(12) United States Patent
Tyler et al.

(10) Patent No.: US 9,879,041 B2
(45) Date of Patent: Jan. 30, 2018

(54) SACCHARIDE DENDRITIC CLUSTER COMPOUNDS AS INHIBITORS OF BACE-1

(71) Applicants: Victoria Link Limited, Wellington (NZ); University of Liverpool, Liverpool (GB)

(72) Inventors: Peter Charles Tyler, Wellington (NZ); Olga Vladimirovna Zubkova, Waikanae Beach (NZ); Jeremy E. Turnbull, Cleobury Mortimer (GB)

(73) Assignees: Victoria Link Limited, Wellington (NZ); University of Liverpool, Liverpool (GB)

( * ) Notice: Subject to any disclaimer, the term of this patent is extended or adjusted under 35 U.S.C. 154(b) by 75 days.

(21) Appl. No.: 14/646,808

(22) PCT Filed: Nov. 28, 2013

(86) PCT No.: PCT/NZ2013/000216
§ 371 (c)(1),
(2) Date: May 22, 2015

(87) PCT Pub. No.: WO2014/084744
PCT Pub. Date: Jun. 5, 2014

(65) Prior Publication Data
US 2015/0291644 A1    Oct. 15, 2015
US 2017/0152279 A9    Jun. 1, 2017

(30) Foreign Application Priority Data

Nov. 28, 2012 (NZ) .......................... 603908
Nov. 28, 2012 (NZ) .......................... 603910

(51) Int. Cl.
*C07H 15/04*    (2006.01)
*C07H 15/08*    (2006.01)

(52) U.S. Cl.
CPC .............. *C07H 15/08* (2013.01); *C07H 15/04* (2013.01)

(58) Field of Classification Search
CPC ................................ C07H 15/04; C07H 15/08
USPC ........................................... 514/25; 536/17.6
See application file for complete search history.

(56) References Cited

FOREIGN PATENT DOCUMENTS

| WO | WO 95/25736 | * | 9/1995 | ............. C07H 15/04 |
|---|---|---|---|---|
| WO | WO1995025736 A1 | | 9/1995 | |
| WO | WO2012037254 A1 | | 3/2012 | |
| WO | WO2012121617 A1 | | 9/2012 | |

OTHER PUBLICATIONS

The Merck Manual, 1992, 16th Edn., pp. 1493-1497.*

* cited by examiner

*Primary Examiner* — Ganapathy Krishnan
(74) *Attorney, Agent, or Firm* — Glenn J. Foulds; Bozicevic, Field & Francis LLP

(57) ABSTRACT

The invention relates to dendritic compounds, the use of these compounds as pharmaceuticals, pharmaceutical compositions containing the compounds, processes for preparing the compounds, and methods of treating diseases or conditions in which it is desirable to inhibit β-secretase.

19 Claims, 1 Drawing Sheet

SACCHARIDE DENDRITIC CLUSTER COMPOUNDS AS INHIBITORS OF BACE-1

TECHNICAL FIELD

This invention relates generally to dendritic compounds, the use of these compounds as pharmaceuticals, pharmaceutical compositions containing the compounds, processes for preparing the compounds, and methods of treating diseases or conditions in which it is desirable to inhibit β-secretase.

BACKGROUND

As populations age neurodegenerative disorders, such as Alzheimer's disease, become more prevalent. Alzheimer's disease is a common form of dementia, and is progressive and irreversible. The pathogenesis of the disease is thought to involve cerebral deposits of aggregated amyloid β-peptide. The first (and rate-limiting) step in the generation of amyloid β-peptide is cleavage of amyloid precursor protein by β-secretase (β-site amyloid precursor protein cleaving enzyme-1, β-secretase-1, hereinafter "BACE-1"). This makes BACE-1 an attractive target for new Alzheimer's therapies.

Heparan sulfate (HS) and its highly sulfated analogue heparin have been shown to inhibit BACE-1 activity. HS and heparin are both glycosaminoglycans comprising 1,4-linked disaccharide units of β-D-iduronic acid or α-L-iduronic acid with N-acetyl-α-D-glucosamine (dominant in the case of HS) or N-sulfo-α-D-glucosamine (dominant in the case of heparin) and additional O-sulfate ester substituents. Heparin is a well-known pharmaceutical with anti-coagulant activity. However, the anti-coagulant properties of heparin need to be attenuated if it is to be used for other pharmaceutical applications otherwise possible side effects, such as internal bleeding and impaired blood clotting, can be problematic.

There is a need for further oligosaccharides which are inhibitors of BACE-1. Furthermore, if such oligosaccharides were synthetic, in other words, if they could be synthesised de novo, they would, advantageously, be well-characterised single chemical entities. This would make them attractive for use as pharmaceuticals. However, long linear heparan sulfate mimics can be complex and expensive to synthesise. Dendrimer constructs would provide the multiple binding epitopes required for tight binding, and are easier to prepare synthetically.

It is therefore an object of the present invention to provide compounds that are inhibitors of BACE-1, or to at least provide a useful choice.

SUMMARY OF INVENTION

In a first aspect, the present invention provides a compound of formula (I)

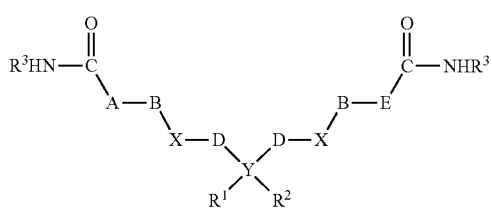

(I)

wherein:

$R^3$ is a radical of formula (iii), a radical of formula (iv) or a radical of formula (iv)(a)

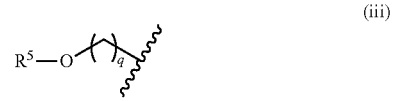

(iii)

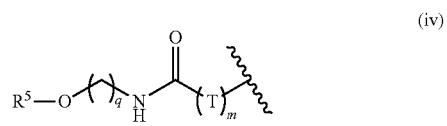

(iv)

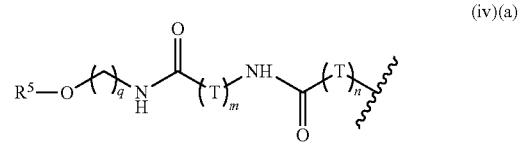

(iv)(a)

$R^5$ is a radical of formula (v), (vi), (vii), (viii) or (ix):

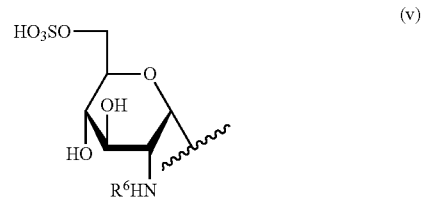

(v)

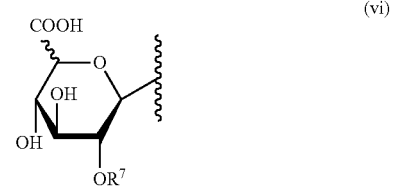

(vi)

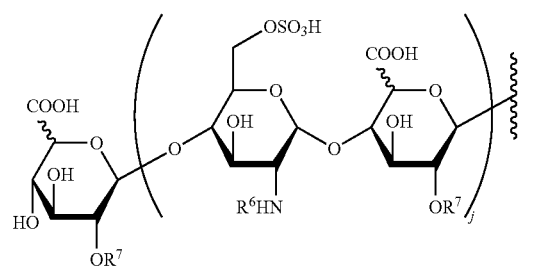

(vii)

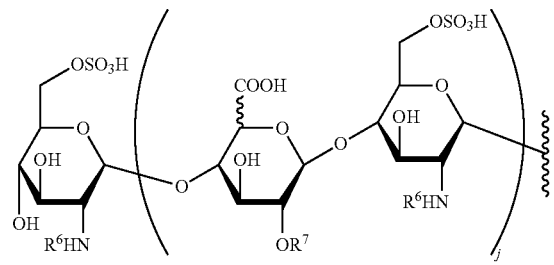

(viii)

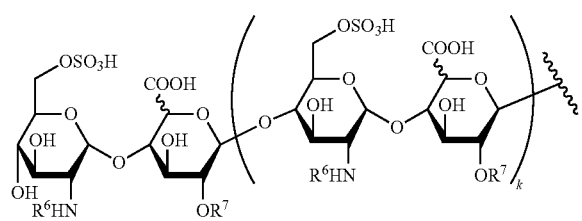

j is an integer from 1 to 6;
k is an integer from 0 to 5;
$R^6$ is H, $SO_3H$, an acyl group which is optionally radiolabelled, or $R^6$ is C(=O)$R^8$ where $R^8$ is aryl or aralkyl;
$R^7$ is H or $SO_3H$;
and:
Y is O;
B is O;
$R^1$ and $R^2$ are absent; and
either A, E, D and X are all $CH_2$; or A, D and X are all $CH_2$ and E is $(CH_2CH_2O)_t{}^\#CH_2$ wherein # indicates a point of attachment of E to its adjacent carbonyl group;
t is an integer from 1 to 10;
or:
Y is C;
$R^1$ and $R^2$ are both H; and
A, E, B and D are $CH_2$ and X is O;
or:
Y is C;
A is $(CH_2)$
$R^1$ and $R^2$ are both H;
B, X, D and E are all absent; and
u is an integer from 1 to 10;
or:
Y is C;
X is O;
B is $(CH_2)_p$;
A, E and D are all $CH_2$; and
$R^1$ is H, NHZ or $C_{1-6}$alkyl and $R^2$ is a radical of formula (i), a radical of formula (ii) or a radical of formula (ii)(a)

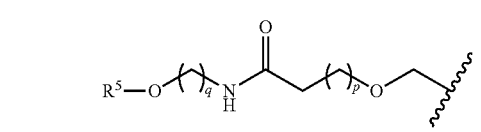 (i)

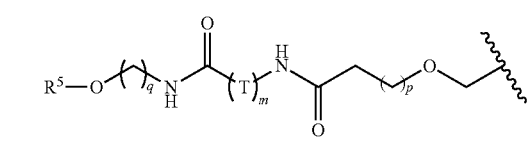 (ii)

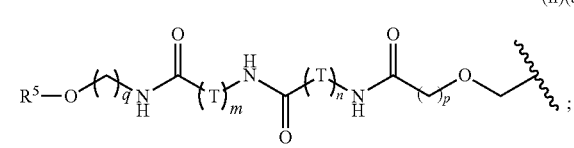 (ii)(a)

Z is H, acyl, C(O)$(CH_2)_w$N(H)G, *$CH_3$*C(O)— where *C denotes $^{13}$C or $^{14}$C, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino) phenyl]ethenyl}pyridinium hexafluorophosphate);

w is an integer from 1 to 11;
G is H, acyl, Boc (t-butoxycarbonyl), Troc (2,2,2-trichloroethyloxycarbonyl), Fmoc (9-fluorenylmethoxycarbonyl), Cbz (benzyloxycarbonyl),*$CH_3$*C(O)— where *C denotes $^{13}$C or $^{14}$C, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino) phenyl]ethenyl}pyridinium hexafluorophosphate);

or:
Y is C;
X is O;
B is $(CH_2)_p$;
A, E and D are all $CH_2$; and
$R^1$ and $R^2$, both the same, are a radical of formula (i), a radical of formula (ii) or a radical of formula (ii)(a)

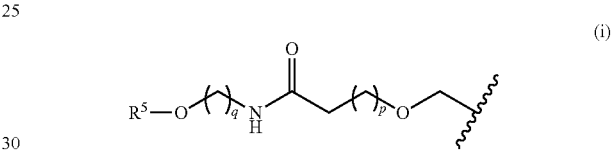 (i)

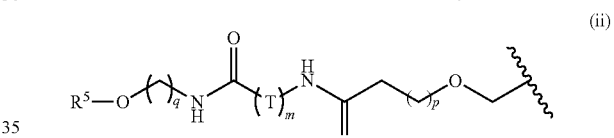 (ii)

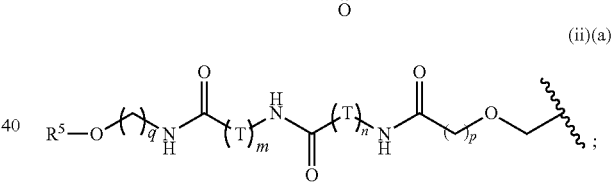 (ii)(a)

each T is independently selected from the group consisting of $(CH_2CH_2O)_xCH_2CH_2$ and $CH_2$;
each x is independently an integer from 1 to 12;
n is an integer from 1 to 11, provided that when T is $(CH_2CH_2O)_xCH_2CH_2$ then n is 1;
q is an integer from 1 to 11;
m is an integer from 1 to 11, provided that when T is $(CH_2CH_2O)_xCH_2CH_2$ then m is 1;
p is an integer from 1 to 5;
or a pharmaceutically acceptable salt thereof, or a prodrug thereof.

Preferably each T is $CH_2$.
Alternatively preferably at least one T is $CH_2$.
Alternatively preferably at least one T is $(CH_2CH_2O)_x CH_2CH_2$.

Preferably the pharmaceutically acceptable salt is an ammonium salt, a metal salt, or a salt of an organic cation, or a mixture thereof. More preferably the pharmaceutically acceptable salt is a sodium salt.

Preferably the radical (vi), (vii) (viii) or (ix) is all glucoform. Alternatively it is preferred that the radical (vi), (vii), (viii) or (ix) is all ido-form.

Preferably radical (vi) is:

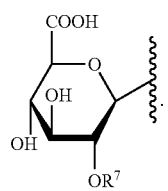

(vi)

Alternatively, preferably radical (vi) is:

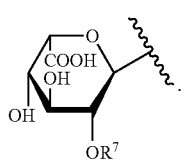

(vi)

Preferably radical (vii) is:

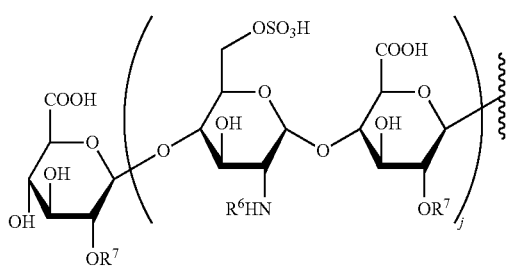

(vii)

where j is as defined above.

Alternatively, preferably radical (vii) is:

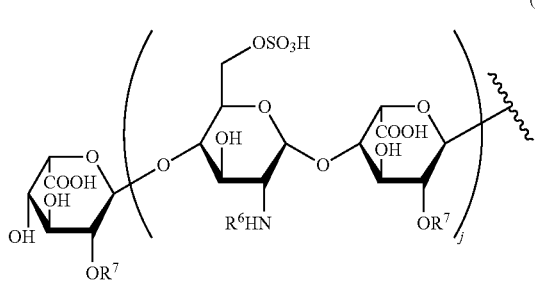

(vii)

where j is as defined above.

Preferably radical (viii) is:

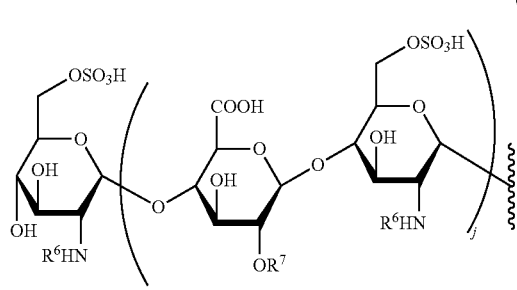

(viii)

where j is as defined above.

Alternatively preferably radical (viii) is:

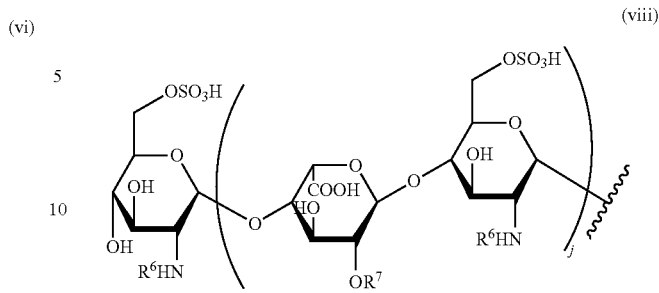

(viii)

where j is as defined above.
Preferably j is 1.
Preferably radical (ix) is:

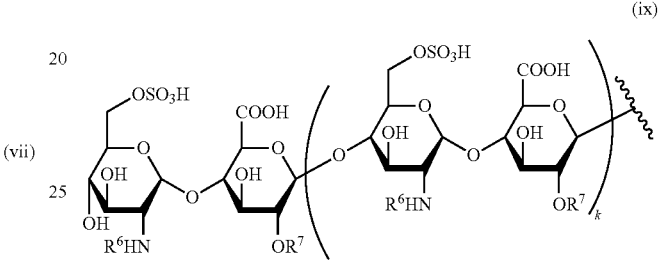

(ix)

where k is as defined above.
Alternatively, preferably radical (ix) is:

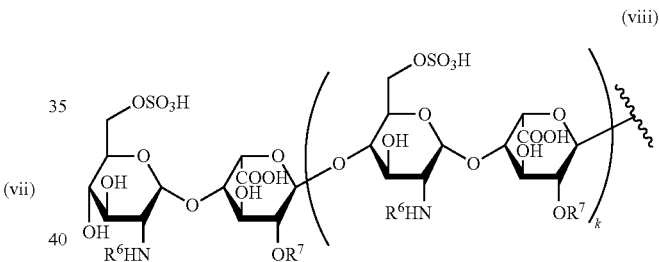

(viii)

where k is as defined above.
Preferably k is 0 or 1.
Alternatively preferably, the radical (vi), (vii), (viii) or (ix) comprises a mixture of gluco-form and ido-form saccharide units.
Preferably $R^6$ is an acetyl group which is optionally radiolabelled.
Preferably Z is acetyl.
Preferably G is acetyl.
Preferably $R^1$ and $R^2$ are both a radical of formula (i)

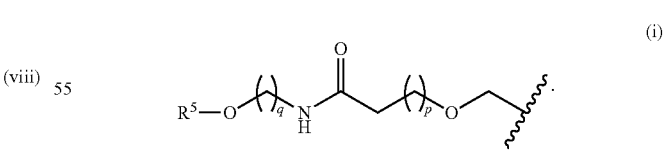

(i)

Alternatively it is preferred that $R^1$ and $R^2$ are both a radical of formula (ii)

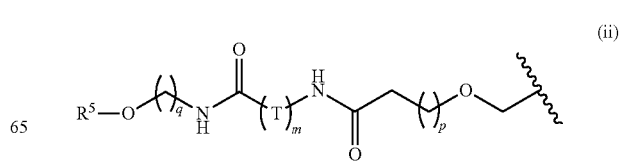

(ii)

Alternatively it is preferred that $R^1$ and $R^2$ are both a radical of formula (ii)(a)

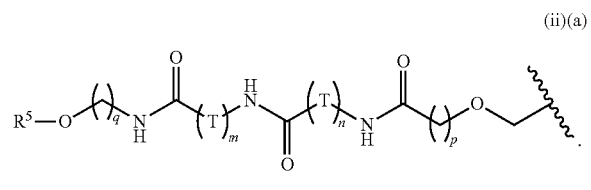
(ii)(a)

It is further preferred that, in $R^1$, one T is $(CH_2CH_2O)_x CH_2CH_2$ and one T is $CH_2$ and in $R^2$ one T is $(CH_2CH_2O)_x CH_2CH_2$ and one T is $CH_2$.

It is further preferred that, in both of $R^1$ and $R^2$, $(T)_m$ is $(CH_2CH_2O)_x CH_2CH_2$ and $(T)_n$ is $(CH_2)_n$. Alternatively it is preferred that, in both of $R^1$ and $R^2$, $(T)_m$ is $(CH_2)_m$ and $(T)_n$ is $(CH_2CH_2O)_x CH_2CH_2$.

Alternatively preferably $R^1$ and $R^2$ are both a radical of formula (ii)(a) wherein each T is $(CH_2CH_2O)_x CH_2CH_2$, wherein each x in each radical of formula (ii)(a) is independently selected.

Preferably $R^3$ is a radical of formula (iii)

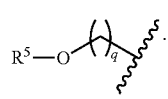
(iii)

Alternatively it is preferred that $R^3$ is a radical of formula (iv)

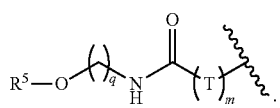
(iv)

Alternatively it is preferred that $R^3$ is a radical of formula (iv)(a)

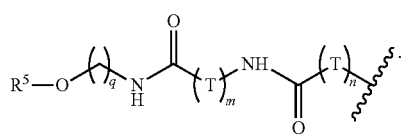
(iv)(a)

It is further preferred that, in $R^3$, one T is $(CH_2CH_2O)_x CH_2CH_2$ and one T is $CH_2$. It is further preferred that, in $R^3$, $(T)_m$ is $(CH_2CH_2O)_x CH_2CH_2$ and $(T)_n$ is $(CH_2)_n$. Alternatively it is preferred that, in $R^3$, $(T)_n$ is $(CH_2CH_2O)_x CH_2CH_2$ and $(T)_m$ is $(CH_2)_m$.

Alternatively preferably $R^3$ is a radical of formula (iv)(a) wherein each T is $(CH_2CH_2O)_x CH_2CH_2$, wherein each x in each radical of formula (iv)(a) is independently selected.

It is preferred that $R^1$ is H or $C_{1-6}$alkyl, e.g. $CH_3$ or $CH_2CH_3$. Alternatively it is preferred that $R^1$ is $NH_2$. Alternatively it is preferred that $R^1$ is NHZ, more preferably wherein Z is $C(O)(CH_2)_w N(H)G$, e.g. where G is Troc (2,2,2-trichloroethyloxycarbonyl), Fmoc (fluorenylmethyloxycarbonyl) or Cbz (benzyloxycarbonyl). Preferably w is 7.

Preferably Y is O; B is O; $R^1$ and $R^2$ are absent; and either A, E, D and X are all $CH_2$ or A, D and X are all $CH_2$ and E is $(CH_2CH_2O)_t CH_2$; and t is an integer from 1 to 10, preferably an integer from 1 to 2.

Alternatively it is preferred that Y is C; $R^1$ and $R^2$ are both H; A, E, B and D are $CH_2$ and X is O.

Alternatively it is preferred that Y is C; A is $(CH_2)_u$; $R^1$ and $R^2$ are both H; B, X, D and E are all absent; and u is an integer from 1 to 10.

Alternatively it is preferred that:
Y is C; X is O; A, E and D are all $CH_2$; B is $(CH_2)_p$;
$R^1$ is H, NHZ or $C_{1-6}$alkyl;
$R^2$ is a radical of formula (i), a radical of formula (ii) or a radical of formula (ii)(a)

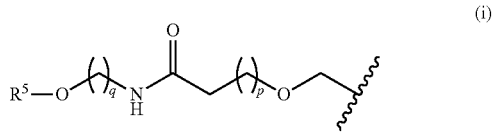
(i)

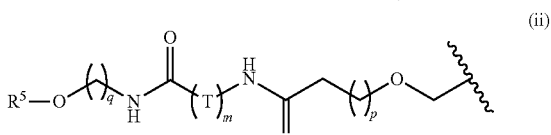
(ii)

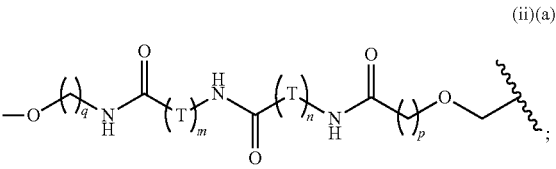
(ii)(a)

Z is H, acyl, $C(O)(CH_2)_w N(H)G$, *$CH_3$*C(O)— where *C denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate);
w is an integer from 1 to 11;
G is H, acyl, Boc (t-butoxycarbonyl), Troc (2,2,2-trichloroethyloxycarbonyl), Fmoc (9-fluorenylmethoxycarbonyl), Cbz (carboxybenzyl),*$CH_3$*C(O)— where *C denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl) benzoyl]amino}propyl}-4-{2-[4-(dimethylamino)phenyl] ethenyl}pyridinium hexafluorophosphate).

Preferably $R^1$ is H, NHZ or $C_{1-6}$alkyl and $R^2$ is a radical of formula (i)

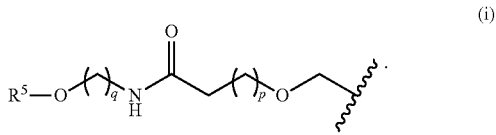
(i)

Alternatively preferably $R^1$ is H, NHZ or $C_{1-6}$alkyl and $R^2$ is a radical of formula (ii)

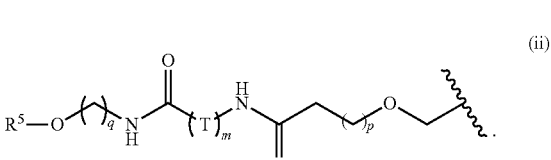
(ii)

Alternatively preferably $R^1$ is H, NHZ or $C_{1-6}$alkyl and $R^2$ is a radical of formula (ii)(a)

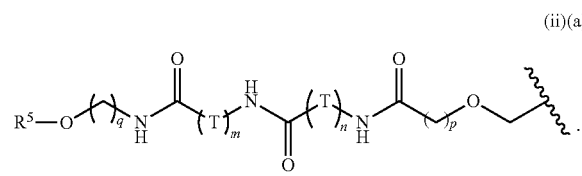

(ii)(a)

It is further preferred that, in $R^2$, is $(T)_m$ is $(CH_2CH_2O)_x$ $CH_2CH_2$ and $(T)_n$ is $(CH_2)_n$. Alternatively it is preferred that, in $R^2$, $(T)_m$ is $(CH_2)_m$ and $(T)_n$ is $(CH_2CH_2O)_xCH_2CH_2$. Alternatively preferably $R^2$ is a radical of formula (ii)(a) wherein each T is $(CH_2CH_2O)_xCH_2CH_2$, wherein each x in each radical of formula (ii)(a) is independently selected.

Alternatively it is preferred that Y is C; X is O; A, E and D are all $CH_2$; B is $(CH_2)_p$;
$R^1$ and $R^2$, both the same, are a radical of formula (i), a radical of formula (ii) or a radical of formula (ii)(a)

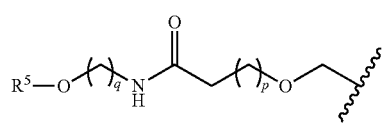

(i)

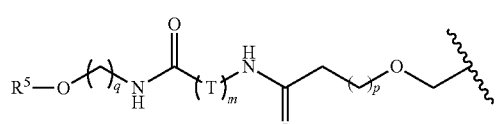

(ii)

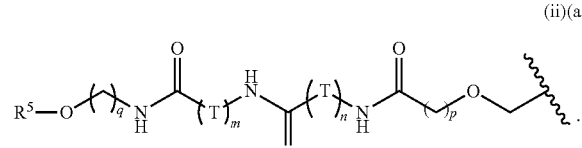

(ii)(a)

Preferably, Y is C; X is O; A, E and D are all $CH_2$; B is $(CH_2)_p$; $R^1$ and $R^2$, both the same, are a radical of formula (i)

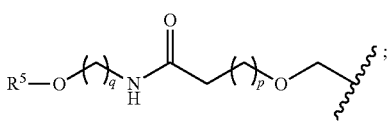

(i)

and $R^3$ is a radical of formula (iii)

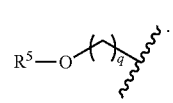

(iii)

More preferably, Y is C; X is O; A, E and D are all $CH_2$; B is $(CH_2)_p$; $R^1$ and $R^2$, both the same, are a radical of formula (i)

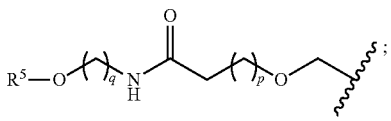

(i)

$R^3$ is a radical of formula (iii)

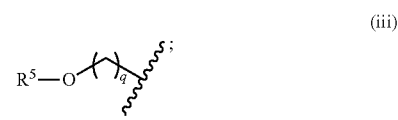

(iii)

and $R^5$ is a radical of formula (ix)

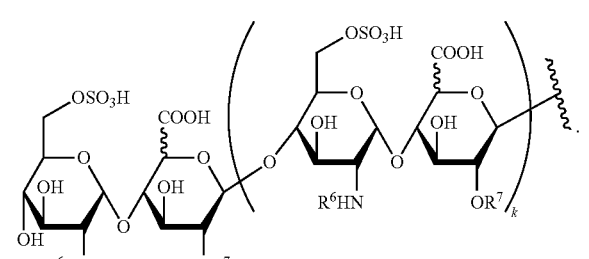

(ix)

Alternatively preferably Y is C; X is O; A, B, E and D are all $CH_2$; $R^1$ and $R^2$, both the same, are a radical of formula (ii)

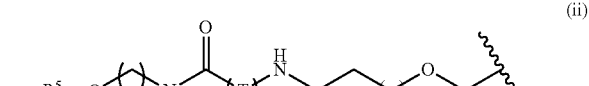

(ii)

and $R^3$ is a radical of formula (iv)

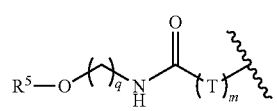

(iv)

Alternatively preferably Y is C; X is O; A, B, E and D are all $CH_2$; $R^1$ and $R^2$, both the same, are a radical of formula (ii)(a)

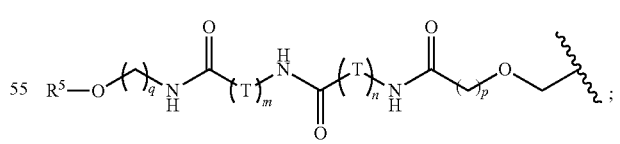

(ii)(a)

and $R^3$ is a radical of formula (iv)(a)

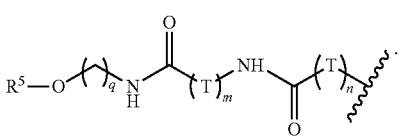

(iv)(a)

More preferably, preferably Y is C; X is O; A, B, E and D are all CH$_2$; R$^1$ and R$^2$, both the same, are a radical of formula (ii)

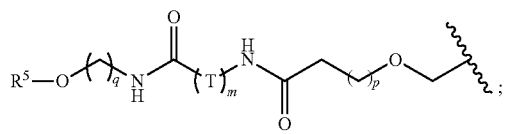
(ii)

R$^3$ is a radical of formula (iv)

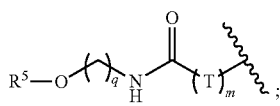
(iv)

and R$^5$ is a radical of formula (ix)

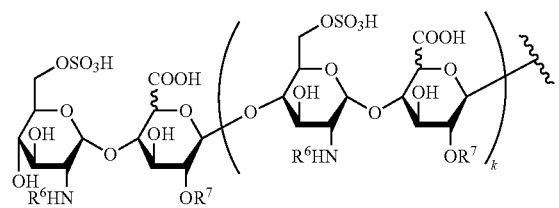
(ix)

Preferably Y is C; R$^1$ and R$^2$ are both H; A, E, B and D are CH$_2$; X is O; and R$^3$ is a radical of formula (iii)

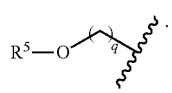
(iii)

Alternatively preferably Y is C; R$^1$ and R$^2$ are both H; A, E, B and D are CH$_2$; X is O; and R$^3$ is a radical of formula (iv)

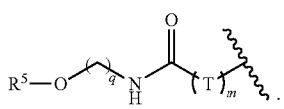
(iv)

Preferably Y is C; X is O; A, B, E and D are all CH$_2$; R$^1$ is H; R$^2$ is a radical of formula (i)

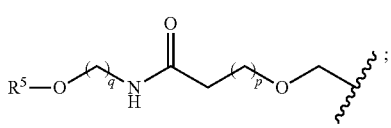
(i)

and R$^3$ is a radical of formula (iii)

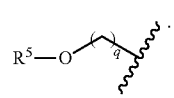
(iii)

Alternatively preferably Y is C; X is O; A, B, E and D are all CH$_2$; R$^1$ is H; R$^2$ is a radical of formula (ii)

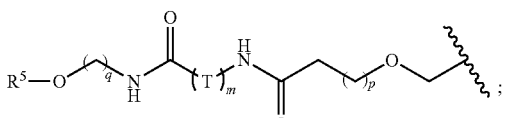
(ii)

and R$^3$ is a radical of formula (iv)

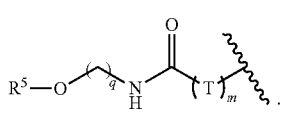
(iv)

Alternatively preferably Y is C; X is O; A, B, E and D are all CH$_2$; R$^1$ is H; R$^2$ is a radical of formula (ii)

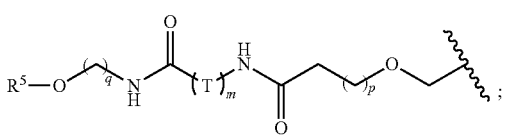
(ii)

and R$^3$ is a radical of formula (iii)

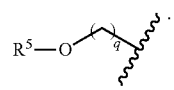
(iii)

Alternatively preferably Y is C; X is O; A, B, E and D are all CH$_2$; R$^1$ is H; R$^2$ is a radical of formula (i)

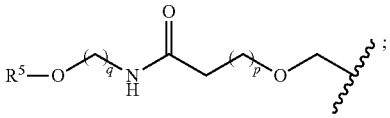
(i)

and R$^3$ is a radical of formula (iv)

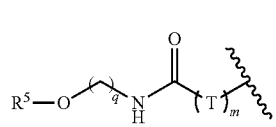
(iv)

Preferably Y is C; A is $(CH_2)_u$; $R^1$ and $R^2$ are both H; B, X, D and E are all absent; u is an integer from 1 to 10; and $R^3$ is a radical of formula (iii)

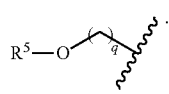 (iii)

Alternatively preferably Y is C; A is $(CH_2)_u$; $R^1$ and $R^2$ are both H; B, X, D and E are all absent; u is an integer from 1 to 10; and $R^3$ is a radical of formula (iv)

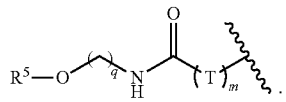 (iv)

Preferably Y is O; B is O; $R^1$ and $R^2$ are absent; and either A, E, D and X are all $CH_2$ or A, D and X are all $CH_2$ and E is $(CH_2CH_2O)_tCH_2$; t is an integer from 1 to 10, preferably an integer from 1 to 2; and $R^3$ is a radical of formula (iii)

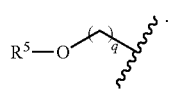 (iii)

Alternatively preferably Y is O; B is O; $R^1$ and $R^2$ are absent; and either A, E, D and X are all $CH_2$ or A, D and X are all $CH_2$ and E is $(CH_2CH_2O)_tCH_2$; t is an integer from 1 to 2; and $R^3$ is a radical of formula (iv)

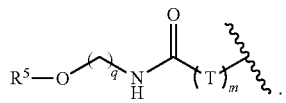 (iv)

Preferably p is 1.

Preferably q is an integer from 3 to 10, e.g. an integer from 4 to 9, e.g. an integer from 5 to 8, e.g. an integer from 6 to 7. Most preferably q is 6.

Preferably n is an integer from 3 to 10, e.g. an integer from 4 to 9, e.g. an integer from 5 to 8, e.g. an integer from 6 to 7. Most preferably n is 7.

Preferably m is an integer from 3 to 10, e.g. an integer from 4 to 9, e.g. an integer from 5 to 8, e.g. an integer from 6 to 7. Most preferably n is 7.

Preferably each T is $CH_2$ and q is an integer from 3 to 10, e.g. an integer from 4 to 9, e.g. an integer from 5 to 8, e.g. an integer from 6 to 7. Most preferably q is 6.

Preferably each T is $CH_2$ and n is an integer from 3 to 10, e.g. an integer from 4 to 9, e.g. an integer from 5 to 8, e.g. an integer from 6 to 7. Most preferably n is 7. More preferably each T is $CH_2$ and q and n are each independently an integer from 3 to 10, e.g. an integer from 4 to 9, e.g. an integer from 5 to 8, e.g. an integer from 6 to 7.

Alternatively preferably at least one T is $CH_2$ and q is an integer from 3 to 10, e.g. an integer from 4 to 9, e.g. an integer from 5 to 8, e.g. an integer from 6 to 7. Most preferably q is 6.

Preferably at least one T is $CH_2$ and n is an integer from 3 to 10, e.g. an integer from 4 to 9, e.g. an integer from 5 to 8, e.g. an integer from 6 to 7. Most preferably n is 7.

Alternatively preferably at least one T is $(CH_2CH_2O)_x CH_2CH_2$ and x is an integer from 2 to 10, e.g. an integer from 2 to 9, e.g. an integer from 2 to 8, e.g. an integer from 2 to 7, e.g. an integer from 2 to 6, e.g. an integer from 2 to 5, e.g. an integer from 2 to 4. Most preferably x is 3.

More preferably at least one T is $CH_2$ and q is 6 and n is 7.

Still more preferably at least one T is $CH_2$ and p is 1 and q is 6. More preferably at least one T is $CH_2$ and p is 1, m is 7 and q is 6.

Preferably the compound of formula (I) is selected from the group consisting of:

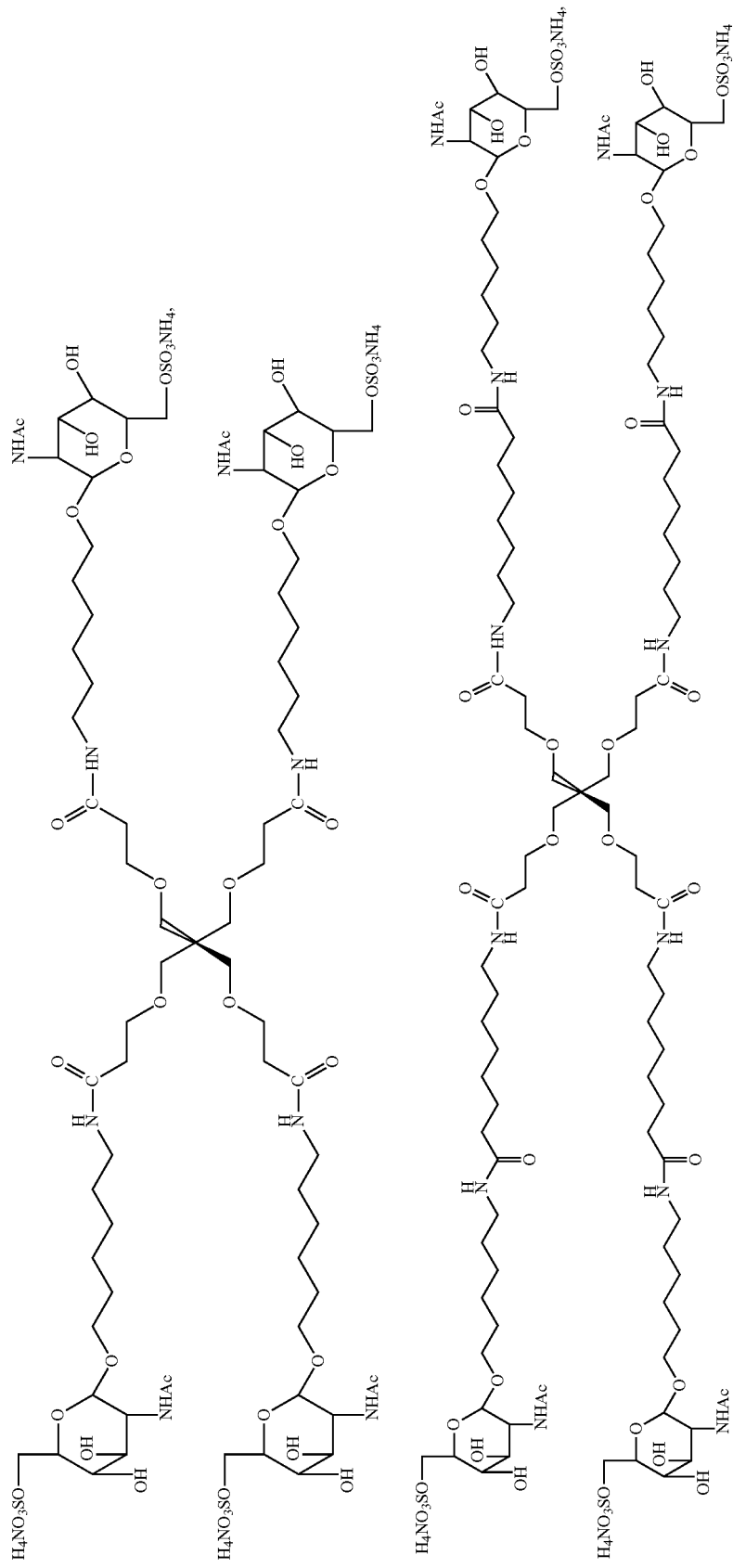

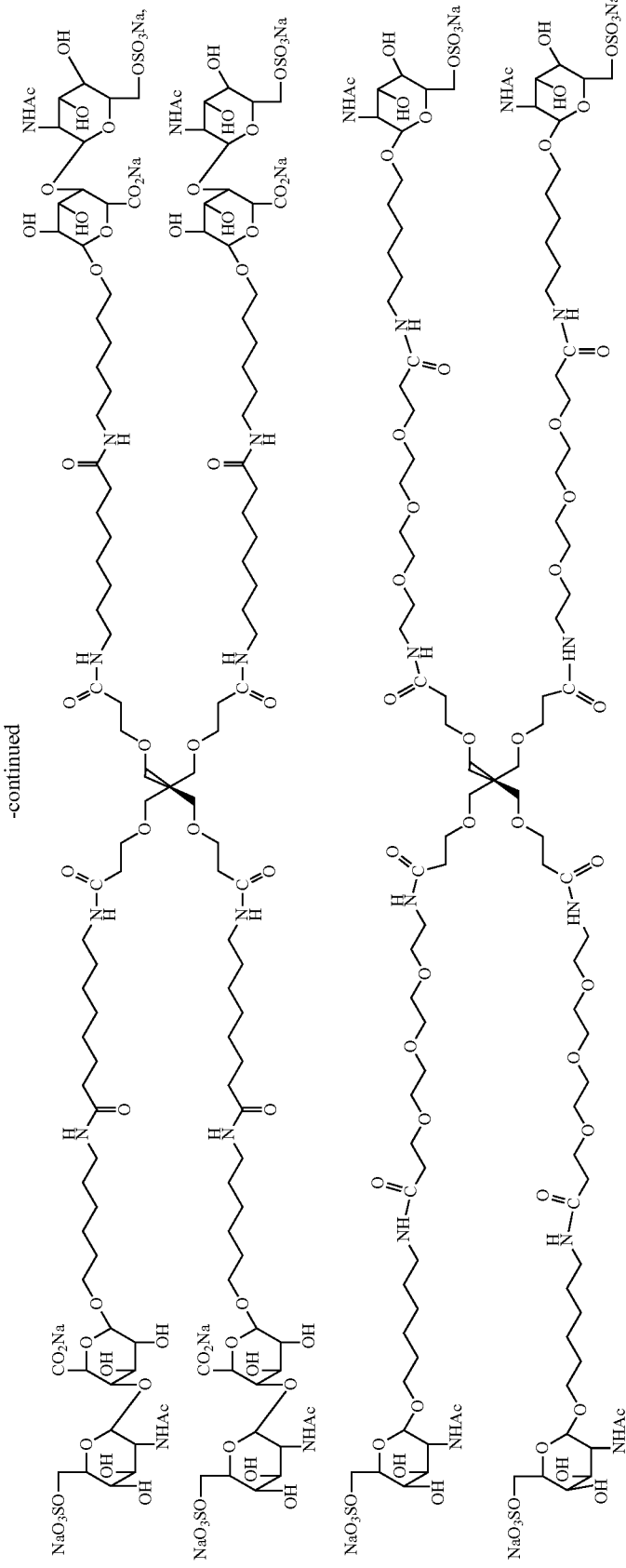

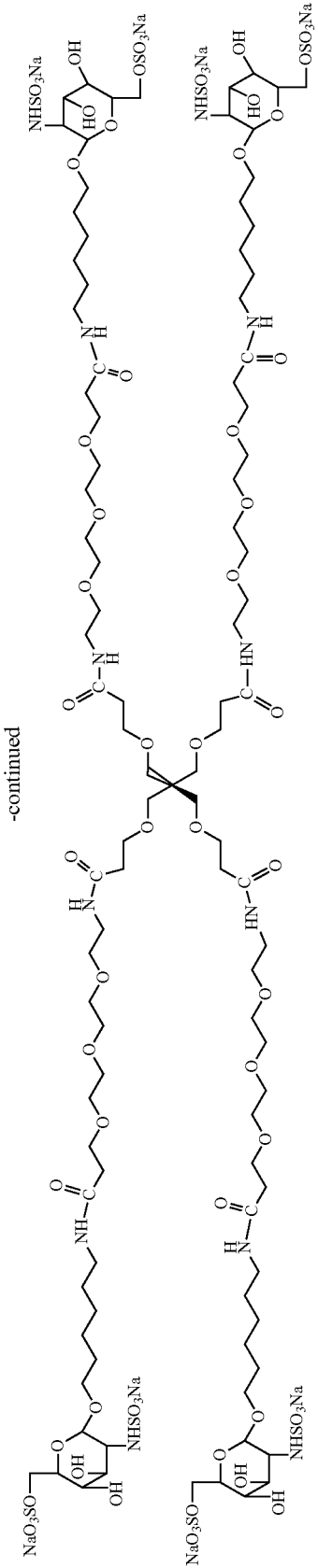
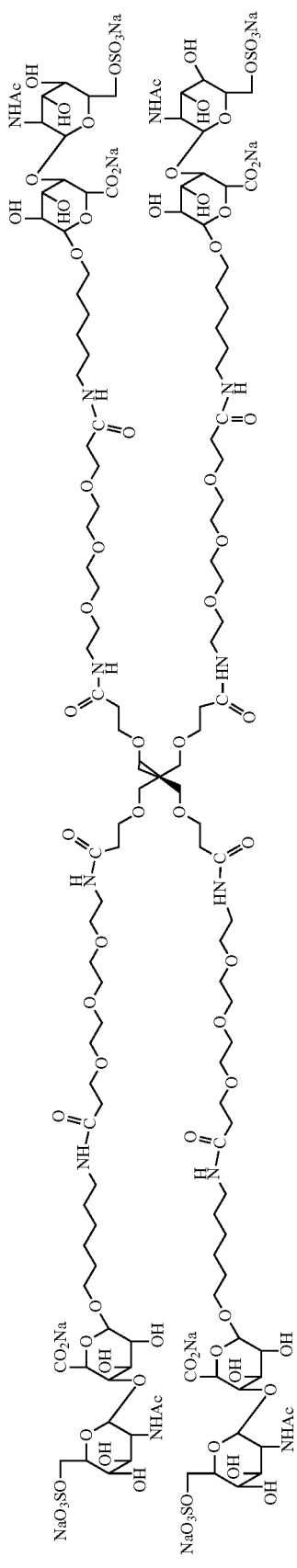

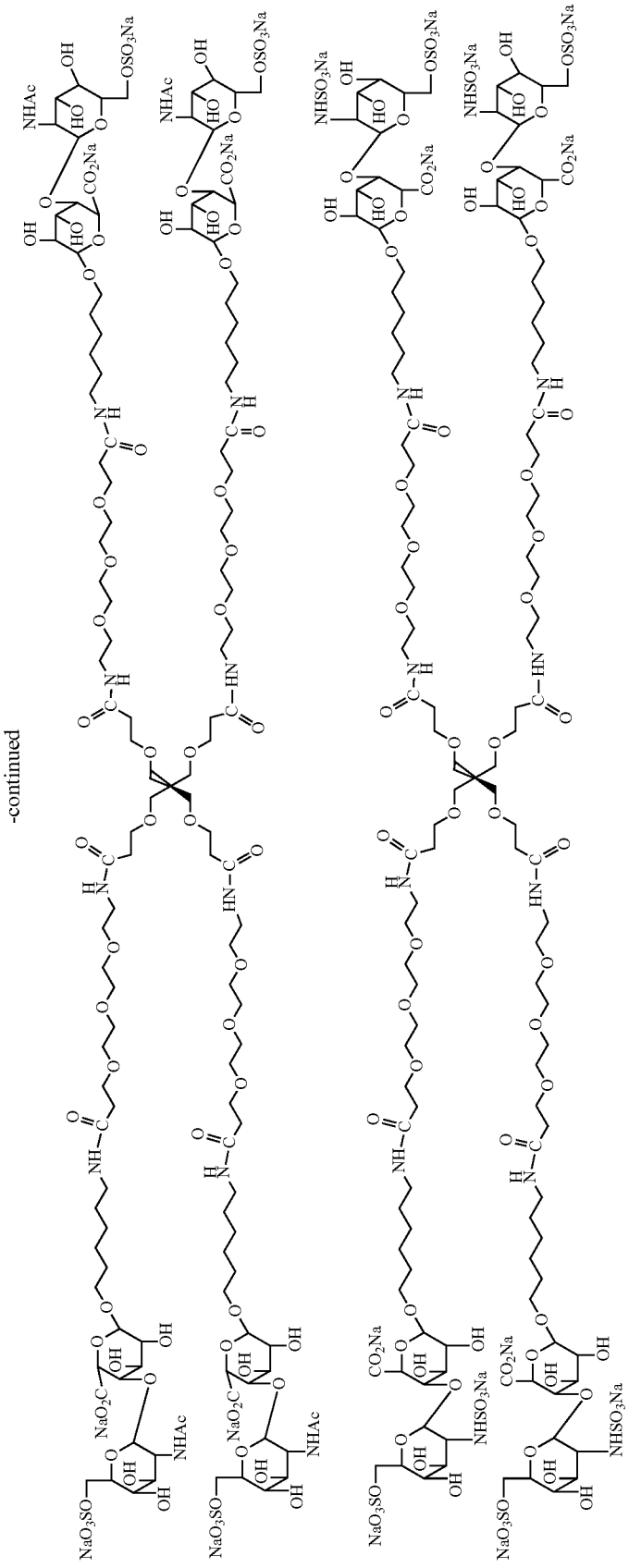

-continued
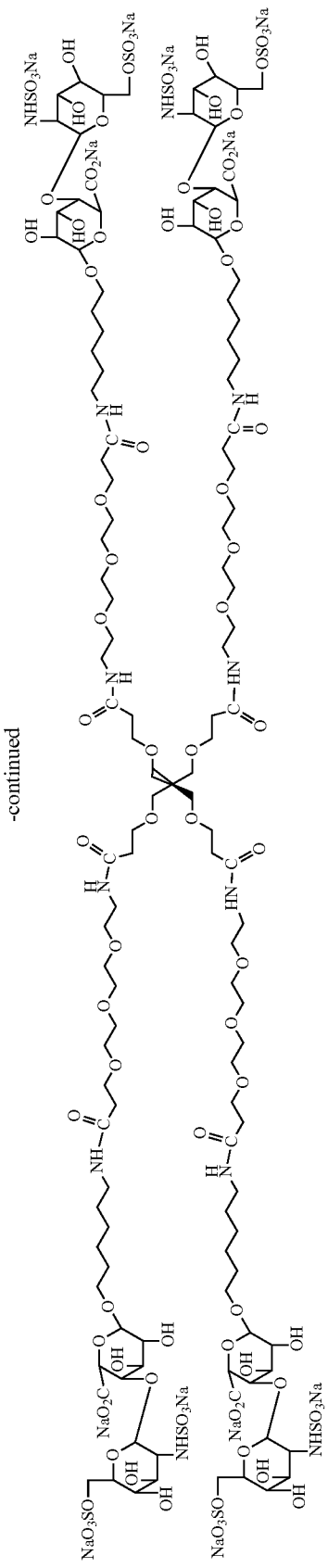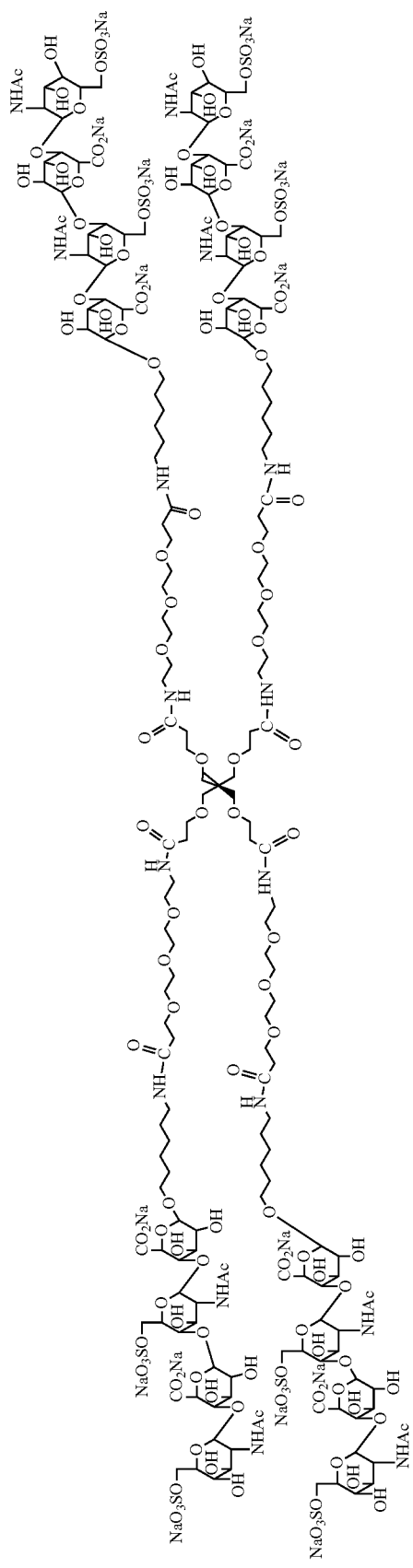

-continued
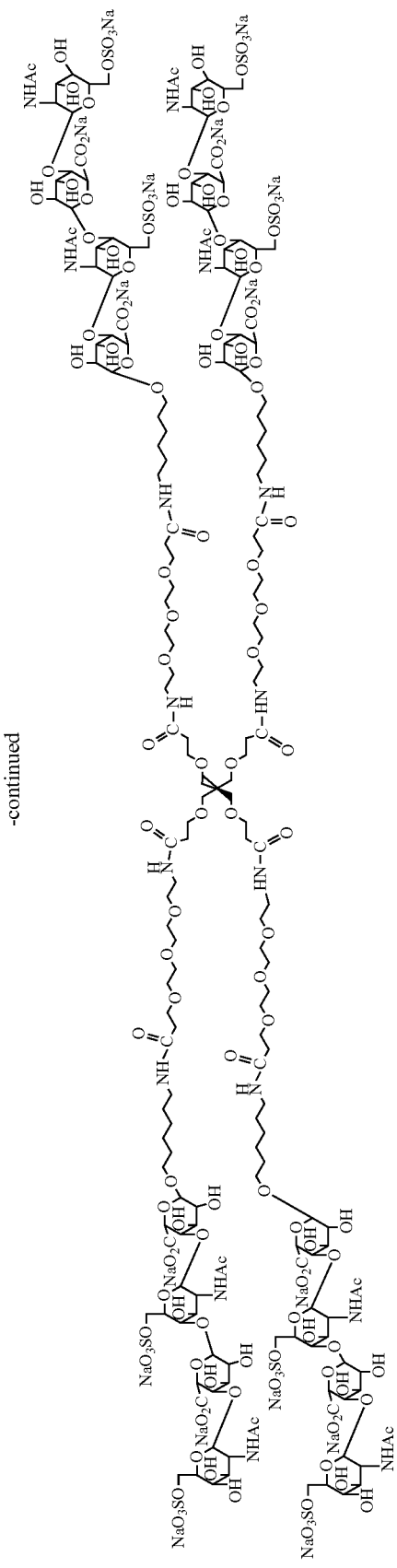
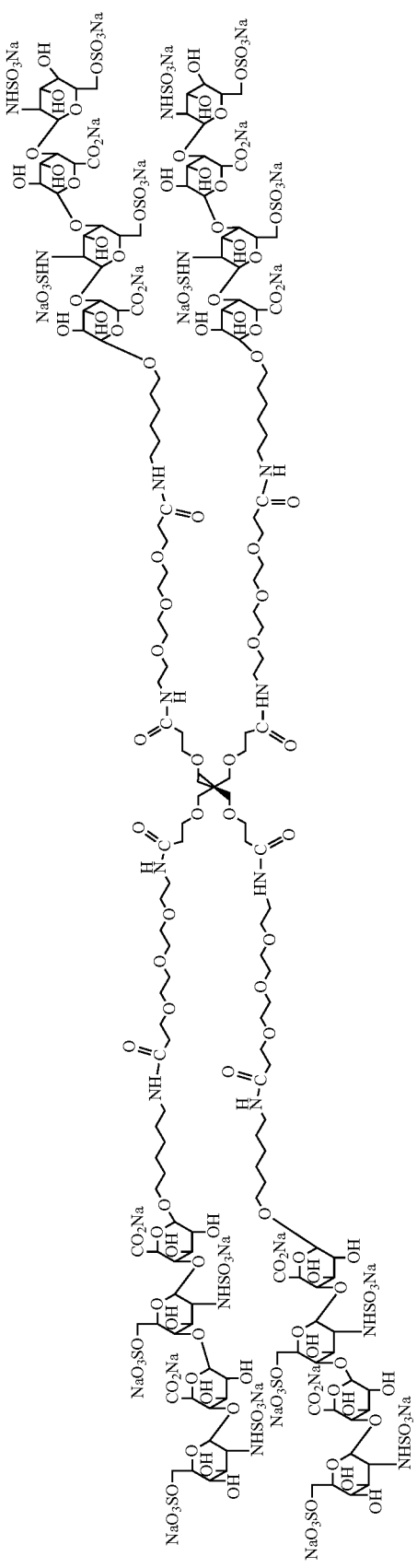

-continued
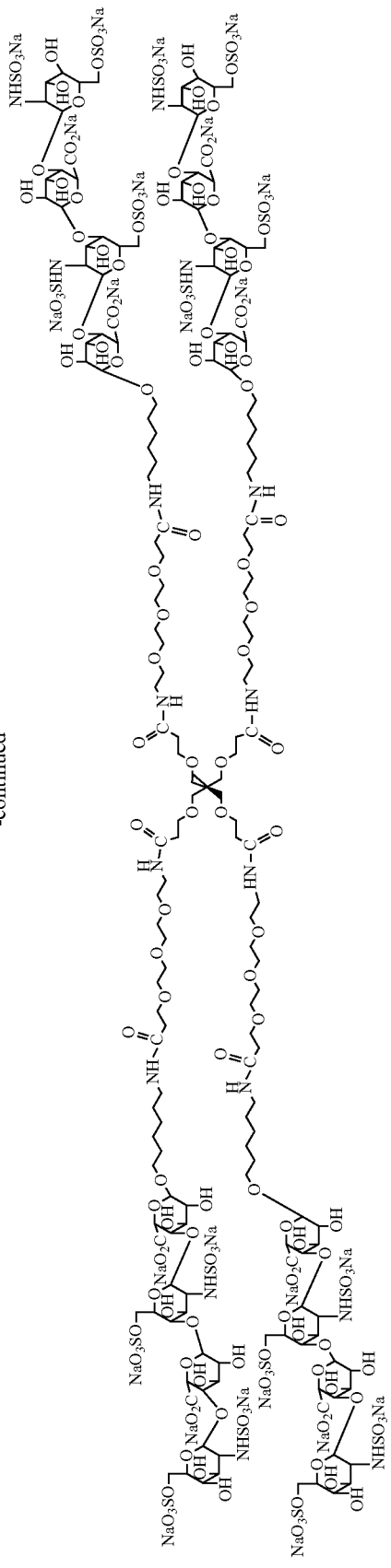
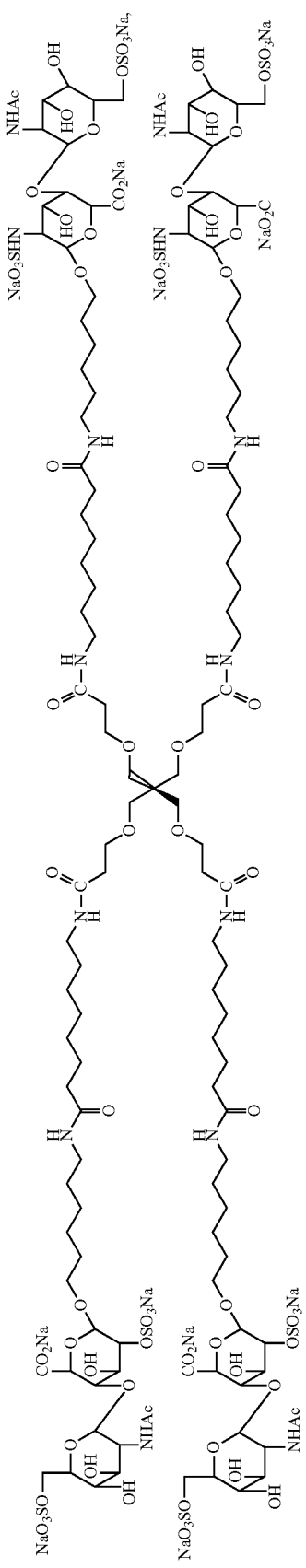

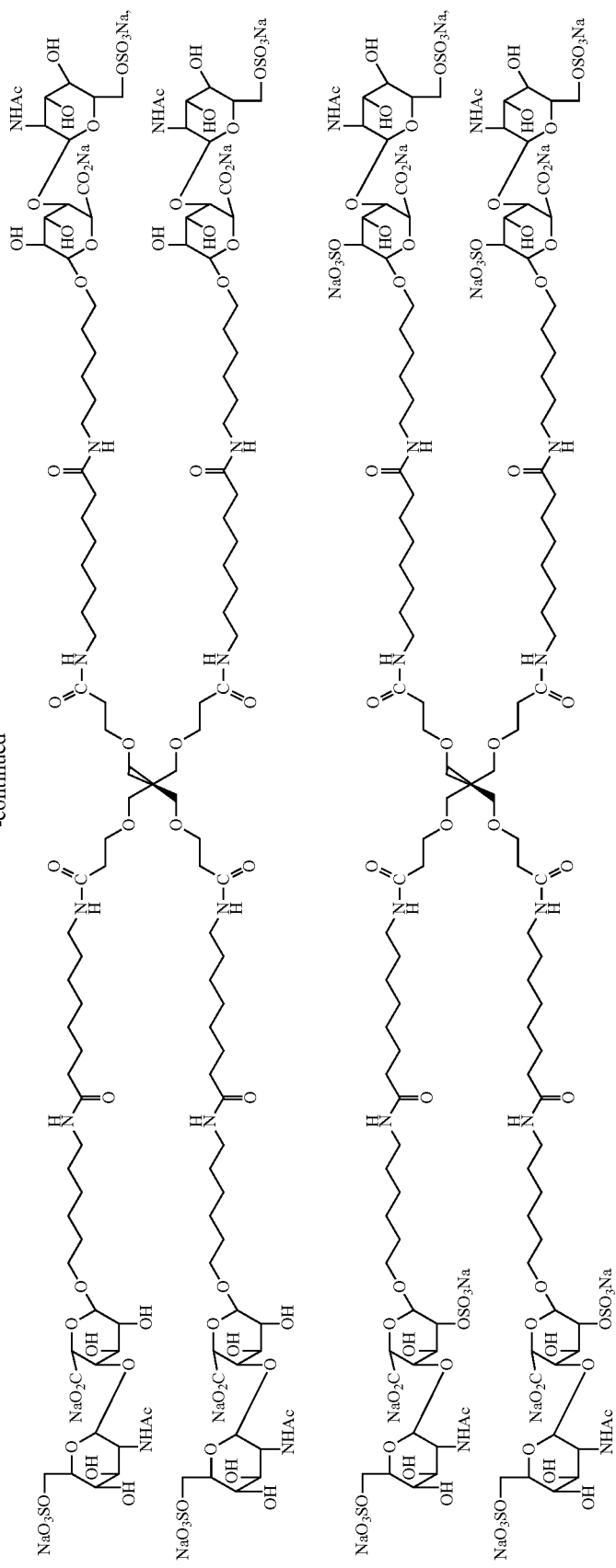

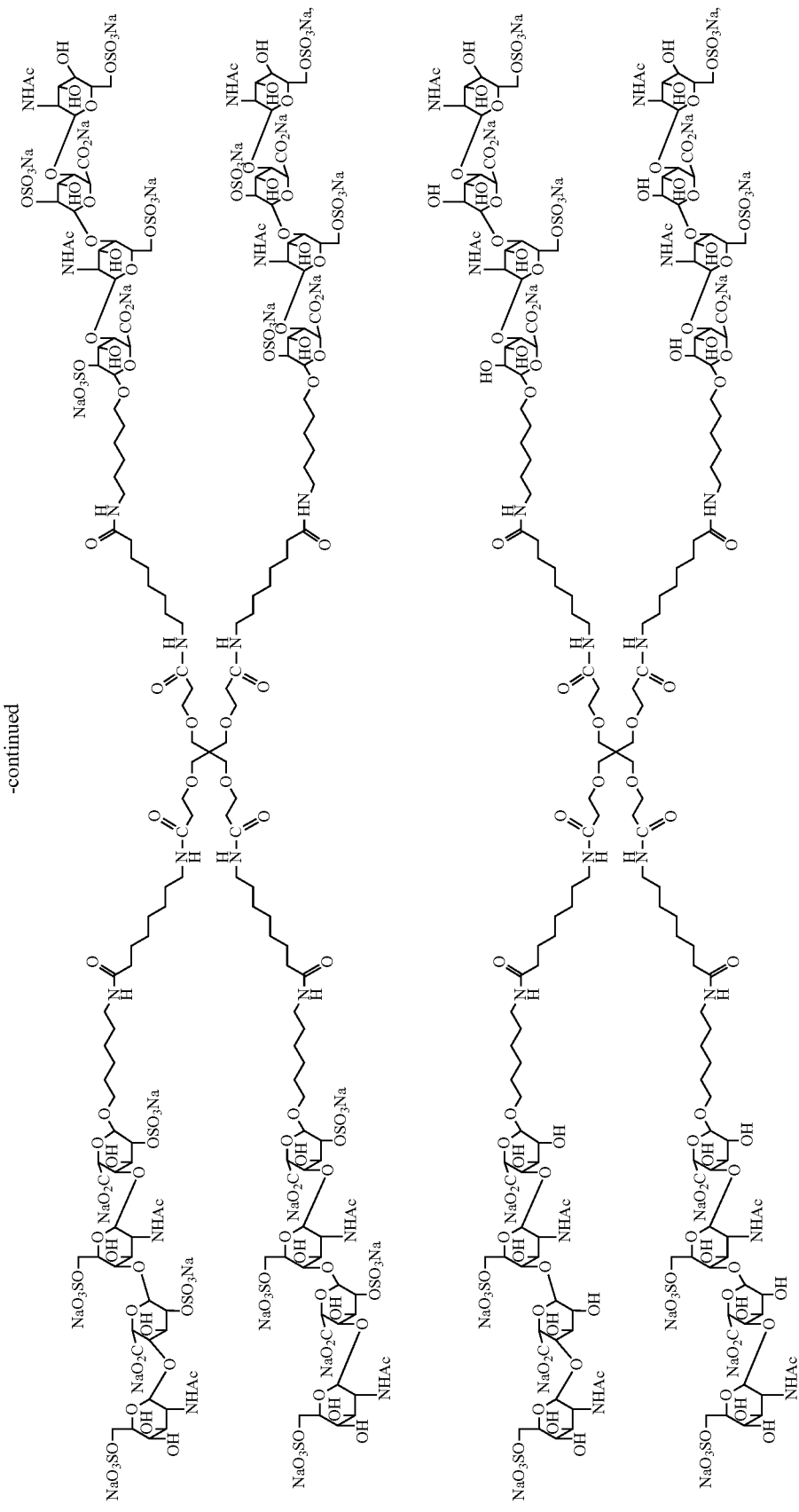

-continued
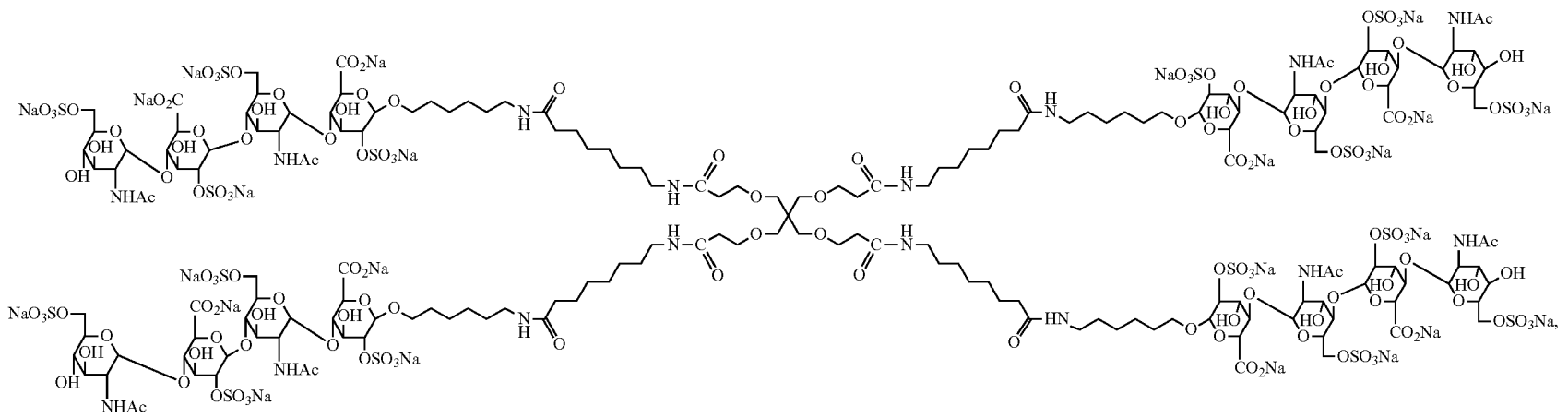

-continued
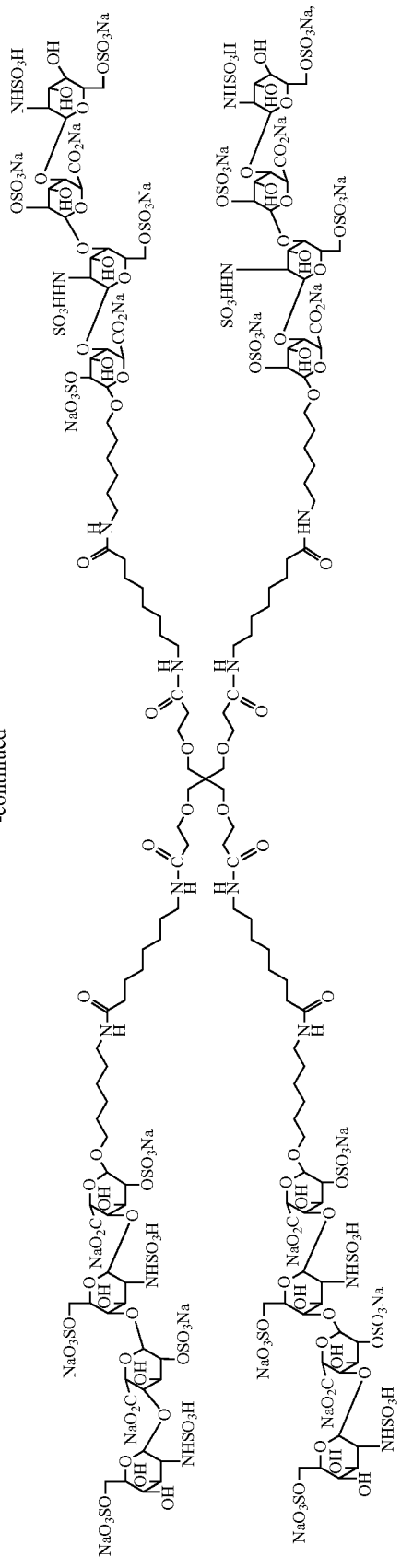
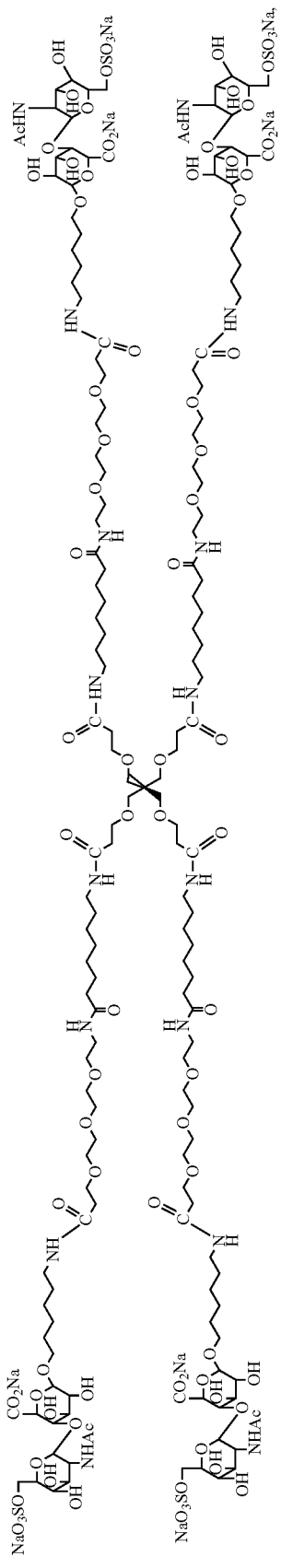

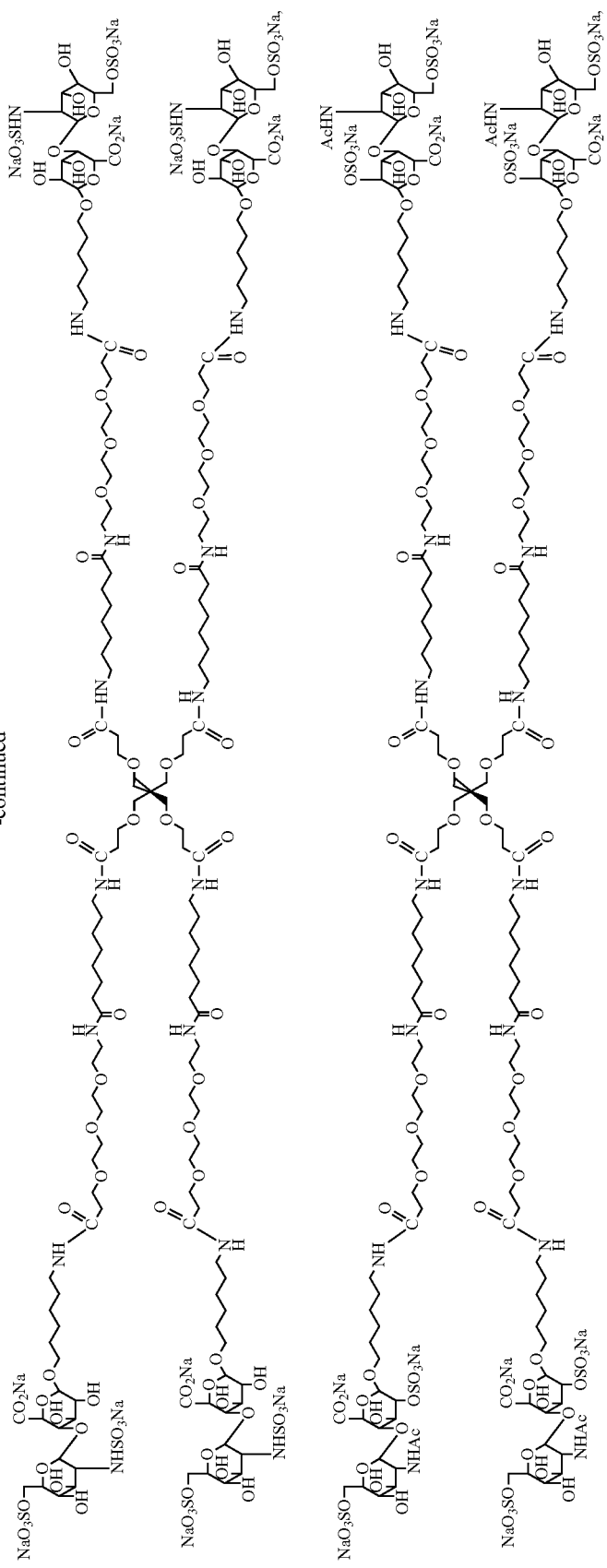

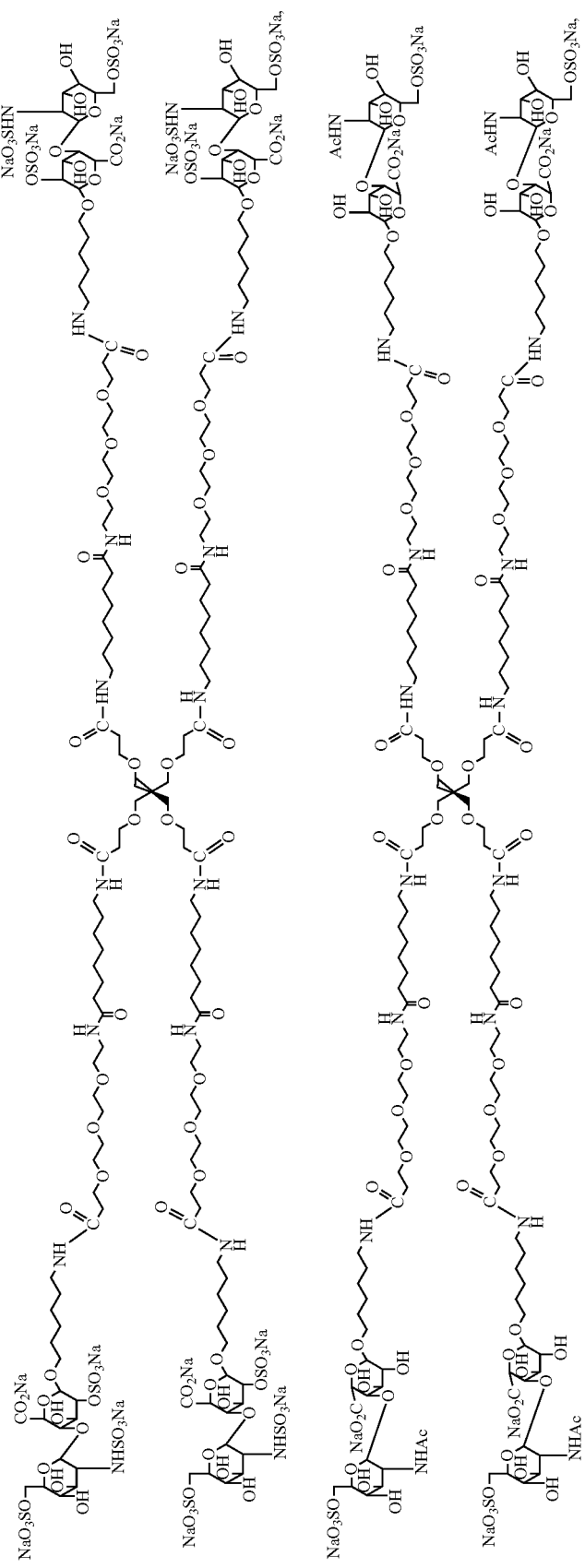

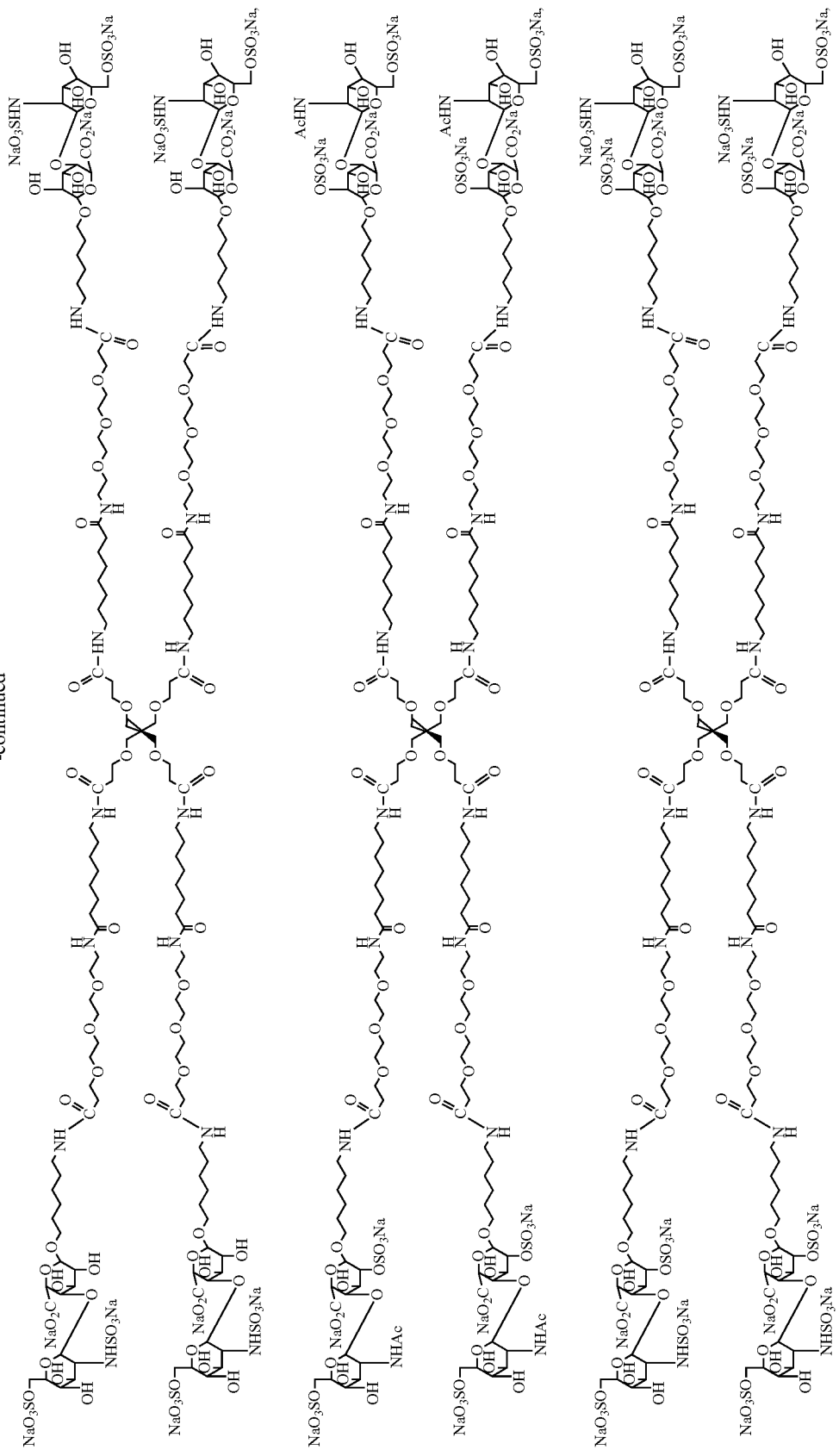

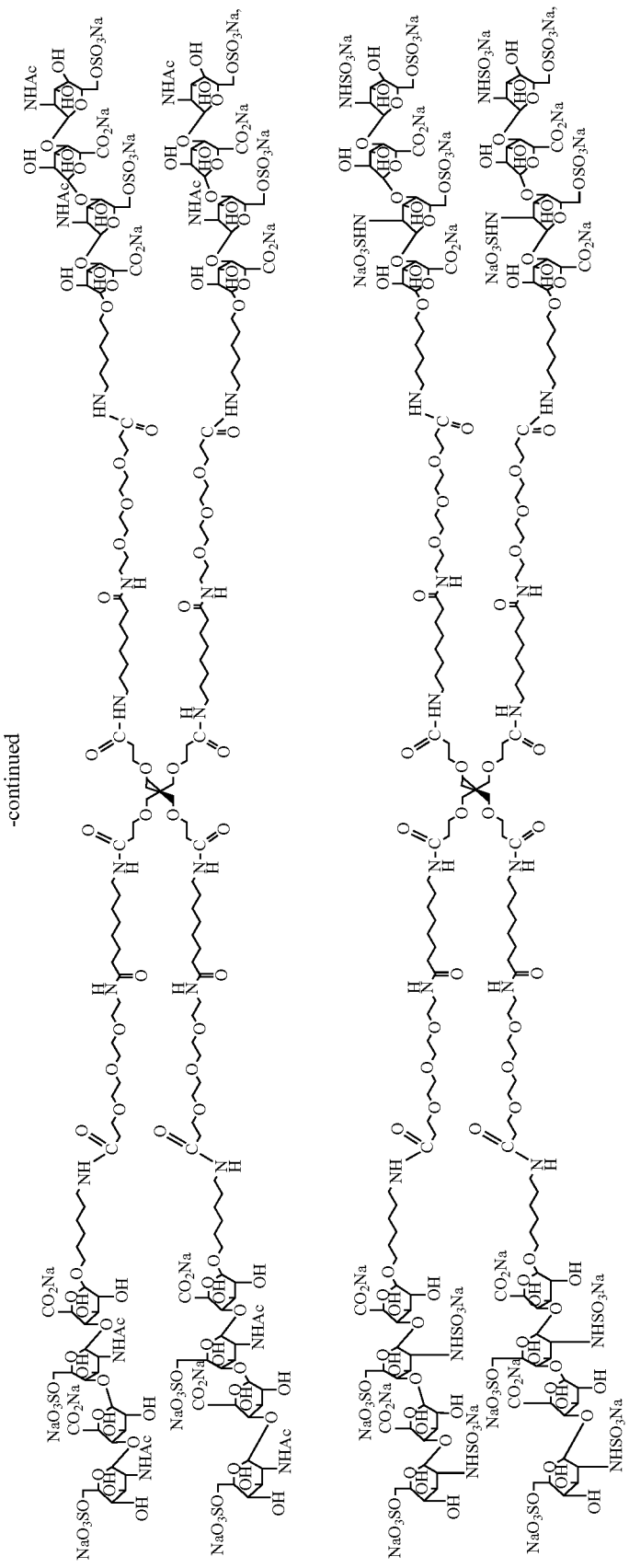

-continued
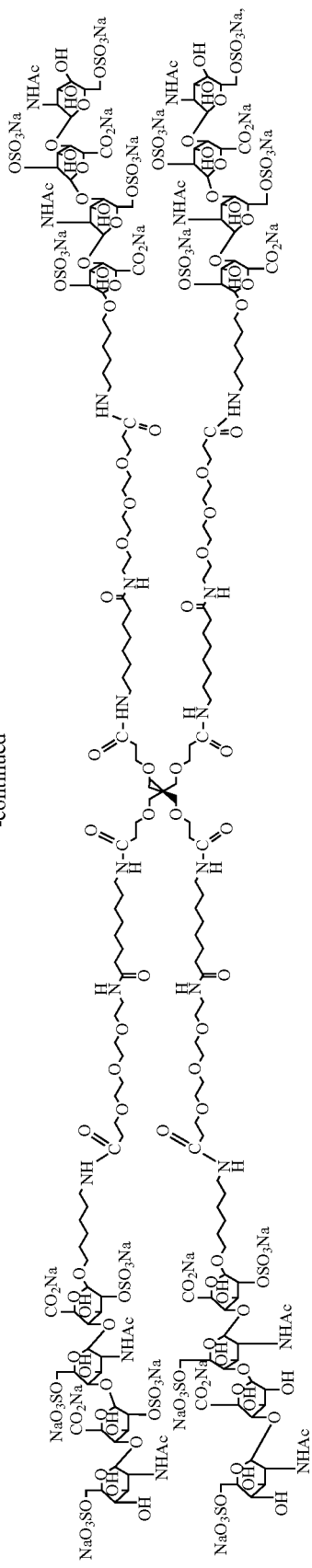
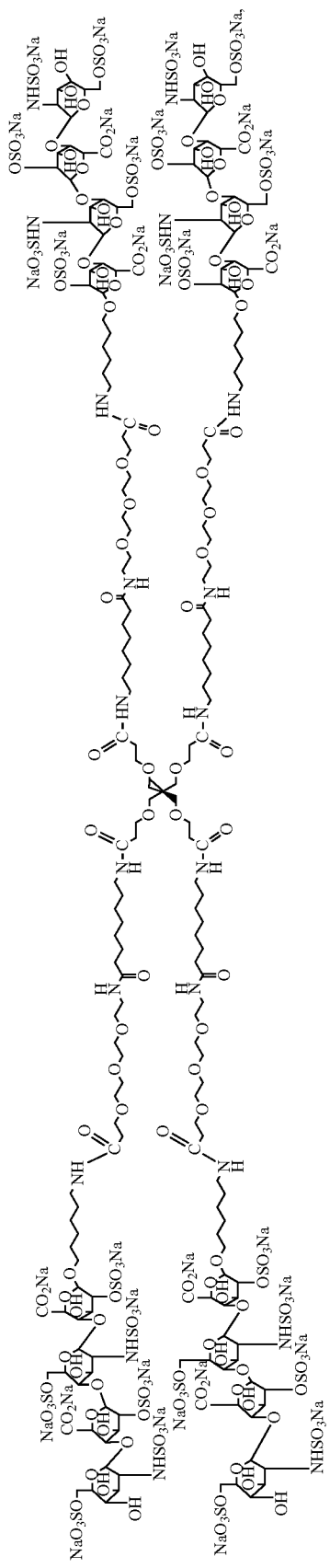

-continued
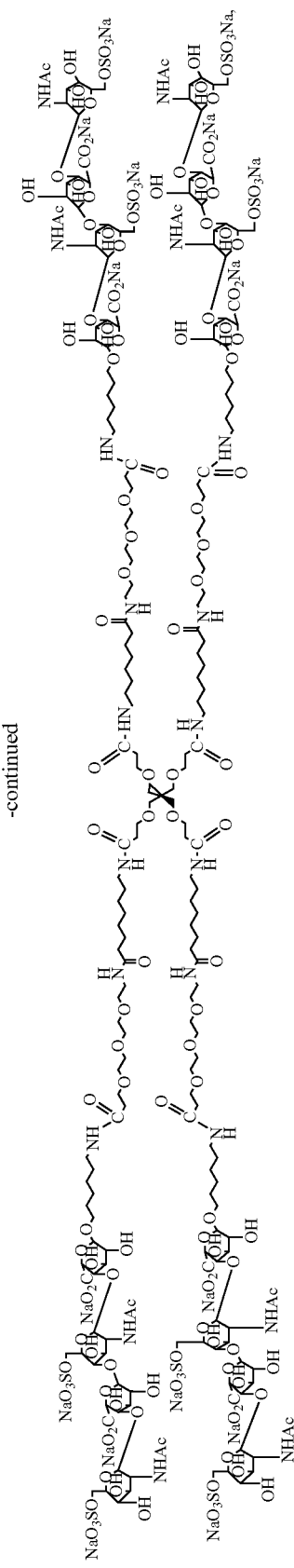
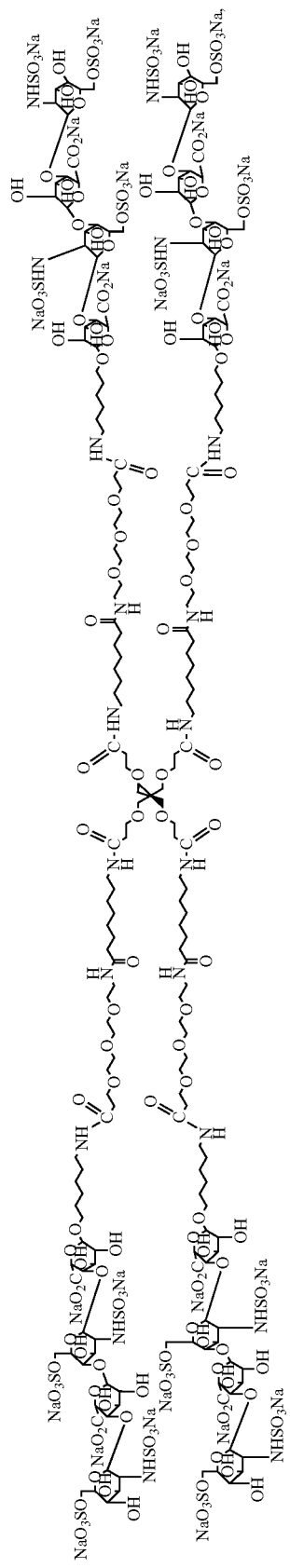

-continued
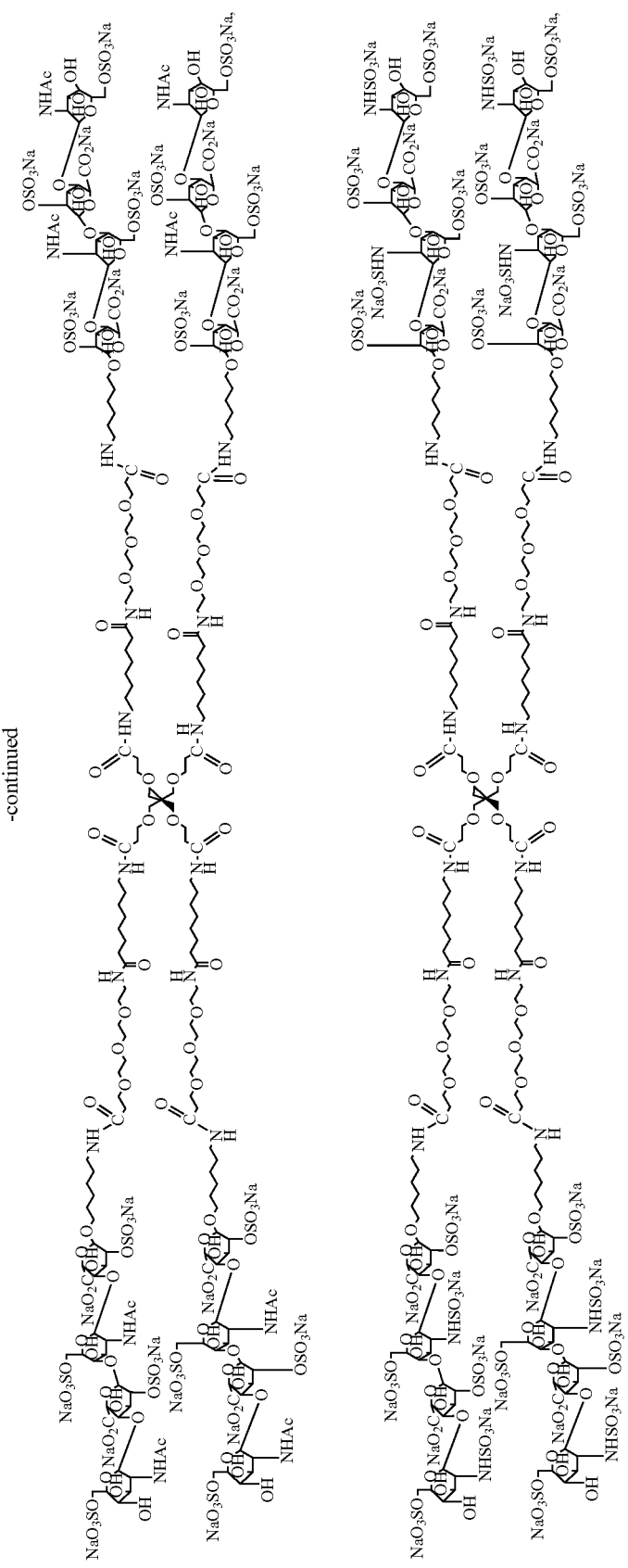

-continued
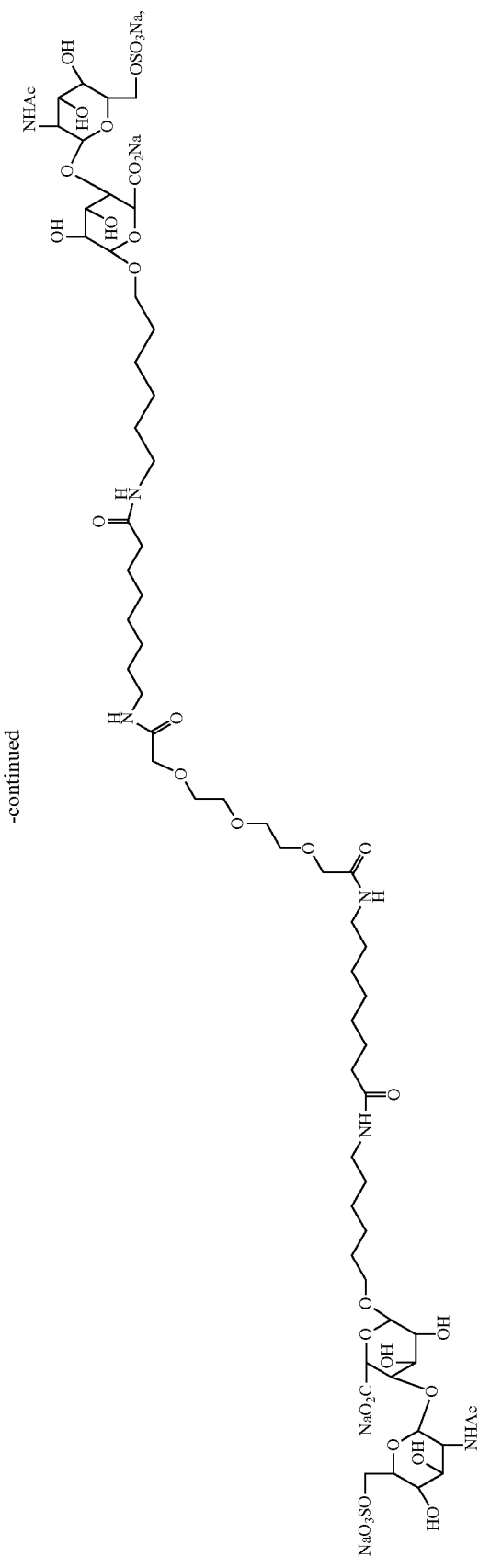
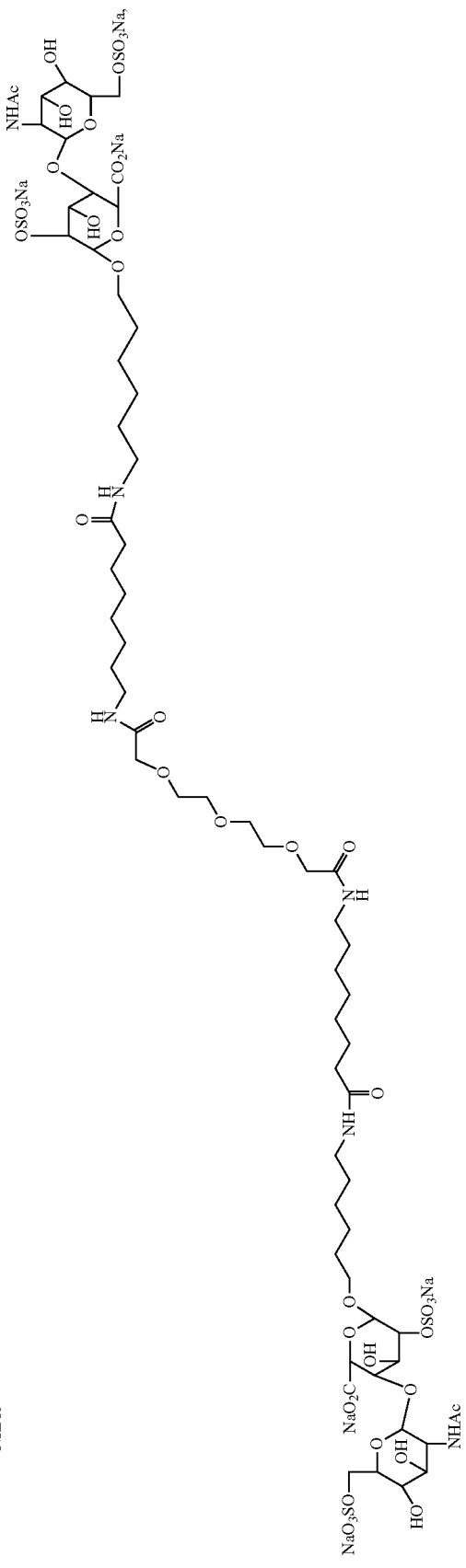

-continued
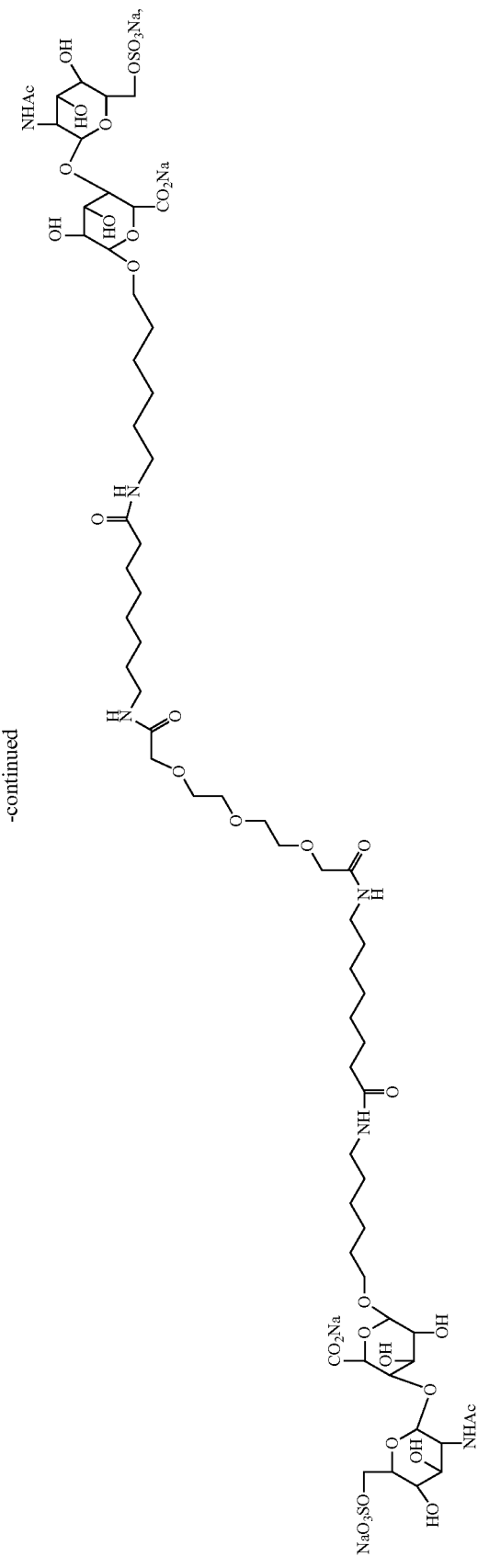
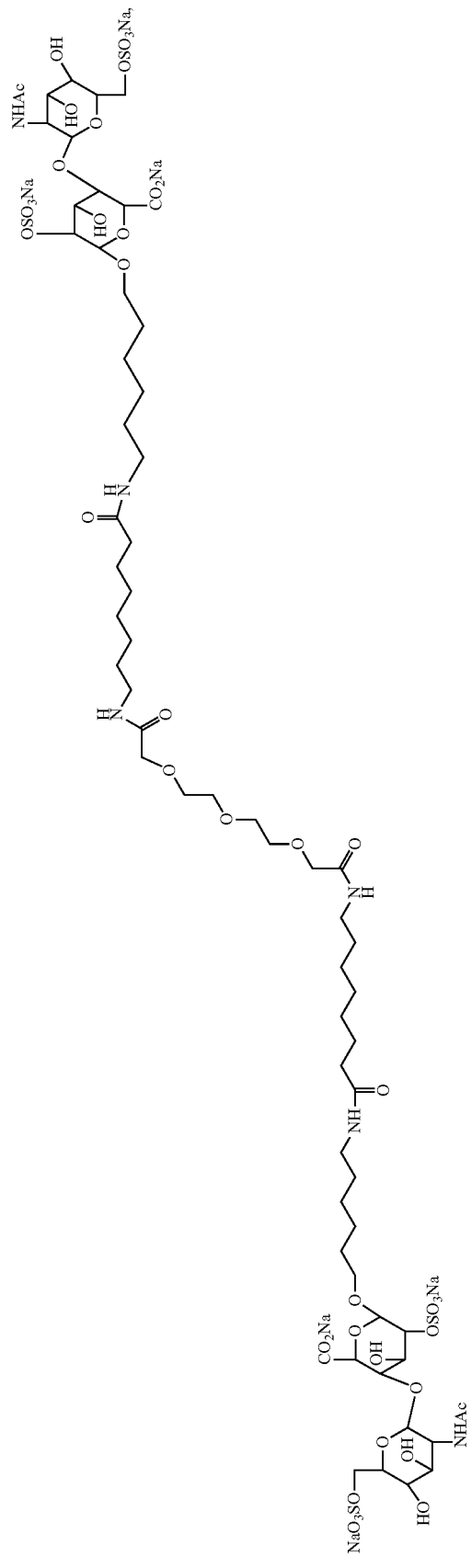

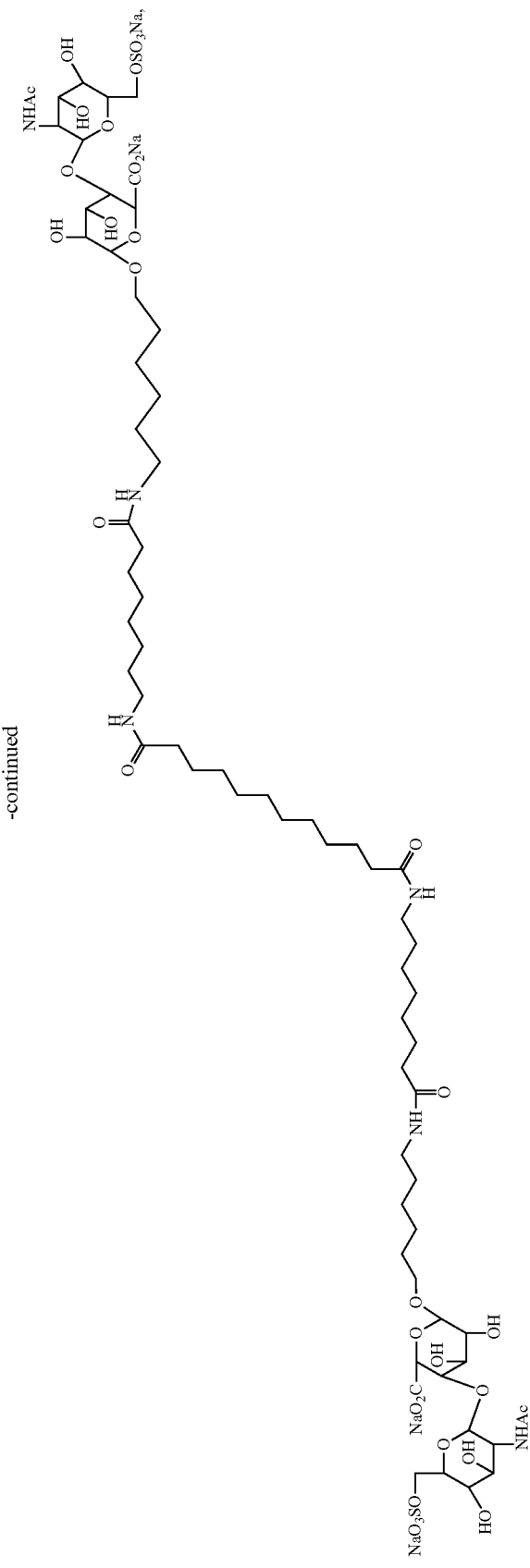
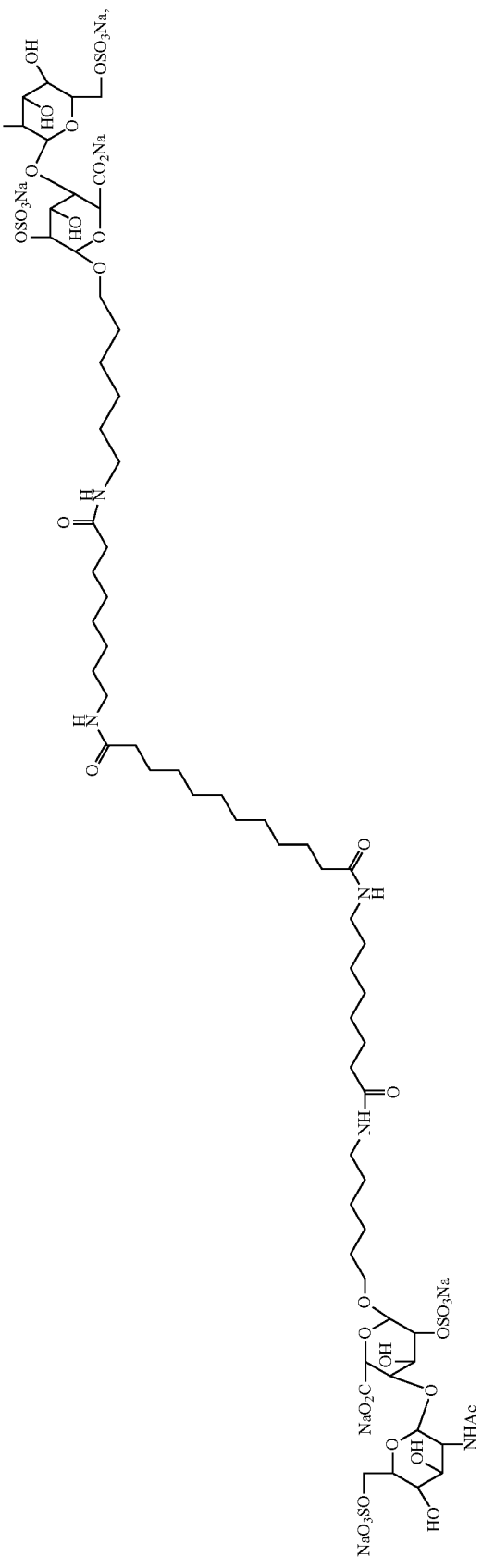

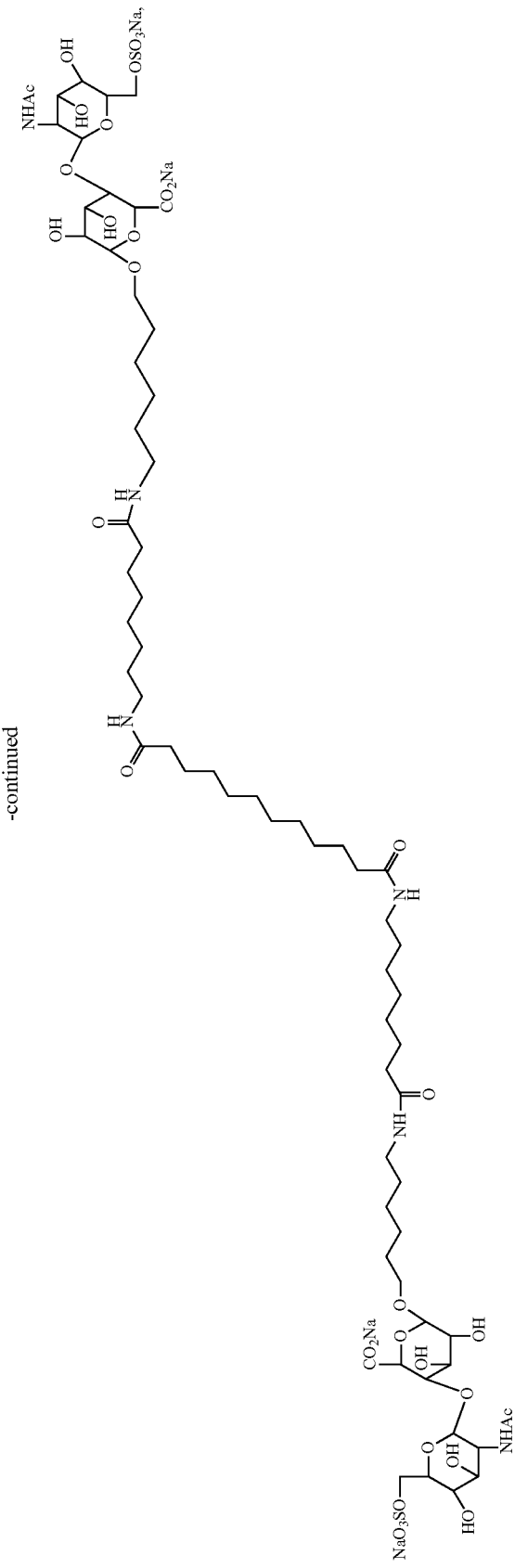
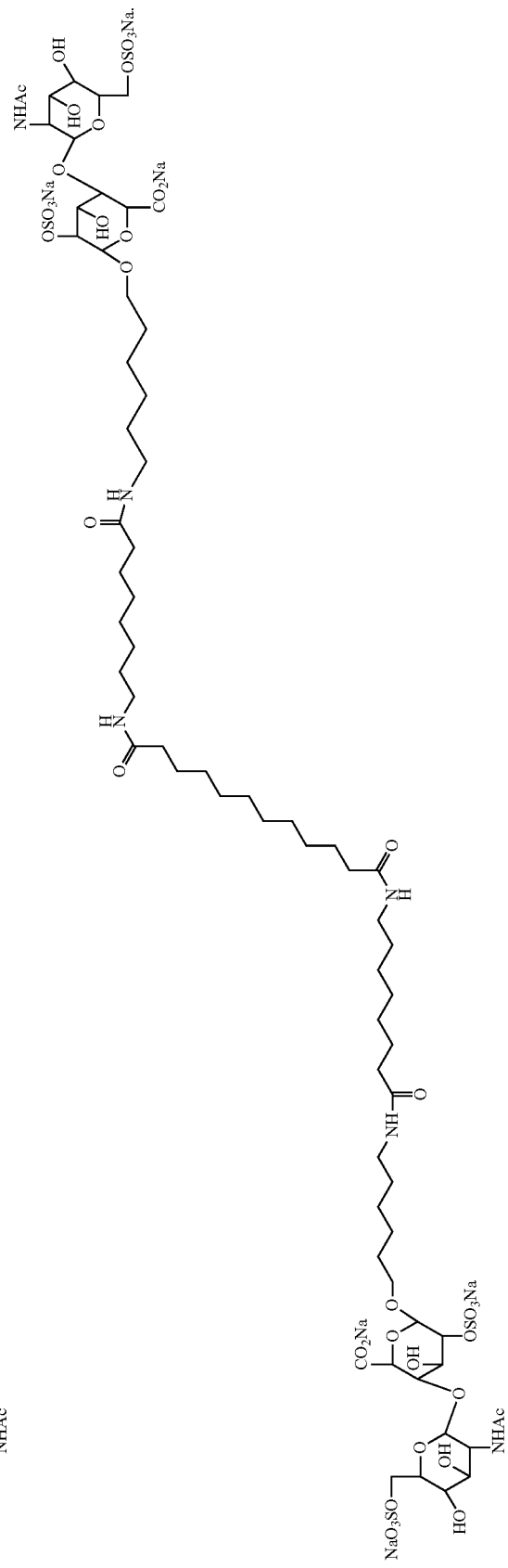

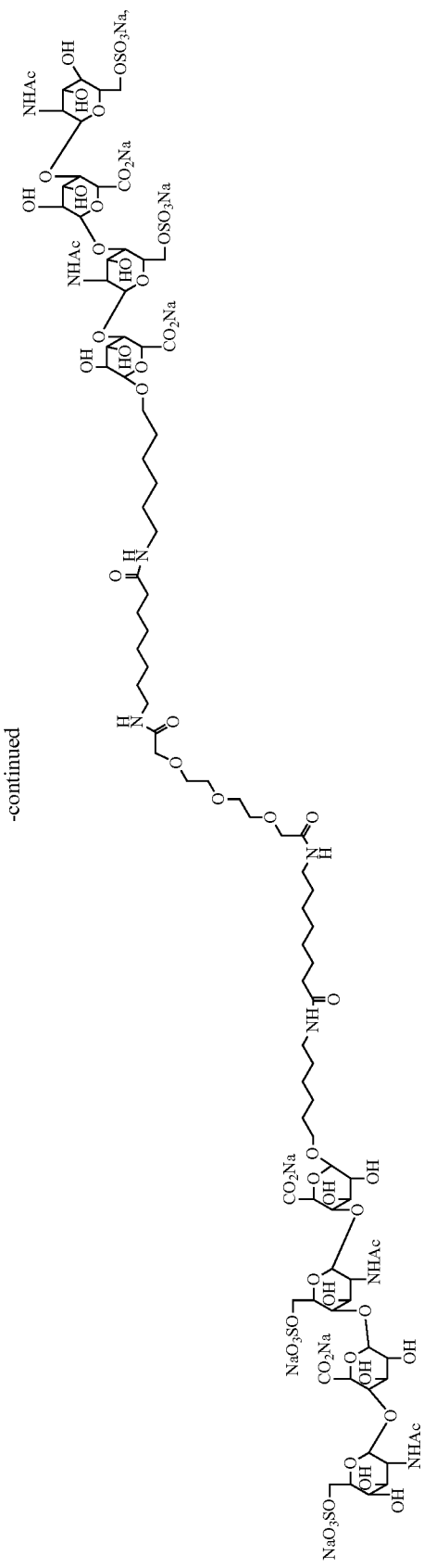
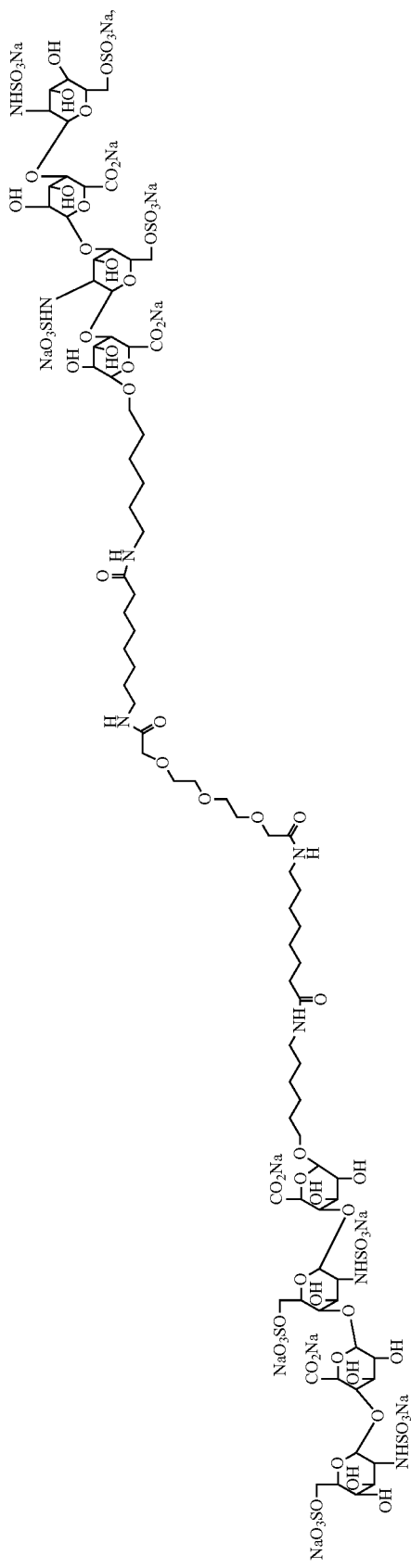

-continued
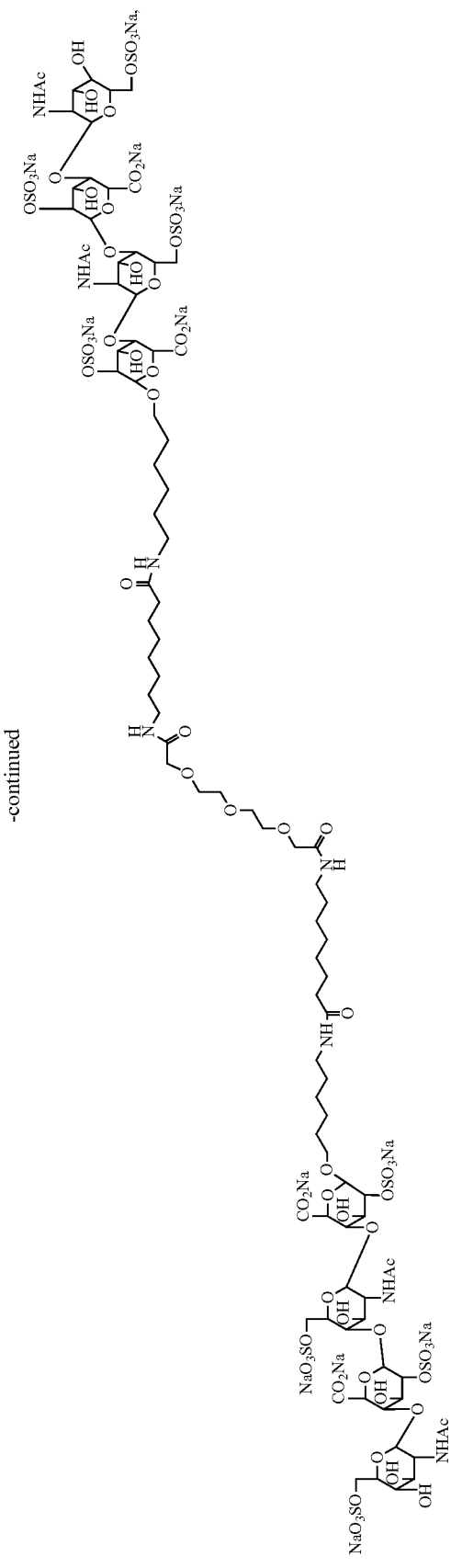
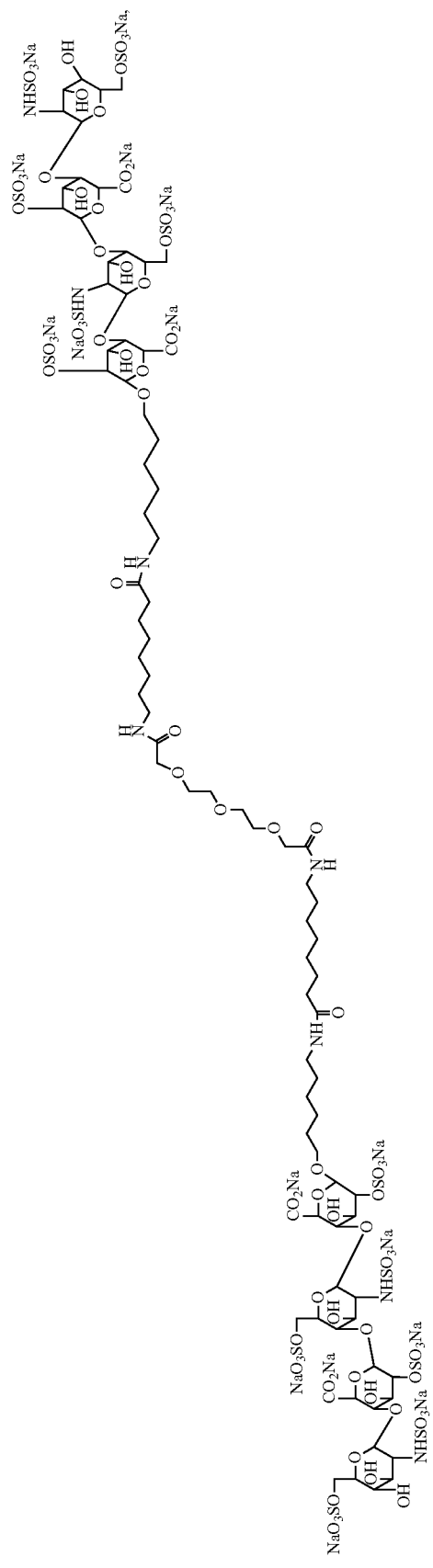

-continued
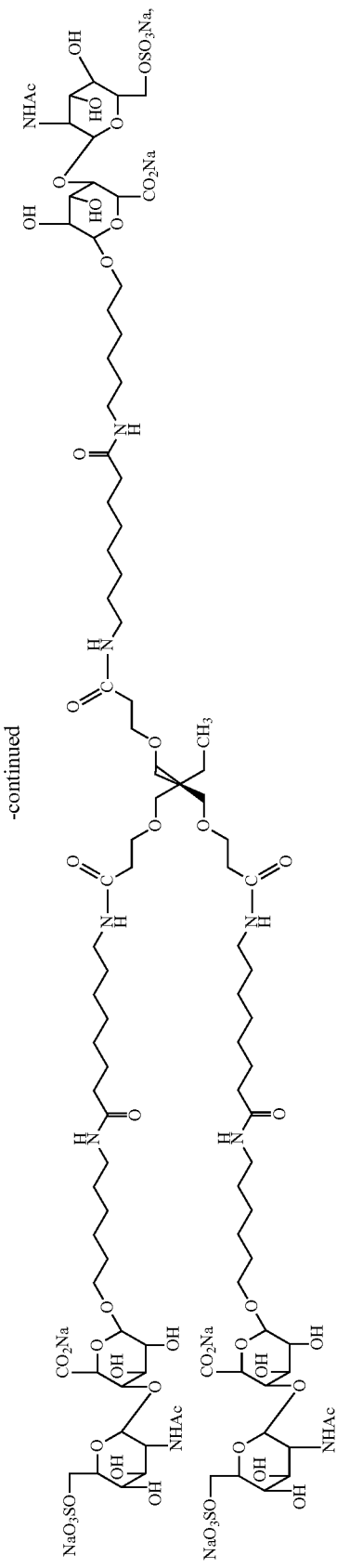
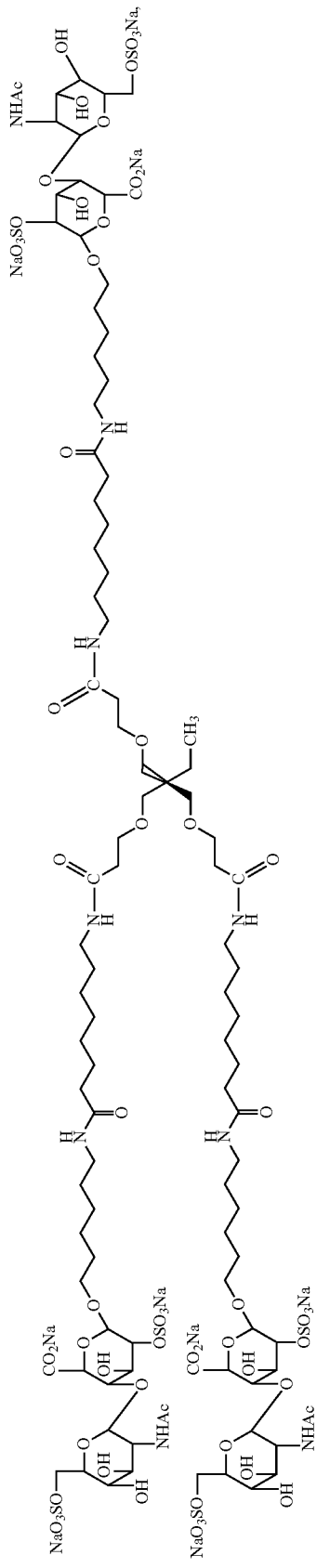

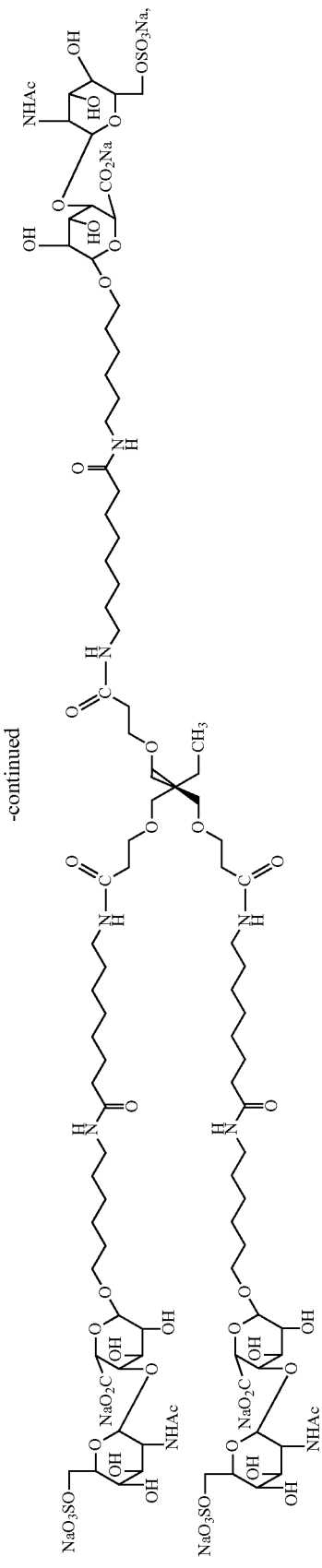
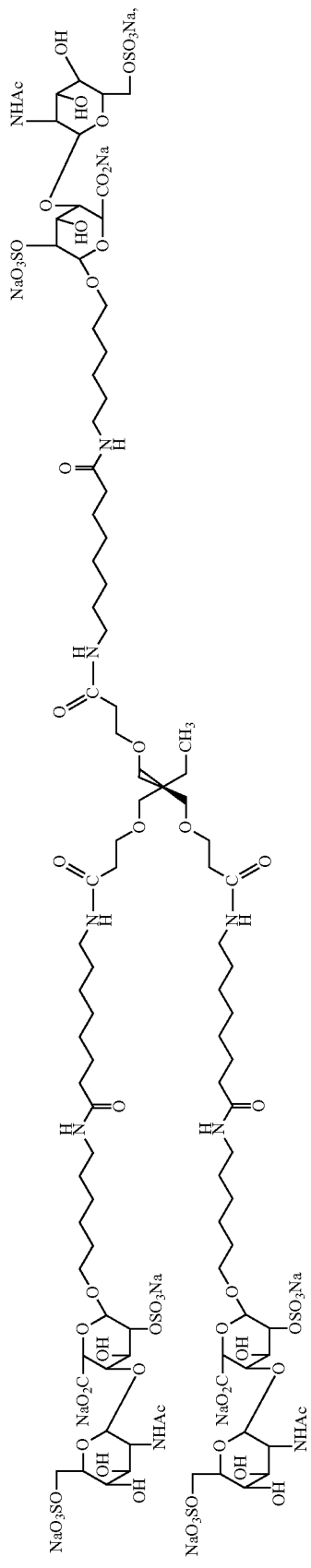

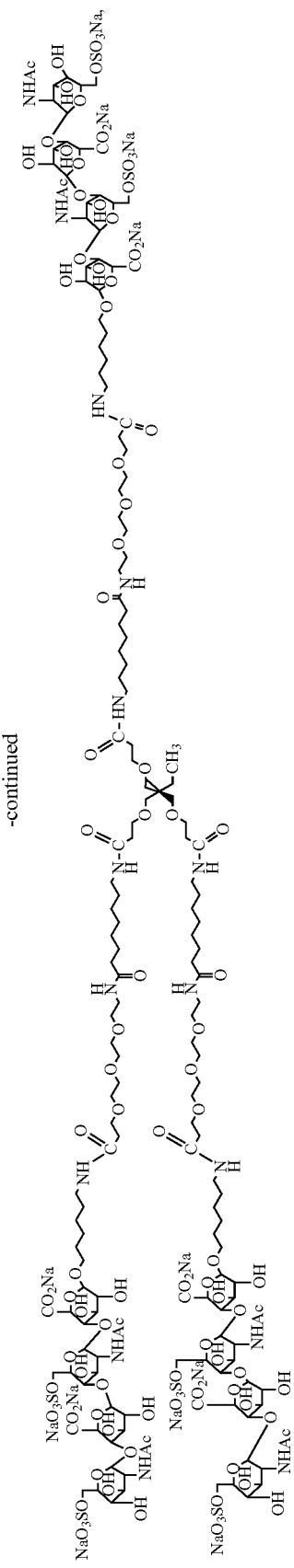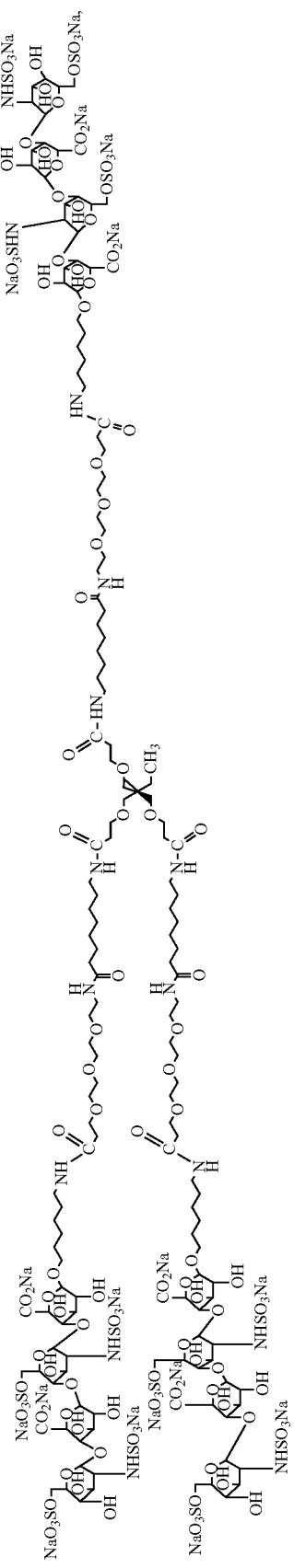

-continued
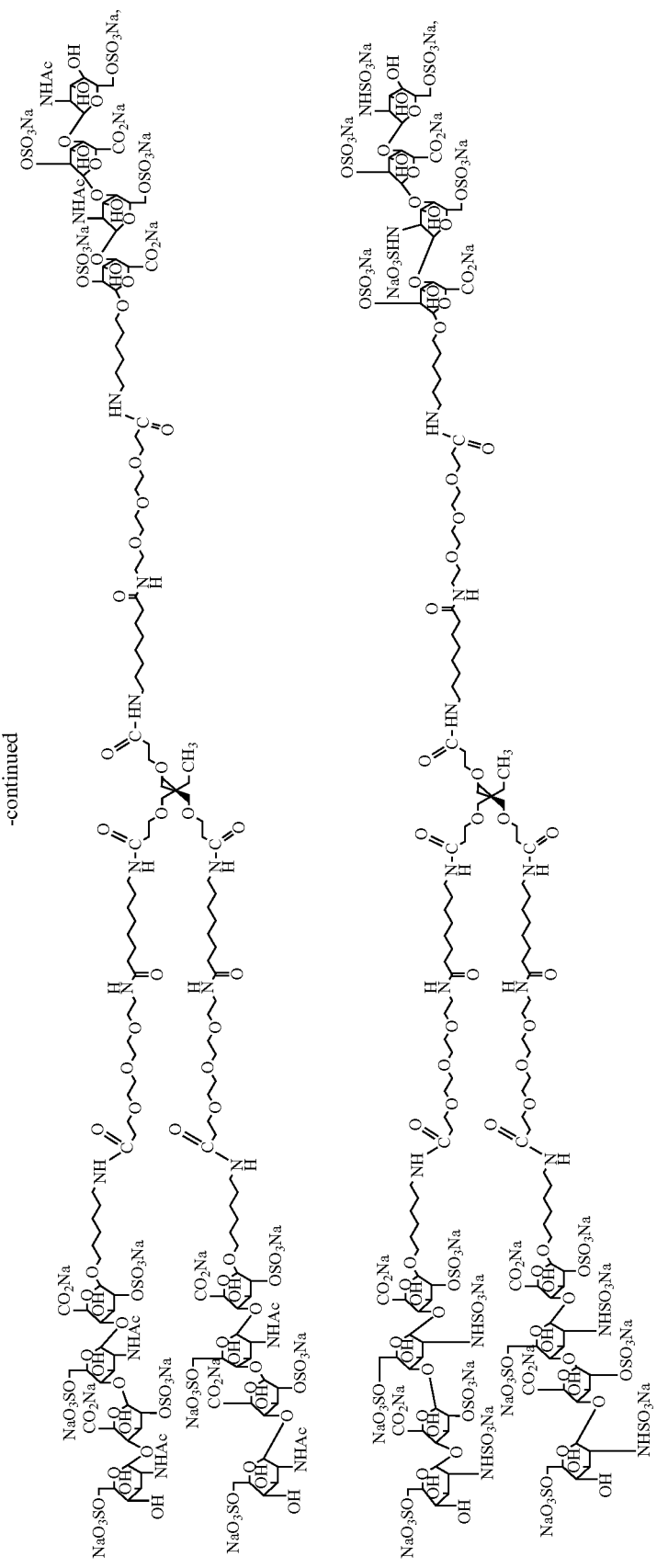

-continued
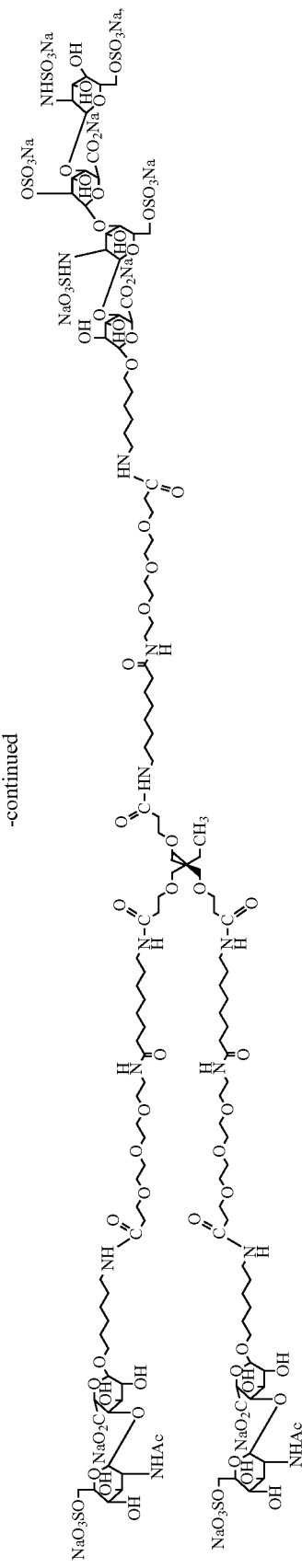
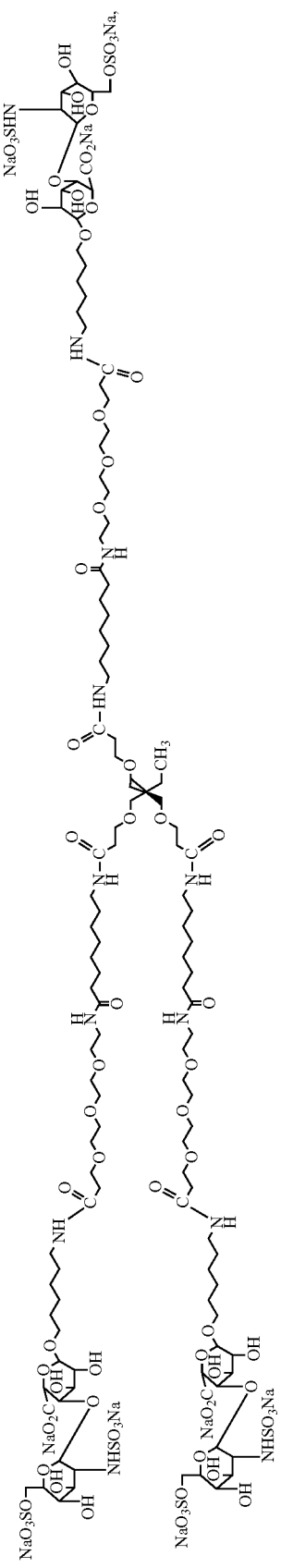

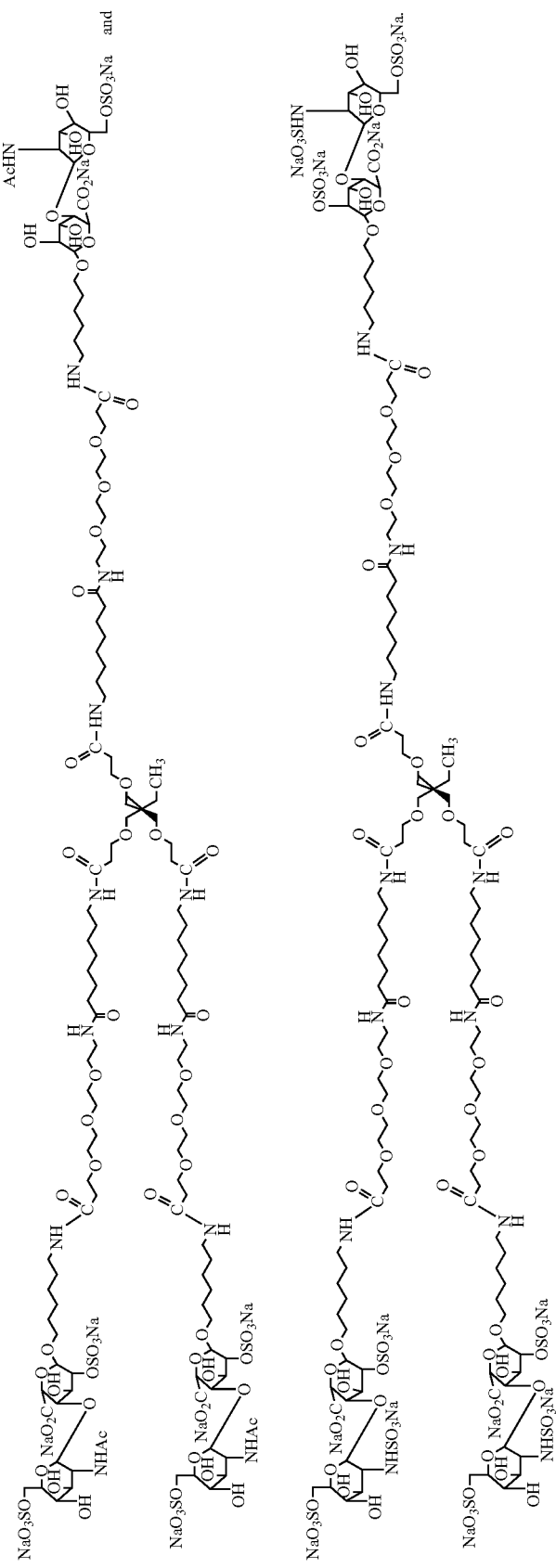

or a pharmaceutically acceptable salt thereof.

In another aspect the invention provides a composition comprising a pharmaceutically effective amount of a compound of formula (I) and optionally a carrier.

In another aspect the invention provides a pharmaceutical composition comprising a pharmaceutically effective amount of a compound of formula (I) and optionally a pharmaceutically acceptable carrier, diluent or excipient.

In another aspect the invention provides a compound of formula (I) in combination with at least one other compound, e.g. a second drug compound. The other compound may be, for example, an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation or memantine.

In another aspect the invention provides the use of a compound of formula (I) for inhibiting BACE-1.

In another aspect the invention provides the use of a compound of formula (I) as a medicament.

In another aspect the invention provides the use of a compound of formula (I) for treating or preventing a disease or disorder in which it is desirable to inhibit BACE-1.

In another aspect the invention provides the use of a compound of formula (I) for treating or preventing a neurodegenerative disorder such as senile dementia, pre-senile dementia, multi-infarct dementia or Alzheimer's disease, preferably Alzheimer's disease.

In another aspect the invention provides the use of a pharmaceutical composition comprising a pharmaceutically effective amount of a compound of formula (I) for treating or preventing a disease or disorder in which it is desirable to inhibit BACE-1.

In another aspect the invention provides the use of a pharmaceutical composition comprising a pharmaceutically effective amount of a compound of formula (I) for treating or preventing a neurodegenerative disorder such as senile dementia, pre-senile dementia, multi-infarct dementia or Alzheimer's disease, preferably Alzheimer's disease.

In another aspect the invention provides the use of a compound of formula (I) for use in the manufacture of a medicament.

In another aspect the invention provides a pharmaceutical composition for treating or preventing a disease or disorder in which it is desirable to inhibit BACE-1, comprising a compound of formula (I).

In another aspect the invention provides a pharmaceutical composition for treating or preventing a neurodegenerative disorder such as senile dementia, pre-senile dementia, multi-infarct dementia or Alzheimer's disease, preferably Alzheimer's disease, comprising a compound of formula (I).

In another aspect the invention provides the use of a compound of formula (I) in the manufacture of a medicament for the treatment or prevention of a disease or disorder in which it is desirable to inhibit BACE-1.

In another aspect the invention provides a method of treating or preventing a disease or disorder in which it is desirable to inhibit BACE-1 comprising administering a pharmaceutically effective amount of a compound of formula (I) to a patient requiring treatment.

In another aspect the invention provides a method of treating or preventing a neurodegenerative disorder such as senile dementia, pre-senile dementia, multi-infarct dementia or Alzheimer's disease, preferably Alzheimer's disease, comprising administering a pharmaceutically effective amount of a compound of formula (I) to a patient requiring treatment.

In another aspect the invention provides the use of a compound of formula (I) in combination with at least one other compound, e.g. a second drug compound, e.g. an oligosaccharide compound, a cyclitol such as scyllo-inositol or D-chiro-inositol, an acetylcholinesterase inhibitor, a nicotinic agonist, an antibody targeting β-amyloid, an inhibitor of β-amyloid, an inhibitor of tau aggregation or memantine, for treating or preventing a disease or disorder in which it is desirable to inhibit BACE-1 (e.g. a neurodegenerative disorder such as senile dementia, pre-senile dementia, multi-infarct dementia or Alzheimer's disease, preferably Alzheimer's disease).

In another aspect the invention provides a method of treating or preventing a disease or disorder in which it is desirable to inhibit BACE-1 (e.g. a neurodegenerative disorder such as senile dementia, pre-senile dementia, multi-infarct dementia or Alzheimer's disease, preferably Alzheimer's disease) comprising administering a pharmaceutically effective amount of a compound of formula (I) in combination with at least one other compound, e.g. a second drug compound, e.g. an oligosaccharide compound, a cyclitol such as scyllo-inositol or D-chiro-inositol, an acetylcholinesterase inhibitor, a nicotinic agonist, an antibody targeting β-amyloid, an inhibitor of (i-amyloid, an inhibitor of tau aggregation or memantine. The compound of formula (I) and the other compound may be administered separately, simultaneously or sequentially.

The diseases or disorders include neurodegenerative disorders such as senile dementia, pre-senile dementia, multi-infarct dementia or Alzheimer's disease, preferably Alzheimer's disease.

The compound of formula (I) may be selected from the group consisting of compounds (a) to (h) and (j) to (u) and (w), (y) and (z) as defined above.

Compounds of formula (I) are hereinafter described as "compounds of the invention". A compound of the invention includes a compound in any form, e.g. in free form or in the form of a salt or a solvate.

DETAILED DESCRIPTION

Definitions

The term "$C_1$-$C_6$alkyl" means any saturated hydrocarbon radical having up to 6 carbon atoms and is intended to include both straight- and branched-chain alkyl groups. Examples of alkyl groups include: methyl group, ethyl group, n-propyl group, iso-propyl group, n-butyl group, iso-butyl group, sec-butyl group, t-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group and 1-methyl-2-ethylpropyl group.

The term "alkylene" means a diradical corresponding to a $C_1$-$C_{12}$alkyl group, where $C_1$-$C_{12}$alkyl means any saturated hydrocarbon radical having up to 12 carbon atoms, and is intended to include straight chain alkyl groups. Examples of alkylene groups include methylene group and ethylene group.

The term "acyl" means C(=O)R' group, where R' is a $C_1$-$C_{30}$alkyl group, where $C_1$-$C_{30}$alkyl means any saturated hydrocarbon radical having up to 30 carbon atoms, and is intended to include straight chain alkyl groups. Examples include acetyl group.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group (including a 1-H-1,2,3-triazol-1-yl and a 1-H-1,2,3-triazol-4-yl group), tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

The term "aralkyl" means an aryl group which is attached to an alkylene moiety, where aryl and alkylene are as defined above. Examples include benzyl group.

The term "prodrug" as used herein means a pharmacologically acceptable derivative of the compounds of formula (I) such that an in vivo biotransformation of the derivative gives the compound as defined in formula (I). Prodrugs of compounds of formulae (I) may be prepared by modifying functional groups present in the compounds in such a way that the modifications are cleaved in vivo to give the parent compound. Typically, prodrugs of the compounds of formula (I) will be ester prodrug forms.

The term "pharmaceutically acceptable salts" is intended to apply to non-toxic salts such as ammonium salts, metal salts, e.g. sodium salts, or salts of organic cations, or a mixture thereof.

The term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in *Protective Groups in Organic Synthesis* (3$^{rd}$ Ed.), T. W. Greene and P. G. M. Wuts, John Wiley & Sons Inc (1999). Examples of protecting groups include, but are not limited to: O-benzyl, O-benzhydryl, O-trityl, O-tert-butyldimethylsilyl, O-tert-butyldiphenylsilyl, O-4-methylbenzyl, O-acetyl, O-chloroacetyl, O-methoxyacetyl, O-benzoyl, O-4-bromobenzoyl, O-4-methylbenzoyl, O-fluorenylmethoxycarbonyl and O-levulinoyl.

The term "patient" includes human and non-human animals.

The terms "treatment", "treating" and the like include the alleviation of one or more symptoms, or improvement of a state associated with the disease or disorder, for example, improvement in cognition, improvement in memory function.

The terms "preventing", "prevention" and the like include the prevention of one or more symptoms associated with the disease or disorder.

Those skilled in the art will appreciate that the compounds of the invention may exist as stereoisomers. For example, structures shown herein which include bonds " " linking the sugar ring with the carboxyl group (such as shown below) are intended to include gluco- and ido-forms of the sugar. Those skilled in the art will also appreciate that it is possible for the compounds of the invention to incorporate only gluco-forms, only ido-forms, or mixtures of gluco- and ido-forms.

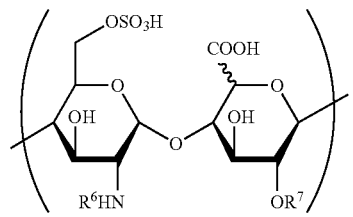

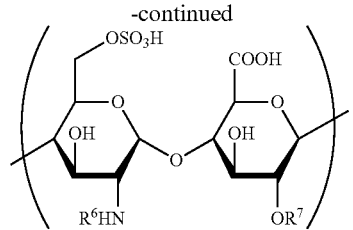

gluco

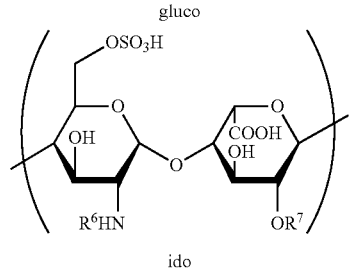

ido

The Compounds of the Invention

The compounds of the invention, particularly those exemplified, are inhibitors of BACE-1 and are useful as pharmaceuticals, particularly for the treatment or prevention of diseases or conditions in which it is desirable to inhibit BACE-1, e.g. neurodegenerative disorders such as senile dementia, pre-senile dementia, multi-infarct dementia or Alzheimer's disease, particularly Alzheimer's disease.

The compounds of the invention are useful in both free base form and in the form of salts and/or solvates.

Without wishing to be bound by theory, the applicants hypothesis that the compounds of the invention can achieve a "clustering effect" through the use of multiple copies of HS fragments in each dendritic structure. Such a clustering effect is advantageous as repetition of individual subunit structures can enhance the usually weak interaction of individual subunit structures in HSs.

As shown in Example 2, compounds of the invention are inhibitors of BACE-1.

Advantageously, certain compounds of the invention, e.g. compounds 18e, 18h, 18b, 18c, 20b, 20c, 22a, do not display any measurable ability to accelerate antithrombin-III mediated inactivation of Factor Xa, as measured by cleavage of a peptide substrate (as described in Example 3). Other compounds of the invention have <5% of the activity of a heparin control as measured in the same assay.

The compounds of the invention also show activity in a brain slice assay (Example 4). Brain slice models can replicate many aspects of the in vivo context. Slices largely preserve the tissue architecture of the brain regions from which they originated, and maintain neuronal activities with intact functional local synaptic circuitry. The use of brain slices in the drug discovery process eliminates lengthy animal surgery to model neuropathology of brain and laborious monitoring of multiple physiological parameters following in vivo manipulation. Slice-based assays provide good experimental access and allow precise control of extracellular environments and facilitate establishing clear correlations between molecular changes with neuropathological outcomes.

A key characteristic of Alzheimer's disease is the deposition of insoluble accumulations of the amyloid/β-peptide (Aβ) in the brain. The Aβ is itself derived from step-wise extracellular enzymatic cleavage of the amyloid precursor protein by BACE-1. The accumulation of Aβ is a critical driving force for Alzheimer's disease pathology according to the amyloid cascade hypothesis.

As shown in Example 4 and FIGS. 1a and 1b, certain compounds of the invention, e.g. compound 18a (called Dendrimer 9 in FIG. 1b), demonstrate the ability to lower amounts of Aβ1-40 in brains of transgenic TG2576 mice.

The compounds of the invention may be administered to a patient by a variety of routes, including orally, parenterally, by inhalation spray, topically, rectally, nasally, buccally or via an implanted reservoir. The compounds may also be administered by intracerebral, intracerebroventricular or intrathecal delivery. For parenteral administration, injections may be given intravenously, intra-arterially, intramuscularly or subcutaneously.

The amount of a compound of the invention to be administered to a patient will vary widely according to the nature of the patient and the nature and extent of the disorder to be treated. Typically the dosage for an adult human will be in the range of about 0.01 µg/kg to about 1 g/kg, preferably about 0.01 mg/kg to about 100 mg/kg. The specific dosage required for any particular patient will depend upon a variety of factors, such as the patient's age, body weight, general health, gender and diet. Optimal doses will depend on other factors such as mode of administration and level of progression of the disease or disorder. Doses may be given once daily, or two or more doses may be required per day. For example, a dosage regime for an Alzheimer's patient might require one dose in the morning and one in the evening. Alternatively, a dosage regime for such a patient might require four hourly doses.

For oral administration the compounds can be formulated into solid or liquid preparations, for example tablets, capsules, granules, powders, solutions, suspensions, syrups, elixirs and dispersions. Such preparations are well known in the art as are other oral dosage regimes not listed here.

For parenteral administration, compounds of the invention can be formulated into sterile solutions, emulsions and suspension.

Compounds of the invention may be mixed with suitable vehicle and then compressed into the desired shape and size. The compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added. Tablets, capsules or powders for oral administration may contain up to about 99% of a compound of the invention.

When liquid preparations are required for oral use, a compound of the invention may be combined with a pharmaceutically acceptable carriers such as water, an organic solvent such as ethanol, or a mixture of both, and optionally other additives such as emulsifying agents, suspending agents, buffers, preservatives, and/or surfactants may be used. Colourings, sweeteners or flavourings may also be added.

The compounds may also be administered by injection in a pharmaceutically acceptable diluent such as water or saline. The diluent may comprise one or more other ingredients such as ethanol, propylene glycol, an oil or a pharmaceutically acceptable surfactant.

The compounds of the invention may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds of the invention may further be administered by means of sustained release systems. For example, they may be incorporated into a slowly dissolving tablet or capsule.

Synthesis of the Compounds of the Invention

The compounds of the invention may be prepared by a variety of different methods. The following are representative non-limiting general methods for synthesising compounds of the invention.

1. Synthesis of the Dendritic "Core" Starting Materials

The "cores" that are used as starting materials for the dendritic compounds of the invention can be synthesised by a variety of methods as described below. (Note: those skilled in the art will realise that Schemes 2 to 7 below show cores which contain succinimidyl group(s). However, cores having other than succinimidyl groups can be prepared analogously. For example, compounds where a hydroxyl replaces the succinimidyl group can be prepared by treatment of the OBn precursors (e.g. Schemes 2-7, below) with palladium on carbon or palladium hydroxide on carbon or platinum on carbon catalysts in solvents such as aqueous THF, methanol, ethanol, ethyl acetate stirred under a hydrogen atmosphere at ambient temperature and pressure or at 5-50 psi, preferably at 5-25 psi.

"Tetrameric" cores are prepared from compound 1, which is synthesised in three steps from pentaerythritol (Scheme 1).

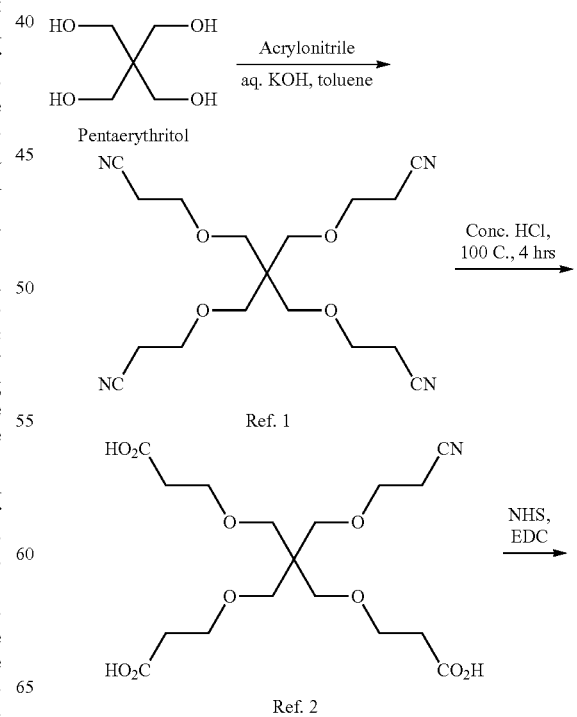

Scheme 1

-continued

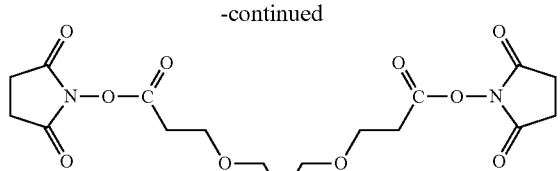

1

(Hukkämaki, J.; Pakkanen, T. T. *Journal of Molecular Catalysis A: Chemical* 2001, 174, 205-211; Ref. 2, Newcombe, G. R.; Mishra, A; Moorfield, C. N. *J. Org. Chem.* 2002, 67, 3957-3960).

Compound 1 is then converted to other core compounds via reaction with a suitable amino-substituted carboxylic acid, such as 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, 11-aminoundecanoic acid or 12-aminododecanoic acid (Scheme 2).

Scheme 2

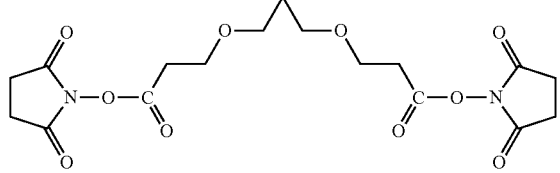

$p$ is an integer from 1 to 5

1

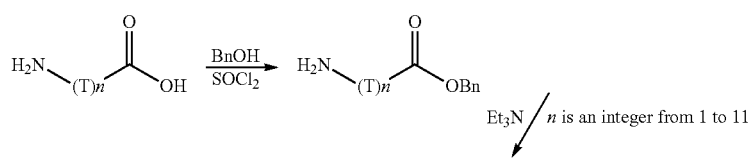

$n$ is an integer from 1 to 11

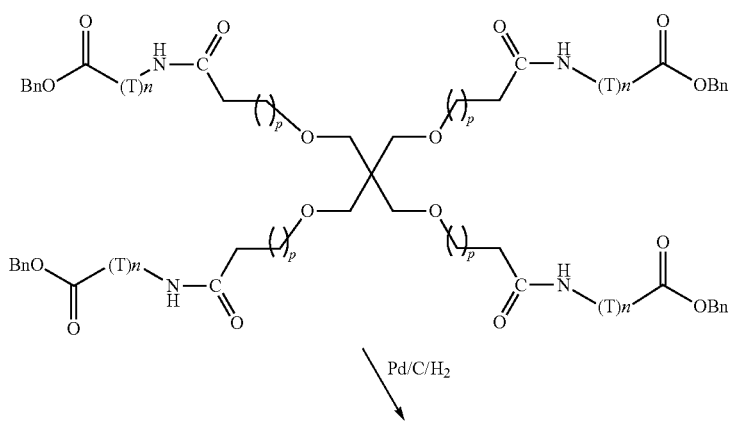

Pd/C/H$_2$

-continued
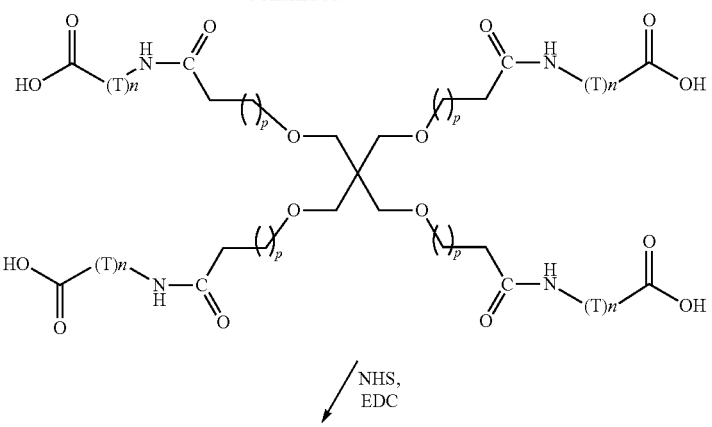
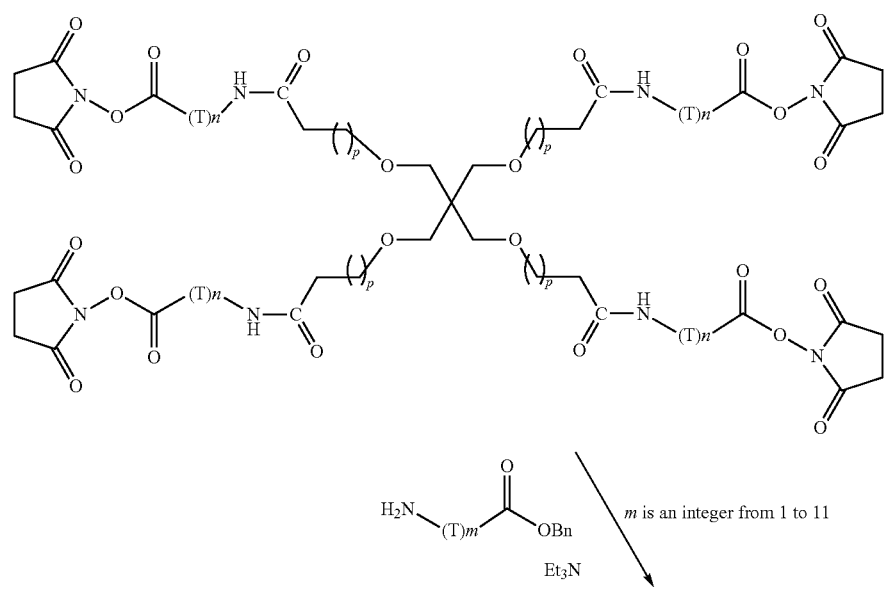
$m$ is an integer from 1 to 11
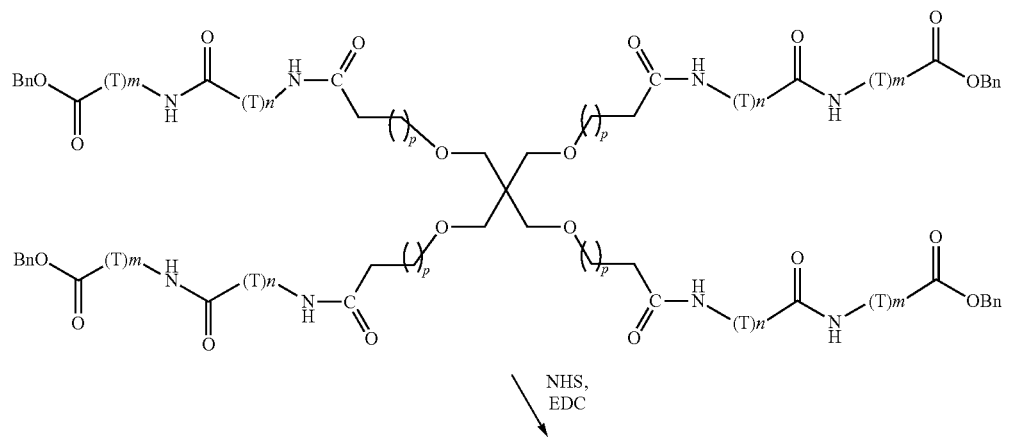

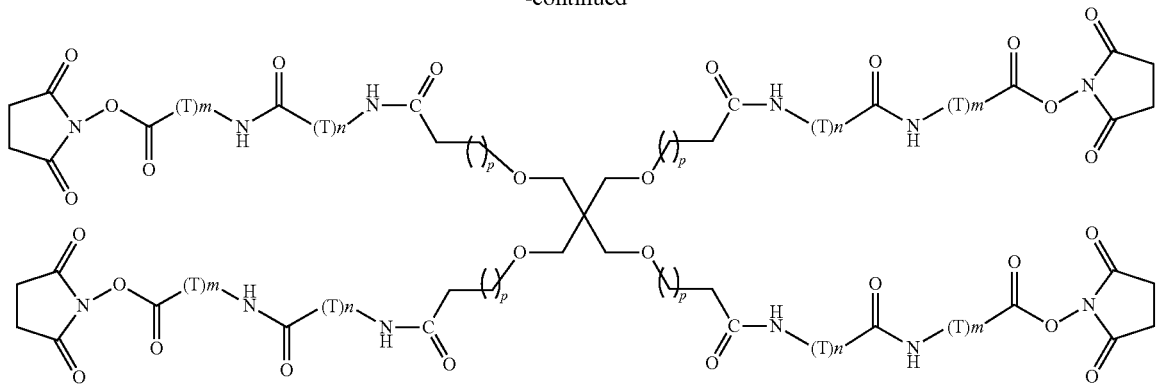

"Dimeric" dendritic cores (where Y is C and $R^1$ and $R^2$ are both H) are prepared from 3,3'-(propane-1,3-diylbis(oxy) dipropanoic acid, using a suitable amino-substituted carboxylic acid, such as 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, 11-aminoundecanoic acid or 12-aminododecanoic acid (Scheme 3).

Scheme 3

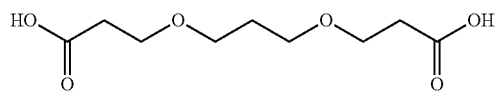

3,3'-(propane-1,3-diylbis(oxy))dipropanoic acid

↓ EDC, NHS

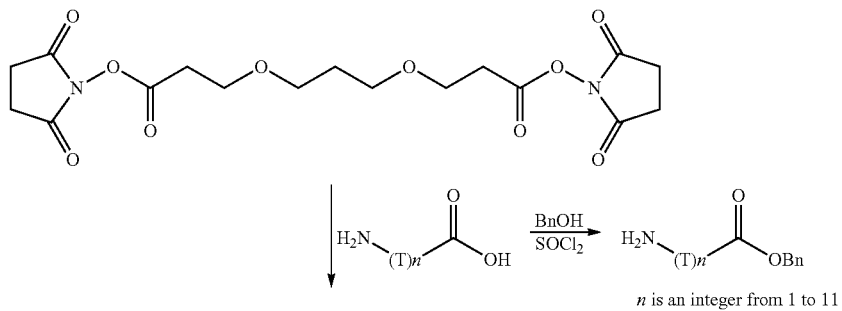

$n$ is an integer from 1 to 11

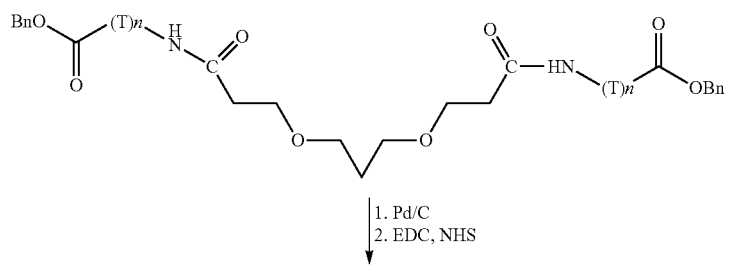

1. Pd/C
2. EDC, NHS

↓

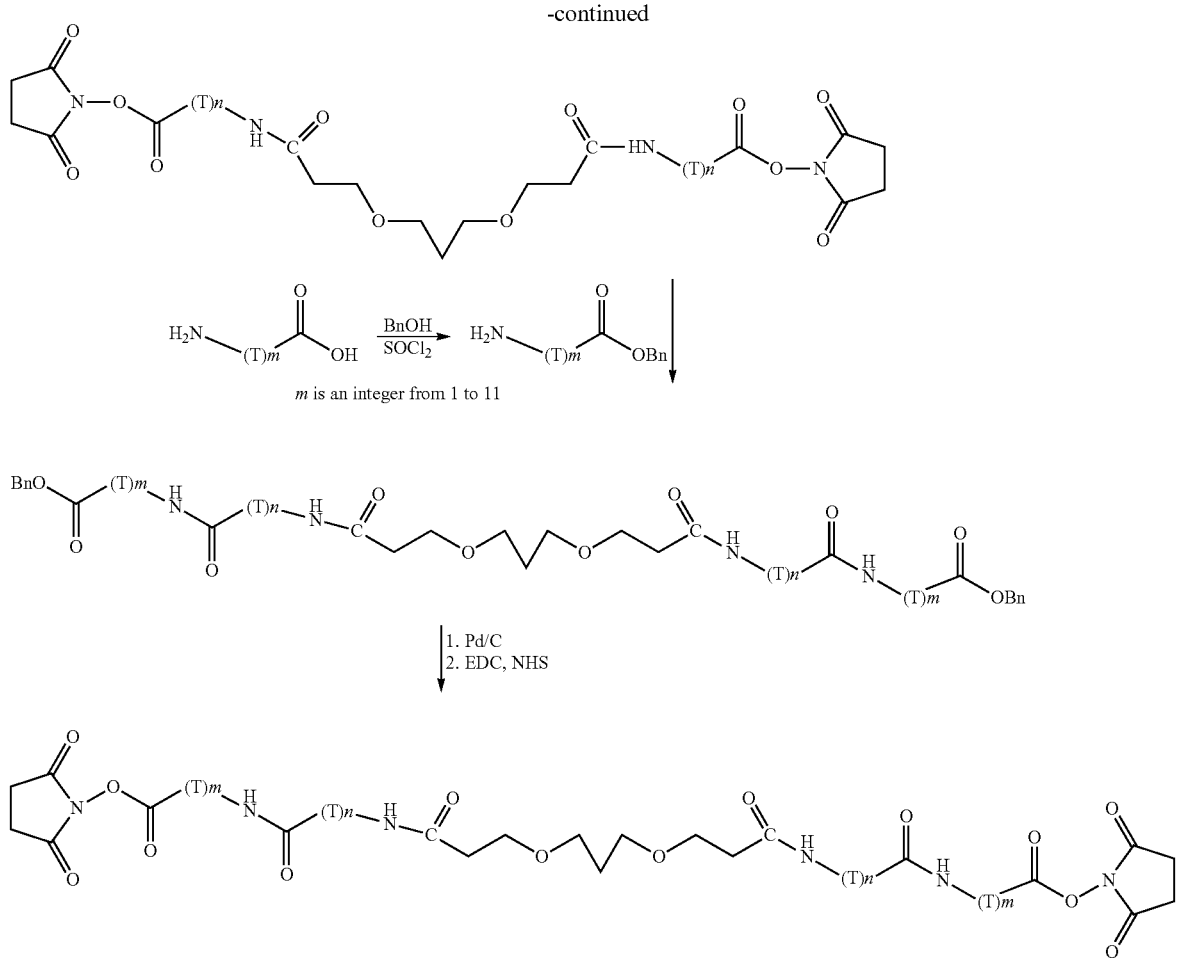
"Dimeric" dendritic core compounds of the invention where Y is C; A is $(CH_2)_n$; and $R^1$ and $R^2$ are both H are prepared from a suitable diacid, as shown in Scheme 4.
Scheme 4
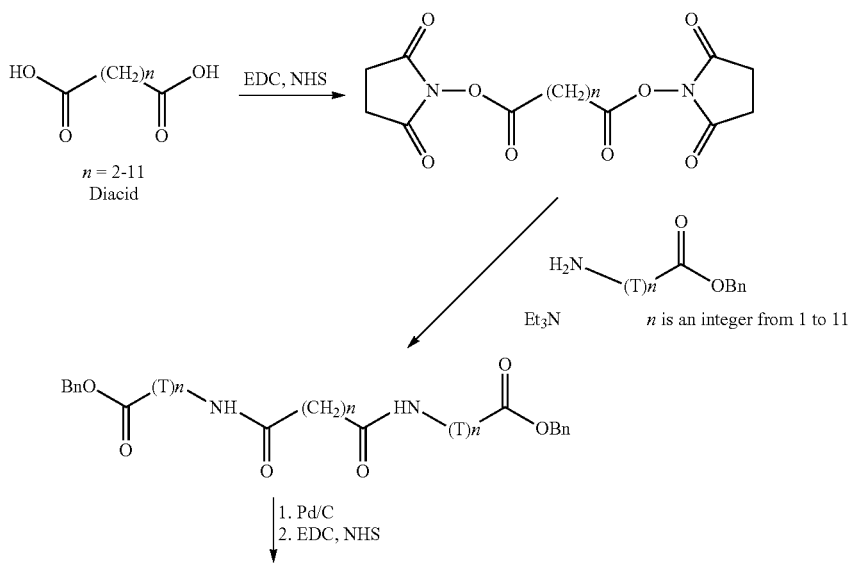

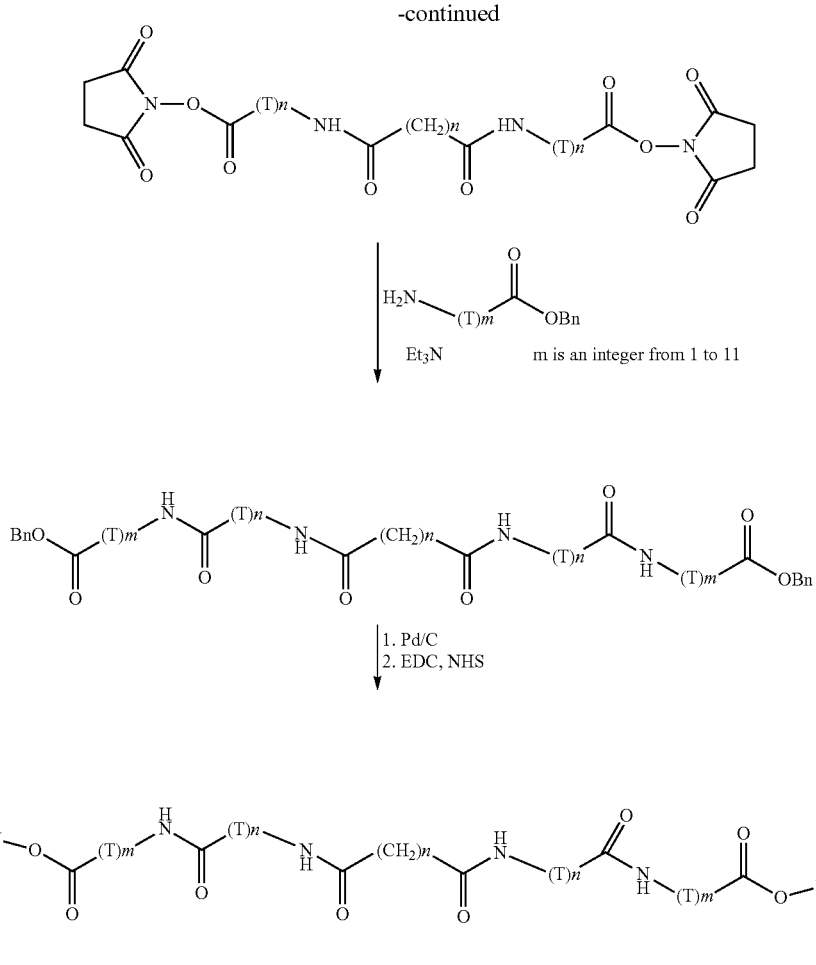
"Dimeric" dendritic core compounds of the invention where Y is O and E is $(CH_2CH_2O)_tCH_2$ are prepared as shown in Scheme 5. Suitable starting materials include, for example, 3,6,9-trioxaundecanedioic acid, 3,6,9,12-tetraoxatetradecanedioic acid or 3,6,9,12,15-pentaoxaheptadecanedioic acid.
Scheme 5
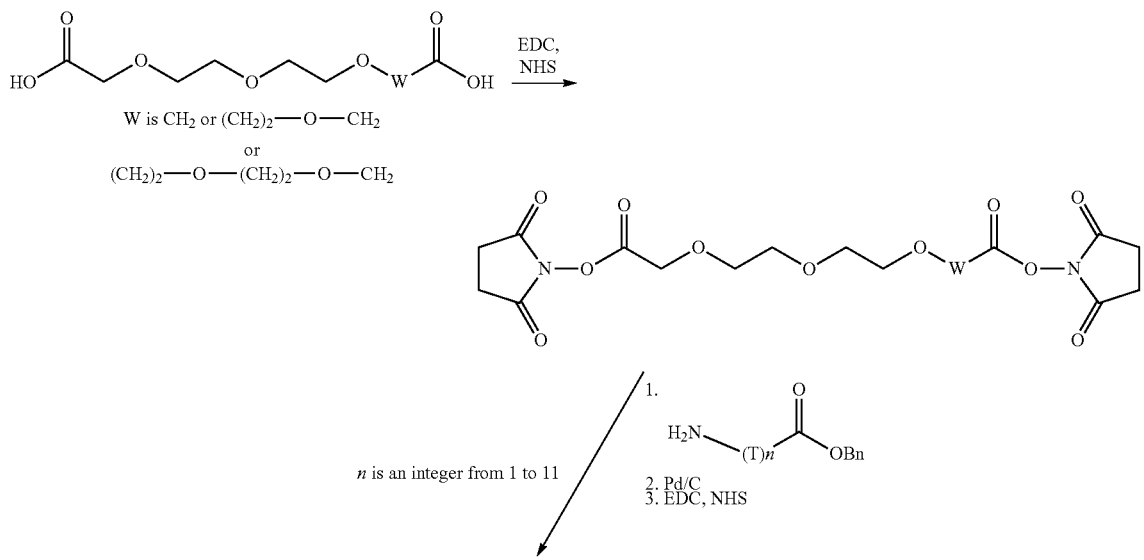

-continued

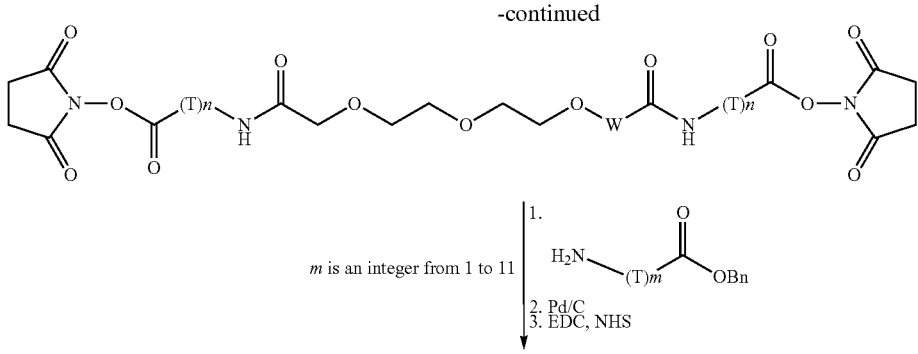

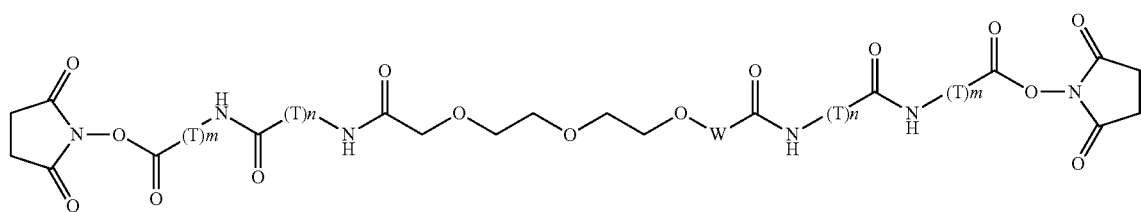

"Trimeric" cores (where Y is C and R[1] is NHZ) are prepared from 2-amino-2-hydroxymethyl-propane-1,3-diol, as shown in Scheme 6. Those skilled in the art will appreciate that trimeric dendritic core compounds where R[1] is NH$_2$ can be used to further elaborate the substitution at the R[1] position. For example, such compounds can be linked to radio- or fluorescent labels or the amino functionality can be converted to other functional groups.

Scheme 6

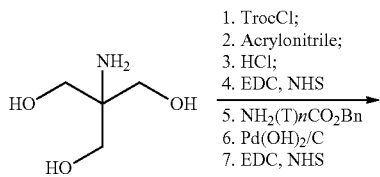

1. TrocCl;
2. Acrylonitrile;
3. HCl;
4. EDC, NHS
5. NH$_2$(T)$n$CO$_2$Bn
6. Pd(OH)$_2$/C
7. EDC, NHS

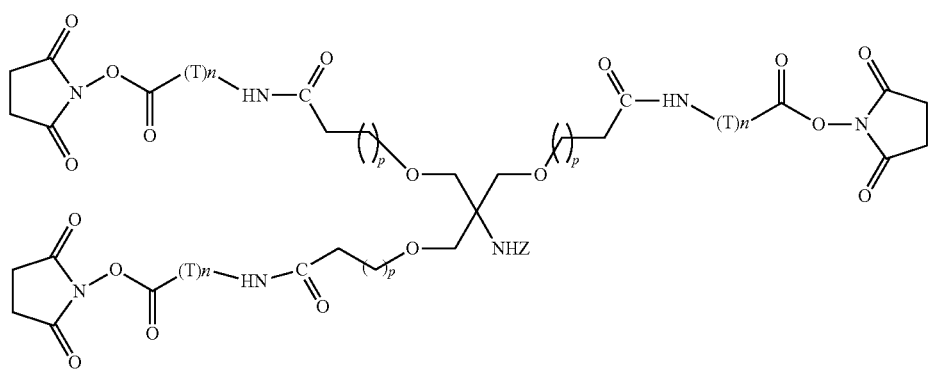

$n$ is an integer from 1 to 11
$m$ is an integer from 1 to 11

1. NH$_2$(T)$_m$CO$_2$Bn
2. Pd(OH)$_2$/C
3. EDC, NHS

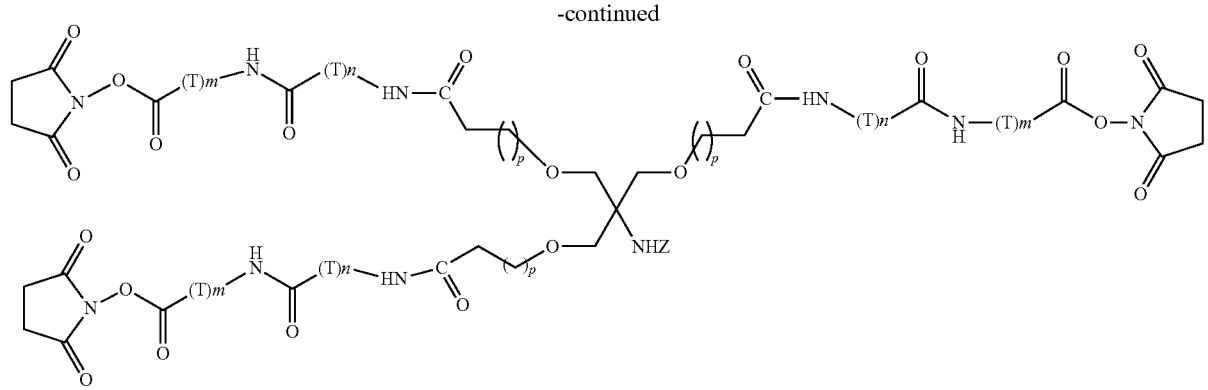
"Trimeric" cores (where Y is C and $R^1$ is H, $CH_3$ or $CH_2CH_3$) are prepared from 2-hydroxymethyl-propane-1,3-diol, 1,1,1-tris(hydroxymethyl)ethane or 1,1,1-tris(hydroxymethyl)propane, respectively (Scheme 7).
Scheme 7
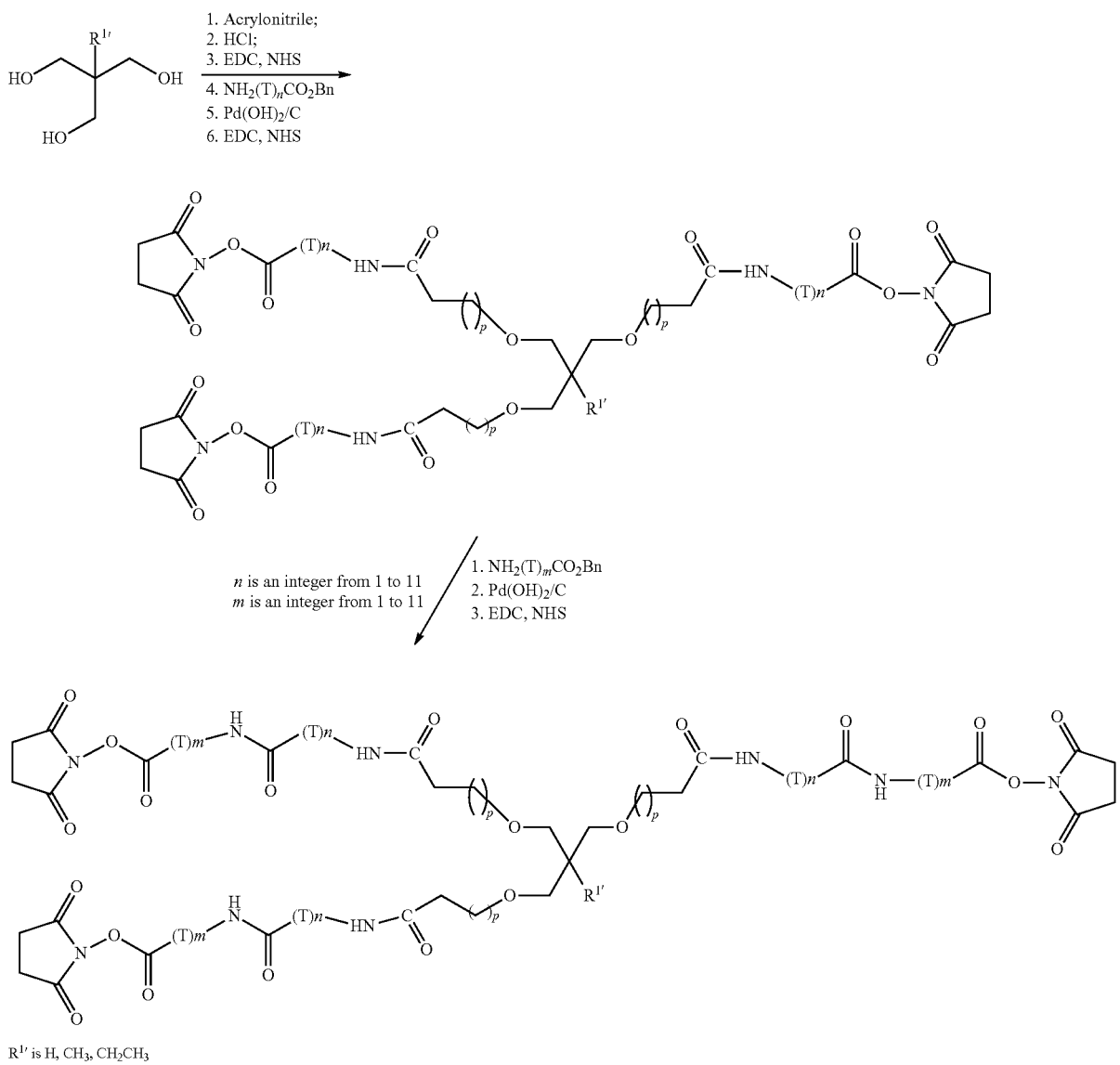
$R^{1'}$ is H, $CH_3$, $CH_2CH_3$ 2. Synthesis of the Glycoside Units The mono-, di- and tetrasaccharide units used as or used to prepare the glycosides that can be coupled to the core starting materials can be synthesised as described in WO 2012/121617.

Scheme 8 shows a general method for the synthesis of glycosides that can be used to prepare tetrameric, trimeric and dimeric compounds of the invention.

(Note: in Schemes 8 to 12, f, g, r and j are each independently an integer from 0 to 6.)

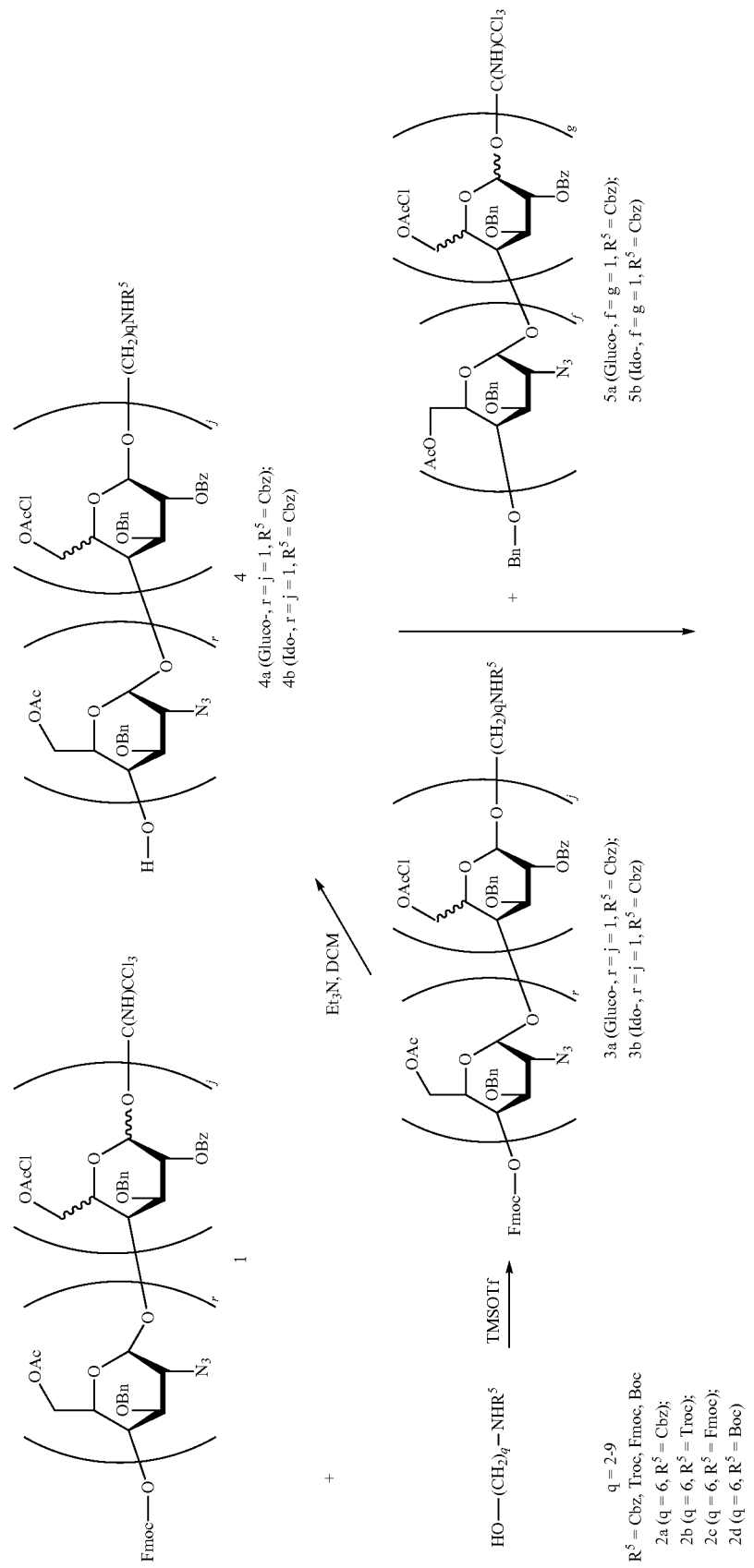

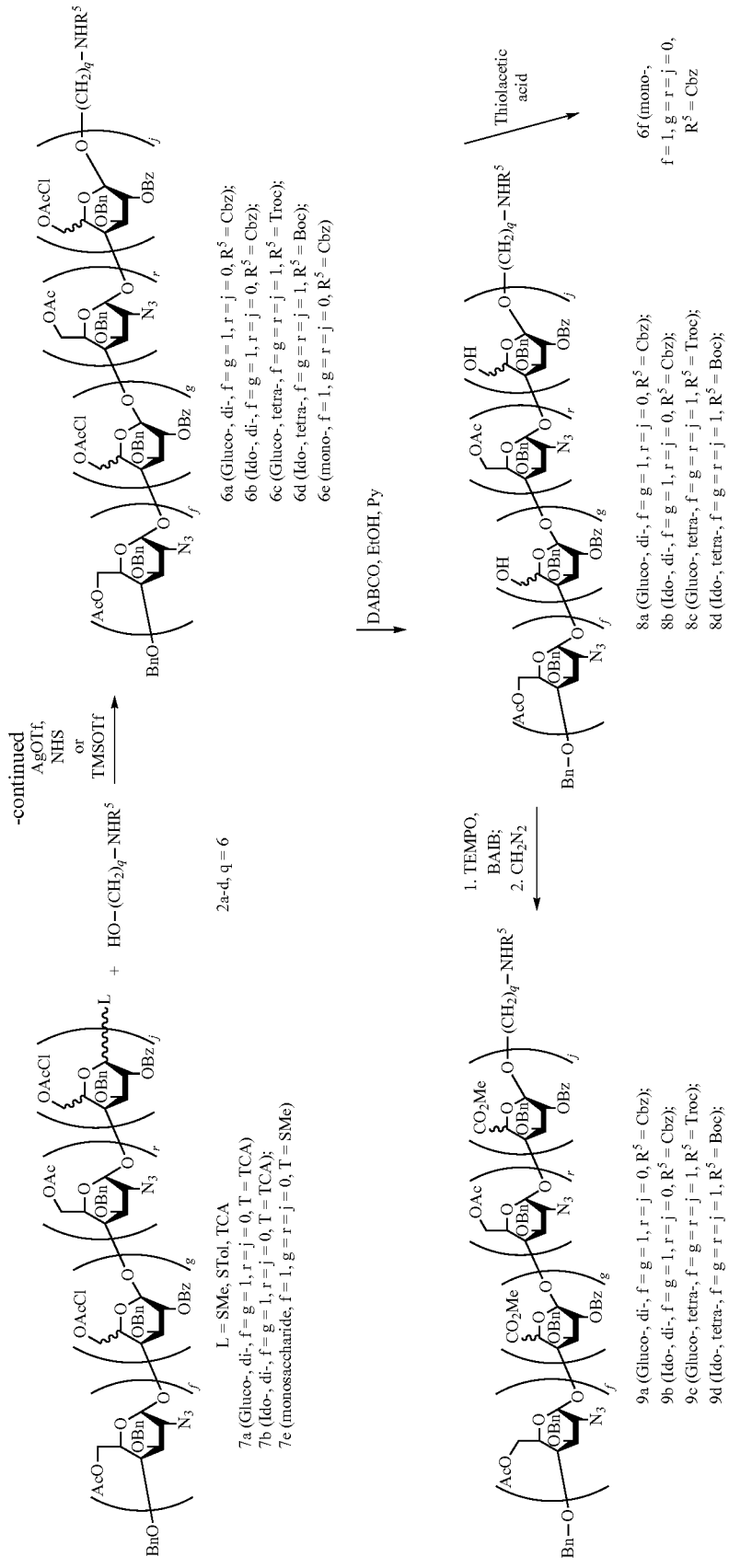

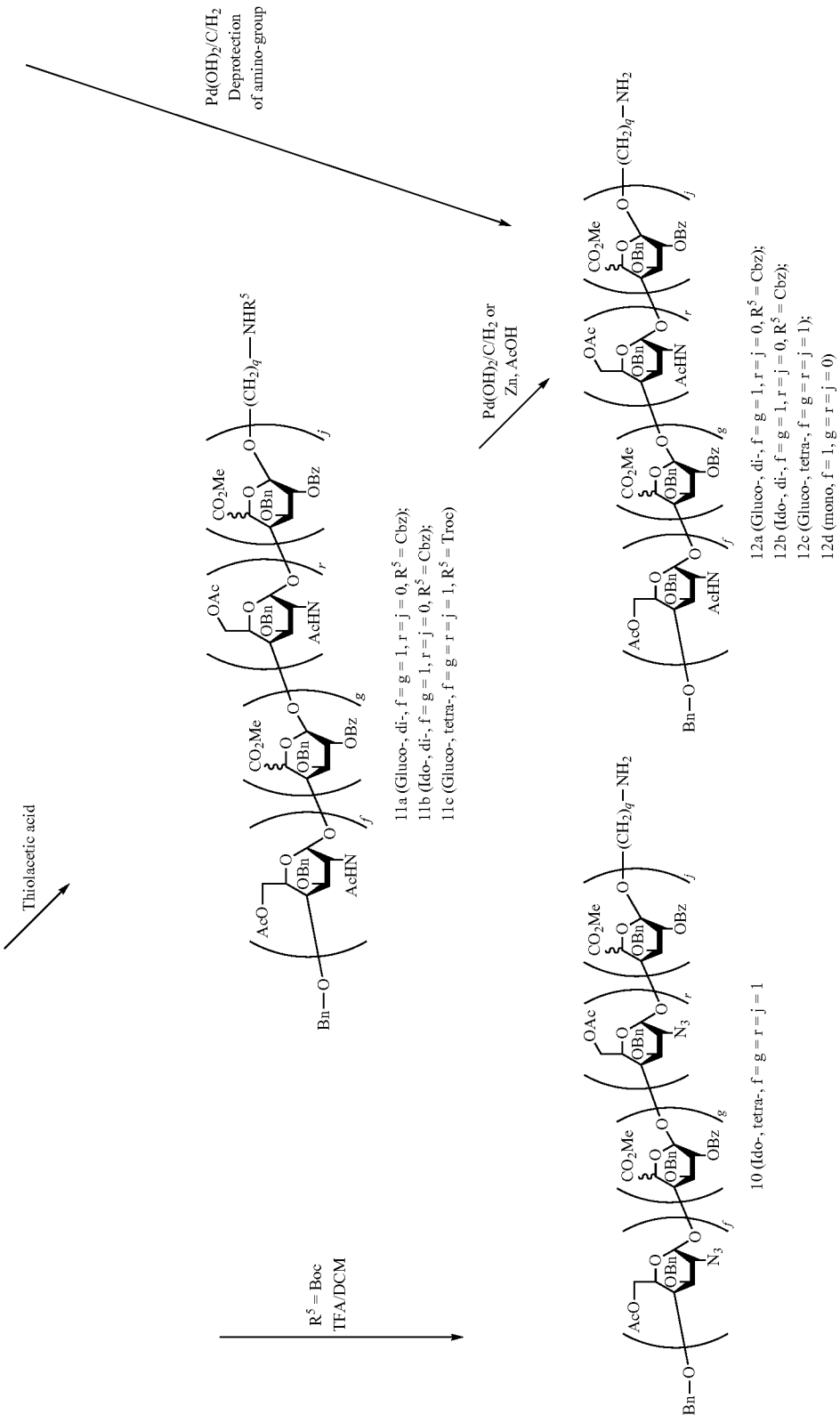

3. Synthesis of the Dendritic Compounds of the Invention

The "core" starting materials can be coupled to a glycoside which has a free amino group, thereby allowing preparation of the dendritic compounds of the invention. The coupling procedure and requires a suitable solvent (DMF, DMSO, water, for example), a small amount of base, e.g. triethylamine, and a suitable glycoside (at least about 2 equivalents of glycoside, e.g. about 2.2 equivalents of glycoside are used for coupling with dimeric cores, at least about 3 equivalents of glycoside, e.g. about 3.3 equivalents of glycoside are used for coupling with trimeric cores and at least about 4 equivalents of glycoside e.g. about 4.4 equivalents of glycoside are used for coupling with tetrameric cores).

Schemes 9-12 show general methods for coupling glycosides to the tetrameric, trimeric and dimeric cores. (Note: those skilled in the art will appreciate that, for the sake of clarity, the group $(CH_2)_p$ is only shown in the structures at the beginning of Schemes 9 and 10 but is intended to be read as included in the remaining structures in the schemes. Furthermore, although the compounds shown in Schemes 9 and 11 are those where each T is $CH_2$, those skilled in the art will understand that compounds where one or more T is $(CH_2CH_2O)_xCH_2$ can also be synthesised in accordance with the procedures shown in Schemes 9 and 11.)

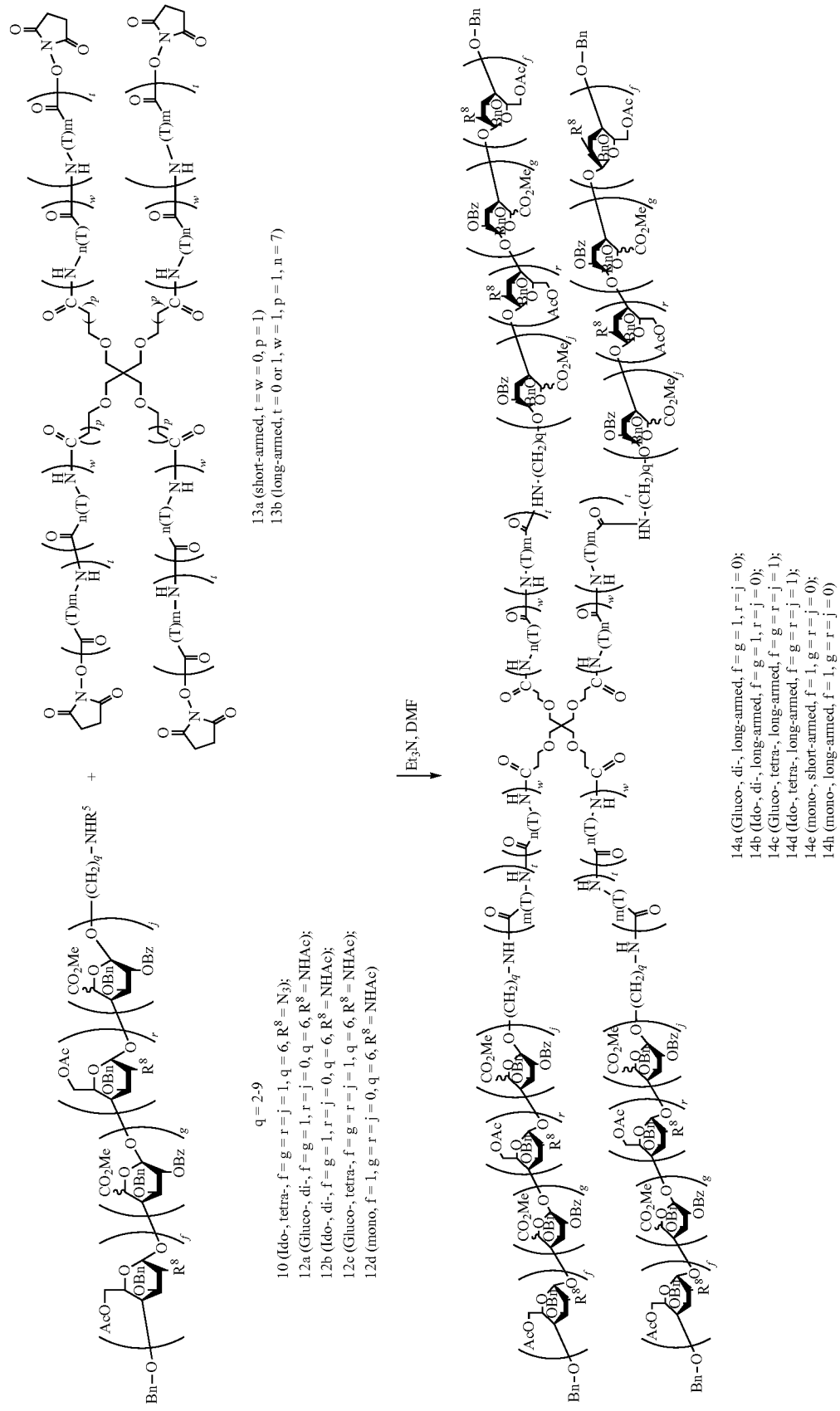

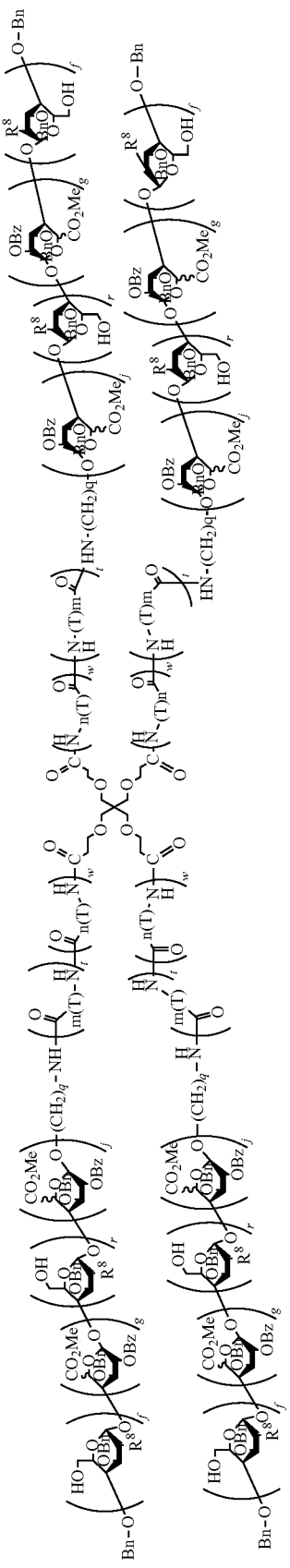

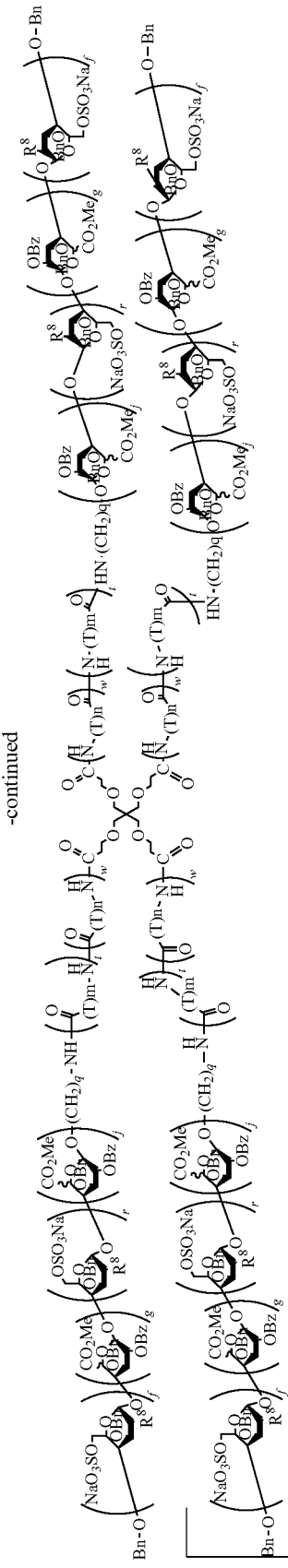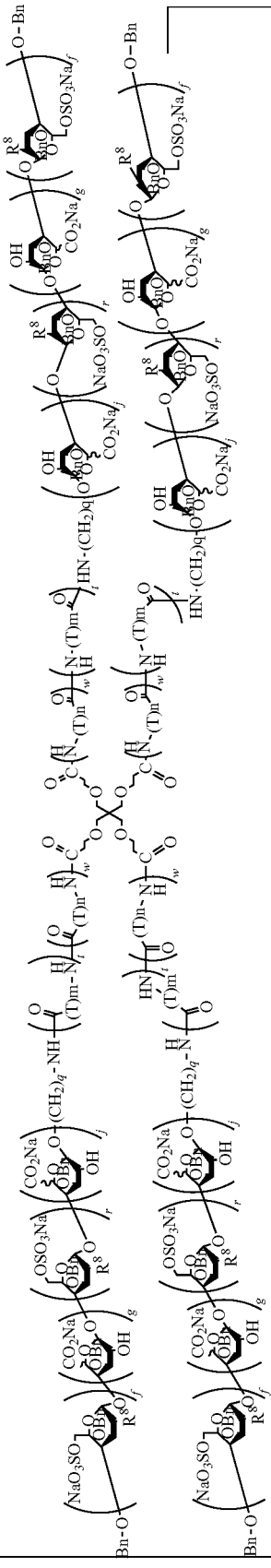

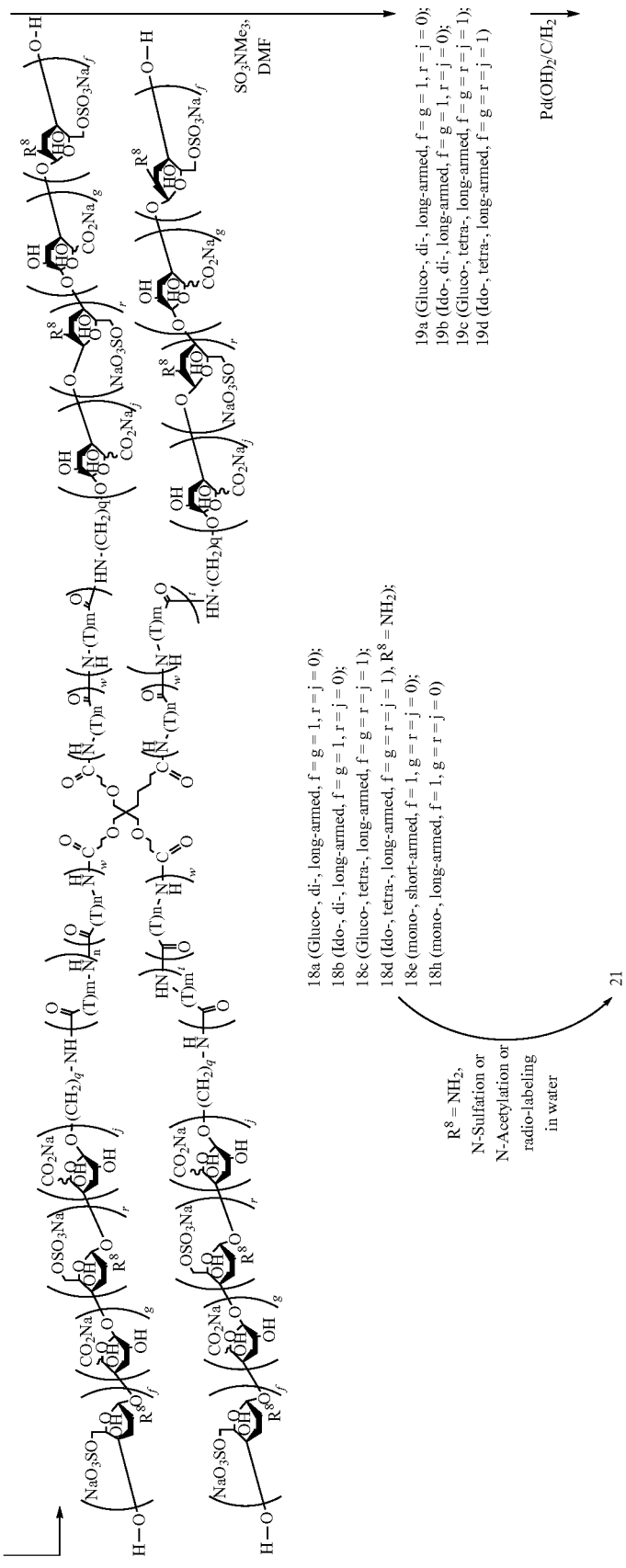

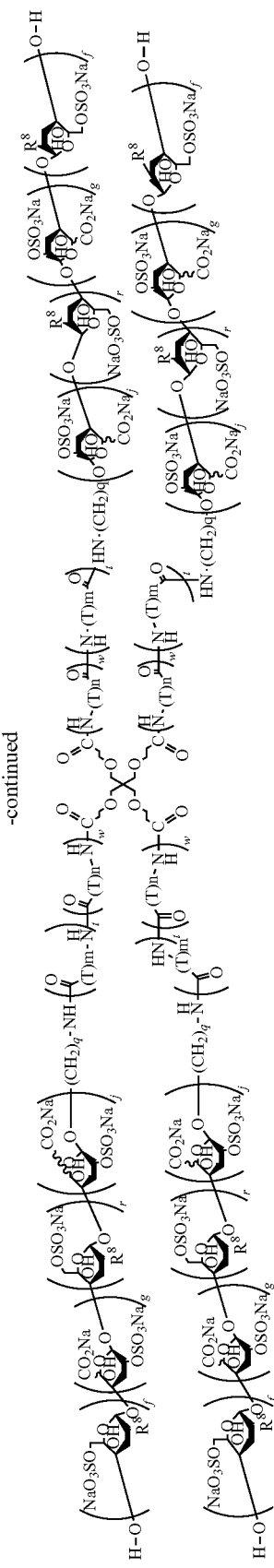

Scheme 10
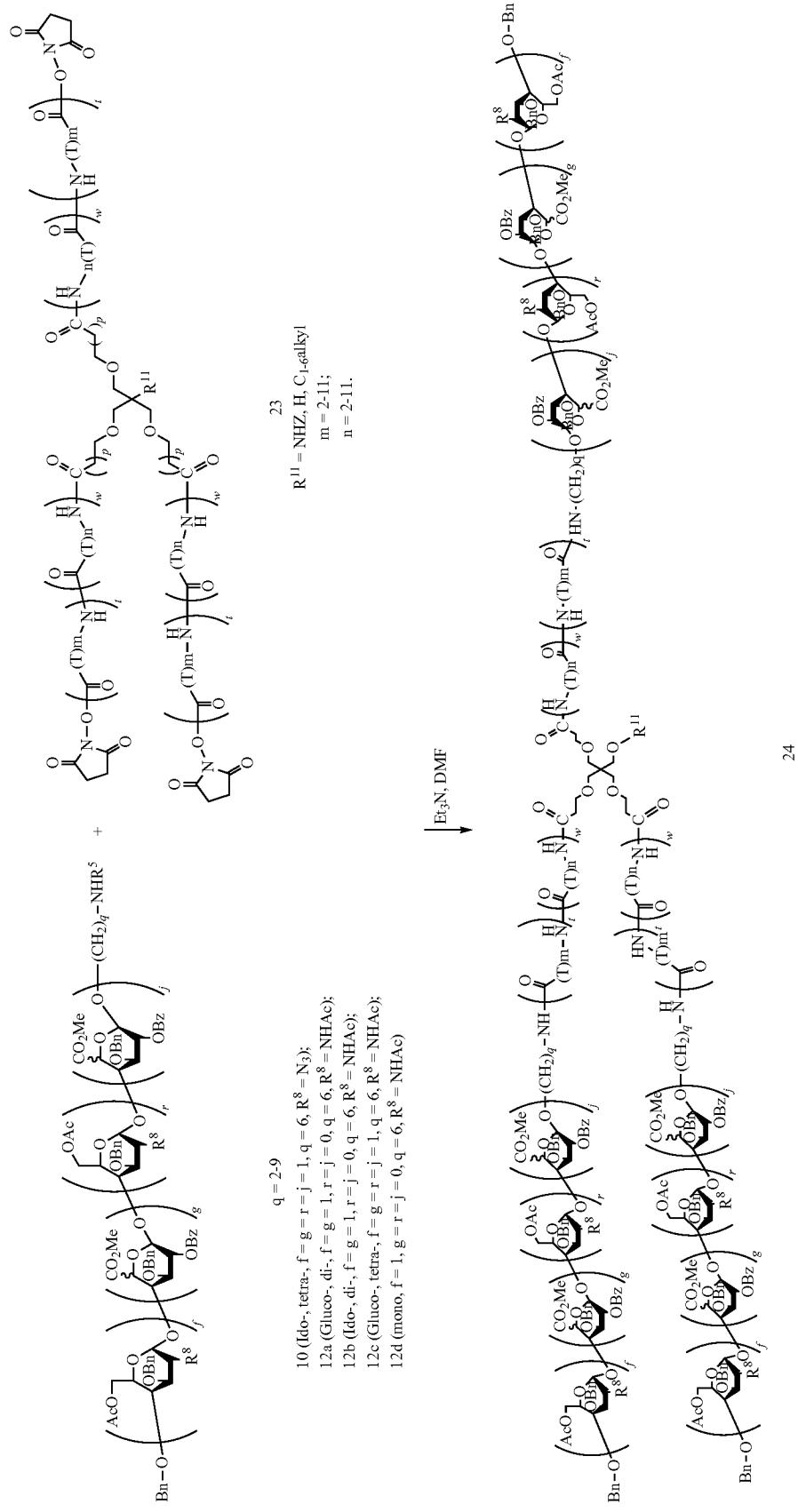

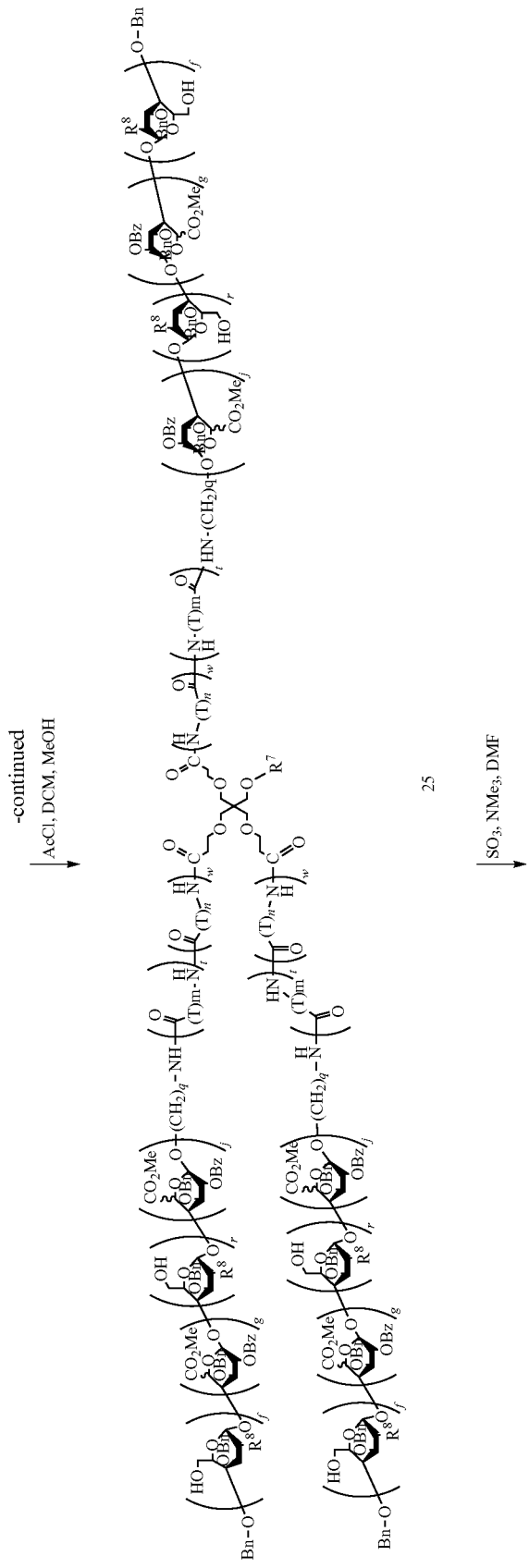

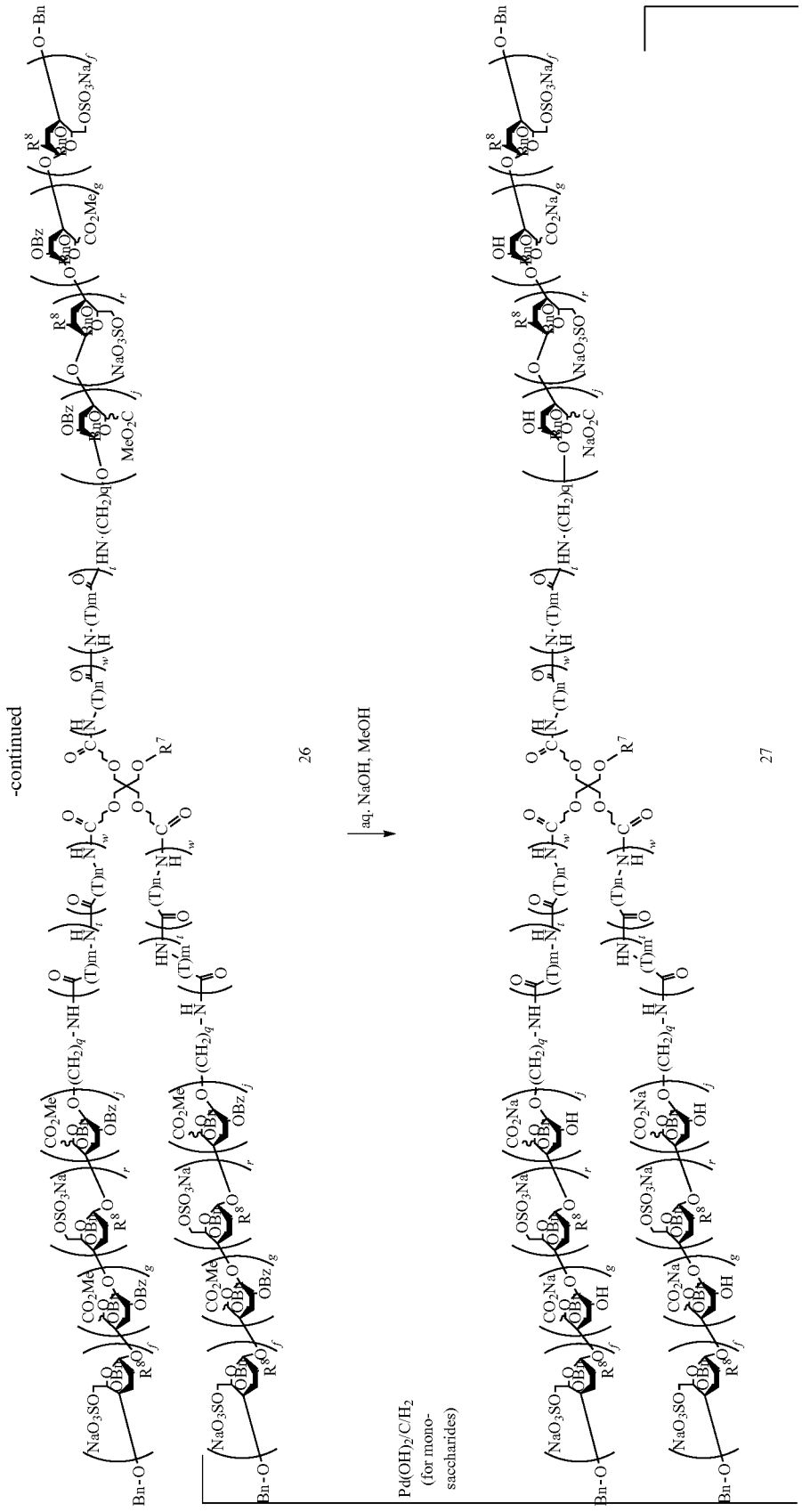

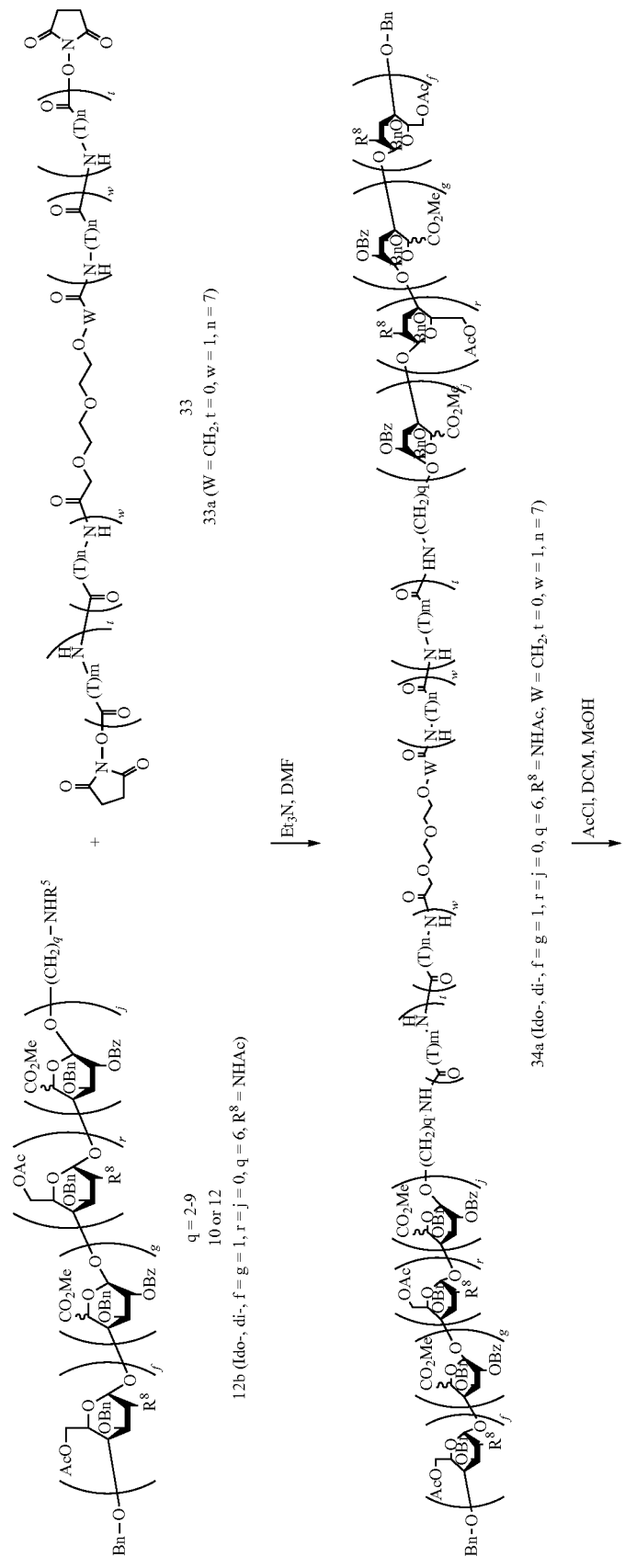
Scheme 11

-continued
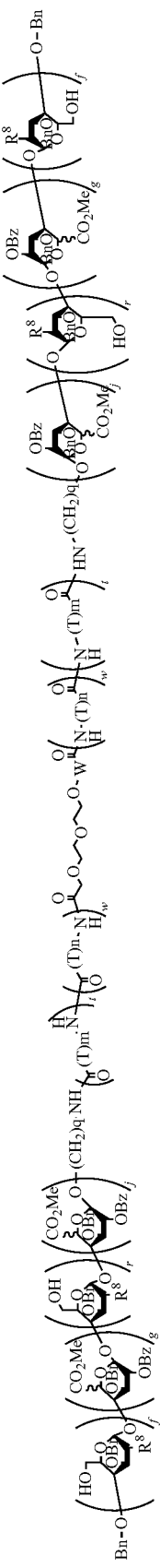
35a (Ido-, di-, f = g = 1, r = j = 0, q = 6, R⁸ = NHAc, W = CH₂, t = 0, w = 1, n = 7)
↓ SO₃·NMe₃, DMF
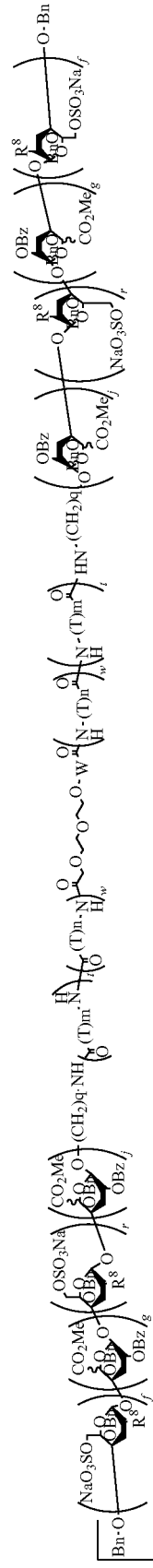
36a (Ido-, di-, f = g = 1, r = j = 0, q = 6, R⁸ = NHAc, W = CH₂, t = 0, w = 1, n = 7)
↓ aq·NaOH, MeOH

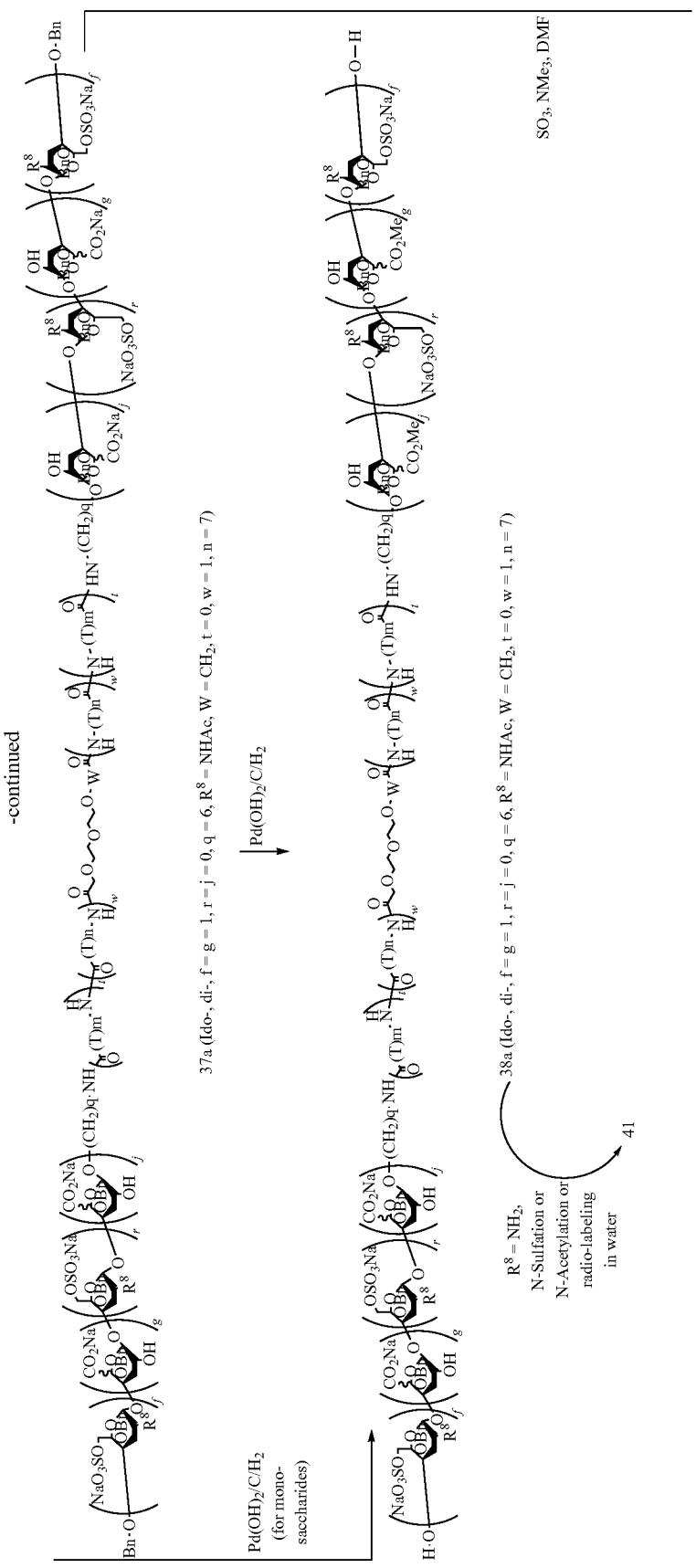

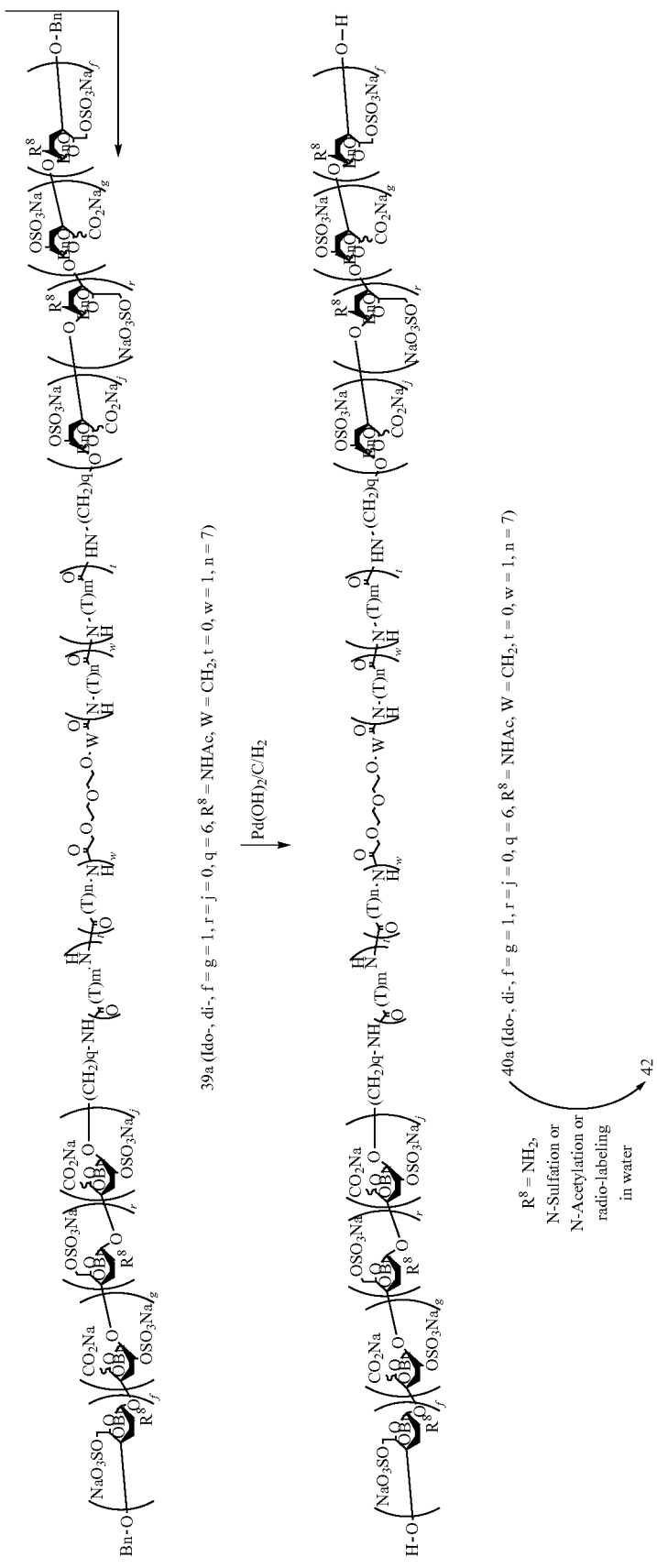

Scheme 12
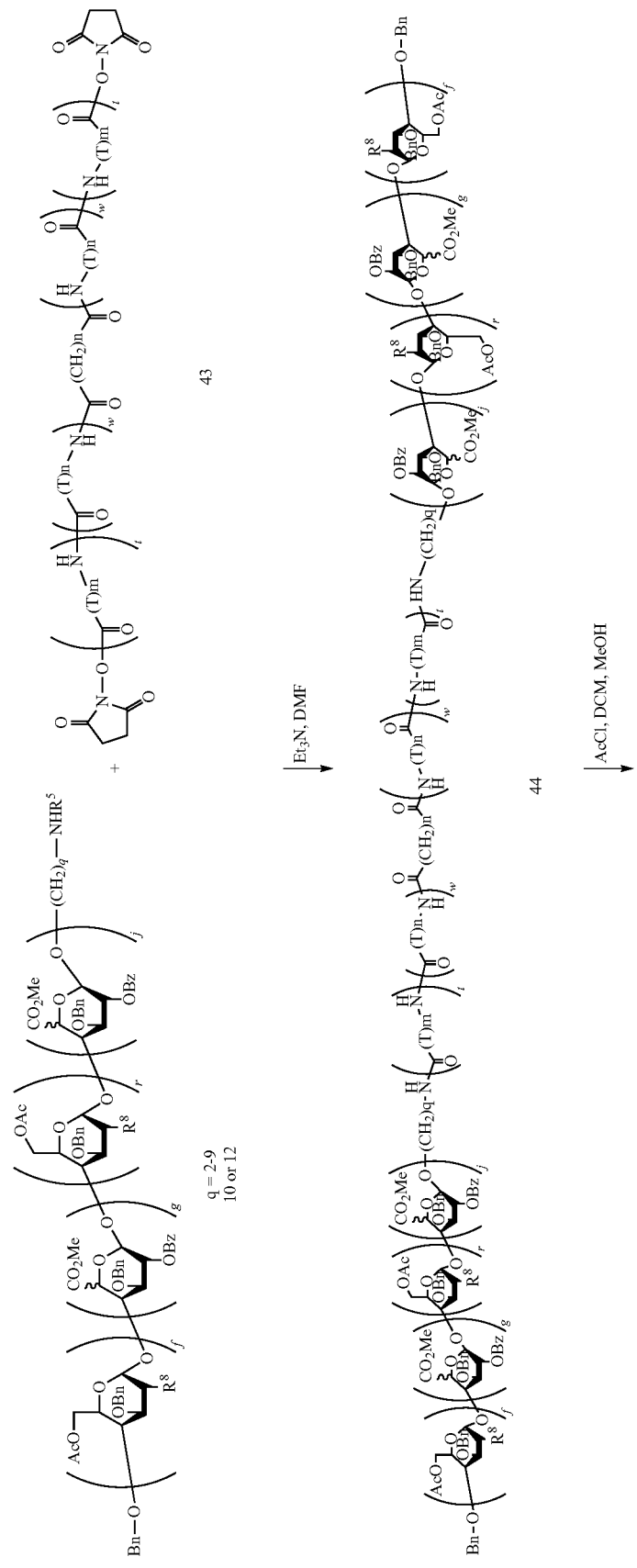

-continued
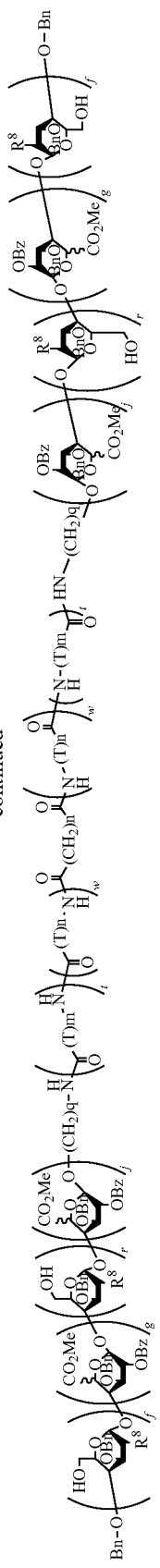
45
↓ SO₃·NMe₃, DMF
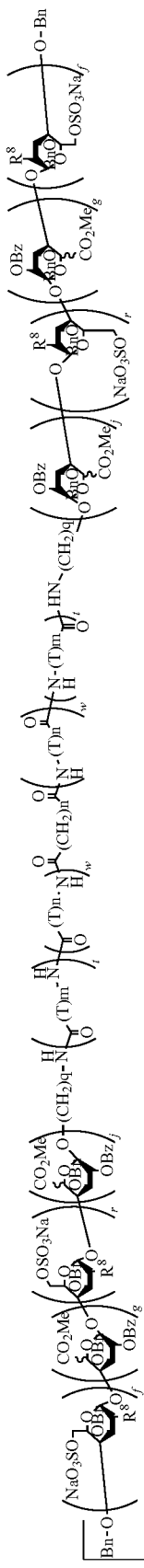
46
↓ aq·NaOH, MeOH

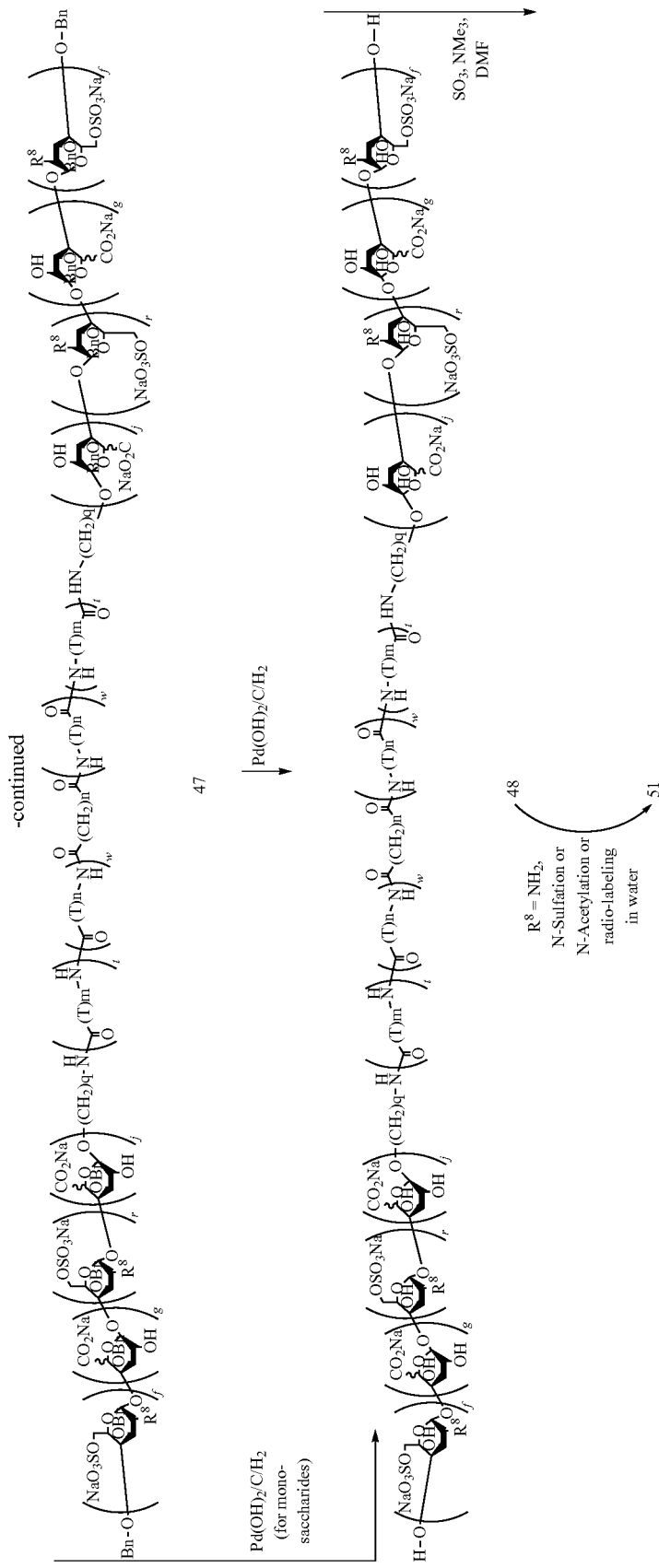

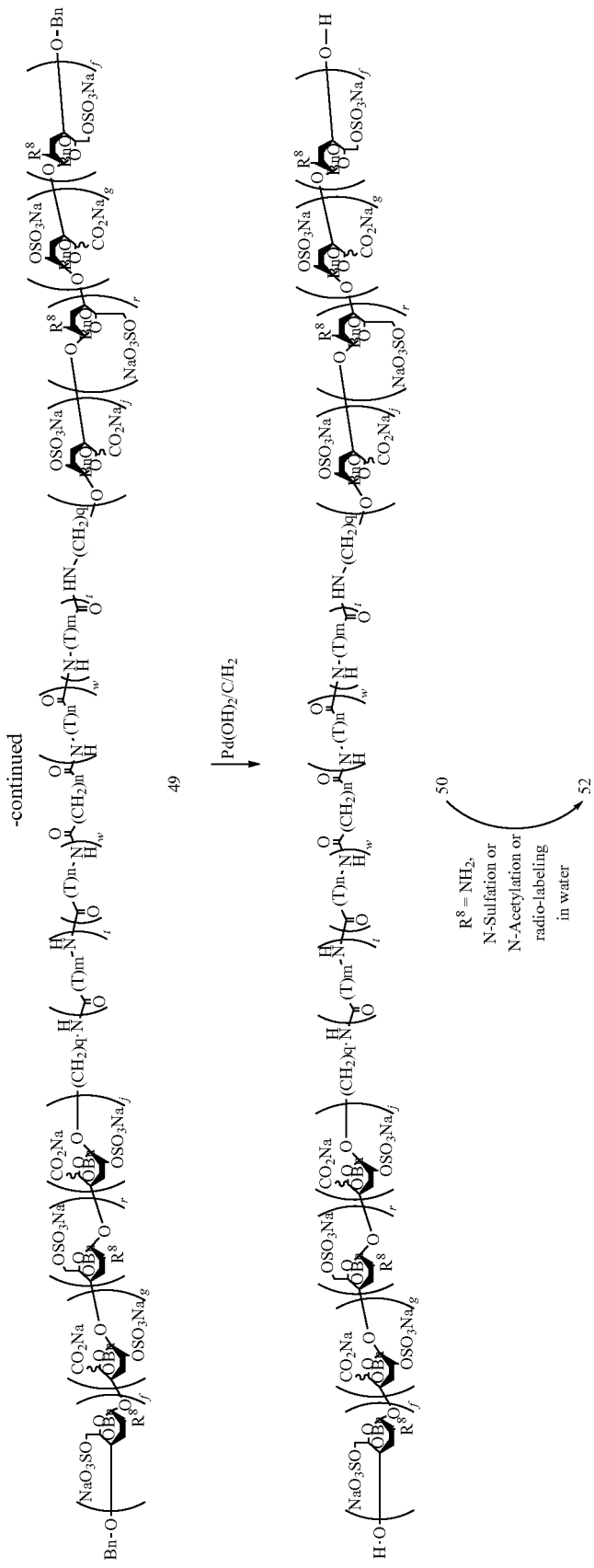

ABBREVIATIONS

Figure 1A:
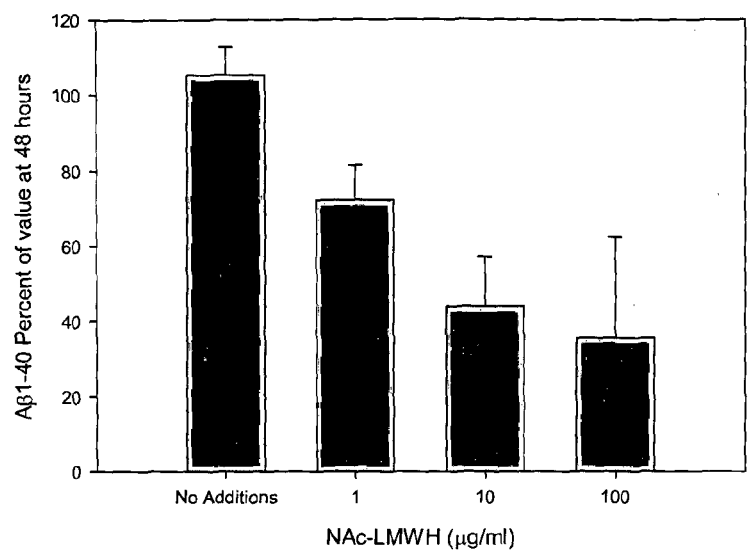
FIG. 1a shows the percentage of Aβ1-40 present in brain slice assays, with addition of various concentrations of NHAc-LMWH (low molecular weight heparin), in accordance with the method described in Example 3.

NMR nuclear magnetic resonance
HRMS high resolution mass spectrometry
ESI electrospray ionisation
TLC thin layer chromatography
RT room temperature
DCM dichloromethane
TEMPO 2,2,6,6-tetramethyl piperidinyloxy
THF tetrahydrofuran
DMF dimethylformamide
TMS trimethylsilyl
TMS-diazomethane trimethylsilyl-diazomethane
NHS N-Hydroxysuccinimide
EDC 1-Ethyl-3-[3-dimethylaminopropyl]carbodiimide hydrochloride
TCA Trichloroacetic acid
DABCO 1,4-diazabicyclo[2.2.2]octane
BAIB [Bis(acetoxy)iodo]benzene

EXAMPLES

The following examples further illustrate the invention. It is to be appreciated that the invention is not limited to the examples.

Example 1: Synthesis of Compounds

Example 1.1: Synthesis of tetra-succinimidyl ester

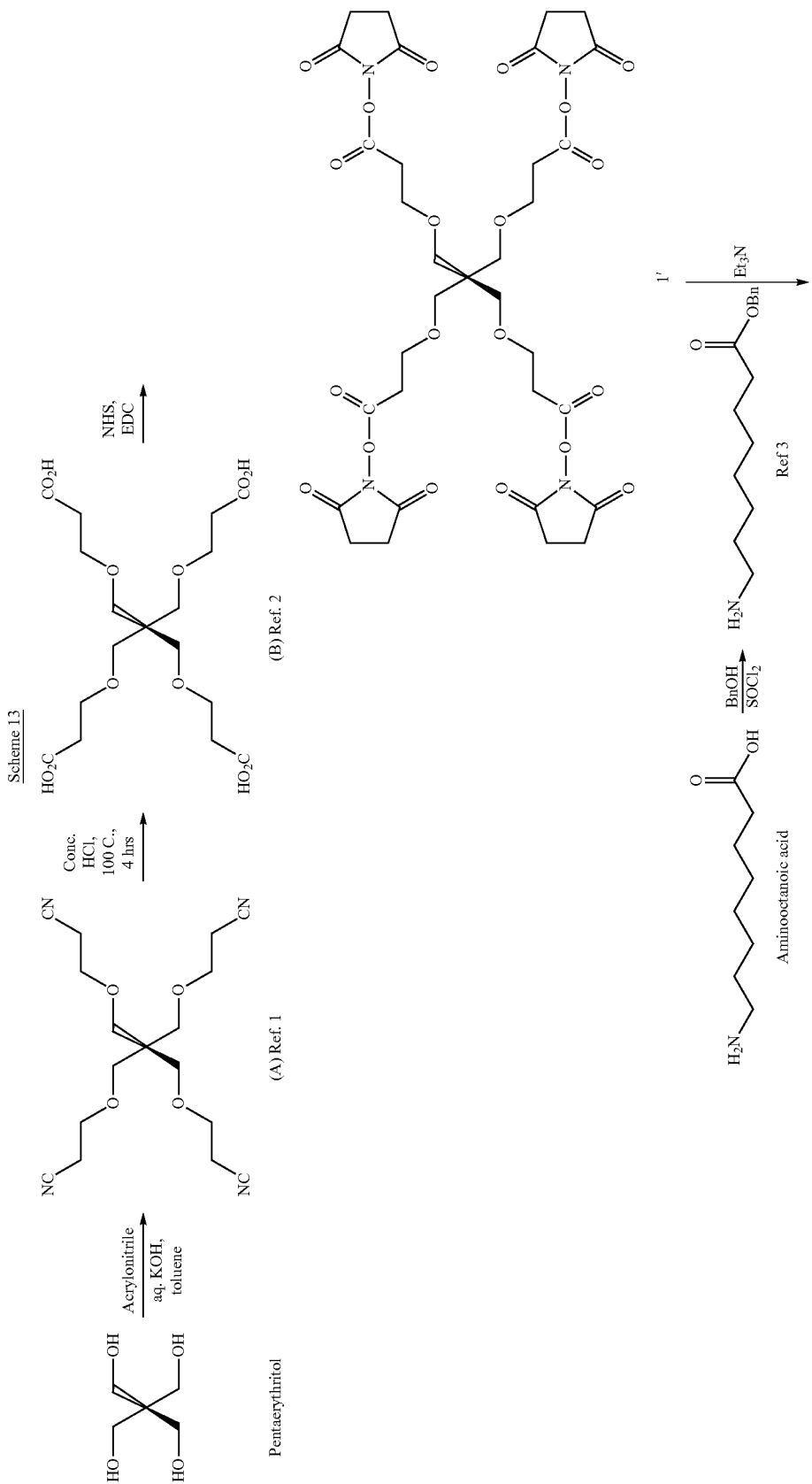

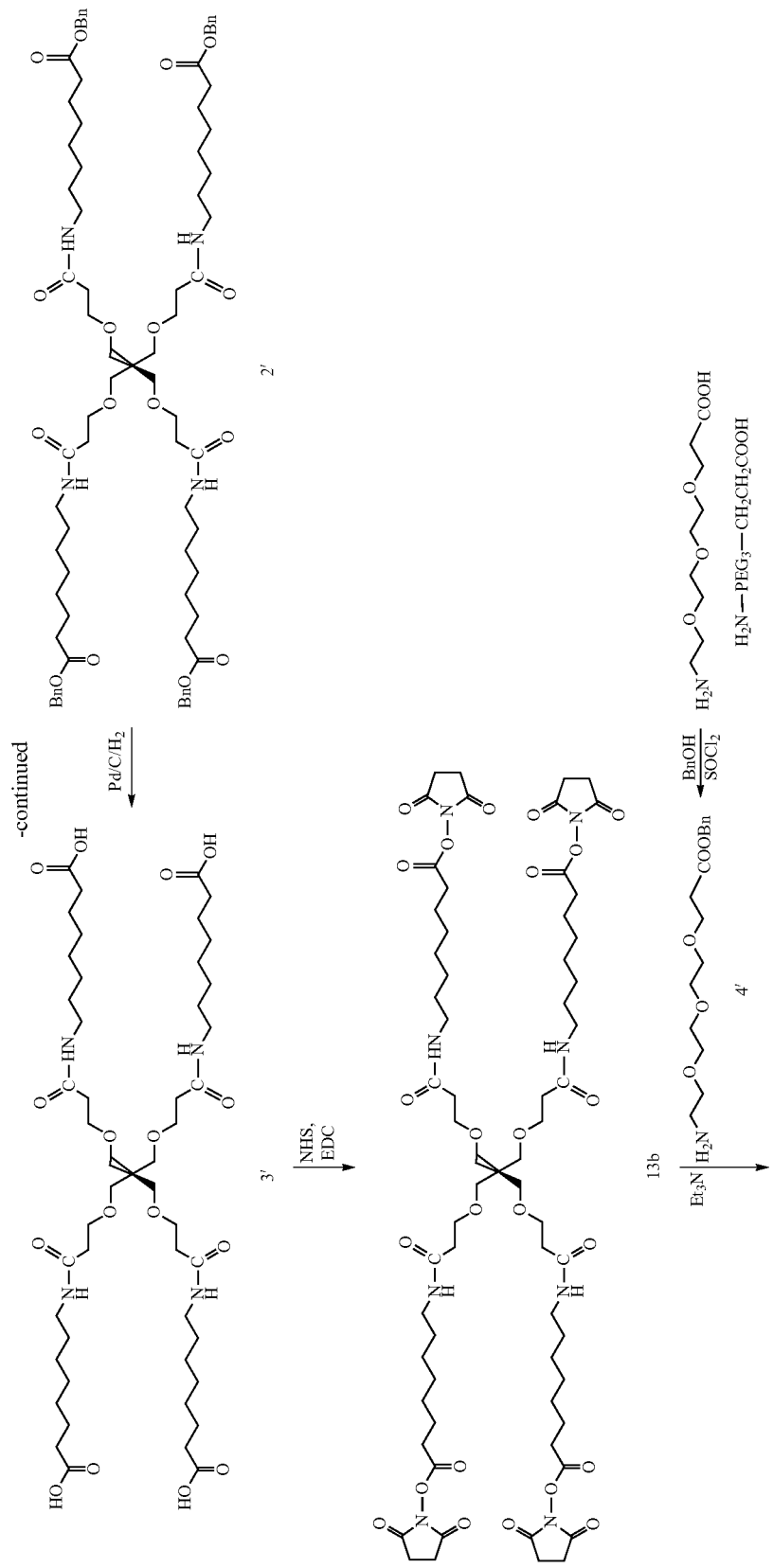

-continued
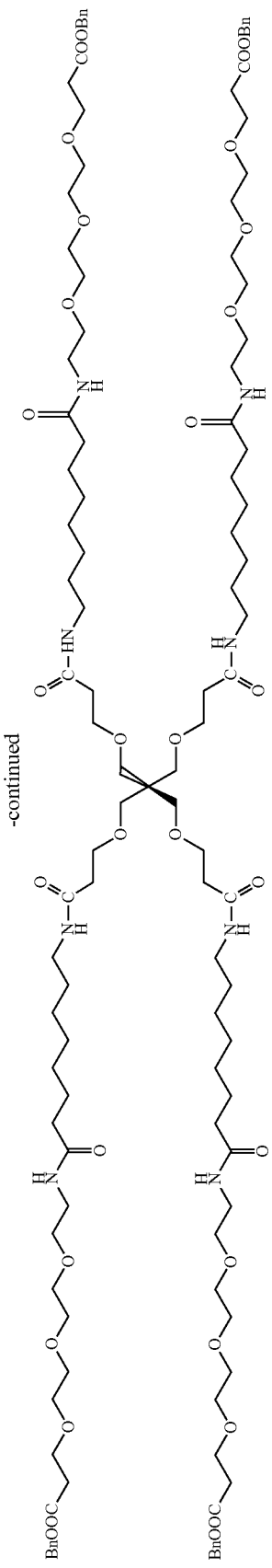
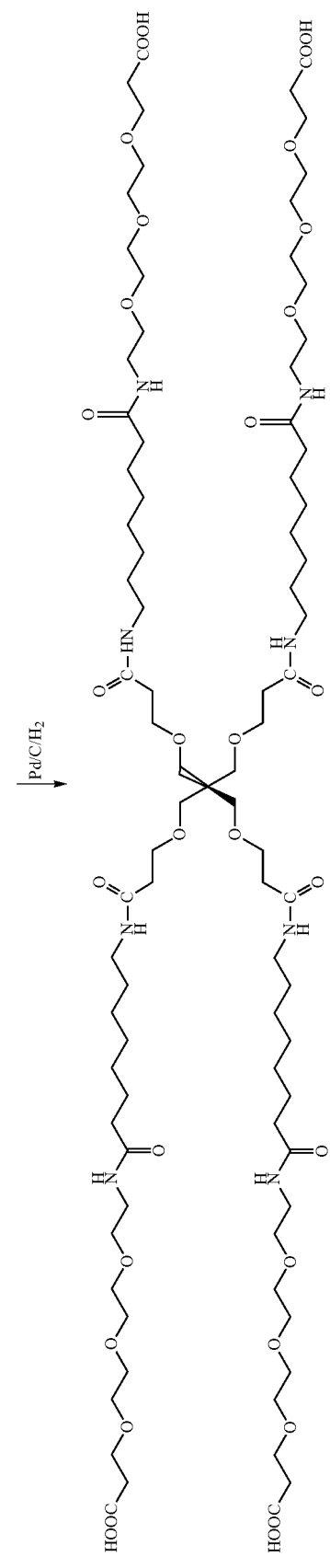
Pd/C/H₂
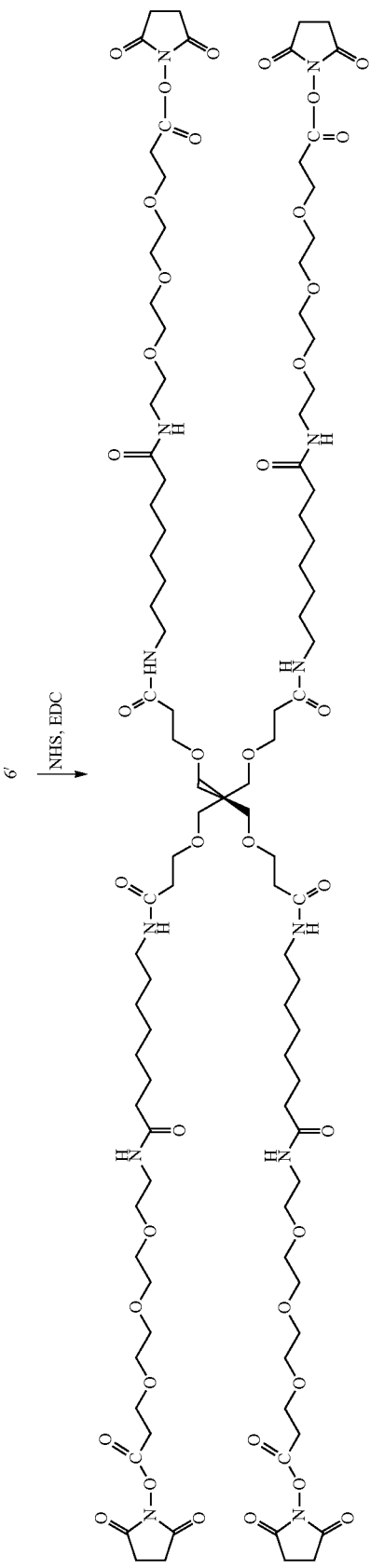
NHS, EDC

Preparation of 1'

Tetranitrile precursor (Ref.1, Hukkämaki, J.; Pakkanen, T. T. *Journal of Molecular Catalysis A: Chemical* 2001, 174, 205-211) is prepared via Michael-type addition of acrylonitrile to pentaerythritol. Acidic hydrolysis of tetranitrile (Ref. 2, Newcombe, G. R.; Mishra, A; Moorfield, C. N. *J. Org. Chem.* 2002, 67, 3957-3960) furnishes the tetraacid. Tetraacid (1.0 g, 2.35 mmol) is dissolved in dry DMF (15 mL). N-Hydroxysuccinimide (1.62 g, 14.14 mmol) and 1-ethyl-3-[3-dimethylaminopropyl]carbodiimide hydrochloride (EDC, 2.71 g, 14.14 mmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with EtOAc followed by EtOAc:MeOH, 19:1→9:1→7:1→4:1 to give the tetra-succinimidyl ester (1', 1.2 g, 1.48 mmol, 63%). $R_f$=0.25 (Ethyl Acetate:MeOH, 9:1). $^{13}$C-NMR (125 MHz, DMSO-D$_6$) δ 170.7, 170.1, 68.7, 65.5, 44.9, 31.5, 25.7. HRMS calcd for $C_{33}H_{40}N_4O_{20}Na$ (M+Na)$^+$ m/z 835.2134, found 835.2128.

Preparation of 2'

Aminooctanoic acid is treated with benzyl alcohol in the presence of thionyl chloride (Ref. 3, Patel, R. P; Price, S. *J. Org Chem.* 1965, 30 (10), 3575-3576) to give a tetra benzyl ester (2 g, 8.12 mmol). This and tetra-succinimidyl ester (1', 1.1 g, 1.35 mmol) are dissolved in a mixture of dry THF (55 mL) and dry DMF (3 mL) and treated with triethylamine (1.5 mL, 10.83 mmol).

After stirring for 24 hrs the mixture is diluted with ethyl acetate and washed with water twice, dried over magnesium sulfate and concentrated. The residue is dissolved in hot EtOAc, the crystals are filtered off and discharged. The mother liquor is concentrated and the residue is purified by flash chromatography on silica gel eluting with Chloroform:EtOAc:MeOH, 5:2:0.5 to afford the tetra-benzyl ester (2', 1.7 g, 1.26 mmol, 93%). $R_f$=0.3 (Chloroform:Ethyl Acetate:MeOH, 5:2:1). $^{13}$C-NMR (125 MHz, CDCl$_3$) δ 173.5, 171.2, 136.1, 128.5, 128.2, 128.1, 69.1, 67.4, 66.1, 45.3, 39.5, 36.9, 34.2, 29.6, 29.4, 28.9, 26.7, 26.6, 24.8. HRMS calcd for $C_{77}H_{112}N_4O_{16}Na$ (M+Na)$^+$ m/z 1371.7971, found 1371.7977.

Preparation of 3'

Tetra benzyl ester (2', 0.595 g, 441 μmol) is dissolved in dry THF (16 mL). Water (4 mL) and glacial acetic acid (5 drops) are added. The reaction mixture is treated with palladium hydroxide on carbon (20% Pd, 1 g) and stirred for 3 hours under hydrogen at ambient temperature and pressure. The catalyst is filtered off and washed with 50% aqueous EtOH. The solution is concentrated to dryness to give a "long-armed" tetraacid (3', 0.42 g, 429 μmol, 97%). The product is used in the next step without further purification. $R_f$=0.0 (base line, Chloroform:Ethyl Acetate:MeOH, 5:2:1). $^{13}$C-NMR (125 MHz, DMSO-D$_6$) δ 174.5, 169.9, 68.8, 67.3, 45.0, 39.0, 38.4, 36.1, 33.8, 29.1, 28.5, 38.4, 26.3, 25.2, 24.5. HRMS calcd for $C_{49}H_{87}N_4O_{16}$ (M−H)$^−$ m/z 987.6117, found 987.6110.

Preparation of 13b

"Long-armed" tetraacid (3', 424 mg, 429 μmol) is dissolved in dry DMF (7 mL). N-Hydroxysuccinimide (296 mg, 2.57 mmol) and 1-ethyl-3-[3-dimethylaminopropyl]carbodiimide hydrochloride (EDC, 493 mg, 2.57 mmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with Chloroform:Ethyl Acetate:MeOH, 5:2:0.5→5:4:1 to give the "long-armed" tetra-succinimidyl ester (13b, 415 mg, 301 μmol, 70.3%). $R_f$=0.25 (DCM:MeOH, 9:1). $^{13}$C-NMR (125 MHz, CDCl$_3$) δ 171.5, 169.4, 168.6, 68.9, 67.4, 45.3, 39.4, 36.7, 30.8, 29.5, 29.4, 28.6, 28.5, 26.6, 25.5, 25.4, 24.4. HRMS calcd for $C_{65}H_{100}N_8O_{24}Na$ (M+Na)$^+$ m/z 1399.6748, found 1399.6737.

Preparation of 4'

$H_2N(PEG)_3CH_2CH_2COOH$ (or PEG aminoacid) (1.0 g, 4.52 mmol) is dissolved in benzyl alcohol (30 mL, 287 mmol) and cooled to 0° C. Thionyl chloride (6 mL, 82.2 mmol) is added slowly dropwise. The reaction mixture is stirred at 0° C. for 15 min followed by heating at 100° C. for 5 hours. Then this is diluted with diethyl ether and the oily residue is collected and purified by flash chromatography on silica gel eluting with Dichloromethane:MeOH, 9:1→1:1 to afford the benzyl ester (4', 1.2 g, 3.9 mmol, 85%). $R_f$=0.15 (Dichloromethane:MeOH, 9:1). $^{13}$C-NMR (125 MHz, CDCl$_3$) δ 171.6, 135.8, 128.5, 128.2, 128.1, 70.2, 70.14, 70.13, 69.9, 66.7, 66.4, 66.3, 50.0, 39.7, 35.0. HRMS calcd for $C_{16}H_{26}NO_5$ (M+H)$^+$ m/z 312.1811, found 312.1806.

Preparation of 5'

The benzyl ester 4' (65 mg, 210 μmol) and tetra-succinimidyl ester (13b, 58 mg, 42.1 μmol) are dissolved in dry DMF (2 mL) and treated with triethylamine (47 μL, 336 μmol). After stirring for 24 hrs the mixture is diluted with ethyl acetate and washed with water twice, dried over magnesium sulfate and concentrated. The residue is dissolved in hot EtOAc, the crystals are filtered off and discharged. The mother liquor is concentrated and the residue is purified by flash chromatography on silica gel eluting with Chloroform:EtOAc:MeOH, 5:2:0.5 to afford the tetra-benzyl ester (5', 71 mg, 32.8 μmol, 78%). $R_f$=0.3 (Chloroform:Ethyl Acetate:MeOH, 5:2:1). $^{13}$C-NMR (125 MHz, CDCl$_3$) δ 173.2, 171.3, 135.8, 128.5, 128.2, 128.1, 70.5, 704, 70.2, 69.9, 69.2, 67.5, 66.5, 66.3, 45.3, 39.4, 39.1, 36.9, 36.5, 35.1, 29.6, 29.1, 29.0, 26.7, 25.5.

Preparation of 6'

Tetra benzyl ester (5', 16 mg, 7.21 μmol) is dissolved in dry THF (4 mL). Water (1 mL) and glacial acetic acid (2 drops) are added. The reaction mixture is treated with palladium hydroxide on carbon (20% Pd, 20 mg) and stirred for 3 hours under hydrogen at ambient temperature and pressure. The catalyst is filtered off and washed with 50% aqueous EtOH. The solution is concentrated to dryness to give a "long-armed" PEG tetraacid (6', 13 mg, 7.21 μmol, 97%). The product is used in the next step without further purification. $R_f$=0.0 (base line, Chloroform:Ethyl Acetate:MeOH, 5:2:1). $^{13}$C-NMR (125 MHz, MeOD) δ 176.7, 174.2, 71.4, 71.3, 71.2, 70.6, 68.8, 67.8, 62.8, 48.5, 40.6, 40.3, 37.8, 37.1, 35.8

Preparation of 7'

"Long-armed" PEG tetraacid (6', 13 mg, 7.21 μmol) is dissolved in dry DMF (1 mL). N-Hydroxysuccinimide (5.1 mg, 43.2 μmol), DIPEA (7.6 μL, 43.2 μmol) and 1-ethyl-3-[3-dimethylaminopropyl]carbodiimide hydrochloride (EDC, 8.3 mg, 43.2 μmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with Chloroform:Ethyl Acetate:MeOH, 5:2:0.5→5:4:1 to give the "long-armed" PEG tetra-succinimidyl ester (7', 15 mg, 6.85 μmol, 94%). $R_f$=0.25 (DCM:MeOH, 9:1).

Example 1.2: Synthesis of di-succinimidyl ester

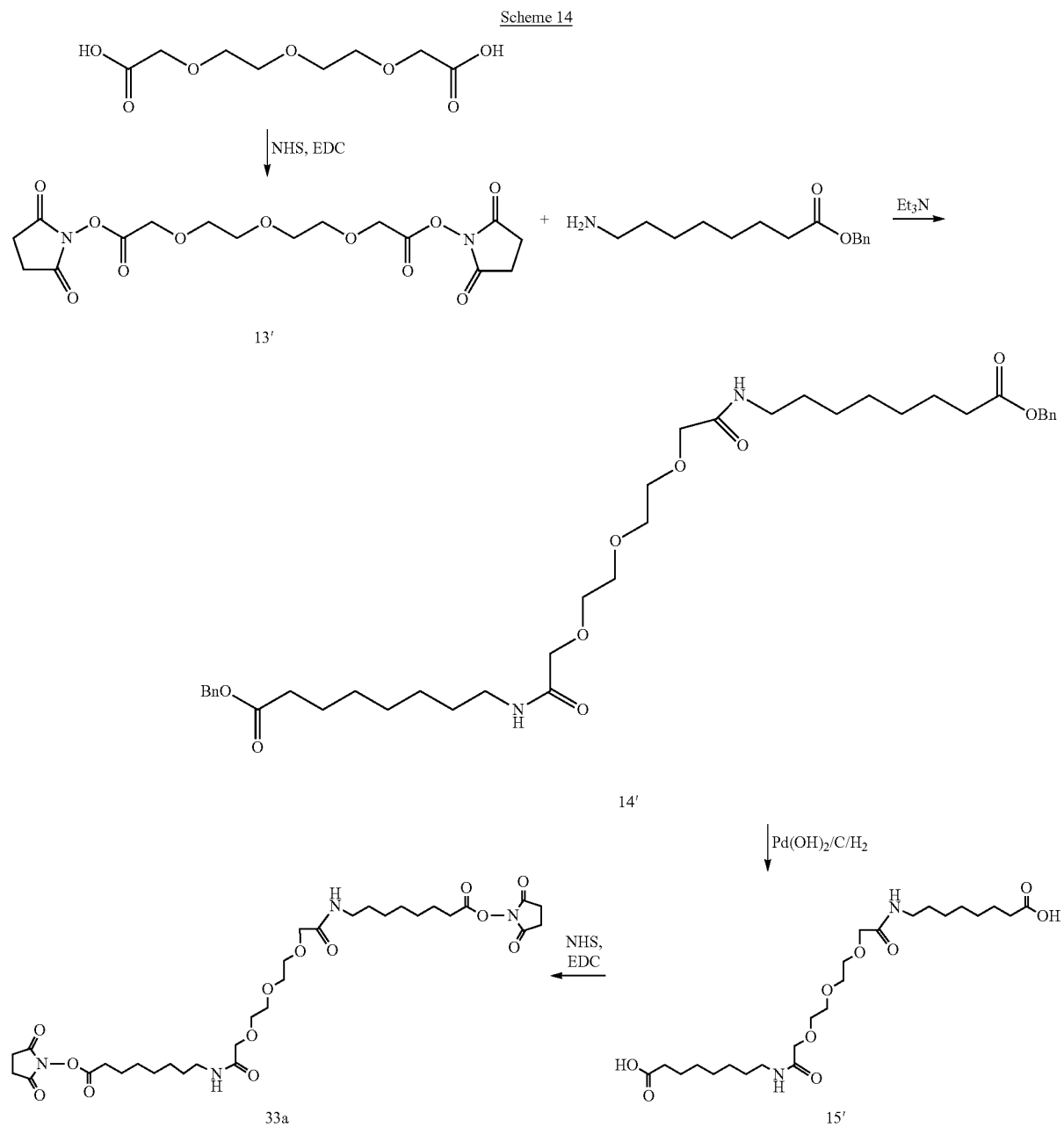

Preparation of 14'

3,6,9-Trioxaundecanedioic acid (500 mg, 2.25 mmol) is dissolved in dry DMF (10 mL). N-Hydroxysuccinimide (785 mg, 6.75 mmol, 3 eq.), 1-ethyl-3-[3-dimethylaminopropyl]carbodiimide hydrochloride (EDC, 1.32 g, 6.75 mmol, 3 eq.) and N,N-diisopropylethylamine (2.38 mL, 13.5 mmol) followed by benzyl 8-aminooctanate (1.68 g, 6.75 mmol, 3 eq.) are added to the reaction mixture at room temperature and stirring continued for 4 hrs. The mixture is diluted with DCM and washed with water, then with diluted HCl and water, dried over magnesium sulfate and concentrated. The residue is dissolved in hot EtOAc, the crystals are filtered off and discharged. The mother liquor is concentrated and the residue is purified by flash chromatography on silica gel eluting with Chloroform:EtOAc:MeOH, 5:2:0.3 to afford the di-benzyl ester (10, 1.1 g, 1.61 mmol, 71%). $^{13}$C-NMR (125 MHz, CDCl$_3$) δ 173.4, 169.9, 136.1, 128.4, 128.3, 128.1, 127.8, 127.7, 65.9, 63.9, 60.3, 39.5, 36.8, 31.9, 30.9, 29.3, 28.8, 26.6, 25.3, 24.7, 24.4, 21.2, 20.9. HRMS calcd for $C_{38}H_{56}N_2O_9Na$ (M+Na)$^+$ m/z 707.3884, found 707.3876.

Preparation of 15'

Di-benzyl ester (14', 204 mg, 297 μmol) is dissolved in dry THF (8 mL). Water (2 mL) and glacial acetic acid (3 drops) are added. The reaction mixture is treated with palladium hydroxide on carbon (20% Pd, 0.5 g) and stirred for 3 hours under hydrogen at ambient temperature and pressure. The catalyst is filtered off and washed with 50% aqueous EtOH. The solution is concentrated to dryness to give a "long-armed" diacid (15', 150 mg, 297 µmol, 99.8%). The product is used in the next step without further purification. $R_f$=0.0 (base line, Chloroform:Ethyl Acetate:MeOH, 5:2:1). $^{13}$C-NMR (125 MHz, MeOD) δ 178.1, 175.3, 172.9, 72.3, 71.7, 71.6, 40.4, 35.5, 30.9, 30.6, 30.5, 28.3, 26.5. HRMS calcd for $C_{24}H_{44}N_2O_9Na$ (M+Na)$^+$ m/z 527.2945, found 527.2943.

Preparation of 33a

"Long-armed" diacid (15', 150 mg, 297 µmol) is dissolved in dry DMF (4 mL). N-Hydroxysuccinimide (104 mg, 892 µmol), 1-ethyl-3-[3-dimethylaminopropyl]carbodiimide hydrochloride (EDC, 174 mg, 892 µmol) and N,N-diisopropylethylamine (0.157 mL, 892 µmol) are added to the reaction mixture at room temperature and stirring continued for 24 hrs. The mixture is diluted with DCM and washed with water, then with diluted HCl and water, dried over magnesium sulfate and concentrated. The residue is purified by flash chromatography on silica gel eluting with Chloroform:Ethyl Acetate:MeOH, 5:2:0.5→5:4:1 to give the "long-armed" di-succinimidyl ester (33a, 188 mg, 269 µmol, 90%). $R_f$=0.25 (DCM:MeOH, 9:1). $^{13}$C-NMR (125 MHz, CDCl$_3$) δ 170.9, 169.9, 169.5, 168.5, 70.7, 70.6, 70.5, 70.4, 70.0, 38.7, 31.4, 30.7, 29.4, 28.6, 28.5, 28.4, 26.5, 25.5, 24.4. HRMS calcd for $C_{32}H_{50}N_4O_{13}Na$ (M+Na)$^+$ m/z 721.3272, found 721.3259.

Example 1.3: Synthesis of Dendritic Cluster Compounds

Preparation of 6e (Scheme 8)

Thioglycoside donor (WO 2012/121617) (1 g, 2.2 mmol) and Cbz-protected hexa-amino alcohol (Chipowsky, S.; Lee, Y. C. *Carb. Res.*, 1973, 31, 339-346) (1 g, 4.3 mmol, 2.0 eq) are dissolved in anhydrous dichloromethane (20 mL) and cooled to −15° C. and powdered molecular sieves (4 Å) are added. After 10 min N-iodosuccinimide (836 mg, 3.7 mmol, 1.7 eq) and silver trifluoromethanesulfonate (281 mg, 1 mmol, 0.5 eq) are added. The reaction mixture is allowed to warm up to room temperature over 1 h. The mixture is diluted with ethyl acetate and filtered through celite. The filtrate is washed with a 1:1 mixture of saturated aq. sodium bicarbonate and aq. thiosulfate (30%), washed with saturated aq. sodium chloride, dried over magnesium sulfate and concentrated. The residue is purified by silica gel chromatography (EtOAc:petroleum ether, 1:2) to furnish the glycoside 6e as a syrup (1.35 g, 2.0 mmol, 93%), TLC (EtOAc:petroleum ether, 1:2 v/v): $R_f$=0.25. Used directly for the synthesis of compound 6f without further purification. HRMS (ESI) calcd for $C_{38}H_{48}N_2O_9Na$ (M+Na)$^+$ m/z 699.3258, found 699.3257.

Preparation of 12d (Scheme 8)

Compound 6f (0.56 g, 0.827 mmol) is dissolved in methanol (12 mL) and treated with palladium hydroxide on carbon (20% Pd, 500 mg). The reaction mixture is stirred for just 20 min under hydrogen at ambient temperature and pressure. The catalyst is filtered off and washed with EtOAc:MeOH, 1:1, 40 mL. The solution is concentrated to dryness and chromatography of the residue (EtOAc:methanol:aq. ammonia, 4:1:0.05) gives compound 12d (0.4 g, 0.75 mmol, 91%); TLC (EtOAc:methanol:aq. ammonia, 4:1:0.05): $R_f$=0.15; $^{13}$C-NMR (125 MHz, CDCl$_3$) δ 170.7, 170.4, 138.3, 137.7, 128.5, 128.4, 127.9, 127.8, 99.8, 80.4, 78.5, 78.1, 75.9, 75.4, 75.0, 74.7, 74.6, 72.8, 69.6, 63.3, 57.2, 41.8, 33.0, 29.3, 26.4, 26.1, 25.7, 25.5, 23.5, 20.8. HRMS (ESI) calcd for $C_{30}H_{43}N_2O_7Na$ (M+H)$^+$ m/z 543.3070, found 543.3077.

Preparation of 12a (Scheme 8)

Compound 11a (0.56 g, 0.528 mmol) is dissolved in methanol (15 mL) and treated with palladium hydroxide on carbon (20% Pd, 500 mg). The reaction mixture is stirred for just 15 min under hydrogen at ambient temperature and pressure. The catalyst is filtered off and washed with EtOAc:MeOH, 1:1, 40 mL. The solution is concentrated to dryness and chromatography of the residue (EtOAc:methanol:aq. ammonia, 4:1:0.05) gives compound 12a (0.45 g, 0.49 mmol, 92%); TLC (EtOAc:methanol:aq. ammonia, 4:1:0.05): $R_f$=0.15; $^{13}$C-NMR (125 MHz, CDCl$_3$) δ 173.3, 172.7, 170.8, 166.7, 139.8, 139.5, 138.5, 134.8, 130.9, 130.8, 129.9, 129.5, 129.1, 128.9, 128.8, 128.7, 128.6, 102.4, 98.9, 83.7, 81.7, 78.9, 76.2, 75.2, 71.5, 70.9, 63.7, 54.1, 53.5, 40.6, 30.2, 28.4, 26.9, 26.5, 22.9, 20.8. HRMS (ESI) calcd for $C_{51}H_{63}N_2O_{14}$ (M+H)$^+$ m/z 927.4279, found 927.4270.

Preparation of 12b (Scheme 8)

Compound 11b (1.0 g, 0.942 mmol) is dissolved in methanol (20 mL) and treated with palladium hydroxide on carbon (20% Pd, 1 g). The reaction mixture is stirred for just 15 min under hydrogen at ambient temperature and pressure. The catalyst is filtered off and washed with EtOAc:MeOH, 1:1, 40 mL. The solution is concentrated to dryness and chromatography of the residue (EtOAc:methanol:aq. ammonia, 4:1:0.05) furnishes compound 12b (0.42 g, 0.45 mmol, 48%); TLC (EtOAc:methanol:aq. ammonia, 4:1:0.05): $R_f$=0.15; $^{13}$C-NMR (125 MHz, CDCl$_3$) δ 170.6, 169.9, 169.5, 165.7, 138.0, 137.9, 137.2, 133.7, 129.7, 129.3, 128.9, 128.8, 128.5, 128.4, 128.0, 127.9, 127.7, 127.6, 99.9, 98.3, 80.5, 74.8, 74.0, 72.9, 72.3, 70.4, 68.9, 68.8, 67.6, 62.4, 59.7, 52.6, 52.3, 51.9, 45.4, 36.3, 29.6, 29.3, 27.6, 27.2, 27.0, 25.9, 22.9, 20.8. HRMS (ESI) calcd for $C_{51}H_{63}N_2O_{14}$ (M+H)$^+$ m/z 927.4279, found 927.4275.

Preparation of 4a (Scheme 8)

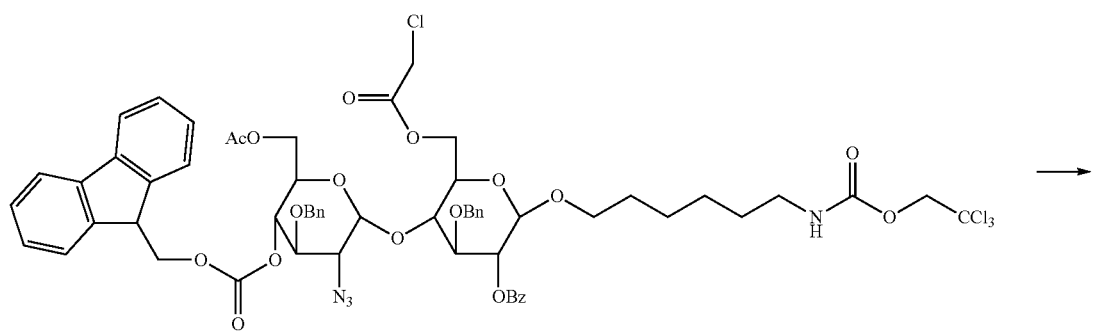

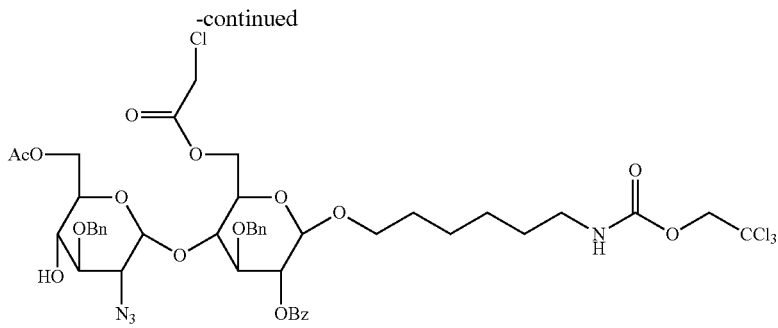
-continued

Triethylamine (8.0 mL) is added to a solution of 3a (1.8 g, 1.42 mmol) in dichloromethane (40 mL) and the solution is stirred at RT for 3 h, then washed with aq HCl, aq NaHCO$_3$, dried and concentrated to dryness. (Chromatography (5-40% EtOAc/Toluene) gives the title compound as a foam (1.19 g, 1.14 mmol, 80%). $^1$H NMR (CDCl$_3$), δ 8.05 (m, 2H), 7.58 (t, J=7.4 Hz, 1H), 7.47-7.44 (m, 2H), 7.41-7.30 (m, 5H), 7.23-7.16 (m, 5H), 5.57 (d, J=3.9 Hz, 1H), 5.31 (dd, J=8.8, 7.8 Hz, 1H), 4.94-4.88 (m, 3H), 4.79-4.71 (m, 4H), 4.62-4.57 (m, 2H), 4.51 (dd, J=12.4, 4.0 Hz, 1H), 4.33 (dd, J=11.8, 5.4 Hz, 1H), 4.15-4.12 (m, 3H), 4.03 (t, J=8.5 Hz, 1H), 3.93 (t, J=9.4 Hz, 1H), 3.86-3.73 (m, 4H), 3.47-3.42 (m, 2H), 3.23 (dd, J=10.3, 3.9 Hz, 1H), 3.07-3.01 (m, 3H), 2.09 (s, 3H), 1.52-1.42 (m, 2H), 1.32-1.13 (m, 6H). $^{13}$C NMR δ 171.87, 167.10, 165.03, 154.51, 137.82, 137.42, 133.38, 129.75, 129.04, 128.65, 128.57, 128.34, 128.18, 128.14, 127.72, 127.64, 100.86, 98.13, 82.99, 79.12, 75.34, 74.55, 74.46, 74.26, 74.06, 72.40, 71.28, 70.69, 69.78, 64.98, 62.89, 62.65, 41.08, 40.70, 29.42, 29.14, 26.12, 25.47, 20.79. HRMS (ESI) Calc for C$_{46}$H$_{54}$Cl$_4$O$_{15}$Na [M+Na]$^+$ m/z 1065.2237, found 1065.2229.

Preparation of 12c (Scheme 8)

Tetrasaccharide 11c (660 mg, 0.37 mmol) is dissolved in dry THF (5 mL) and glacial AcOH (4.5 mL) at RT. The reaction mixture is treated with pre-activated Zn (1.9 g, 29 mmol, 80 eq.) and stirred at RT for 3.5 hours. The solvents are removed in vacuo and the residue is dissolved in chloroform, washed with ice-cold saturated aq. sodium bicarbonate and water, dried over magnesium sulfate and concentrated to furnish the glycoside 12c as a foam (610 mg, 0.37 mmol, 100%), TLC (DCM:MeOH, 1:9 v/v): R$_f$=0.2. The product is very pure and is used in the next step without further purification. $^{13}$C-NMR (125 MHz, CDCl$_3$) δ 170.7, 170.6, 170.2, 170.1, 167.9, 167.5, 164.9, 138.7, 138.1, 137.7, 136.5, 136.4, 133.8, 133.4, 129.8, 129.7, 129.5, 128.8, 128.6, 128.5, 128.4, 128.3, 128.2, 128.1, 128.0, 127.9, 127.8, 127.4, 127.3, 127.1, 101.3, 101.2, 99.5, 99.1, 81.4, 81.2, 80.5, 78.1, 77.2, 77.1, 76.9, 75.4, 75.2, 74.9, 74.8, 74.7, 74.4, 73.8, 73.6, 70.7, 70.2, 70.0, 62.5, 62.2, 61.5, 52.8, 52.7, 52.5, 52.2, 49.6, 49.3, 41.9, 32.6, 30.3, 29.7, 29.4, 29.2, 28.8, 26.8, 26.3, 25.6, 22.6, 22.5, 20.8, 20.7. HRMS (ESI) calcd for C$_{89}$H$_{104}$N$_3$O$_{27}$ (M+H)$^+$ m/z 1646.6857, found 1646.6847.

Preparation of 4b (Scheme 8)

Disaccharide 3b (2.4 g, 2.0 mmol) is dissolved in a mixture of dry dichloromethane (32 mL) and triethylamine (8 mL) and stirred at RT for 3 hours. The mixture is diluted with dichloromethane, washed with diluted aq. HCl, water and saturated aq. sodium chloride, dried over magnesium sulfate and concentrated. The residue is purified by silica gel chromatography (Ethyl Acetate:petroleum ether, 1:3→1:2) to furnish the glycoside 4b as a foam (1.75 g, 1.8 mmol, 90%), TLC (Ethyl Acetate:petroleum ether, 1:32 v/v): R$_f$=0.25. $^{13}$C-NMR (125 MHz, CDCl$_3$) δ 171.7, 171.5, 167.0, 166.1, 156.0, 138.1, 137.7, 137.6, 133.3, 129.9, 129.8, 128.6, 128.5, 128.3, 128.1, 128.0, 127.9, 127.8, 127.7, 127.3, 98.7, 98.4, 82.5, 79.7, 76.1, 75.3, 75.1, 74.9, 74.7, 74.2, 73.6, 73.0, 72.9, 72.6, 72.4, 72.1, 71.3, 71.1, 70.7, 70.6, 70.1, 69.5, 68.8, 66.4, 65.9, 65.4, 65.3, 64.9, 64.1, 63.2, 60.4, 40.7, 40.6, 29.9, 29.7, 29.3, 28.4, 28.1, 26.5, 25.9, 25.6, 20.7, 20.6. HRMS (ESI) calcd for C$_{48}$H$_{61}$N$_4$ClO$_{15}$Na (M+Na)$^+$ m/z 991.3720, found 991.3711.

Preparation of 10 (Scheme 8)

Tetra-saccharide 9d (110 mg, 64 μmol) is dissolved in dry dichloromethane (5 mL) and cooled to 0 C. TFA (0.5 mL) is added and stirred at RT for 18 hours. The mixture is diluted with dichloromethane, washed with saturated aq. sodium bicarbonate, water, dried over magnesium sulfate and concentrated to furnish the glycoside 10 as a foam (98 mg, 61 μmol, 95%), TLC (Ethyl Acetate:petroleum ether, 1:2, v/v): R$_f$=0.25. The product is very pure and is used in the next step without further purification. $^{13}$C-NMR (125 MHz, CDCl$_3$) δ 170.7, 170.5, 169.7, 169.4, 165.7, 165.2, 137.8, 137.7, 137.6, 137.3, 133.4, 130.9, 130.0, 129.9, 129.7, 129.3, 128.8, 128.7, 128.5, 128.4, 128.3, 128.2, 128.1, 127.9, 127.8, 127.6, 99.1, 99.0, 98.9, 98.5, 79.9, 78.7, 76.8, 75.7, 75.6, 75.5, 75.0, 74.8, 74.6, 73.9, 73.6, 72.9, 72.3, 70.5, 70.2, 70.1, 69.7, 68.7, 68.3, 67.5, 64.7, 63.6, 63.5, 62.3, 61.8, 52.1, 52.0, 41.4, 31.9, 30.5, 29.9, 29.7, 26.5, 25.8, 20.8. HRMS (ESI) calcd for C$_{85}$H$_{96}$N$_7$O$_{25}$ (M+H)$^+$ m/z 1614.6456, found 1614.6440.

Preparation of 22a (Scheme 9)

Ido-configured tetramer 20d (7 mg, 1.3 μmol) is dissolved in water (1 mL). Sulfur trioxide trimethylamine complex (20 mg, 144 μmol) and sodium carbonate (20 mg) are added at RT. The mixture is stirred at RT for 72 h and poured on top of silica gel column. The residue is purified by chromatography (dichloromethane:methanol:aq. ammonia, 7:2:0.5→5:4:1→methanol:water:aq. Ammonia, 3:1:1) to afford the N-sulfated tetramer 22a as a foam (6 mg, 1.1 μmol, 89% yield); TLC (EtOAc:ethanol:water, 2:1:1): R$_f$=0.12.

General Procedure A (GPA): Coupling with Tetra-Succinimidyl Ester

A solution of tetra-succinimidyl ester 13a or 13b (1 eq) in dry DMF (40 mg per 1 mL of DMF) is added to the solution of glycoside with a 6 carbon linker and an unmasked amino-function (6 eq.) in dry DMF (100 mg per 1 mL of DMF) at room temperature. The reaction mixture is treated with triethylamine (8 eq) and stirred at RT for 1-24 hrs. DMF is removed in vacuo and the residue is purified by flash chromatography on silica gel eluting with EtOAc followed by Ethyl Acetate:MeOH, 9:1→3:2 to give the tetra-succinimidyl ester.

Synthesis of 14e (Scheme 9)

Compound 14e is prepared from compounds 12d and 13a following general procedure A: The residue is purified by silica gel chromatography (Ethyl Acetate:MeOH, 9:1→3:2) to give the tetramer 14e as a foam (135 mg, 53.5 mmol, 92% yield); TLC (EtOAc:MeOH, 9:1, v/v): $R_f$=0.65. $^{13}$C-NMR (125 MHz, MeOD) δ 173.8, 173.2, 172.5, 140.0, 139.8, 139.4, 129.5, 129.4, 129.1, 129.0, 128.9, 128.8, 128.7, 102.5, 84.4, 79.6, 79.5, 77.2, 76.3, 76.1, 75.8, 74.2, 70.7, 70.6, 70.5, 68.8, 64.3, 62.3, 56.8, 46.7, 40.5, 37.8, 30.5, 27.8, 26.8, 26.3, 23.3, 20.8. HRMS (ESI) calcd for $C_{137}H_{188}N_8O_{36}Na$ (M+Na)$^+$ m/z 2544.3024, found 2544.3049.

Synthesis of 14h (Scheme 9)

Compound 14h is prepared from compounds 12d and 13b following general procedure A: The residue is purified by silica gel chromatography (EtOAc→Ethyl Acetate:MeOH, 9:1→3:2) to furnish the tetramer 14h as a foam (176 mg, 57 mmol, 95% yield); TLC (EtOAc:MeOH, 9:1, v/v): $R_f$=0.55. $^{13}$C-NMR (125 MHz, MeOD) δ 174.6, 174.2, 172.3, 171.7, 138.4, 138.1, 128.2, 128.1, 127.7, 127.6, 127.4, 101.1, 82.7, 78.2, 77.9, 77.7, 77.4, 75.7, 75.6, 74.8, 74.6, 69.7, 69.3, 67.4, 61.7, 61.0, 55.6, 45.3, 39.3, 39.0, 36.9, 36.5, 36.4, 35.9, 34.8, 32.9, 32.2, 29.8, 29.2, 29.1, 28.9, 28.8, 26.6, 26.5, 26.4, 25.7, 25.4, 25.3, 24.9, 22.2.

Synthesis of 14a (Scheme 9)

Compound 14a is prepared from compounds 12a and 13b following general procedure A: The residue is purified by silica gel chromatography (EtOAc→Ethyl Acetate:MeOH, 9:1→4:1) to give the tetramer 14a as a foam (314 mg, 67.9 mmol, 93% yield); TLC (EtOAc:MeOH, 9:1, v/v): $R_f$=0.55. $^{13}$C-NMR (125 MHz, CDCl$_3$) δ 170.6, 169.9, 169.5, 165.7, 156.4, 138.1, 137.9, 137.8, 137.2, 136.7, 133.7, 129.7, 129.3, 129.1, 129.0, 128.8, 128.5, 128.4, 128.2, 128.1, 127.9, 127.7, 127.6, 125.3, 98.9, 98.3, 80.5, 74.8, 74.7, 73.9, 72.9, 72.4, 70.4, 68.9, 68.8, 67.7, 66.5, 62.5, 52.6, 52.4, 40.9, 29.8, 29.2, 26.4, 25.7, 22.9, 21.4, 20.8. HRMS (ESI) Calc for $C_{253}H_{326}N_{12}O_{68}Na_2$ [M+2Na]$^{2+}$ m/z (%), 2334.1187 (20), 2334.6204 (65), 2335.1218 (98), 2335.6235 (100), 2336.1250 (80), 2336.6267 (50), 2337.1282 (30), found, 2334.6121 (50), 2335.1125 (85), 2335.6130 (100), 2336.1157 (98), 2336.6216 (85), 2337.1265 (70), 2337.6304 (50), 2338.1331 (40), 2338.6350 (30).

Synthesis of 14b (Scheme 9)

Compound 14b is prepared from compounds 12b and 13b following general procedure A: The residue is purified by silica gel chromatography (EtOAc→Ethyl Acetate:MeOH, 9:1→4:1→methanol) to afford the tetramer 14b as a foam (394 mg, 85 mmol, 96% yield); TLC (EtOAc:MeOH, 9:1, v/v): $R_f$=0.55. $^{13}$C-NMR (125 MHz, MeOD) δ 173.9, 173.5, 172.5, 172.1, 171.2, 170.2, 165.9, 163.6, 138.5, 138.2, 137.9, 133.5, 129.8, 129.7, 128.9, 128.4, 128.3, 128.2, 128.1, 127.9, 127.8, 127.5, 127.4, 99.2, 97.1, 80.6, 78.3, 78.1, 77.9, 77.8, 74.9, 74.8, 73.7, 73.5, 72.6, 72.5, 72.4, 70.6, 69.7, 69.4, 68.8, 68.7, 68.3, 68.2, 67.6, 62.9, 53.1, 51.9, 49.9, 45.5, 39.4, 39.2, 36.7, 36.1, 35.9, 35.1, 33.3, 32.9, 32.7, 30.7, 29.3, 29.2, 29.1, 28.9, 28.3, 27.0, 26.8, 26.6, 26.5, 25.9, 25.5, 25.2, 25.1.

Synthesis of 14c (Scheme 9)

Compound 14c is prepared from compounds 12c and 13b following general procedure A: The residue is purified by silica gel chromatography (EtOAc→Ethyl Acetate:MeOH, 9:1→4:1→methanol) to afford the tetramer 14c as a foam (544 mg, 0.072 mmol, 99% yield); TLC (EtOAc:MeOH, 9:1, v/v): $R_f$=0.45. $^{13}$C-NMR (125 MHz, CDCl$_3$) δ 174.2, 172.0, 171.0, 168.5, 168.0, 165.1, 164.8, 163.0, 138.7, 137.9, 137.5, 136.3, 133.7, 133.3, 129.5, 129.3, 128.6, 128.3, 128.1, 127.9, 127.7, 127.3, 126.9, 100.9, 100.8, 97.8, 97.2, 81.9, 80.2, 78.0, 74.5, 74.3, 74.1, 73.4, 69.9, 69.8, 69.5, 69.0, 67.2, 62.2, 61.6, 52.3, 52.0, 51.9, 48.8, 48.6, 48.4, 48.3, 48.1, 47.9, 47.8, 39.1, 38.9, 36.4, 36.2, 35.9, 30.9, 29.3, 29.1, 28.8, 26.5, 26.2, 25.5, 21.9, 20.1.

Synthesis of 14d (Scheme 9)

Compound 14d is prepared from compounds 10 and 13b following general procedure A: The residue is purified by silica gel chromatography (EtOAc→Ethyl Acetate:MeOH, 9:1→4:1→methanol) to afford the tetramer 14d as a foam (83 mg, 11.3 μmol, 93% yield); TLC (EtOAc:MeOH, 9:1, v/v): $R_f$=0.55. $^{13}$C-NMR (125 MHz, DMSO-D$_6$) δ 171.9, 171.8, 170.1, 169.9, 169.0, 168.9, 168.5, 164.9, 164.5, 162.3, 137.8, 137.7, 137.5, 133.5, 133.3, 129.4, 129.3, 129.1, 128.8, 128.6, 128.3, 128.2, 128.1, 128.0, 127.8, 127.7, 127.6, 127.5, 127.4, 127.3, 127.2, 98.1, 98.0, 97.7, 97.0, 79.7, 79.2, 78.9, 78.7, 78.3, 77.2, 74.9, 74.3, 74.2, 73.9, 73.5, 73.3, 73.2, 72.5, 72.3, 71.7, 69.7, 69.6, 69.2, 69.1, 68.8, 68.7, 67.9, 67.6, 67.3, 62.5, 62.4, 61.8, 61.6, 51.8, 51.5, 45.0, 39.0, 38.5, 38.3, 38.2, 36.1, 35.7, 35.4, 30.7, 29.1, 29.0, 28.9, 28.7, 28.5, 26.3, 26.2, 25.3, 25.2, 20.4.

General Procedure B (GPB): Glycosylation—TCA chemistry

A solution of the trichloroacetimidate donor (1.3 eq) and the glycosyl acceptor alcohol (1 eq) in anhydrous toluene (40 mL per mmol acceptor) is cooled to reaction temperature (between −10 and −20° C.), powdered molecular sieves (4 Å) are added and the suspension stirred at the temperature. After 15 min, trimethylsilyl trifluoromethanesulfonate (0.3 eq) is added and the reaction mixture stirred at reaction temperature until TLC (toluene/ethyl acetate 4:1) indicated completion. The mixture is diluted with ethyl acetate and filtered through celite into aq. sodium bicarbonate, the organic layer is washed with water and saturated aq. sodium chloride, dried over magnesium sulfate and concentrated. The residue is purified by flash chromatography to yield the fully protected oligosaccharides.

Synthesis of 6a (Scheme 8)

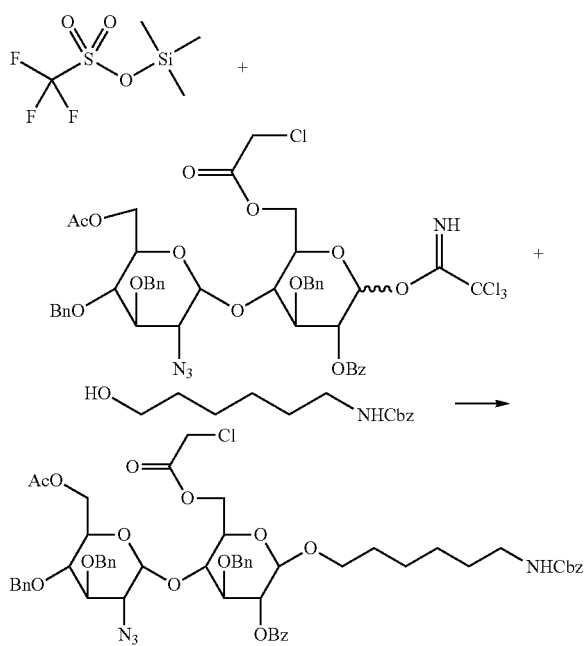

A mixture of imidate 7a (1.7 g, 1.69 mmol), N-benzyloxycarbonyl-6-hydroxyhexyl amine (2a) (0.85 g, 3.38 mmol) and dried 4 Å molecular sieves (1.0 g) in dry DCM (10 mL) is stirred for 1 h, then cooled in an ice bath and trimethylsilyltrifluoromethane sulfonate (0.092 mL, 0.508 mmol) is added. After 30 mins the reaction is quenched with triethylamine, filtered and the filtrate is washed with aq NaHCO$_3$, dried and concentrated. Chromatography (15-40% EtOAc in hexanes) gives the title compound (1.42 g, 1.3 mmol, 77%). $^1$H NMR (CDCl$_3$) δ 8.05-8.03 (m, 2H), 7.55-7.17 (m, 23H), 5.55 (d, J=3.9 Hz, 1H), 5.30 (dd, J=8.7, 7.7 Hz, 1H), 5.08 (bs, 2H), 4.88 (bs, 2H), 4.83 (d, J=10.8 Hz, 1H), 4.77 (d, J=10.5 Hz, 1H), 4.73 (d, J=10.5 Hz, 1H), 4.60-4.56 (m, 3H), 4.34 (dd, J=11.8, 5.5 Hz, 1H), 4.27-4.19 (m, 2H), 4.14-4.09 (m, 3H), 4.02 (t, J=8.5 Hz, 1H), 3.94-3.90 (m, 2H), 3.85-3.82 (m, 2H), 3.74-3.71 (m, 1H), 3.50 (dd, J=9.8, 8.9 Hz, 1H), 3.44-3.39 (m, 1H), 3.29 (dd, J=10.4, 3.9 Hz, 1H), 3.04-2.98 (m, 2H), 2.03 (s, 3H), 1.51-1.41 (m, 2H), 1.26-1.12 (m, 6H). $^{13}$C NMR δ 170.51, 167.01, 165.00, 156.33, 137.57, 137.48, 137.25, 136.77, 133.33, 129.72, 128.61, 128.53, 128.34, 128.19, 128.13, 128.02, 127.69, 127.61, 100.83, 97.98, 83.35, 82.93, 80.08, 77.90, 75.51, 75.23, 74.76, 74.24, 74.02, 73.17, 72.36, 70.29, 69.76, 67.04, 66.53, 65.03, 63.22, 62.57, 60.38, 40.88, 40.69, 29.65, 29.19, 26.21, 25.48, 20.77. HRMS (ESI) Calc for C$_{58}$H$_{65}$ClN$_4$O$_{15}$Na [M+Na]$^+$ m/z, 1115.4033, found, 1115.4033.

Synthesis of 6b (Scheme 8)

Compound 6b is prepared from trichloroacetimidate disaccharide donor (WO 2012/121617) (1 g) and Cbz-protected hexa-amino alcohol (Chipowsky, S.; Lee, Y. C. Carb. Res., 1973, 31, 339-346) (2.0 eq) following general procedure B: The residue is purified by silica gel chromatography (Ethyl Acetate:Petroleum ether, 1:3→1:2) to furnish the glycoside 6b as a foam (1.7 g, 1.55 mmol, 82% yield); TLC (EtOAc:Petroleum ether, 1:2, v/v): R$_f$=0.45. $^{13}$C-NMR (125 MHz, CDCl$_3$) 170.6, 166.9, 166.1, 165.6, 156.4, 137.7, 137.5, 137.4, 136.7, 133.2, 129.9, 129.8, 128.6, 128.5, 128.4, 128.3, 128.1, 127.9, 98.8, 98.4, 80.6, 80.3, 76.8, 75.2, 75.1, 74.7, 74.1, 72.9, 72.4, 70.4, 70.2, 69.7, 68.7, 68.2, 66.5, 65.8, 65.3, 65.2, 63.8, 63.6, 62.7, 60.4, 40.6, 29.8, 29.3, 26.4, 25.9, 25.7, 20.7. HRMS (ESI) Calc for C$_{58}$H$_{65}$ClN$_4$O$_{15}$Na [M+Na]$^+$ m/z, 1115.4033, found, 1115.4031.

Synthesis of 3a (Scheme 8)

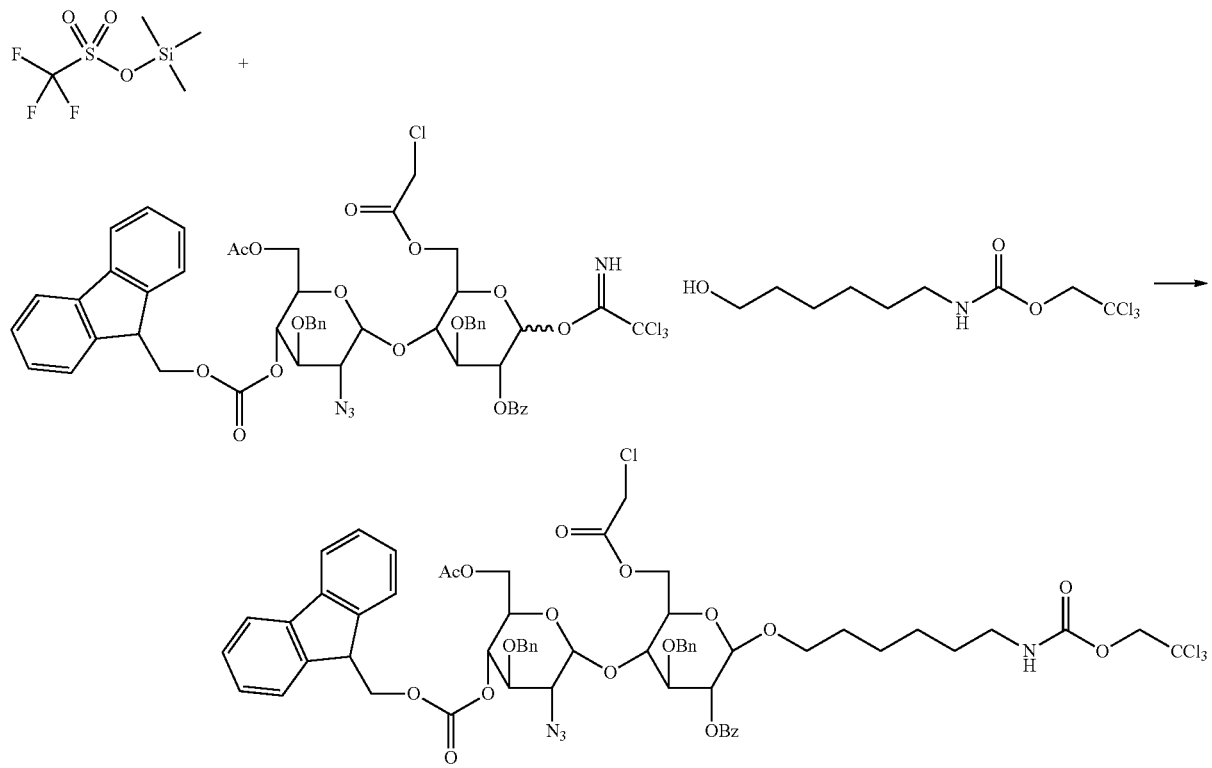

Imidate (2.14 g, 1.88 mmol) (1) (WO 2012/121617) and 2,2,2-trichloroethyl 6-hydroxyhexylcarbamate (2b) (1.10 g, 3.76 mmol) are dissolved in dry acetonitrile (15 mL) and then concentrated to dryness. The residue is dissolved in dry dichloromethane (15 mL) and cooled in an ice bath under argon with stirring while trimethylsilyl trifluoromethanesulfonate (0.068 mL, 0.376 mmol) is added. After 30 mins the solution is washed with aq NaHCO$_3$, dried and concentrated to dryness. Chromatography [25-60% (EtOAc/CHCl$_3$ 1:2) in hexanes] gives the title compound as a foam (1.84 g, 1.45 mmol, 77%). $^1$H NMR (CDCl$_3$), δ 8.07-8.05 (m, 2H), 7.76-7.74 (m, 2H), 7.61-7.54 (m, 3H), 7.47-7.44 (m, 2H), 7.40-7.37 (m, 2H), 7.30-7.16 (m, 12H), 5.60 (d, J=3.9 Hz, 1H), 5.31 (dd, J=8.7, 7.7 Hz, 1H), 4.90 (bs, 1H), 4.87 (t, J=9.3 Hz, 1H), 4.76-4.72 (m, 4H), 4.66-4.58 (m, 3H), 4.48 (dd, J=10.5, 6.7 Hz, 1H), 4.38-4.25 (m, 3H), 4.18 (t, J=6.9 Hz, 1H), 4.14 (s, 2H), 4.09-3.92 (m, 4H), 3.87-3.83 (m, 1H), 3.78-3.74 (m, 1H), 3.45-3.43 (m, 1H), 3.35 (dd, J=10.3, 3.9 Hz, 1H), 3.08-3.04 (m, 2H), 2.05 (s, 3H), 1.54-1.43 (m, 6H). $^{13}$C NMR δ 170.49, 167.05, 165.01, 154.50, 154.14, 143.24, 143.01, 141.32, 137.35, 137.13, 133.40, 129.75, 129.71, 128.58, 128.39, 127.97, 127.89, 127.79, 127.61, 127.25, 125.10, 124.91, 120.11, 100.83, 95.80, 82.79, 77.38, 75.11, 74.88, 74.72, 74.47, 74.25, 73.97, 72.31, 70.39, 69.77, 68.71, 64.98, 62.60, 61.98, 46.71, 41.08, 40.68, 29.44, 29.15, 26.13, 25.47, 20.69. HRMS (ESI) Calc for $C_{61}H_{64}Cl_4N_4O_{17}Na$ [M+Na]$^+$ m/z 1287.2918, found 1287.2927.

Synthesis of 6c (Scheme 8)

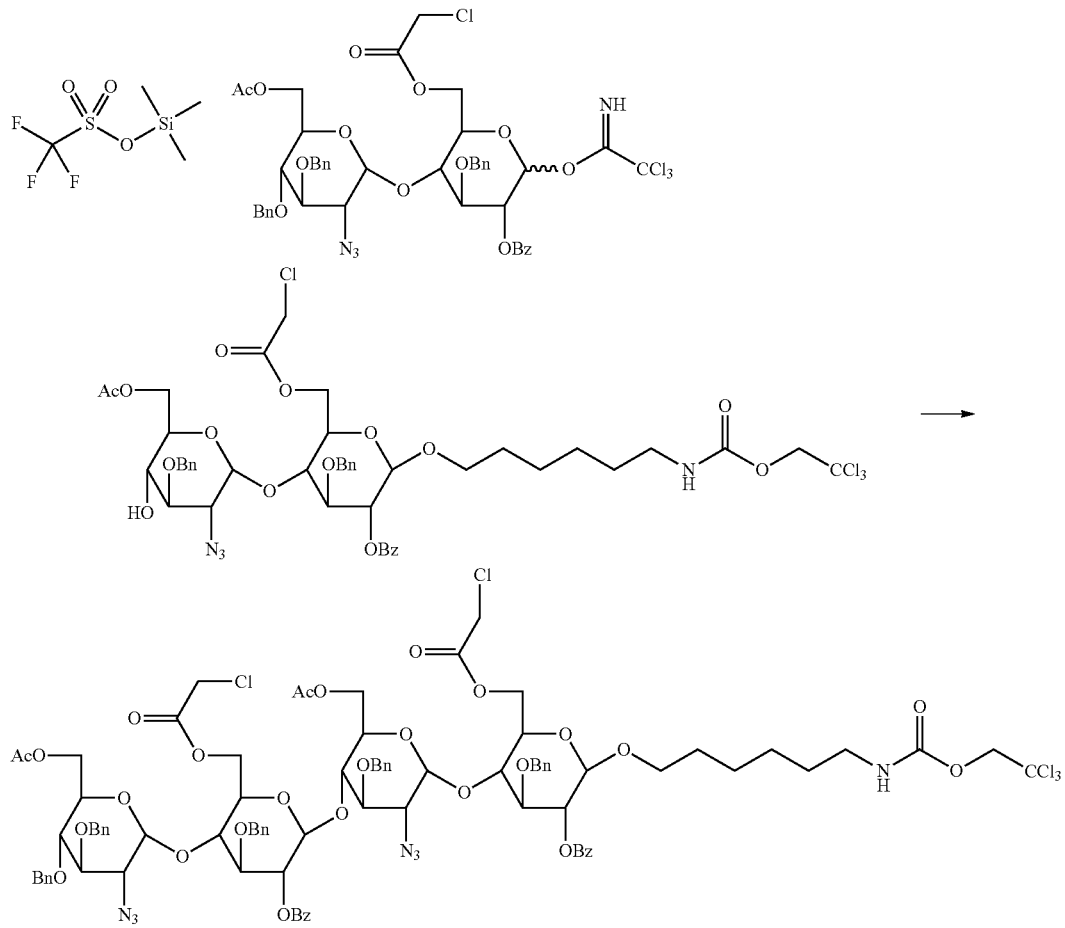

A solution of acetimidate donor (WO 2012/121617) (5a) (1.37 g, 1.36 mmol) and 4a (1.19 g, 1.14 mmol) in dry DCM (10 mL) is cooled in an ice bath and trimethylsilyltrifluoromethanesulfonate (0.062 mL, 0.34 mmol) is added with stirring. After 30 mins, the solution is washed with aq NaHCO₃, dried and concentrated to dryness. Chromatography (10-30% EtOAc/Hexanes) gives the title compound as a syrup. $^1$H NMR (CDCl₃) δ 8.07-8.02 (m, 4H), 7.62-7.55 (m, 2H), 7.48-7.42 (m, 4H), 7.37-7.11 (m, 25H), 5.49-5.46 (m, 2H), 5.37 (dd, J=8.6, 8.1 Hz, 1H), 5.23 (dd, J=8.8, 7.8 Hz, 1H), 5.10 (d, J=11.2 Hz, 1H), 4.91-4.87 (m, 3H), 4.83-4.79 (m, 2H), 4.72-4.62 (m, 7H), 4.56 (d, J=10.9 Hz, 1H), 4.51 (d, J=7.7 Hz, 1H), 4.39-4.32 (m, 2H), 4.24-4.08 (m, 6H), 4.01-3.57 (m, 15H), 3.49 (t, J=9.4 Hz, 1H), 3.41-3.37 (m, 1H), 3.30 (dd, J=10.3, 3.9 Hz, 1H), 3.22 (dd, J=10.2, 4.0 Hz, 1H), 3.07-3.03 (m, 2H), 2.02, 2.00 (s, 3H each), 1.50-1.37 (m, 2H), 1.30-1.12 (m, 6H); $^{13}$C NMR δ 170.50, 170.44, 166.88, 166.48, 164.99, 164.95, 154.50, 138.30, 137.52, 137.40, 137.32, 137.24, 133.80, 133.35, 129.77, 129.73, 129.05, 128.90, 128.81, 128.61, 128.57, 128.37, 128.32, 128.25, 128.21, 128.11, 128.05, 127.75, 127.69, 127.49, 127.41, 125.32, 100.98, 100.81, 98.08, 97.66, 95.81, 82.95, 82.83, 80.14, 77.81, 77.77, 77.60, 75.58, 75.23, 75.05, 74.72, 74.64, 74.47, 74.20, 74.01, 72.41, 72.32, 70.37, 69.73, 69.68, 65.01, 64.26, 63.23, 62.65, 62.42, 61.90, 41.09, 40.53, 40.47, 29.42, 29.12, 26.10, 25.45, 20.77. HRMS (ESI) Calc for $C_{90}H_{98}Cl_5N_7O_{27}Na$ [M+Na]$^+$ m/z (%), 1906.4851 (62), 1907.4885 (61), 1908.4821 (100), 1909.4855 (97), 1910.4792 (64), 1911.4826 (62), found, 1906.4845 (50), 1907.4875 (60), 1908.4772 (100), 1909.4808 (90), 1910.4786 (90), 1911.4829 (70). HRMS (ESI) calcd for $C_{90}H_{98}N_7Cl_5O_{27}Na$ (M+Na)$^+$ m/z 1906.4851, found 1906.4861.

Synthesis of 3b (Scheme 8)

Compound 3b is prepared from trichloroacetimidate disaccharide donor (WO 2012/121617) (1 g) and Boc-protected hexa-amino alcohol (2d) (Pichot, C., Delair, T., Mandrand, B. and Llauro, M. F.; *Makromol. Chem.*, 1993, 194, 117-135) following general procedure B: The residue is purified by silica gel chromatography (Ethyl Acetate:Chloroform:Petroleum ether, 1:3:3) to afford the glycoside 3b as a foam (3.0 g, 2.56 mmol, 86% yield); TLC (EtOAc: Petroleum ether, 1:2, v/v): R$_f$=0.45. $^{13}$C-NMR (125 MHz, CDCl₃) 170.5, 166.9, 165.6, 156.0, 154.2, 143.3, 143.1, 141.4, 141.3, 137.7, 137.2, 133.4, 129.9, 129.8, 129.1, 128.7, 128.5, 128.4, 128.3, 128.1, 128.0, 127.8, 127.7, 127.3, 125.1, 124.9, 120.1, 98.9, 98.5, 78.9, 78.2, 75.8, 74.9, 74.6, 72.8, 72.4, 70.2, 69.8, 68.9, 68.5, 68.2, 65.2, 65.0, 63.3, 62.1, 60.4, 46.8, 40.6, 30.0, 29.4, 28.5, 26.6, 25.9, 25.7, 20.7. HRMS (ESI) calcd for $C_{63}H_{71}N_4ClO_{17}Na$ (M+Na)$^+$ m/z 1213.4400, found 1213.4409.

Synthesis of 6d (Scheme 8)

Compound 6d is prepared from trichloroacetimidate disaccharide donor (WO 2012/121617) (1 g) and the glycoside 4b following general procedure B: The residue is purified by silica gel chromatography (Ethyl Acetate:Petroleum ether, 1:1) to afford the glycoside 6d as a foam in a moderate yield due to the partial loss of N-Boc protecting group (1.2 g, 0.66 mmol, 45% yield); TLC (EtOAc:Petroleum ether, 1:2, v/v): $R_f$=0.35. $^{13}$C-NMR (125 MHz, CDCl$_3$) 170.6, 170.5, 167.1, 167.0, 166.9, 165.9, 165.7, 165.5, 156.0, 137.7, 137.5, 137.3, 136.5, 133.4, 133.3, 129.8, 129.5, 128.7, 128.6, 128.5, 128.4, 128.3, 128.2, 128.1, 128.0, 127.9, 127.7, 98.8, 98.4, 98.1, 97.9, 80.6, 78.9, 77.2, 76.9, 75.6, 75.3, 75.2, 74.9, 74.7, 74.5, 74.1, 73.4, 73.2, 72.4, 70.5, 70.3, 70.1, 69.8, 68.8, 68.2, 67.4, 65.5, 65.2, 65.1, 64.7, 63.9, 63.8, 63.7, 62.7, 62.3, 60.4, 40.6, 40.5, 29.9, 29.7, 29.3, 28.5, 26.5, 25.9, 20.8. HRMS (ESI) calcd for $C_{92}H_{105}N_7Cl_2O_{27}Na$ (M+Na)$^+$ m/z 1832.6333, found 1832.6316.

General Procedure C (GPC): Selective De-Chloroacetylation

DABCO (6 equiv. per chloroacetyl group) is added to the starting material in dry ethanol (5 mL for 40 μmol) at room temperature. The mixture is heated at 60-70° C. under argon for 2 h. After TLC (EtOAc:petroleum ether, 3:2) indicated the completion of the reaction Dowex 50WX8-200 ion-exchange resin is added to neutralize the solution. After 15 min the resin is filtered off and the solution is concentrated to dryness. Chromatography (EtOAc:petroleum ether, 3:2) affords the products with unblocked primary hydroxyl groups.

Synthesis of 8a (Scheme 8)

4.59-4.55 (m, 2H), 4.29 (dd, J=11.9, 2.0 Hz, 1H), 4.23 (dd, J=12.0, 4.8 Hz, 1H), 4.07-4.00 (m, 2H), 3.95-3.77 (m, 5H), 3.54-3.41 (m, 3H), 3.27 (dd, J=10.4, 4.0 Hz, 1H), 3.03-2.98 (m, 2H), 2.03 (s, 3H), 1.51-1.41 (m, 2H), 1.26-1.11 (m, 6H). $^{13}$C NMR δ 170.63, 165.01, 156.34, 137.66, 137.53, 137.36, 136.75, 133.26, 129.82, 129.70, 128.57, 128.52, 128.31, 128.10, 128.00, 127.68, 101.18, 97.64, 83.47, 80.17, 78.04, 75.49, 75.18, 74.89, 74.41, 74.29, 72.82, 70.06, 69.88, 66.54, 63.24, 62.96, 61.93, 40.86, 29.64, 29.22, 26.19, 25.46, 20.78.

Synthesis of 8b (Scheme 8)

Compound 8b is prepared from compound 6b following general procedure C: The residue is purified by silica gel chromatography (EtOAc:PE, 1:2→1:1) to give 8b as a foam (1.8 g, 1.77 mmol, 92% yield); TLC (EtOAc:PE, 1:2, v/v): $R_f$=0.15. $^{13}$C-NMR (125 MHz, CDCl$_3$) δ 170.6, 165.7, 156.5, 137.8, 137.5, 137.4, 136.7, 133.1, 130.1, 129.8, 128.5, 128.4, 128.3, 128.1, 128.0, 127.9, 127.8, 127.7, 98.6, 98.4, 80.7, 80.5, 76.8, 75.8, 75.1, 74.5, 73.5, 72.7, 72.1, 70.3, 69.8, 68.8, 67.8, 67.3, 66.6, 63.9, 63.7, 63.1, 61.7, 60.4, 40.9, 29.8, 29.4, 29.2, 26.3, 25.7, 20.7. HRMS (ESI) Calc for $C_{56}H_{64}N_4O_{14}Na$ [M+Na]$^+$ m/z 1039.4317, found 1039.4310.

Synthesis of 8c (Scheme 8)

Compound 8c is prepared from compound 6c following general procedure C: The residue is purified by silica gel chromatography (EtOAc:Toluene, 1:9→1:1) to afford 8c as a foam (1.6 g, 0.923 mmol, 87% yield); TLC (EtOAc:Toluene, 2:1, v/v): $R_f$=0.45. $^{13}$C-NMR (125 MHz, CDCl$_3$) δ 170.4, 166.9, 166.5, 164.9, 138.2, 137.5, 137.4, 137.3, 137.2, 133.8, 133.3, 129.7, 128.9, 128.8, 128.6, 128.5, 128.4, 128.3, 128.2, 128.1, 128.0, 127.7, 127.5, 127.4, 100.9, 100.8, 98.1, 97.6, 82.9, 82.8, 80.1, 77.0, 76.8, 75.6, 75.2, 75.0, 74.7, 74.6, 74.5, 74.2, 74.0, 72.4, 72.3, 70.3, 69.7, 65.0, 64.3, 63.2, 62.6, 62.4, 61.9, 41.1, 40.5, 29.4, 29.1, 26.1,

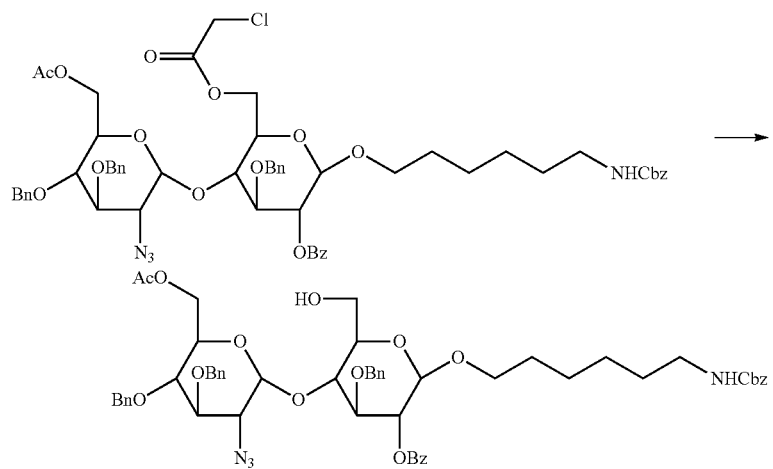

1,4-Diazabicyclo(2.2.2)octane (0.338 g, 3.02 mmol) is added to a solution of the chloroacetate 6a (1.1 g, 1.006 mmol) in EtOH (20 mL) and pyridine (2 mL), and the solution is heated at ~70-80° C. for 3 h. Chloroform is added and the mixture is washed with water, aq HCl, aq NaHCO$_3$, dried and concentrated. Chromatography (20-60% EtOAc/Hex) gives the product 8a as a foam (0.932 g, 0.916 mmol, 91%). $^1$H NMR (CDCl$_3$) δ 8.04-8.02 (m, 2H), 7.54-7.15 (m, 23H), 5.62 (d, J=3.9 Hz, 1H), 5.29 (t, J=8.4 Hz, 1H), 5.08 (bs, 2H), 4.89 (bs, 2H), 4.82 (d, J=10.9 Hz, 1H), 4.76 (d, J=10.4 Hz, 1H), 4.72 (d, J=10.4 Hz, 1H), 4.65 (bs, 1H), 25.4, 20.7. HRMS (ESI) calcd for $C_{86}H_{96}N_7Cl_3O_{25}Na$ (M+Na)$^+$ m/z 1754.5419, found 1754.5426.

Synthesis of 8d (Scheme 8)

Compound 51 is prepared from compound 50 following general procedure C: The residue is purified by silica gel chromatography (EtOAc:PE, 1:1→2:1) to furnish 51 as a foam (215 mg, 140 μmol, 93% yield); TLC (EtOAc:PE, 3:2, v/v): $R_f$=0.25. $^{13}$C-NMR (125 MHz, CDCl$_3$) δ 171.1, 170.6, 170.5, 165.8, 165.7, 156.1, 137.8, 137.5, 137.4, 133.3, 130.3, 130.1, 129.8, 129.7, 128.6, 128.5, 128.4, 128.39, 128.33, 128.2, 128.1, 128.0, 127.9, 127.8, 98.5, 98.2, 98.0, 97.9, 80.6, 79.3, 79.0, 76.9, 75.6, 75.2, 74.9, 74.6, 74.2, 74.0, 73.6, 73.5, 72.9, 72.4, 72.1, 70.3, 70.0, 69.4, 69.0, 68.1, 67.9, 67.2, 64.1, 63.8, 62.7, 62.6, 61.9, 61.7, 60.4, 31.9, 29.7, 29.4, 28.8, 26.4, 25.8, 20.74, 20.73. HRMS (ESI) calcd for $C_{88}H_{103}N_7O_{25}Na$ (M+Na)$^+$ m/z 1680.6901, found 1680.6919.

General Procedure D1 (GPD): TEMPO/BAIB Oxidation and Esterification by Diazomethane A solution of starting material in acetonitrile (5 mL for 32 μmol) and water (0.9 mL) is treated with TEMPO (0.2 equiv.) and BAIB (2.5 equiv. per hydroxyl group) at room temperature for 4-24 hours. After TLC (EtOAc:petroleum ether, 3:2) indicates the completion of the reaction chloroform and water are added. The solution is acidified with diluted HCl, back-extracted with chloroform, dried and concentrated. The residue is dissolved in dry ether and treated with an excess of freshly prepared diazomethane solution in ether until TLC (EtOAc:petroleum ether, 2:3) indicates the formation of methyl esters. The residues are purified by silica gel chromatography (EtOAc:petroleum ether, 2:3) to furnish the esters.

Synthesis of 9b (Scheme 8)

Compound 9b is prepared from compound 8b following general procedure D1: The residue is purified by silica gel chromatography (EtOAc:PE, 1:2→1:1) to furnish 9b as a foam (1.1 g, 1.0 mmol, 84% yield); TLC (EtOAc:PE, 1:1, v/v): $R_f$=0.75. $^{13}$C-NMR (125 MHz, CDCl$_3$) δ 170.5, 169.7, 165.5, 156.4, 137.8, 137.7, 136.7, 133.2, 129.9, 129.7, 129.0, 128.7, 128.5, 128.4, 128.3, 128.2, 128.0, 127.9, 127.8, 127.7, 125.3, 99.5, 99.2, 80.1, 76.8, 76.0, 74.8, 74.7, 73.4, 72.3, 70.1, 68.7, 68.0, 67.4, 66.6, 63.8, 62.4, 52.3, 40.9, 29.8, 29.3, 26.5, 25.8, 20.8. HRMS (ESI) calcd for $C_{57}H_{64}N_4O_{15}Na$ (M+Na)$^+$ m/z 1067.4266, found 1067.4269.

General Procedure D2 (GPD): TEMPO/BAIB Oxidation and Esterification with TMS-Diazomethane A solution of starting material in acetonitrile (5 mL for 32 μmol) and water (0.9 mL) is treated with TEMPO (0.2 equiv.) and BAIB (2.5 equiv. per hydroxyl group) at room temperature for 4-24 hours. After TLC (EtOAc:petroleum ether, 3:2) indicated the completion of the reaction chloroform and water are added. The solution is acidified with diluted HCl, back-extracted with chloroform, dried and concentrated. The residue is dissolved in diethyl ether/methanol (3:2) and a 2M solution of TMS-diazomethane in hexane (1.5 eq per carboxylate) is added dropwise at 0° C. After completion (TLC:Tol/EtOAc 3:2), 0.5 mL acetic acid are added to quench the reaction. Solvents are evaporated in vacuo and the residues are purified by silica gel chromatography to furnish the esters.

Synthesis of 9a (Scheme 8)

To a solution of the alcohol 8a (0.93 g, 0.914 mmol) in acetonitrile (10 mL) and water (2 mL) is added iodobenzene diacetate (0.589 g, 1.829 mmol) and TEMPO (2,2,6,6-tetramethyl piperidinyloxy, free radical) (0.043 g, 0.274 mmol) then the solution is stirred at RT for 24 h. Most of the solvent is evaporated, chloroform is added and the mixture is washed with 2M aq HCl, then dried and concentrated to dryness. A solution of the crude residue in ether (15 mL) and MeOH (5 mL) is cooled in an ice bath and (trimethylsilyl)diazomethane 2M in hexanes (0.429 ml, 2.74 mmol) is added. After 30 mins the excess diazomethane is quenched with a little acetic acid, then the solution is concentrated to dryness. Chromatography (10-40% EtOAc/hexanes) gives the title compound 9a as a syrup (0.844 g, 0.808 mmol, 88%). $^1$H NMR (CDCl$_3$) δ 8.03-8.01 (m, 2H), 7.55-7.16 (m, 23H), 5.50 (d, J=3.7 Hz, 1H), 5.32 (dd, J=8.4, 7.1 Hz, 1H), 5.08 (bs, 2H), 4.87 (bs, 2H), 4.81 (d, J=11.0 Hz, 1H), 4.78 (d, J=10.6 Hz, 1H), 4.71 (d, J=10.6 Hz, 1H), 4.69 (bs, 1H), 4.62 (d, J=7.1 Hz, 1H), 4.56 (d, J=11.0 Hz, 1H), 4.33-4.27 (m, 2H), 4.22 (dd, J=12.1, 3.6 Hz, 1H), 4.07 (d, J=9.3 Hz, 1H), 4.00 (t, J=8.5 Hz, 1H), 3.92-3.82 (m, 2H), 3.77 (s, 3H), 3.66-3.63 (m, 1H), 3.51 (t, J=9.4 Hz, 1H), 3.44-3.39 (m, 1H), 3.29 (dd, J=10.4, 3.7 Hz, 1H), 3.04-3.00 (m, 2H), 2.03 (s, 3H), 1.51-1.41 (m, 2H), 1.28-1.12 (m, 6H). $^{13}$C NMR δ 170.63, 168.63, 164.96, 156.34, 137.66, 137.56, 137.41, 136.79, 133.33, 129.74, 129.68, 128.52, 128.31, 128.04, 127.94, 127.78, 127.72, 101.20, 97.66, 82.26, 80.11, 77.60, 75.48, 75.01, 74.95, 74.49, 74.32, 73.81, 69.89, 69.79, 66.52, 63.40, 62.31, 52.75, 40.89, 29.66, 29.11, 26.23, 25.47, 20.82. HRMS (ESI) Calc for $C_{57}H_{64}N_4O_{15}Na$ [M+Na]$^+$ m/z, 1067.4266, found, 1067.4269.

Synthesis of 9c (Scheme 8)

Compound 9c is prepared from compound 8c following general procedure D2: The residue is purified by silica gel chromatography (EtOAc:Toluene, 1:9→1:1) to furnish 9c as a foam (1.0 g, 0.56 mmol, 71% yield); TLC (EtOAc:PE, 1:1, v/v): $R_f$=0.75. $^{13}$C-NMR (125 MHz, CDCl$_3$) 170.6, 168.5, 167.7, 164.9, 164.7, 154.5, 138.2, 137.8, 137.6, 137.5, 137.3, 137.2, 133.8, 133.3, 129.9, 129.7, 129.6, 129.1, 128.9, 128.8, 128.5, 128.3, 128.2, 128.1, 128.0, 127.9, 127.8, 127.7, 127.6, 127.5, 125.3, 101.2, 101.1, 97.7, 97.3, 82.6, 80.2, 77.7, 76.8, 75.6, 75.5, 75.3, 75.0, 74.9, 74.8, 74.5, 74.1, 73.8, 73.5, 69.8, 69.1, 63.4, 62.7, 62.2, 61.5, 52.7, 52.1, 41.1, 29.4, 29.0, 26.1, 25.5, 21.5, 20.8. HRMS (ESI) calcd for $C_{88}H_{96}N_7Cl_3O_{27}Na$ (M+Na)$^+$ m/z 1810.5317, found 1810.5317.

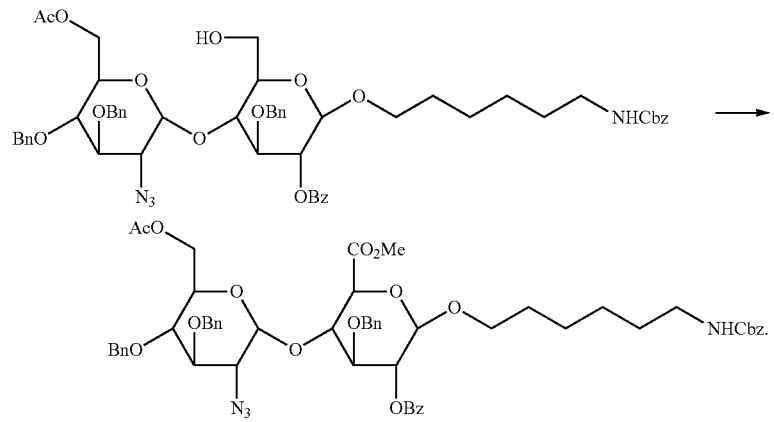

Synthesis of 9d (Scheme 8)

Compound 9d is prepared from compound 8d following general procedure D2: The residue is purified by silica gel chromatography (EtOAc:PE, 1:2→1:1) to furnish 9d as a foam (165 mg, 96 µmol, 93% yield); TLC (EtOAc:PE, 1:1, v/v): $R_f$=0.75. $^{13}$C-NMR (125 MHz, CDCl$_3$) δ 170.7, 170.5, 169.7, 169.4, 165.7, 165.2, 155.9, 137.8, 137.7, 137.6, 137.3, 133.4, 130.0, 129.9, 129.7, 129.4, 128.8, 128.7, 128.5, 128.4, 128.3, 128.2, 128.0, 127.9, 127.8, 127.6, 99.2, 99.1, 98.9, 98.5, 79.9, 79.0, 78.7, 76.8, 75.8, 75.6, 75.5, 75.0, 74.8, 74.6, 73.9, 72.9, 72.3, 70.5, 70.2, 70.1, 69.7, 68.7, 68.2, 67.5, 63.6, 63.5, 62.3, 62.2, 61.8, 60.4, 40.5, 29.9, 29.7, 29.3, 28.5, 26.5, 25.8, 20.8. HRMS (ESI) calcd for $C_{90}H_{103}N_7O_{27}Na$ (M+Na)$^+$ m/z 1736.6800, found 1736.6814.

General Procedure E (GPE): Reduction of Azide Group

Thiolacetic acid (1 mL for 20 µmol) is added to the starting material in dry pyridine (1 mL for 20 µmol) at room temperature. The reaction mixture is stirred at room temperature for 48-72 hours. After TLC (EtOAc:Toluene, 4:1) indicates the completion of the reaction toluene is added and the solution is washed with water, diluted HCl and NaHCO$_3$ solution (sat., aq.), dried and concentrated. Chromatography (EtOAc:Toluene, 4:1) affords N-acetylated products.

Synthesis of 6f (Scheme 8)

Compound 6f is prepared as a foam from compound 6e following general procedure E: The residue is purified by silica gel chromatography (Toluene→EtOAc:Toluene, 3:1→1:1) to afford 6f (0.98 g, 1.45 mmol, 96% yield); TLC (EtOAc:toluene, 1:1, v/v): $R_f$=0.15; $^{13}$C-NMR (125 MHz, CDCl$_3$) δ 170.7, 170.4, 156.5, 138.4, 137.7, 136.7, 129.0, 128.5, 128.4, 128.2, 128.0, 127.9, 127.8, 127.7, 125.3, 99.8, 80.5, 78.3, 74.6, 74.5, 72.8, 69.3, 66.5, 63.3, 56.9, 40.7, 29.7, 29.1, 26.1, 25.4, 23.5, 21.4, 20.9. HRMS (ESI) calcd for $C_{38}H_{48}N_2O_9$ (M+H)$^+$ m/z 699.3258, found 699.3257.

Synthesis of 11a (Scheme 8)

J=10.0, 3.5 Hz, 1H), 4.21-4.14 (m, 2H), 3.95 (d, J=9.2 Hz, 1H), 3.89-3.80 (m, 3H), 3.78 (s, 3H), 3.69 (t, J=10.0 Hz, 1H), 3.63 (t, J=9.3 Hz, 1H), 3.43-3.38 (m, 1H), 3.04-3.00 (m, 2H), 2.04 (s, 3H), 1.51-1.40 (m, 2H), 1.36 (s, 3H), 1.27-1.11 (m, 6H). $^{13}$C NMR δ 170.69, 170.15, 167.94, 164.97, 156.34, 138.17, 137.73, 136.75, 136.60, 133.48, 129.71, 129.45, 128.67, 128.54, 128.52, 128.47, 128.38, 128.29, 128.17, 128.15, 128.08, 128.05, 127.90, 127.79, 101.44, 100.00, 81.01, 80.81, 77.93, 77.25, 75.52, 75.06, 74.94, 74.80, 73.88, 70.77, 69.98, 66.54, 62.31, 52.92, 52.71, 40.88, 29.67, 29.08, 26.22, 25.45, 22.57, 20.81. HRMS (ESI) Calc for $C_{59}H_{68}N_2O_{16}Na$ [M+Na]$^+$ m/z, 1083.4467, found, 1083.4462.

Synthesis of 11 b (Scheme 8)

Compound 11b is prepared as a foam from compound 9b following general procedure E: The residue is purified by silica gel chromatography (Toluene→EtOAc:Toluene, 3:1→1:1) to afford 11b (1.0 g, 0.95 mmol, 99% yield); TLC (EtOAc:toluene, 1:1, v/v): $R_f$=0.2; $^{13}$C-NMR (125 MHz, CDCl$_3$) δ 170.6, 169.9, 169.5, 165.7, 156.4, 138.1, 137.9, 137.3, 137.2, 136.7, 133.7, 129.8, 129.3, 129.0, 128.9, 128.8, 128.7, 128.5, 128.4, 128.2, 127.9, 127.7, 127.6, 127.3, 125.3, 99.9, 98.3, 81.7, 80.5, 76.8, 75.9, 74.8, 74.7, 74.0, 73.0, 72.7, 72.4, 70.4, 68.9, 68.8, 67.7, 66.5, 62.5, 52.6, 52.3, 40.9, 29.8, 29.2, 26.4, 25.7, 22.9, 21.4, 20.8. HRMS (ESI) calcd for $C_{59}H_{68}N_2O_{16}Na$ (M+Na)$^+$ m/z 1083.4467, found 1083.4471.

Synthesis of 11c (Scheme 8)

Compound 11c is prepared as a foam from compound 9c following general procedure E: The residue is purified by silica gel chromatography (Toluene EtOAc:Toluene, 9:1→1:1) to furnish 11c (681 mg, 0.38 mmol, 75% yield); TLC (EtOAc:toluene, 4:1, v/v): $R_f$=0.75; $^{13}$C-NMR (125 MHz, CDCl$_3$) δ 172.7, 170.7, 170.6, 170.2, 170.1, 167.9, 167.4, 164.9, 154.5, 138.8, 138.1, 137.9, 137.7, 136.5, 136.4, 133.8, 133.5, 136.4, 133.8, 133.5, 129.8, 129.7, 129.5,

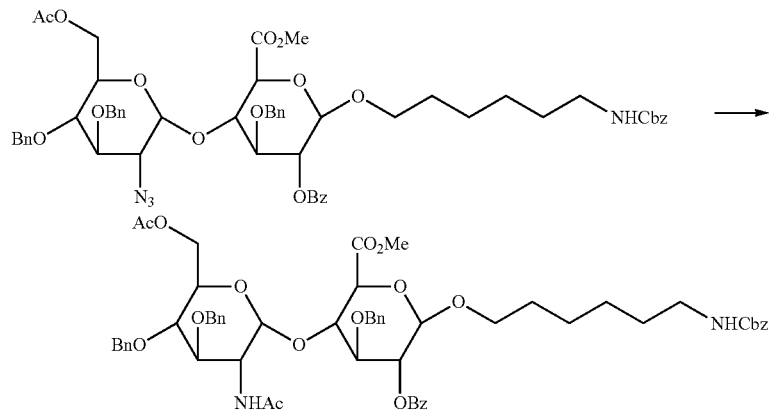

A solution of azide 9a (0.84 g, 0.804 mmol) in pyridine (3 mL) and thioacetic acid (3 mL) is stirred at RT for 24 h. Then toluene is added and the solution is washed with water, aq HCl, then aq NaHCO$_3$, dried and concentrated to dryness. Chromatography (20-60% EtOAc/Hexanes) gives the product (0.649 g, 0.612 mmol, 76%) as a foam. $^1$H NMR (CDCl$_3$) δ 8.01-7.99 (m, 2H), 7.56-7.52 (m, 1H), 7.43-7.40 (m, 2H), 7.36-7.25 (m, 16H), 7.17-7.12 (m, 4H), 5.81 (d, J=9.7 Hz, 1H), 5.34 (dd, J=8.7, 7.0 Hz, 1H), 5.09 (bs, 2H), 4.96 (d, J=3.4 Hz, 1H), 4.83 (d, J=10.8 Hz, 1H), 4.78 (d, J=11.2 Hz, 1H), 4.70 (d, J=10.7 Hz, 1H), 4.68 (bs, 1H), 4.62-4.52 (m, 4H), 4.35 (dd, J=12.0, 2.1 Hz, 1H), 4.28 (dt, 129.0, 128.9, 128.8, 128.6, 128.5, 128.3, 128.2, 128.1, 128.0, 127.9, 127.8, 127.7, 127.5, 127.4, 127.3, 127.1, 125.3, 101.3, 101.2, 99.5, 99.2, 81.4, 81.2, 80.5, 78.1, 77.2, 77.1, 76.8, 76.1, 75.4, 75.2, 75.1, 74.9, 74.8, 74.7, 74.5, 74.3, 74.0, 73.8, 73.6, 70.7, 70.2, 69.9, 69.0, 62.2, 61.5, 52.8, 52.7, 52.5, 52.2, 41.0, 29.4, 29.0, 26.1, 25.4, 22.6, 22.5, 21.5, 20.8. HRMS (ESI) calcd for $C_{92}H_{104}N_3Cl_3O_{29}Na$ (M+Na)$^+$ m/z 1842.5719, found 1842.5718.

General Procedure F (GPF): Zemplen De-O-Acetylation

Starting material is dissolved in dry methanol (10 mL for 50 µmol) at RT and treated with a 1% freshly prepared solution of sodium methoxide (20 µL for 150 mg). Stirring of the reaction mixture is continued for 24 h at RT. After TLC (DCM:MeOH, 9:1) indicates the completion of the reaction the solution is concentrated and dried. The residues are purified by silica gel chromatography (DCM:MeOH, 9:1→5:1) to give de-O-acetylated products.

Synthesis of 15e (Scheme 9)

Compound 15e is prepared from compound 14e following general procedure F: The residue is purified by silica gel chromatography (DCM:MeOH, 9:1→5:1) to furnish the tetraol 15e as a foam (85 mg, 36 µmol, 83% yield); TLC (DCM:MeOH, 9:1, v/v): $R_f$=0.55. $^{13}$C-NMR (125 MHz, MeOD) δ 172.4, 171.7, 138.4, 138.1, 128.1, 128.0, 127.7, 127.5, 127.3, 101.1, 82.7, 78.2, 77.9, 77.7, 77.4, 75.7, 74.7, 74.6, 69.2, 67.4, 61.0, 55.5, 45.3, 39.2, 36.5, 29.2, 26.4, 25.5, 22.2. HRMS (ESI) calcd for $C_{129}H_{180}N_8O_{32}Na$ $(M+Na)^+$ m/z 2376.2601, found 2376.2625.

Synthesis of 14 (Scheme 9)

Compound 15h is prepared from compound 14h following general procedure F: The residue is purified by silica gel chromatography (EtOAc:MeOH, 9:1→4:1) to furnish the tetraol 15h as a foam (72 mg, 24.7 µmol, 76% yield); TLC (EtOAc:MeOH, 4:1, v/v): $R_f$=0.51. $^{13}$C-NMR (125 MHz, MeOD) δ 174.6, 174.2, 172.3, 171.8, 171.2, 139.4, 138.3, 138.2, 137.8, 128.2, 128.1, 128.0, 127.8, 127.7, 127.6, 127.5, 127.4, 101.2, 101.1, 82.7, 77.6, 75.5, 74.8, 74.6, 72.8, 69.4, 69.3, 67.4, 63.0, 60.9, 55.5, 45.3, 39.2, 39.0, 36.9, 36.5, 35.9, 34.8, 32.9, 29.2, 29.1, 28.9, 28.8, 26.6, 26.4, 25.7, 25.4, 24.9, 22.2, 19.9. HRMS (ESI) calcd for $C_{161}H_{240}N_{12}O_{36}Na$ $(M+Na)^+$ m/z 2940.7216, found 2940.7217.

General Procedure G (GPG): Selective De-O-Acetylation

Starting material is dissolved in dry dichloromethane (2 mL for 9 µmol) at 0° C. and treated with a solution of cold dry methanol (4 mL) containing 80 µL of acetyl chloride. Stirring of the reaction, mixture is continued for 30 min at 0° and then at 23° C. for 48 h. After TLC (EtOAc) indicates the completion of the reaction dichloromethane is added and the solution is washed with water and NaHCO$_3$ solution (sat., aq.), dried and concentrated. The residues are purified by silica gel chromatography (EtOAc:MeOH, 9:1) to give de-O-acetylated products.

Synthesis of 15a (Scheme 9)

Compound 15a is prepared from compound 14a following general procedure G: The residue is purified by silica gel chromatography (EtOAc→EtOAc:MeOH, 9:1→4:1) to furnish the tetraol 15a as a foam (250 mg, 56.1 µmol, 91% yield); TLC (EtOAc:MeOH, 4:1, v/v): $R_f$=0.51. $^{13}$C-NMR (125 MHz, MeOD) δ 175.9, 173.8, 173.1, 170.7, 166.7, 140.1, 139.9, 138.4, 134.8, 131.0, 130.8, 129.9, 129.5, 129.46, 129.42, 129.1, 128.8, 128.7, 128.6, 128.5, 128.2, 102.5, 99.1, 83.8, 81.6, 78.9, 76.0, 75.9, 75.8, 75.6, 75.3, 75.2, 73.8, 71.1, 70.7, 68.8, 61.5, 54.2, 53.5, 46.8, 40.5, 40.3, 37.9, 37.2, 30.6, 30.5, 30.3, 30.2, 27.9, 27.6, 27.1, 26.7, 23.1.

Synthesis of 15b (Scheme 9)

Compound 15b is prepared from compound 14b following general procedure G: The residue is purified by silica gel chromatography (EtOAc→EtOAc:MeOH, 9:1→4:1) to give the tetraol 15b as a foam (343 mg, 77 µmol, 96% yield); TLC (EtOAc:MeOH, 4:1, v/v): $R_f$=0.51. $^{13}$C-NMR (125 MHz, MeOD) δ 175.2, 173.8, 173.3, 171.6, 167.1, 139.9, 139.8, 139.2, 134.6, 130.9, 130.1, 129.5, 129.4, 129.1, 128.9, 128.8, 128.7, 128.5, 100.4, 98.7, 81.7, 79.4, 76.1, 75.9, 75.7, 74.6, 74.1, 74.0, 73.9, 73.8, 71.6, 70.7, 70.2, 70.1, 70.0, 69.9, 68.8, 62.0, 54.4, 53.1, 51.1, 46.8, 40.5, 37.2, 36.1, 34.5, 34.0, 33.8, 30.6, 30.5, 30.3, 30.2, 29.4, 28.2, 28.0, 27.7, 27.6, 27.4, 27.0, 26.7, 26.3, 22.9.

Synthesis of 15c (Scheme 9)

Compound 15c is prepared from compound 14c following general procedure G: The residue is purified by silica gel chromatography (Chloroform→Chloroform:MeOH, 19:1→9:1→4:1) to afford the octaol 55 as a foam (255 mg, 40.7 µmol, 89% yield); TLC (EtOAc:MeOH, 9:1, v/v): $R_f$=0.65. $^{13}$C-NMR (125 MHz, MeOD) δ 175.9, 173.8, 173.0, 172.9, 170.4, 170.1, 166.8, 166.5, 140.6, 139.9, 139.8, 138.2, 138.1, 135.3, 134.9, 130.9, 130.8, 130.5, 130.2, 129.9, 129.6, 129.5, 129.2, 129.0, 128.9, 128.8, 128.6, 126.5, 102.5, 102.1, 99.1, 98.8, 83.9, 83.8, 81.6, 79.4, 79.3, 79.2, 78.9, 78.4, 76.2, 76.0, 75.9, 75.7, 75.5, 75.2, 73.9, 73.3, 71.3, 70.7, 68.9, 61.7, 60.4, 54.2, 53.7, 53.4, 46.8, 40.7, 40.5, 38.0, 37.5, 30.7, 30.5, 30.4, 30.3, 28.1, 27.7, 27.2, 26.7, 23.5, 22.2.

General Procedure H (GPH): O-Sulfation

Sulfur trioxide trimethylamine complex (5 equiv per hydroxyl group) is added to the starting materials in dry DMF (3 mL for 50 mg). The mixture is heated at 50-60° C. under argon for 48-72 h. MeOH (1 mL) is added and the mixture stirred for 15 min and concentrated in vacuo. Chromatography (dichloromethane:methanol:aq. ammonia, 7:2:0.5) affords O-sulfated products.

Synthesis of 16e (Scheme 9)

Compound 16e is prepared from compound 15e following general procedure H: The residue is purified by silica gel chromatography (dichloromethane:methanol:aq. ammonia, 7:2:0.5) to furnish the tetra-sulfate 16e as a foam (83 mg, 31 mmol, 96% yield); TLC (dichloromethane:methanol:aq. ammonia, 7:2:0.5): $R_f$=0.15. $^{13}$C-NMR (125 MHz, MeOD) δ 173.9, 173.3, 140.0, 139.7, 129.3, 128.8, 128.7, 128.6, 102.6, 84.1, 79.5, 76.2, 75.8, 74.9, 70.7, 68.8, 67.7, 56.8, 46.7, 40.5, 37.8, 30.5, 27.7, 26.7, 23.2. HRMS (ESI, negative mode) calcd for $C_{129}H_{179}N_8O_{44}S_4$ $(M-H)^-$ m/z 2672.0898, found 2672.0876.

Synthesis of 16h (Scheme 9)

Compound 16h is prepared from compound 15h following general procedure H: The residue is purified by silica gel chromatography (dichloromethane:methanol:aq. ammonia, 7:2:0.5) to furnish the tetra-sulfate 16h as a foam (70 mg, 21.6 mmol, 90% yield); TLC (dichloromethane:methanol: aq. ammonia, 7:2:0.5): $R_f$=0.25. $^{13}$C-NMR (125 MHz, MeOD) δ 176.1, 175.7, 173.9, 173.2, 140.0, 139.6, 129.4, 129.3, 128.8, 128.7, 128.6, 102.6, 84.1, 79.5, 76.0, 75.9, 75.0, 70.7, 70.5, 68.8, 67.7, 56.8, 46.7, 40.5, 40.3, 37.9, 37.8, 37.2, 35.8, 34.2, 30.5, 30.4, 30.2, 30.1, 27.9, 27.7, 27.0, 26.7, 26.3, 23.1.

Synthesis of 16a (Scheme 9)

Compound 16a is prepared from compound 15a following general procedure H: The residue is purified by silica gel chromatography (dichloromethane:methanol:aq. ammonia, 7:2:0.5) to furnish the tetra-sulfate 16a as a foam (252 mg, 52.7 mmol, 95% yield); TLC (dichloromethane:methanol: aq. ammonia, 7:2:0.5): $R_f$=0.25. $^{13}$C-NMR (125 MHz, MeOD) δ 176.0, 173.9, 173.2, 170.9, 166.8, 140.1, 139.8, 138.6, 134.8, 130.9, 130.8, 129.9, 129.5, 129.4, 129.38, 129.32, 128.9, 128.7, 128.6, 102.5, 99.2, 83.5, 81.6, 78.9, 76.1, 76.0, 75.9, 75.7, 75.5, 75.3, 71.9, 71.2, 70.7, 68.8, 66.8, 55.2, 54.2, 53.6, 46.8, 40.5, 40.3, 37.8, 37.2, 30.6, 30.5, 30.3, 30.2, 27.9, 27.6, 27.1, 26.7, 23.1.

Synthesis of 19a (Scheme 9)

Compound 19a is prepared from compound 17a following general procedure H: The residue is purified by silica gel chromatography (dichloromethane:methanol:aq. ammonia, 7:2:0.5) to give the octa-sulfate 19a as a foam (89 mg, 19.2 mmol, 89% yield); TLC (dichloromethane:methanol:aq. ammonia, 7:2:0.5): $R_f$=0.25. $^{13}$C-NMR (125 MHz, MeOD)

δ 176.2, 175.5, 173.9, 173.1, 140.3, 139.9, 139.3, 129.7, 129.5, 129.3, 129.2, 128.7, 128.6, 128.5, 102.3, 98.6, 84.1, 82.0, 80.7, 79.3, 77.4, 76.3, 75.9, 75.4, 74.4, 71.5, 70.7, 68.8, 67.3, 54.4, 44.7, 40.5, 40.4, 37.8, 37.2, 30.5, 30.3, 30.2, 27.9, 27.8, 27.1, 26.7, 23.0.

Synthesis of 16b (Scheme 9)

Compound 16b is prepared from compound 15b following general procedure H: The residue is purified by silica gel chromatography (dichloromethane:methanol:aq. ammonia, 7:2:0.5→5:4:1) to afford the tetra-sulfate 16b as a foam (330 mg, 69.1 mmol, 99% yield); TLC (dichloromethane:methanol:aq. ammonia, 7:2:0.5): $R_f$=0.21. $^{13}$C-NMR (125 MHz, MeOD) δ 175.3, 173.8, 173.3, 171.7, 167.1, 140.0, 139.9, 139.2, 134.6, 130.9, 130.1, 129.6, 129.5, 129.4, 128.9, 128.8, 128.6, 128.4, 100.5, 98.8, 81.5, 79.2, 76.2, 75.9, 75.5, 75.4, 75.3, 74.2, 73.7, 72.4, 71.2, 70.7, 69.9, 69.8, 69.6, 69.5, 68.8, 67.2, 54.4, 53.2, 51.1, 46.8, 40.5, 40.4, 37.8, 37.2, 34.5, 33.9, 33.8, 30.5, 30.4, 30.3, 30.2, 30.1, 29.4, 28.2, 28.0, 27.8, 27.6, 27.4, 27.0, 26.7, 26.3, 22.8.

Synthesis of 19b (Scheme 9)

Compound 19b is prepared from compound 17b following general procedure H: The residue is purified by silica gel chromatography (dichloromethane:methanol:aq. ammonia, 7:2:0.5→5:4:1) to furnish the octa-sulfate 19b as a foam (120 mg, 25.9 mmol, 94% yield); TLC (dichloromethane:methanol:aq. ammonia, 7:2:0.5): $R_f$=0.15. $^{13}$C-NMR (125 MHz, MeOD) δ 174.4, 174.3, 174.2, 174.1, 173.2, 173.1, 172.9, 172.8, 139.2, 138.7, 138.3, 138.2, 128.7, 128.5, 128.4, 128.3, 128.2, 127.9, 127.8, 127.6, 117.4, 100.1, 98.6, 80.9, 78.2, 75.5, 75.1, 74.1, 72.5, 72.4, 72.1, 71.5, 70.6, 70.5, 69.6, 68.2, 68.1, 67.8, 67.2, 66.2, 54.3, 53.7, 50.2, 45.7, 40.3, 39.5, 39.4, 38.7, 36.8, 36.2, 35.2, 34.1, 33.4, 33.0, 32.8, 29.6, 29.5, 29.4, 29.3, 29.2, 29.1, 28.5, 27.2, 26.9, 26.8, 26.7, 26.5, 26.2, 26.1, 26.0.

Synthesis of 16c (Scheme 9)

Compound 16c is prepared from compound 15c following general procedure H: The residue is purified by silica gel chromatography (dichloromethane:methanol:aq. ammonia, 7:2:0.5→5:4:1) to give the octa-sulfate 16c as a foam (278 mg, 35.6 mmol, 100% yield); TLC (dichloromethane:methanol:aq. ammonia, 7:2:0.5): $R_f$=0.2. $^{13}$C-NMR (125 MHz, MeOD) δ 176.0, 173.9, 173.3, 173.2, 170.6, 170.4, 166.8, 166.6, 140.4, 140.1, 139.9, 138.6, 138.5, 135.1, 1334.9, 131.3, 130.9, 130.8, 130.6, 130.2, 129.9, 129.4, 129.3, 129.2, 128.9, 128.6, 128.5, 102.4, 101.7, 98.9, 98.8, 84.0, 83.7, 81.8, 79.5, 79.0, 78.3, 76.3, 75.9, 75.8, 75.5, 75.3, 75.1, 74.9, 71.8, 71.3, 71.2, 70.7, 68.8, 66.8, 65.7, 54.1, 53.4, 52.9, 46.8, 40.5, 40.3, 37.9, 37.2, 30.5, 30.4, 30.3, 30.2, 30.1, 27.9, 27.6, 27.1, 26.7, 23.1, 23.0.

Synthesis of 19c (Scheme 9)

Compound 19c is prepared from compound 17c following general procedure H: The residue is purified by silica gel chromatography (dichloromethane:methanol:aq. ammonia, 7:2:0.5→5:4:1) to afford the hexadeca-sulfate 19c as a foam (99 mg, 14.6 μmol, 90% yield); TLC (dichloromethane:methanol:aq. ammonia, 7:2:0.5): $R_f$=0.2. $^{13}$C-NMR (125 MHz, MeOD) 176.2, 175.8, 175.1, 173.9, 173.4, 140.5, 139.9, 139.7, 139.6, 139.5, 129.8, 129.6, 129.5, 129.4, 129.39, 129.35, 129.3, 129.2, 128.8, 128.7, 128.6, 128.5, 102.4, 101.4, 98.7, 97.4, 83.8, 81.8, 80.9, 80.4, 79.3, 77.3, 76.5, 76.3, 75.9, 75.5, 74.5, 74.2, 71.6, 71.2, 70.9, 70.7, 68.8, 67.2, 66.8, 55.2, 54.4, 53.2, 46.8, 41.1, 40.5, 40.4, 37.8, 37.2, 35.5, 30.5, 30.3, 30.2, 30.1, 27.9, 27.8, 27.1, 26.8, 23.3, 23.1.

Synthesis of 16d (Scheme 9)

Compound 16d is prepared from compound 15d following general procedure H: The residue is purified by silica gel chromatography (dichloromethane:methanol:aq. ammonia, 7:2:0.5→5:4:1) to furnish the sulfate 16d as a foam (13.3 mg, 1.8 μmol, 99% yield); TLC (EtOAc:ethanol:water, 3:1:1): $R_f$=0.15. $^{13}$C-NMR (125 MHz, MeOD) δ 176.2, 173.9, 139.9, 139.6, 138.8, 129.5, 129.3, 129.2, 129.1, 128.8, 128.7, 101.3, 99.8, 97.8, 95.1, 82.3, 79.0, 76.3, 76.1, 73.1, 72.7, 71.6, 71.3, 70.7, 69.1, 68.8, 67.2, 65.9, 48.5, 40.5, 40.4, 37.8, 37.2, 30.5, 30.4, 30.3, 30.2, 27.9, 27.8, 27.1.

General Procedure I (GPI): Saponification

Starting material is dissolved in methanol and water (4/1, v/v, 1.25 mL for 20 mg) containing 2M solution of sodium hydroxide (50 μL per 1.25 mL of reaction mixture) at 0° C. The reaction mixture is stirred at room temperature for 48-72 hours. After TLC (EtOAc:EtOH:water, 3:1:1) indicates the completion of the reaction, the volume of the solvents is reduced in vacuo. The solution is applied to a column of silica for flash chromatography (dichloromethane:methanol:aq. ammonia, 7:2:0.5) to furnish the de-O-benzoylated products.

Synthesis of 17a (Scheme 9)

Compound 17a is prepared from compound 16a following general procedure I: The residue is purified by silica gel chromatography (dichloromethane:methanol, 9:1→dichloromethane:methanol:aq. ammonia, 7:2:0.5→5:4:1) to afford the tetramer 17a as a foam (219 mg, 50.9 mmol, 99% yield); TLC (acetonitrile:water:aq. ammonia, 3:1:1): $R_f$=0.15. $^{13}$C-NMR (125 MHz, MeOD) δ 176.2, 175.4, 173.9, 172.9, 140.2, 139.8, 139.7, 138.7, 130.8, 129.9, 129.5, 129.4, 129.38, 129.31, 128.9, 128.7, 128.6, 104.6, 98.8, 86.3, 81.9, 79.3, 77.9, 76.3, 76.1, 75.9, 75.8, 75.6, 75.4, 71.4, 71.1, 70.7, 68.8, 67.4, 55.2, 54.4, 46.8, 40.5, 40.4, 37.9, 37.2, 30.7, 30.5, 30.4, 30.3, 30.2, 27.9, 27.8, 27.6, 27.1, 26.8, 23.1.

Synthesis of 17b (Scheme 9)

Compound 17b is prepared from compound 16b following general procedure I: The residue is purified by silica gel chromatography (dichloromethane:methanol, 9:1→dichloromethane:methanol:aq. ammonia, 7:2:0.5→5:4:1) to furnish the tetramer 17b as a foam (255 mg, 59.2 mmol, 96% yield); TLC (EtOAc:ethanol:water, 3:1:1): $R_f$=0.15. $^{13}$C-NMR (125 MHz, MeOD) δ 176.1, 175.4, 174.8, 174.7, 173.9, 173.2, 140.2, 139.8, 139.6, 139.5, 129.5, 129.4, 129.3, 128.9, 128.8, 128.7, 128.6, 102.7, 97.2, 82.2, 79.1, 76.3, 76.0, 74.9, 73.2, 72.8, 72.1, 70.7, 69.2, 69.1, 68.8, 68.7, 67.8, 67.7, 67.2, 54.4, 51.2, 46.8, 40.6, 40.4, 37.9, 37.2, 36.2, 34.5, 34.0, 33.8, 30.7, 30.5, 30.4, 30.35, 30.3, 30.2, 29.5, 28.2, 28.0, 27.9, 27.7, 27.6, 27.2, 27.1, 26.7, 26.4, 23.1.

Synthesis of 17c (Scheme 9)

Compound 17c is prepared from compound 16c following general procedure I: The residue is purified by silica gel chromatography (dichloromethane:methanol, 9:1→dichloromethane:methanol:aq. ammonia, 7:2:0.5→5:4:1) to furnish the tetramer 16c as a foam (88 mg, 12.8 μmol, 86% yield); TLC (EtOAc:ethanol:water, 3:1:1): $R_f$=0.15. $^{13}$C-NMR (125 MHz, MeOD) δ 176.3, 176.2, 175.1, 173.9, 173.1, 172.9, 140.3, 140.2, 139.9, 139.8, 139.7, 129.5, 129.4, 129.38, 129.31, 129.0, 128.9, 128.6, 104.7, 104.1, 98.7, 98.2, 86.6, 85.8, 81.9, 80.4, 79.3, 78.2, 77.8, 76.5, 76.3, 76.1, 75.9, 75.5, 75.3, 75.1, 74.9, 71.9, 71.3, 71.1, 70.7, 68.8, 67.4, 67.1, 54.4, 53.4, 46.8, 40.5, 40.4, 37.9, 37.2, 30.7, 30.5, 30.4, 30.3, 30.2, 27.9, 27.8, 27.1, 26.8, 23.0.

Synthesis of 17d (Scheme 9)

Compound 17d is prepared from compound 16d following general procedure I: The residue is purified by silica gel chromatography (dichloromethane:methanol:aq. ammonia, 7:2:0.5→4 5:4:1, MeOH:aq.ammonia→7:1) to furnish the tetramer 17d as a foam (59 mg, 9.7 μmol, 94% yield); TLC (EtOAc:ethanol:water, 3:1:1): $R_f$=0.12. $^{13}$C-NMR (125 MHz, MeOD) δ 176.4, 176.1, 175.2, 173.9, 129.3, 129.2, 129.0, 128.9, 128.8, 128.7, 128.5, 102.7, 101.1, 97.2, 96.0, 82.1, 79.6, 76.3, 75.8, 74.9, 73.6, 73.4, 72.7, 71.9, 70.7, 69.1, 68.8, 68.0, 65.6, 62.1, 61.8, 46.7, 40.5, 40.4, 37.8, 37.2, 30.7, 30.5, 30.4, 30.3, 30.2, 27.9, 27.8, 27.2, 27.1, 26.8.

General Procedure J (GPJ): Global Debenzylation

Starting material is dissolved in THF and water (1/1, v/v, 3 mL for 10 mg) containing aqueous ammonia solution (10% of reaction mixture) and treated with palladium hydroxide on carbon (20% Pd, 5 times the weight of starting material). The reaction mixture is stirred for 24-48 hours under hydrogen at ambient temperature and pressure. After TLC (EtOAc:EtOH:water, 2:1:1) indicates the completion of the reaction the catalyst is filtered off and washed with 50% aqueous THF. The solution is concentrated to dryness and chromatography of the residue (dichloromethane:methanol:aq. ammonia, 5:4:1) gives the final products as ammonium salts. The resulting materials are dissolved in water, passed through a Dowex 50WX8-200 (Na$^+$) resin column (8×1 cm) and eluted with water. Fractions containing the products are evaporated and dried in vacuo to furnish sodium salts of final products.

Synthesis of 18e (Scheme 9)

Compound 18e is prepared from compound 16e following general procedure J: The residue is purified by silica gel chromatography (acetonitrile:water:aq. ammonia, 6:2:1) to furnish the tetramer 18e as a foam (52 mg, 26.6 mmol, 89% yield); TLC (acetonitrile:water:aq. ammonia, 6:2:1): $R_f$=0.33. $^{13}$C-NMR (125 MHz, D$_2$O) δ 174.4, 174.1, 173.9, 101.3, 73.7, 70.5, 69.7, 69.4, 69.0, 67.7, 67.1, 61.1, 55.6, 45.3, 39.5, 36.5, 28.7, 28.6, 25.9, 24.9, 22.37. HRMS (ESI, negative mode) calcd for C$_{73}$H$_{131}$N$_8$O$_{44}$S$_4$ (M–H)$^-$ m/z 1951.7142, found 1951.7120.

Synthesis of 18h (Scheme 9)

Compound 18h is prepared from compound 16h following general procedure J: The residue is purified by silica gel chromatography (acetonitrile:water:aq. ammonia, 6:2:1) to furnish the tetramer 18h as a foam (30 mg, 11.9 mmol, 86% yield); TLC (acetonitrile:water:aq. ammonia, 6:2:1): $R_f$=0.4. $^{13}$C-NMR (125 MHz, D$_2$O) δ 176.6, 176.4, 174.3, 173.8, 101.3, 73.8, 70.5, 69.7, 69.2, 67.7, 67.2, 55.6, 45.4, 39.5, 39.3, 37.7, 36.5, 35.8, 35.5, 32.9, 28.6, 28.5, 28.4, 28.3, 28.2, 26.2, 25.8, 25.5, 24.9, 24.8, 22.3.

Synthesis of 18a (Scheme 9)

Compound 18a is prepared from compound 17a following general procedure J: The residue is purified by silica gel chromatography (acetonitrile:water:aq. ammonia, 6:2:1) to furnish the tetramer 18a as a foam (57 mg, 17.7 mmol, 91% yield); TLC (acetonitrile:water:aq. ammonia, 6:2:1): $R_f$=0.4. $^{13}$C-NMR (125 MHz, D$_2$O) δ 176.6, 174.4, 174.1, 173.8, 102.3, 97.3, 76.6, 76.3, 73.5, 70.7, 70.2, 69.3, 69.1, 67.7, 66.4, 53.6, 45.4, 39.5, 39.3, 36.5, 35.9, 29.7, 28.7, 28.6, 28.4, 28.3, 26.2, 25.9, 25.5, 24.8, 22.0.

Synthesis of 20a (Scheme 9)

Compound 20a is prepared from compound 19a following general procedure J: The residue is purified by silica gel chromatography (dichloromethane:methanol, 9:1→dichloromethane:methanol:aq. ammonia, 7:2:0.5→5:4:1→methanol:aq. Ammonia, 7:1) to afford the tetramer 20a as a foam (45 mg, 12.7 mmol, 98% yield); TLC (EtOAc:ethanol:water, 2:1:1): $R_f$=0.15. $^{13}$C-NMR (125 MHz, D$_2$O) δ 176.7, 174.5, 173.9, 173.8, 100.6, 97.6, 80.4, 76.5, 75.8, 75.2, 70.8, 70.6, 70.3, 69.2, 69.1, 67.7, 66.4, 53.6, 45.4, 39.5, 39.3, 36.5, 35.9, 29.5, 28.7, 28.6, 28.3, 28.2, 28.1, 25.9, 25.5, 24.7, 22.0.

Synthesis of 18b (Scheme 9)

Compound 18b is prepared from compound 17b following general procedure J: The residue is purified by silica gel chromatography (dichloromethane:methanol, 9:1→dichloromethane:methanol:aq. ammonia, 7:2:0.5→5:4:1→methanol:aq. Ammonia, 7:1) to furnish the tetramer 18b as a foam (55 mg, 17.1 mmol, 92% yield); TLC (EtOAc:ethanol:water, 2:1:1): $R_f$=0.15. $^{13}$C-NMR (125 MHz, D$_2$O) δ 175.6, 175.1, 174.9, 173.5, 173.4, 172.8, 99.8, 93.8, 72.8, 70.2, 69.4, 68.2, 67.7, 67.6, 67.5, 67.3, 66.8, 65.6, 52.5, 49.5, 48.0, 46.8, 44.4, 38.6, 38.4, 35.6, 34.9, 32.7, 32.3, 31.7, 32.3, 31.7, 29.2, 27.7, 27.5, 27.4, 26.8, 25.5, 25.3, 25.0, 24.9, 24.8, 24.6, 24.5, 24.4, 24.3, 24.2, 24.1, 24.0, 21.1.

Synthesis of 20b (Scheme 9)

Compound 20b is prepared from compound 19b following general procedure J: The residue is purified by silica gel chromatography (dichloromethane:methanol, 9:1→dichloromethane:methanol:aq. ammonia, 7:2:0.5→5:4:1→methanol:aq. Ammonia, 7:1) to give the tetramer 20b as a foam (49 mg, 13.8 mmol, 91% yield); TLC (EtOAc:ethanol:water, 2:1:1): $R_f$=0.15. $^{13}$C-NMR (125 MHz, D$_2$O) δ 175.7, 175.2, 175.0, 173.9, 173.8, 172.9, 97.5, 93.2, 72.6, 70.3, 70.2, 69.3, 68.3, 68.2, 67.7, 67.6, 66.7, 65.7, 65.6, 62.8, 56.5, 52.4, 49.5, 46.8, 44.4, 38.6, 38.4, 35.6, 34.9, 32.7, 32.3, 31.6, 29.2, 27.6, 27.5, 27.4, 27.3, 26.8, 25.5, 25.3, 24.9, 24.8, 24.7, 24.6, 24.5, 24.3, 24.1, 21.4.

Synthesis of 18c (Scheme 9)

Compound 18c is prepared from compound 17c following general procedure J: The residue is purified by silica gel chromatography (dichloromethane:methanol, 9:1→dichloromethane:methanol:aq. ammonia, 7:2:0.5→5:4:1→methanol:aq. Ammonia, 7:1) to give the octasulfated tetramer 18c as a foam (66 mg, 13.1 μmol, 99% yield); TLC (EtOAc:ethanol:water, 2:1:1): $R_f$=0.15. $^{13}$C-NMR (125 MHz, D$_2$O) δ 176.6, 174.5, 174.4, 174.3, 173.9, 102.3, 101.9, 97.2, 97.0, 77.4, 76.6, 76.4, 76.3, 76.2, 76.1, 73.5, 70.6, 70.2, 69.3, 69.2, 69.0, 68.9, 67.7, 66.4, 65.8, 60.3, 53.5, 53.2, 45.4, 39.5, 39.3, 36.5, 35.9, 29.5, 28.7, 28.6, 28.4, 28.3, 26.2, 25.9, 25.5, 24.8, 22.0.

Synthesis of 20c (Scheme 9)

Compound 20c is prepared from compound 19c following general procedure J: The residue is purified by silica gel chromatography (dichloromethane:methanol, 9:1→dichloromethane:methanol:aq. ammonia, 7:2:0.5→5:4:1→methanol:aq. Ammonia, 7:1) to furnish the hexadeca-sulfated tetramer 20c as a foam (79 mg, 14 μmol, 99% yield); TLC (EtOAc:ethanol:water, 2:1:1): $R_f$=0.15. $^{13}$C-NMR (125 MHz, D$_2$O) δ 177.9, 176.7, 174.5, 174.4, 173.9, 173.4, 100.6, 99.8, 97.8, 97.3, 80.4, 80.0, 77.8, 77.5, 76.1, 75.6, 75.3, 74.9, 70.8, 70.6, 70.2, 69.3, 69.2, 68.8, 67.7, 66.4, 65.8, 53.5, 53.3, 45.4, 39.5, 39.3, 36.5, 35.9, 29.6, 28.7, 28.6, 28.4, 28.3, 26.2, 25.9, 25.5, 24.7, 22.0.

Synthesis of 18d (Scheme 9)

Compound 18d is prepared from compound 17d following general procedure J: The residue is purified by silica gel chromatography (dichloromethane:methanol, 9:1→dichloromethane:methanol:aq. ammonia, 7:2:0.5→5:4:1→methanol:water:aq. Ammonia, 3:1:1) to afford the sulfated tetramer 18d as a foam (7 mg, 1.3 μmol, 74% yield); TLC (EtOAc:ethanol:water, 2:1:1): $R_f$=0.15. $^{13}$C-NMR (125 MHz, D$_2$O) δ 176.8, 175.3, 173.9, 98.6, 97.9, 91.3, 90.9, 75.3, 72.8, 70.4, 69.6, 69.3, 68.8, 68.1, 67.7, 67.2, 66.2, 62.7, 62.5, 54.3, 54.1, 45.3, 39.5, 39.3, 36.5, 35.9, 28.5, 28.4, 28.2, 26.1, 25.9, 25.5, 25.0.

General Procedure A2 (GPA2): Coupling with di-succinimidyl ester.

A solution of di-succinimidyl ester 33a (1 eq) in dry DMF (40 mg per 1 mL of DMF) is added to the solution of glycoside with a 6 carbon linker and an unmasked amino-function (3 eq.) in dry DMF (100 mg per 1 mL of DMF) at room temperature. The reaction mixture is treated with triethylamine (4 eq) and stirred at RT for 1-24 hrs. DMF is removed in vacuo and the residue is purified by flash chromatography on silica gel eluting with EtOAc followed by Ethyl Acetate:MeOH, 9:1→3:2 to give the di-succinimidyl ester.

Synthesis of 34a (Scheme 11)

Compound 34a is prepared from compounds 12b and 33a following general procedure A2: The residue is purified by silica gel chromatography (Ethyl Acetate:MeOH, 9:1→3:2) to give the dimer 34a as a foam (330 mg, 142 µmol, 93% yield); TLC (EtOAc:MeOH, 9:1, v/v): $R_f$=0.55. $^{13}$C-NMR (125 MHz, CDCl$_3$) δ 173.1, 170.5, 169.6, 165.6, 138.1, 137.8, 137.2, 133.6, 129.7, 129.3, 128.9, 128.6, 128.4, 128.3, 128.1, 128.0, 127.9, 127.8, 127.7, 127.6, 127.5, 98.9, 98.3, 80.3, 74.8, 74.7, 73.9, 73.1, 72.3, 70.8, 70.4, 70.3, 70.1, 68.9, 68.8, 67.7, 62.4, 60.3, 52.6, 52.3, 39.3, 38.8, 36.5, 29.5, 29.4, 29.2, 29.0, 28.8, 26.6, 25.3, 22.8, 20.7. HRMS (ESI) calcd for $C_{126}H_{164}N_6O_{35}Na$ (M+Na)$^+$ m/z 2344.1135, found 2344.1116.

Synthesis of 35a (Scheme 11)

Compound 35a is prepared from compound 34a following general procedure G: The residue is purified by silica gel chromatography (EtOAc→EtOAc:MeOH, 9:1→7:1→6:1) to furnish the diol 35a as a foam (209 mg, 93.3 µmol, 92% yield); TLC (EtOAc:MeOH, 4:1, v/v): $R_f$=0.5. $^{13}$C-NMR (125 MHz, CDCl$_3$) δ 173.0, 169.9, 169.7, 169.5, 138.2, 138.1, 137.2, 133.7, 129.8, 129.3, 128.9, 128.7, 128.5, 128.4, 128.1, 128.0, 127.9, 127.7, 127.6, 127.5, 99.1, 98.6, 79.9, 76.9, 75.0, 74.6, 74.5, 73.6, 73.2, 72.4, 70.8, 70.5, 70.2, 68.9, 68.8, 67.7, 61.7, 52.8, 52.4, 39.3, 38.8, 36.5, 29.5, 29.4, 29.2, 29.1, 28.8, 26.6, 26.5, 25.7, 25.6, 22.9. HRMS (ESI) calcd for $C_{122}H_{160}N_6O_{33}Na$ (M+Na)$^+$ m/z 2260.0924, found 2260.0906.

Synthesis of 36a (Scheme 11)

Compound 36a is prepared from compound 35a following general procedure H: The residue is purified by silica gel chromatography (dichloromethane:methanol:aq. ammonia, 7:2:0.5) to furnish the di-sulfate 36a as a foam (138 mg, 57.5 µmol, 91% yield); TLC (dichloromethane:methanol:aq. ammonia, 7:2:0.5): $R_f$=0.15. $^{13}$C-NMR (125 MHz, MeOD) δ 176.2, 176.0, 173.4, 172.5, 171.7, 167.1, 139.9, 139.8, 139.2, 134.6, 131.1, 130.9, 130.1, 129.8, 129.6, 129.5, 129.4, 129.0, 128.9, 128.8, 128.6, 128.5, 100.5, 98.9, 81.4, 79.2, 76.2, 76.0, 75.4, 74.3, 73.7, 72.4, 71.6, 71.2, 69.9, 69.5, 67.2, 54.4, 53.2, 40.5, 40.3, 40.1, 37.2, 37.0, 30.5, 30.4, 30.2, 30.0, 27.8, 27.7, 27.0, 26.9, 22.8. HRMS (ESI, negative mode) calcd for $C_{122}H_{158}N_6O_{39}S_2Na$ (M−2H)$^{2-}$ m/z 1198.5031, found 1198.5035.

Synthesis of 39a (Scheme 11)

Compound 39a is prepared from compound 37a following general procedure H: The residue is purified by silica gel chromatography (dichloromethane:methanol:aq. ammonia, 7:2:0.5) to furnish the tetra-sulfate 39a as a foam (51 mg, 21.9 µmol, 89% yield); TLC (dichloromethane:methanol:aq. ammonia, 7:2:0.5): $R_f$=0.15. $^{13}$C-NMR (125 MHz, MeOD) δ 176.1, 175.9, 174.1, 172.4, 169.2, 140.3, 139.8, 139.3, 129.8, 129.6, 129.4, 129.3, 129.1, 129.0, 128.8, 128.7, 128.5, 100.4, 98.9, 82.0, 79.2, 76.5, 76.1, 74.9, 73.5, 72.5, 71.9, 71.5, 71.3, 71.2, 71.0, 69.0, 68.4, 67.2, 54.7, 40.4, 40.1, 37.1, 30.6, 30.5, 30.4, 30.2, 30.1, 27.9, 27.8, 27.1, 27.0, 23.4. HRMS (ESI, negative mode) calcd for $C_{106}H_{146}N_6O_{43}S_4Na$ (M−2H)$^{2-}$ m/z 1159.9169, found 1159.9193.

Synthesis of 37a (Scheme 11)

Compound 37a is prepared from compound 36a following general procedure I: The residue is purified by silica gel chromatography (dichloromethane:methanol, 9:1→dichloromethane:methanol:aq. ammonia, 7:2:0.5→5:4:1) to afford the tetramer 37a as a foam (94 mg, 43.4 µmol, 87% yield); TLC (acetonitrile:water:aq. ammonia, 3:1:1): $R_f$=0.15. $^{13}$C-NMR (125 MHz, MeOD) δ 176.1, 175.5, 173.1, 172.4, 140.2, 139.8, 139.5, 139.1, 129.5, 129.4, 129.3, 129.2, 128.9, 128.8, 128.7, 128.6, 102.5, 97.2, 82.3, 79.1, 76.3, 76.0, 74.9, 73.4, 72.7, 71.8, 71.6, 71.3, 71.2, 69.2, 67.9, 67.2, 54.5, 40.4, 40.0, 37.2, 30.7, 30.5, 30.4, 30.2, 30.1, 27.8, 27.1, 27.0, 23.1. HRMS (ESI, negative mode) calcd for $C_{106}H_{146}N_6O_{37}S_2Na$ (M−2H)$^{2-}$ m/z 1079.9601, found 1079.9614.

Synthesis of 38a (Scheme 11)

Compound 38a is prepared from compound 37a following general procedure J: The residue is purified by silica gel chromatography (acetonitrile:water:aq. ammonia, 6:2:1) to furnish the tetramer 38a as a foam (38 mg, 23.4 µmol, 95% yield); TLC (acetonitrile:water:aq. ammonia, 6:2:1): $R_f$=0.3. $^{13}$C-NMR (125 MHz, D$_2$O) δ 176.8, 174.9, 174.3, 172.2, 100.7, 94.5, 73.7, 71.0, 70.4, 69.6, 69.5, 69.4, 69.2, 68.8, 68.5, 68.4, 66.5, 53.4, 39.3, 39.0, 35.8, 28.5, 28.4, 28.3, 28.1, 25.9, 25.8, 25.4, 25.0, 22.0. HRMS (ESI, negative mode) calcd for $C_{64}H_{110}N_6O_{37}S_2Na$ (M−2H)$^{2-}$ m/z 1641.6250, found 1641.6233.

Synthesis of 40a (Scheme 11)

Compound 40a is prepared from compound 39a following general procedure J: The residue is purified by silica gel chromatography (acetonitrile:water:aq. ammonia, 6:2:1) to furnish the dimer 40a as a foam (29 mg, 16.3 µmol, 84% yield); TLC (acetonitrile:water:aq. ammonia, 6:2:1): $R_f$=0.32. $^{13}$C-NMR (125 MHz, D$_2$O) δ 176.0, 174.3, 173.9, 171.3, 97.5, 92.9, 72.7, 70.3, 70.0, 69.5, 69.2, 68.7, 68.6, 68.4, 67.6, 65.9, 65.7, 62.7, 60.3, 52.4, 38.4, 38.1, 34.9, 27.5, 27.4, 27.1, 25.1, 24.9, 24.5, 24.1, 21.4.

Example 2: Determination of BACE-1 Inhibition by In Vitro FRET Peptide Cleavage Assay The ability of compounds of the invention to inhibit BACE-1 cleavage of APP is assessed using a fluorescent resonance energy transfer (FRET) peptide cleavage assay employing the FRET peptide HiLyte 488-Glu-Val-Asn-Leu-Asp-Ala-Glu-Phe-Lys(QXL520)-OH (Anaspec, Inc., CA, USA; Cat no. 60604-01). When intact, the amino terminal fluorophore is quenched, but upon enzymatic cleavage the fluorophore is released from quencher and fluoresces (520 nm). Assays are performed in triplicate in 96 well black plates (20 mM sodium acetate, 0.1% Triton-X-100, pH 4.5; 2.2 ng peptide per well and 25 ng/well of recombinant human BACE-1 (R & D Systems Cat no. 931-AS). The appropriate controls for enzyme activity (substrate plus enzyme, and substrate only) are employed and plates are incubated (1 h, 25° C., with activity stopped with 2.5 M sodium acetate). Compounds of the invention are added in the concentration range from 100-0.0001 µg/mL. Fluorescence 480ex/520em is measured on a Polarstar plate reader (BMG LabTechnologies, UK) and data are analysed by plotting $\log_{10}$ concentration of compound against percent inhibition and fitting a logistic dose response sigmoidal curve using OriginPro 8 (OriginLabs, Mass, USA).

TABLE 1

Inhibition of BACE-1 by Compounds of the Invention

| Compound | Structure | IC50 μg/mL |
|---|---|---|
| Heparin | | 0.002 |
| Monomer-sulfated GlcNAc | | >>50 |
| 18e | 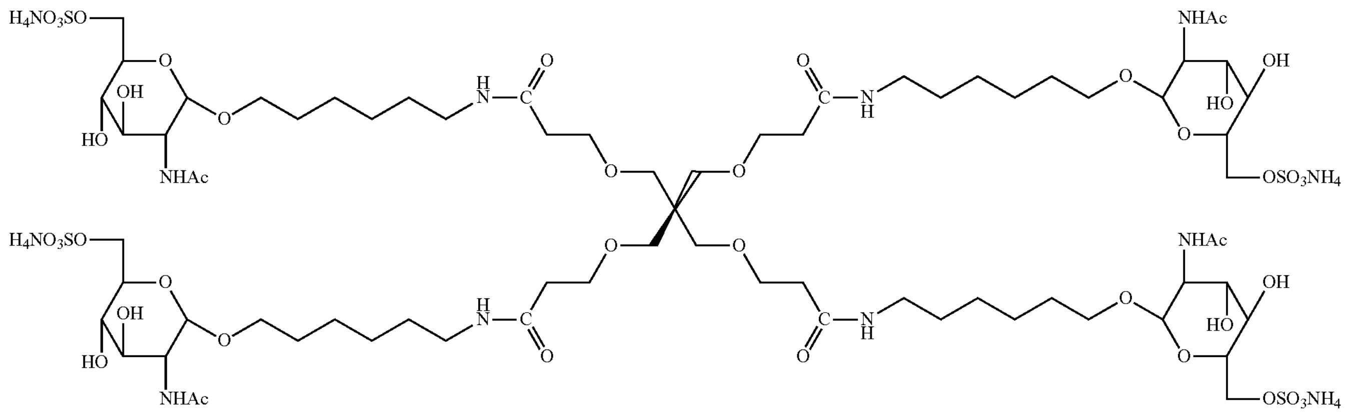 | ~50 |
| 18h | 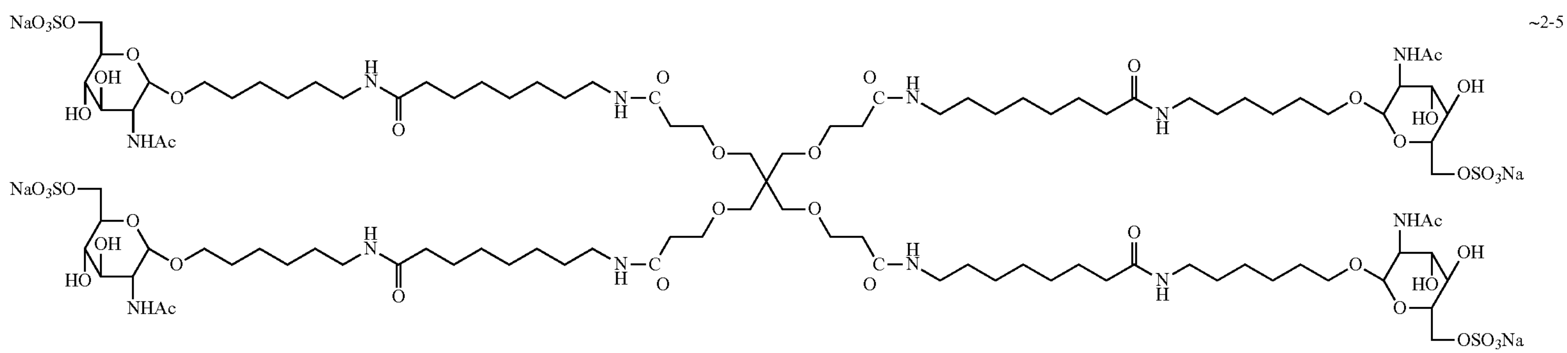 | ~2-5 |

TABLE 1-continued

Inhibition of BACE-1 by Compounds of the Invention

| Compound | Structure | IC50 µg/mL |
|---|---|---|
| 18b | 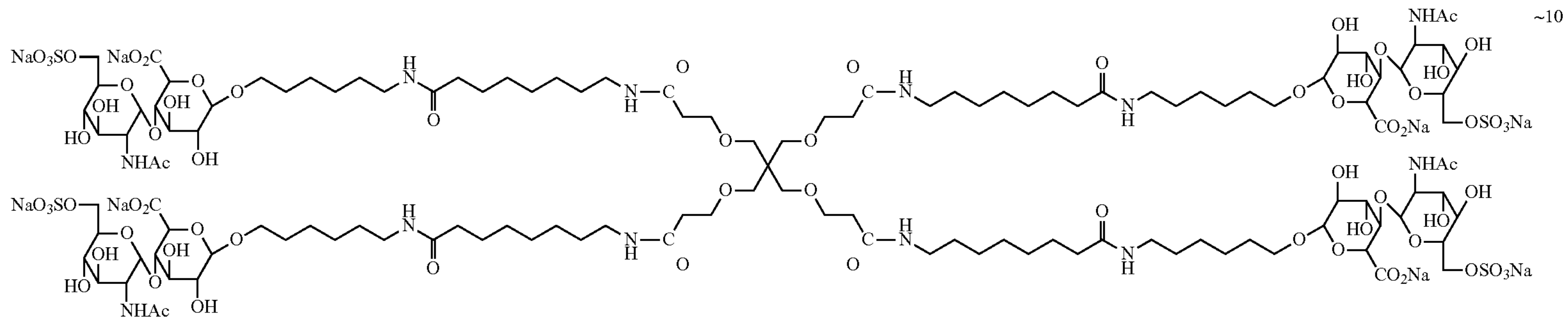 | ~10 |
| 20a | 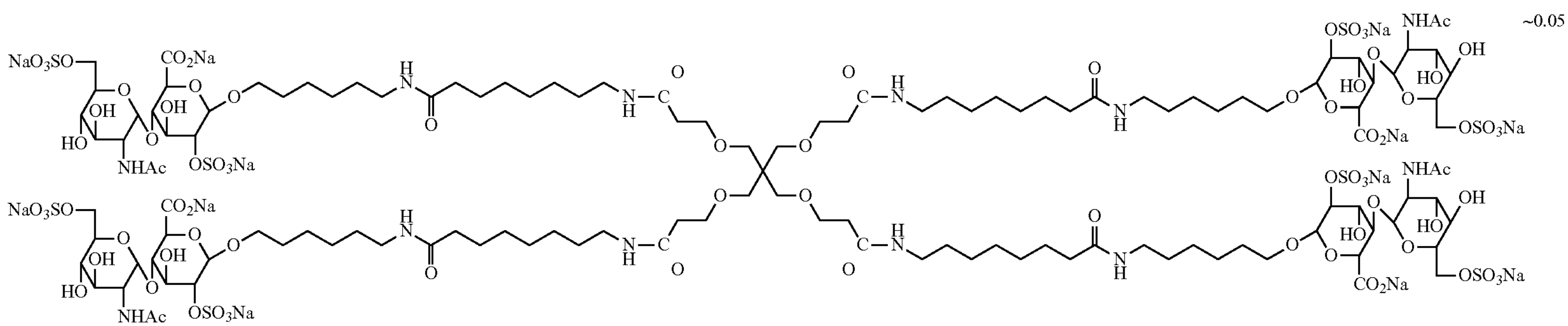 | ~0.05 |
| 20b | 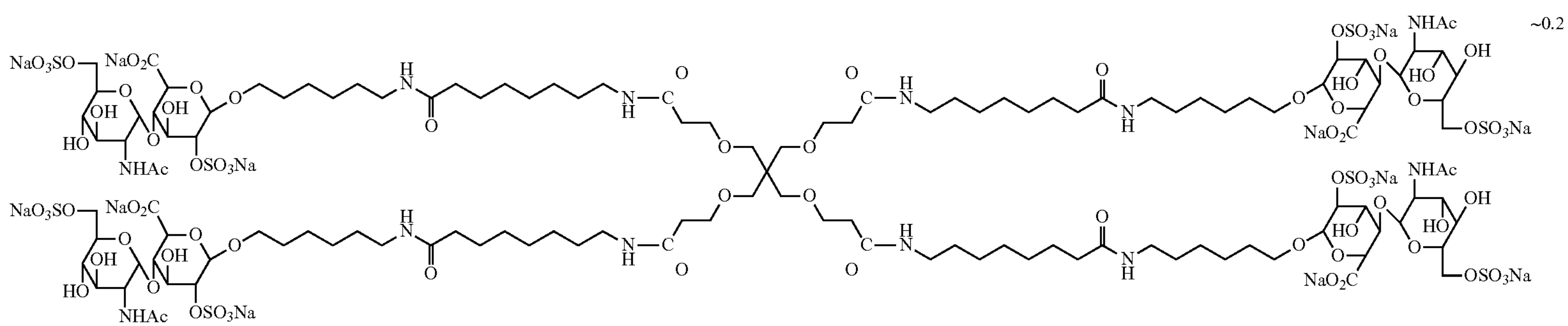 | ~0.2 |

TABLE 1-continued

Inhibition of BACE-1 by Compounds of the Invention

| Compound | Structure | IC50 µg/mL |
|---|---|---|
| 22a | 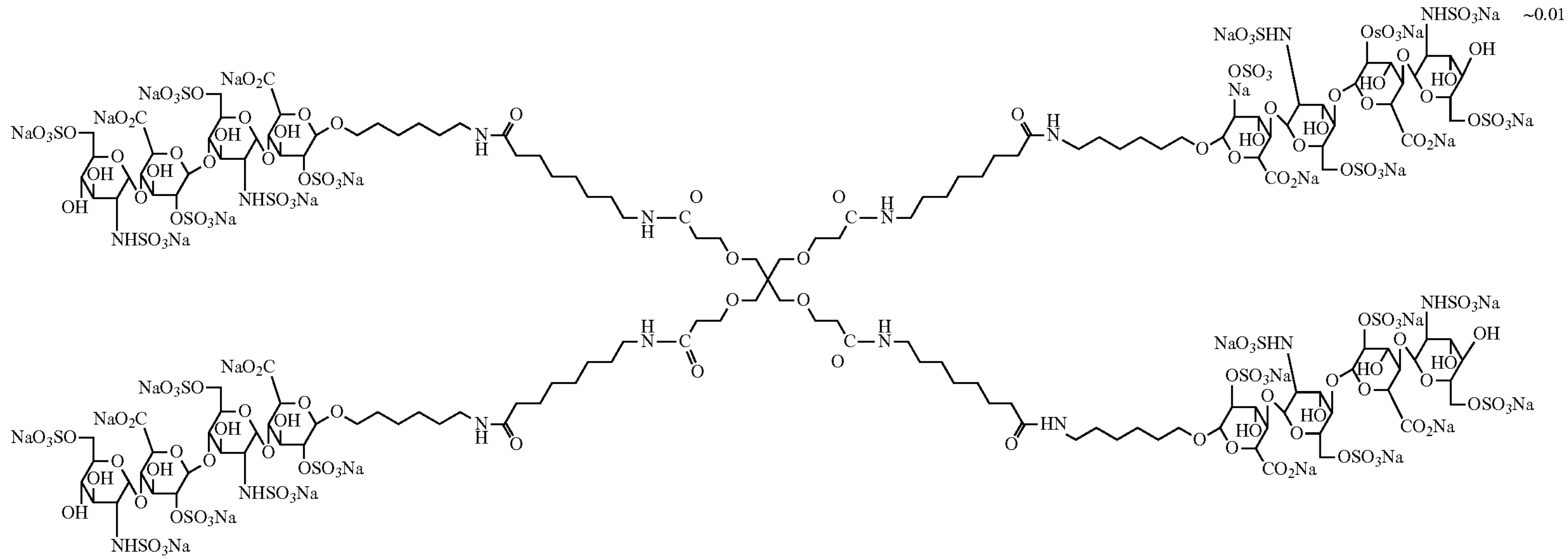 | ~0.01 |

TABLE 1-continued
Inhibition of BACE-1 by Compounds of the Invention
| Compound | Structure | IC50 μg/mL |
|---|---|---|
| 18c | 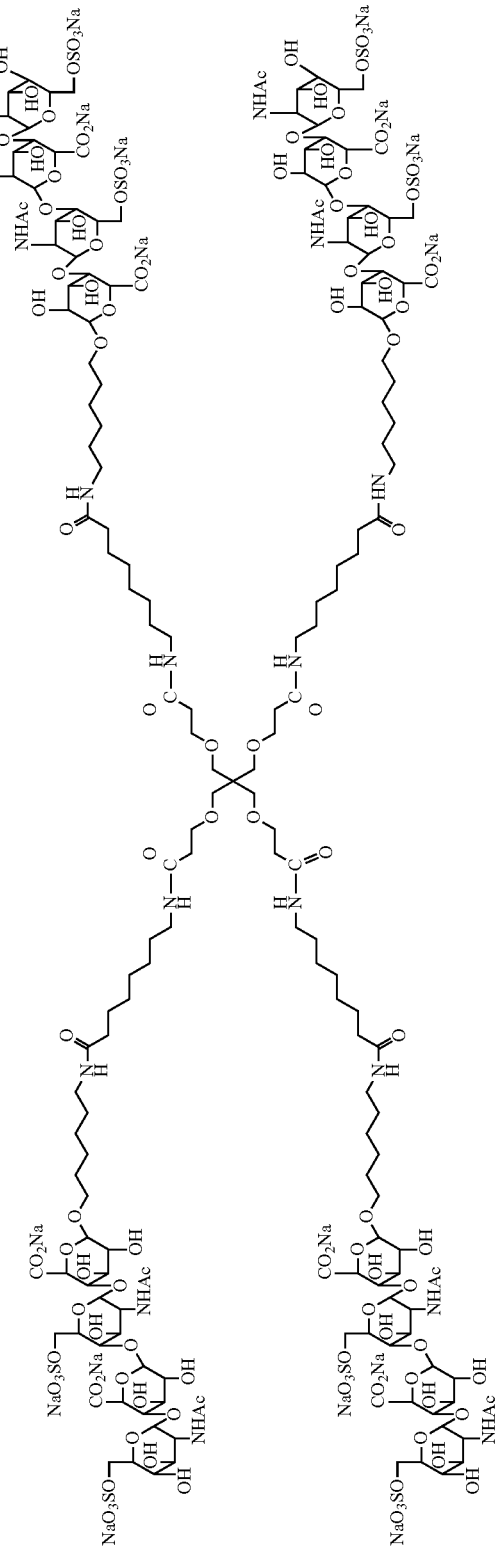 | ~0.2 |

TABLE 1-continued

Inhibition of BACE-1 by Compounds of the Invention

| Compound | Structure | IC50 µg/mL |
|---|---|---|
| 20c | 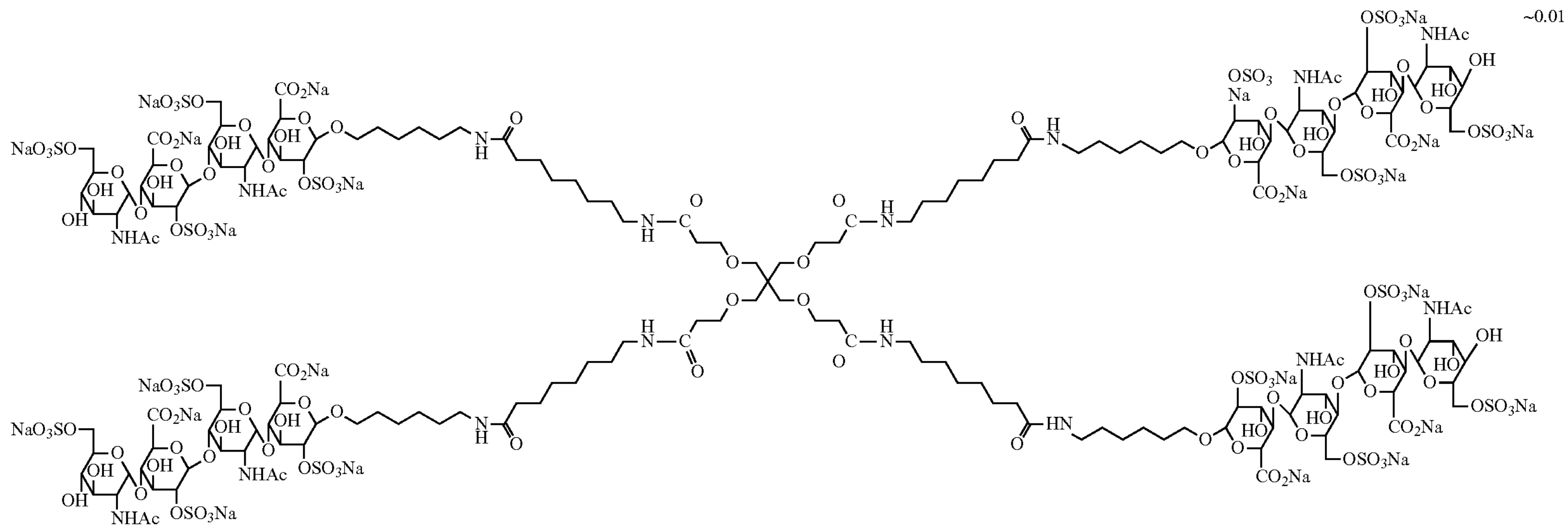 | ~0.01 |
| 18a | 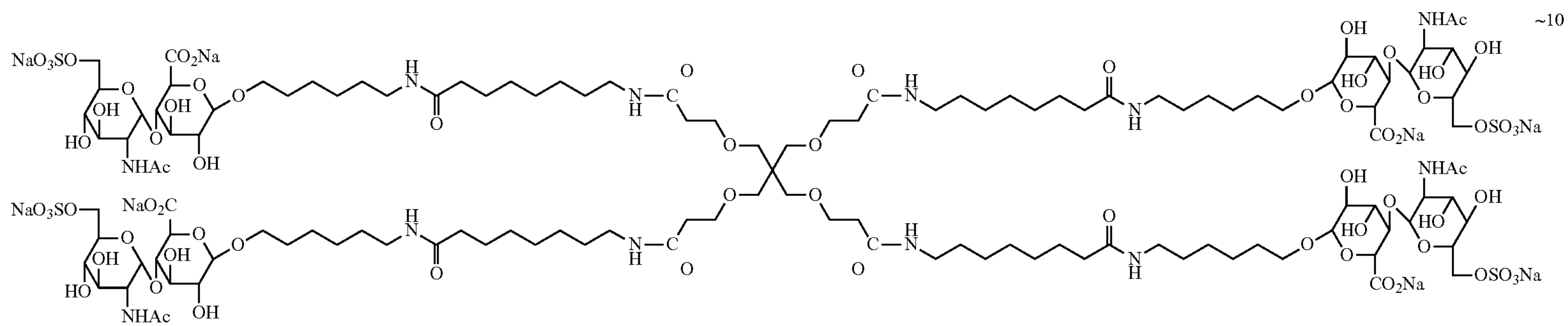 | ~10 |

Example 3: Factor Xa Anticoagulant Assay Protocol

The compound of the invention, standard or control (5 µl), is pipetted in assay buffer (0.9% sodium chloride) into a 96 well plate (Costar 3595) and 19 µl of 0.03 IU/ml human Antithrombin III (American Diagnostica Inc., product No. 433) in assay buffer is added to each well. The plate is incubated for two minutes at 37° C. 19 µl of bovine Factor Xa (14 nkat/ml; Thermo Scientific; product No. 32521) in assay buffer is added to each well and incubated for one minute at 37° C. 19 µl of 2.5 mM chromogenic substrate (American Diagnostica Inc. Spectrozyme FXa Product No 222L) in assay buffer is added to each well and incubated for 2 hours at 37° C., followed by addition of 5 µl of 30% acetic acid to each well. Absorbance at 405 nm is read on a multiplate reader.

All compounds are tested in the dose range 0.004 to 50 µg/ml and none display any measurable ability to accelerate antithrombin-III mediated inactivation of Factor Xa, as measured by cleavage of a peptide substrate.

Example 4: Brain Slice Assay

Figure 1B:
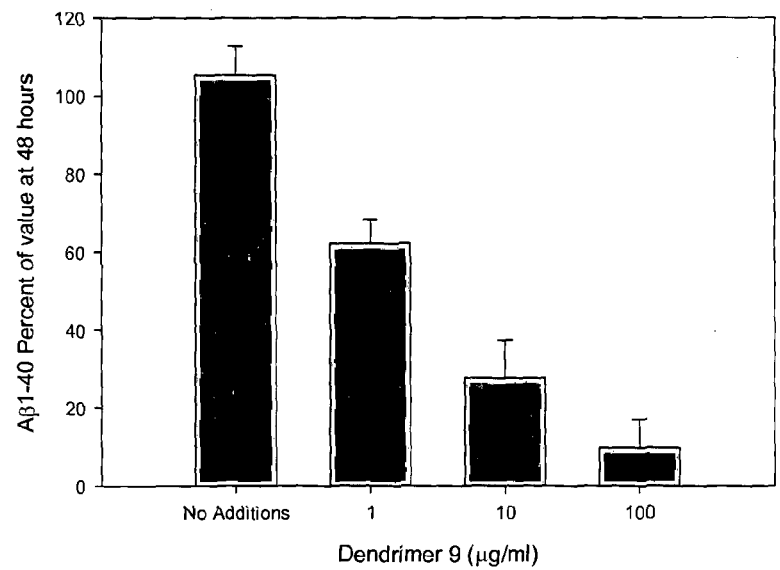
FIG. 1b shows the percentage of Aβ1-40 present in brain slice assays, with addition of various concentrations of Compound 18a (called "Dendrimer 9" in FIG. 1b), in accordance with the method described in Example 3.

Transgenic TG2576 mice expressing the human SWE-mutated amyloid precursor protein are sacrificed by cervical dislocation at 8-10 months of age. The brain is removed and 400 µm coronal sections are obtained using a manual tissue chopper (Leica Microsystems). Slices are washed briefly in HBSS (Hank balanced salt solution, Life Technologies) supplemented with 4.5 mg/ml glucose (Sigma-Aldrich) and 3.75 µg/ml amphotericin B (Sigma-Aldrich) and transferred to a transwell plate (Costar 3396 HTS 24 well transwell plate with 0.4 µm polycarbonate membrane) in 1 ml of 50% MEM (minimal essential medium, Life Technologies) supplemented with 25% heat-inactivated horse serum (Life Technologies), 25% HBSS, 0.5 mM glutamine (Life Technologies), 4.5 mg/ml glucose and 3.75 µg/ml amphotericin B. Slices are incubated 48 hours at 37 C, 5% CO$_2$. After 48 hours the medium is collected from each well and reserved. 1 ml of fresh medium with or without a compound of the invention or NAc-LMWH (at concentrations of 1, 10 and 100 µg/ml) is added to each well. Slices are incubated a further 48 hours and the medium is collected and reserved. Soluble Aµ1-40 in the medium is quantified using a SensoLyte™ Anti-Human βeta-Amyloid (1-40) ELISA kit (Anaspec) in accordance with the manufacturer's instructions. Briefly, medium is diluted 1:4 in Sample Dilution Buffer and 100 µl is added to the appropriate wells. Detection Antibody (50 µl) is added to each well and the plate is incubated overnight at 4° C. in the dark. Wells are washed 7× with 350 µl of Wash Buffer with 30 seconds of soaking time for each wash. TMB Color Substrate Solution (100 µl) is added to each well and the plate is incubated at room temperature in the dark for 15 minutes. The color reaction is stopped with 50 µl of Stop Solution and the plate is read at 450 nm using an absorbance plate reader (Thermo Multiskan EX). The amount of Aβ-40 is quantified by reference to a standard curve of Aβ1-40 (supplied in the SensoLyte™ kit). Data are expressed as a percentage of the Aβ1-40 present at 96 hours vs. 48 hours for each condition. Results are shown in FIGS. 1a and 1b.

Although the invention has been described by way of example, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The invention relates to compounds that are inhibitors of BACE-1. The compounds are therefore indicated for the treatment or prevention of diseases in which the inhibition of BACE-1 is desirable, e.g. neurodegenerative disorders such as senile dementia, pre-senile dementia, multi-infarct dementia or Alzheimer's disease.

The invention claimed is:

1. A compound of formula (I)

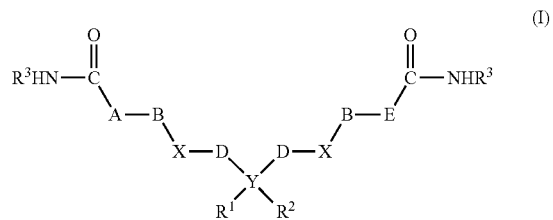

wherein:

R$^3$ is a radical of formula (iv) or a radical of formula (iv)(a)

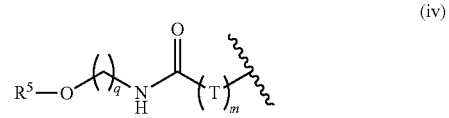

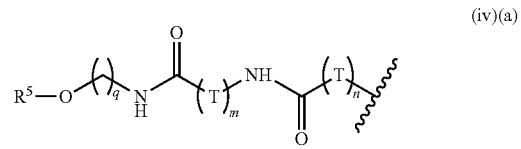

R$^5$ is a radical of formula (v), (vi), (vii), (viii) or (ix):

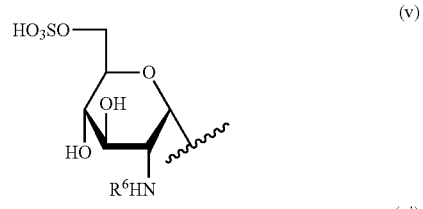

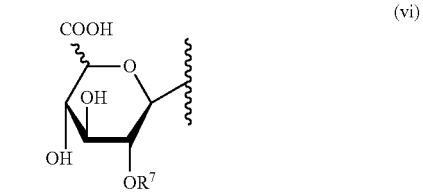

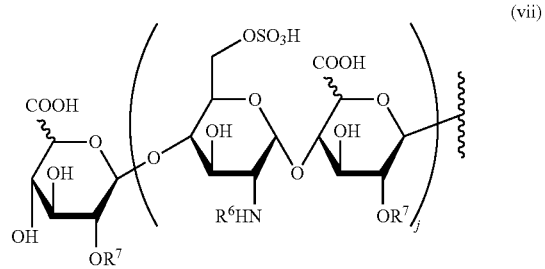

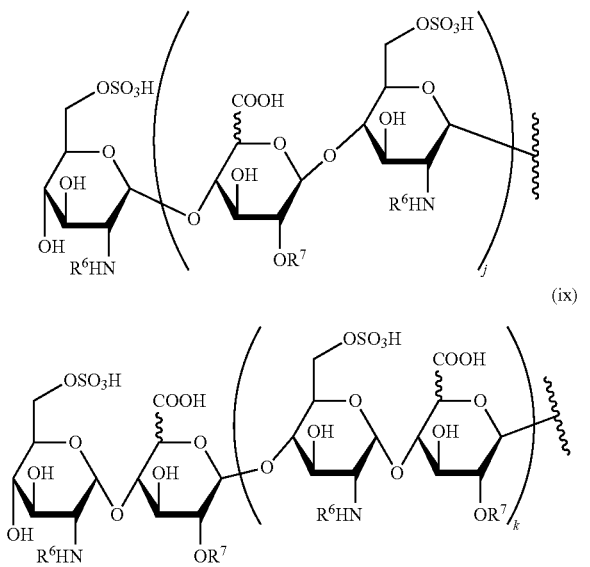

(viii)

(ix)

j is an integer from 1 to 6;
k is an integer from 0 to 5;
$R^6$ is H, $SO_3H$, an acyl group which is optionally radiolabelled, or $R^6$ is $C(=O)R^8$ where $R^8$ is aryl or aralkyl;
$R^7$ is H or $SO_3H$;
and:
Y is O;
B is O;
$R^1$ and $R^2$ are absent; and
either A, E, D and X are all $CH_2$; or A, D and X are all $CH_2$ and E is $(CH_2CH_2O)_t{}^\#CH_2$
wherein $^\#$ indicates a point of attachment of E to its adjacent carbonyl group;
t is an integer from 1 to 10;
or:
Y is C;
$R^1$ and $R^2$ are both H; and
A, E, B and D are $CH_2$ and X is O;
or:
Y is C;
A is $(CH_2)_u$
$R^1$ and $R^2$ are both H;
B, X, D and E are all absent; and
u is an integer from 1 to 10;
or:
Y is C;
X is O;
B is $(CH_2)_p$;
A, E and D are all $CH_2$;
$R^1$ is H, NHZ or $C_{1-6}$alkyl and $R^2$ is a radical of formula (i), a radical of formula (ii) or a radical of formula (ii)(a)

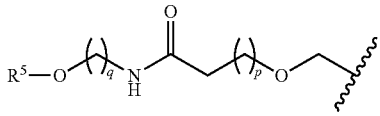

(i)

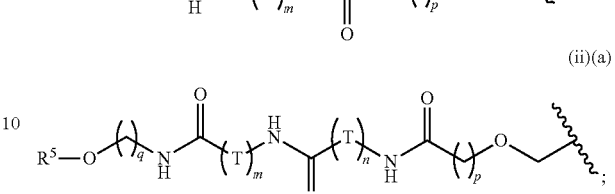

(ii)

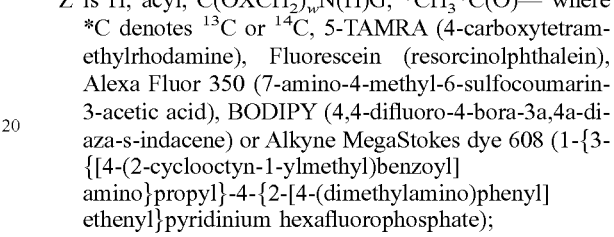

(ii)(a)

Z is H, acyl, $C(OXCH_2)_wN(H)G$, $*CH_3*C(O)—$ where $*C$ denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate);
w is an integer from 1 to 11; and
G is H, acyl, Boc (t-butoxycarbonyl), Troc (2,2,2-trichloroethyloxycarbonyl), Fmoc (9-fluorenylmethoxycarbonyl), Cbz (benzyloxycarbonyl), $*CH_3*C(O)—$ where $*C$ denotes $^{13}C$ or $^{14}C$, 5-TAMRA (4-carboxytetramethylrhodamine), Fluorescein (resorcinolphthalein), Alexa Fluor 350 (7-amino-4-methyl-6-sulfocoumarin-3-acetic acid), BODIPY (4,4-difluoro-4-bora-3a,4a-diaza-s-indacene) or Alkyne MegaStokes dye 608 (1-{3-{[4-(2-cyclooctyn-1-ylmethyl)benzoyl]amino}propyl}-4-{2-[4-(dimethylamino)phenyl]ethenyl}pyridinium hexafluorophosphate);
or:
Y is C;
X is O;
B is $(CH_2)_p$;
A, E and D are all $CH_2$; and
$R^1$ and $R^2$, both the same, are a radical of formula (i), a radical of formula (ii) or a radical of formula (ii)(a)

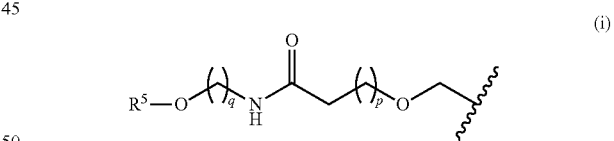

(i)

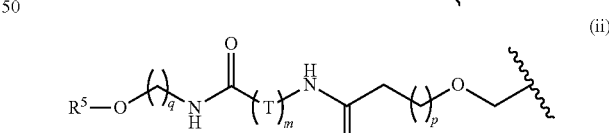

(ii)

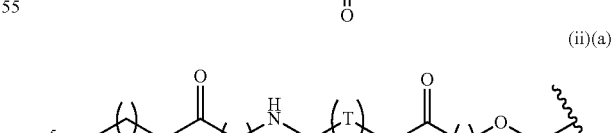

(ii)(a)

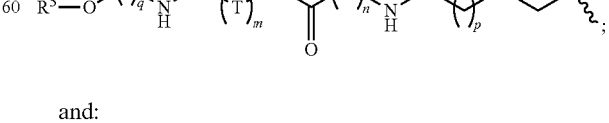

and:
each T is independently selected from the group consisting of $(CH_2CH_2O)_xCH_2CH_2$ and $CH_2$, wherein each T is $CH_2$ or at least one T is $(CH_2CH_2O)_xCH_2CH_2$;

each x is independently an integer from 1 to 12;

n is an integer from 1 to 11, provided that when T is $(CH_2CH_2O)_xCH_2CH_2$ then n is 1;

q is an integer from 1 to 11;

m is an integer from 1 to 11, provided that when T is $(CH_2CH_2O)_xCH_2CH_2$ then m is 1; and p is an integer from 1 to 5;

or a pharmaceutically acceptable salt thereof, or a prodrug thereof.

2. The compound of claim 1, wherein each T is $CH_2$.

3. The compound of claim 1, wherein $R^3$ is a radical of formula (iv).

4. The compound of claim 1, wherein $R^1$ and $R^2$, both the same, are a radical of formula (i) or a radical of formula (ii), or wherein $R^1$ is H, NHZ or $C_{1-6}$alkyl and $R^2$ is a radical of formula (i) or a radical of formula (ii).

5. The compound of claim 1, wherein at least one T is $(CH_2CH_2O)_xCH_2CH_2$.

6. The compound of claim 1, wherein $R^5$ is a radical of formula (vi), (vii), (viii) or (ix) wherein radical (vi), (vii), (viii) or (ix) contains no ido-form saccharide units.

7. The compound of claim 1, wherein $R^5$ is a radical of formula (vi), (vii), (viii) or (ix) wherein radical (vi), (vii), (viii) or (ix) contains no gluco-form saccharide units.

8. The compound of claim 1, wherein $R^5$ is a radical of formula (vi), (vii), (viii) or (ix) wherein radical (vi), (vii), (viii) or (ix) comprises a mixture of gluco-form and ido-form saccharide units.

9. The compound of claim 1, wherein $R^1$ and $R^2$, both the same, are a radical of formula (ii)(a)

(ii)(a)

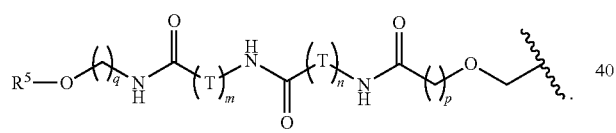

10. The compound of claim 1, wherein Y is O; B is O; $R^1$ and $R^2$ are absent; and either A, E, D and X are all $CH_2$ or A, D and X are all $CH_2$ and E is $(CH_2CH_2O)_tCH_2$; and t is an integer from 1 to 10.

11. The compound of claim 1, wherein Y is C; $R^1$ and $R^2$ are both H; A, E, B and D are $CH_2$ and X is O.

12. The compound of claim 1, wherein Y is C; A is $(CH_2)_u$; $R^1$ and $R^2$ are both H; B, X, D and E are all absent; and u is an integer from 1 to 10.

13. The compound of claim 1, wherein:

Y is C; X is O; A, E and D are all $CH_2$, B is $(CH_2)_p$;

$R^1$ is H, NHZ or $C_{1-6}$alkyl;

$R^2$ is a radical of formula (i), a radical of formula (ii) or a radical of formula (ii)(a)

(i)

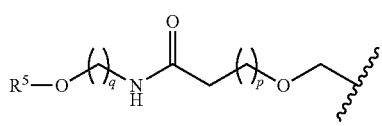

(ii)

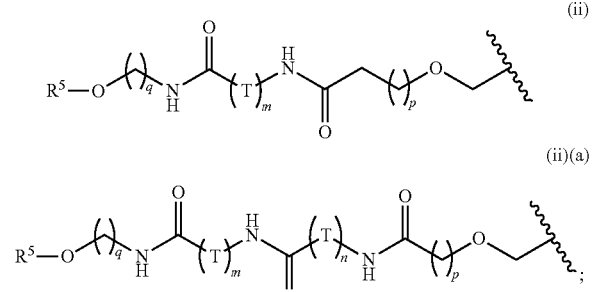

(ii)(a)

Z is H, acyl, $CO(CH_2)_wN(H)G$, *$CH_3$*CO— where *C denotes $^{13}C$ or $^{14}C$, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate;

w is an integer from 1 to 11;

G is H, acyl, t-butoxycarbonyl, 2,2,2-trichloroethyloxycarbonyl, 9-fluorenylmethoxycarbonyl, carboxybenzyl, *$CH_3$*CO— where *C denotes $^{13}C$ or $^{14}C$, 4-carboxytetramethylrhodamine, resorcinolphthalein, 7-amino-4-methyl-6-sulfocoumarin-3-acetic acid, 4,4-difluoro-4-bora-3a,4a-diaza-s-indacene or 1-{3-{[4-(2-cyclooctyn-1-ylmethyl)benzoyl]amino}propyl}-4-{2-[4-(dimethylamino)phenyl]ethenyl}pyridinium hexafluorophosphate.

14. The compound of claim 1, wherein Y is C; X is O; A, E and D are all $CH_2$; B is $(CH_2)_p$;

$R^1$ and $R^2$, both the same, are a radical of formula (i), a radical of formula (ii) or a radical of formula (ii)(a)

(i)

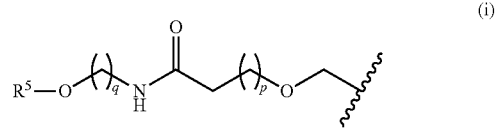

(ii)

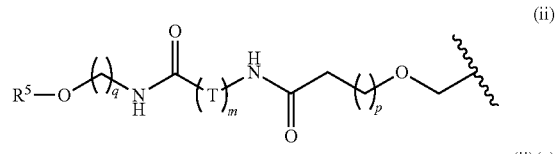

(ii)(a)

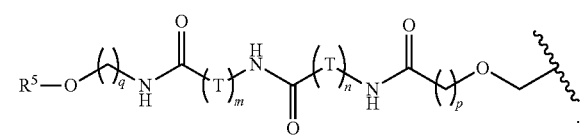

15. The compound of claim 1, wherein $R^5$ is a radical of formula (viii) wherein j is 1.

16. The compound of claim 1, wherein $R^5$ is a radical of formula (ix) wherein k is 0 or 1.

17. The compound of claim 1, selected from the group consisting of:

191 192
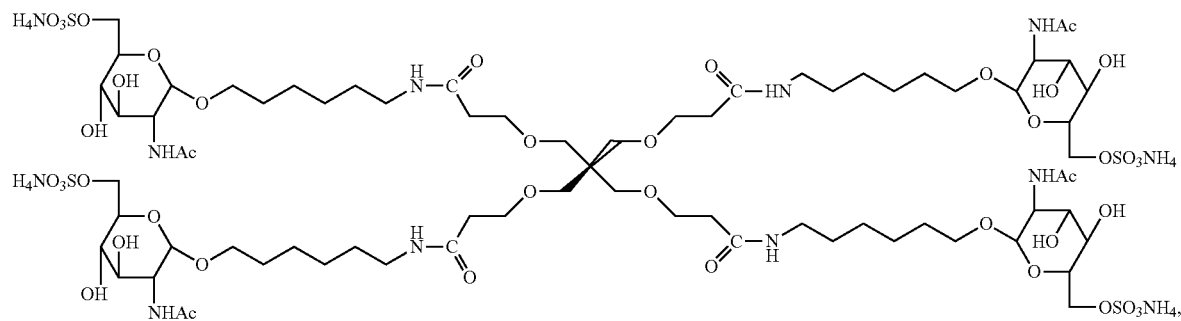
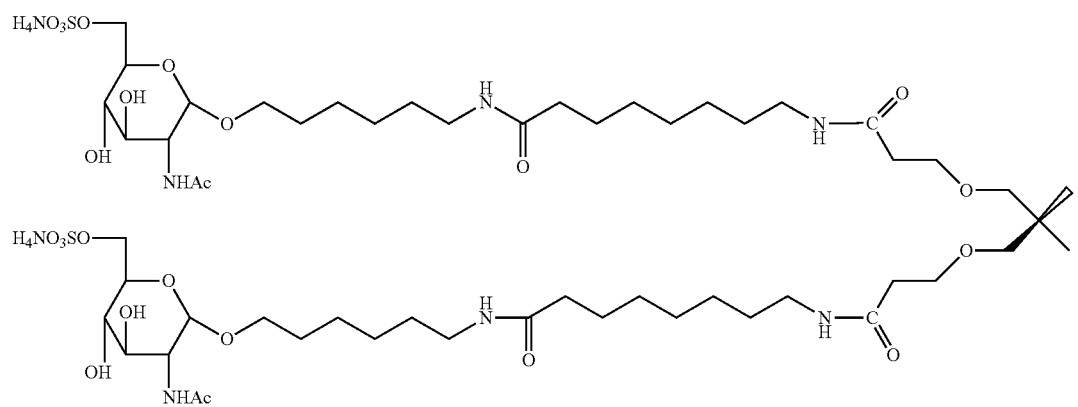
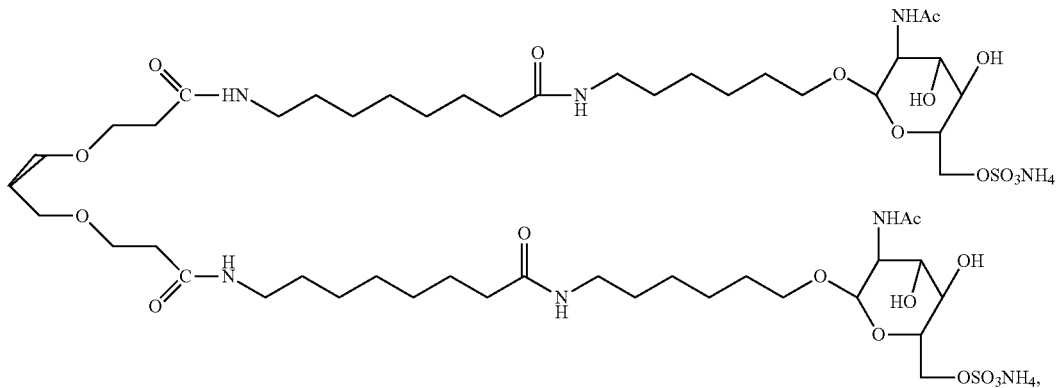
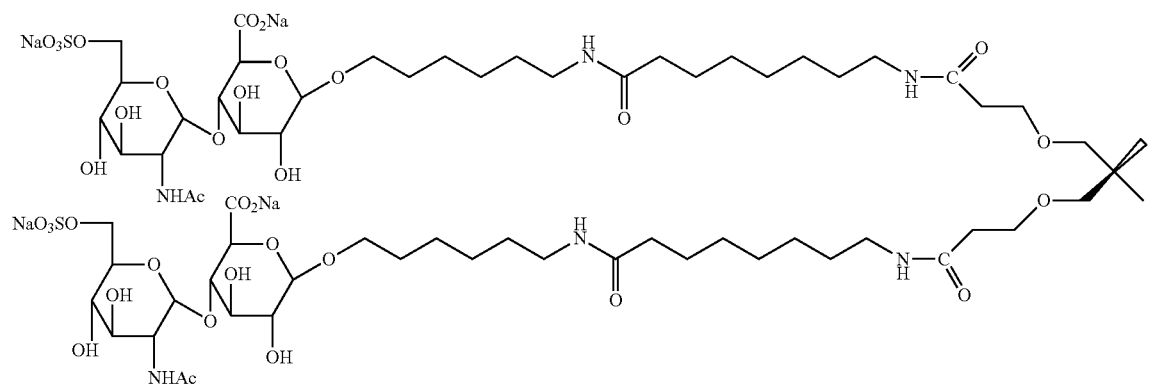

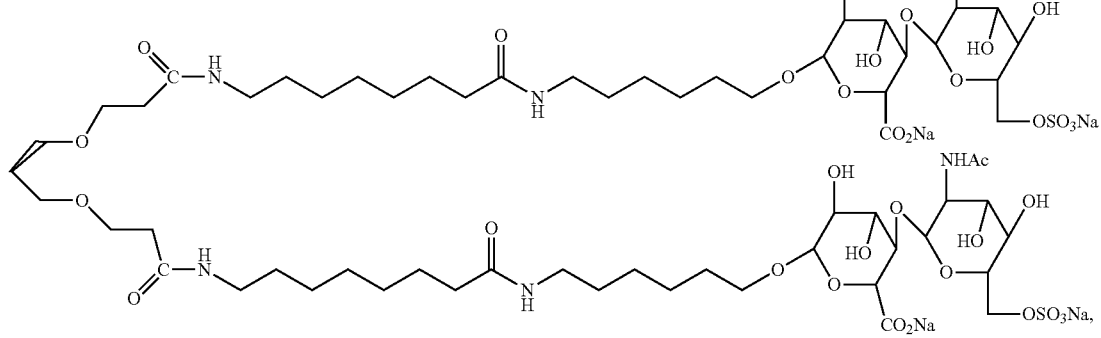
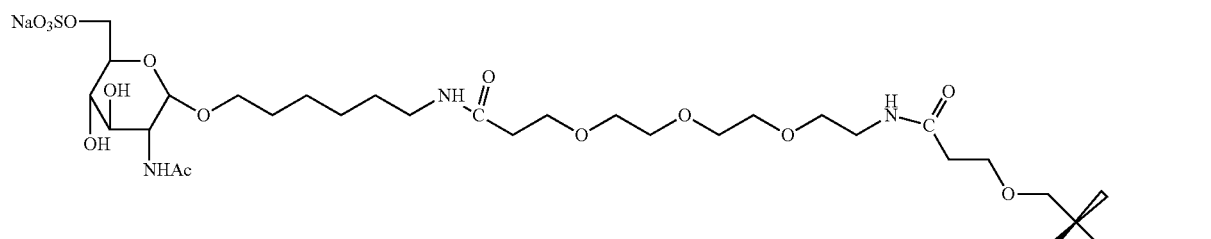
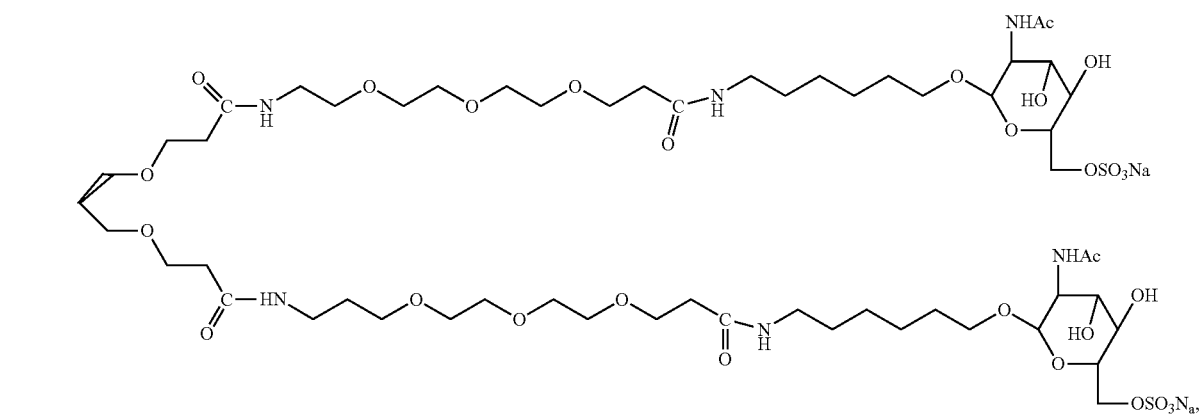
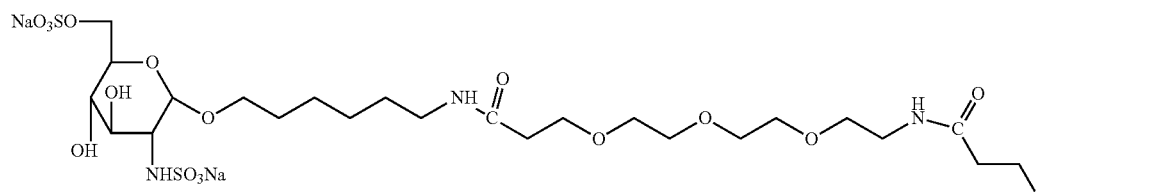
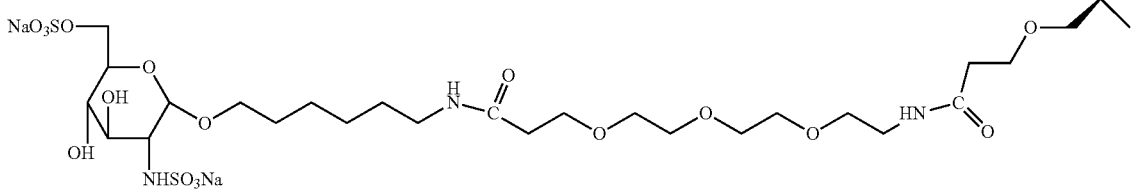

-continued
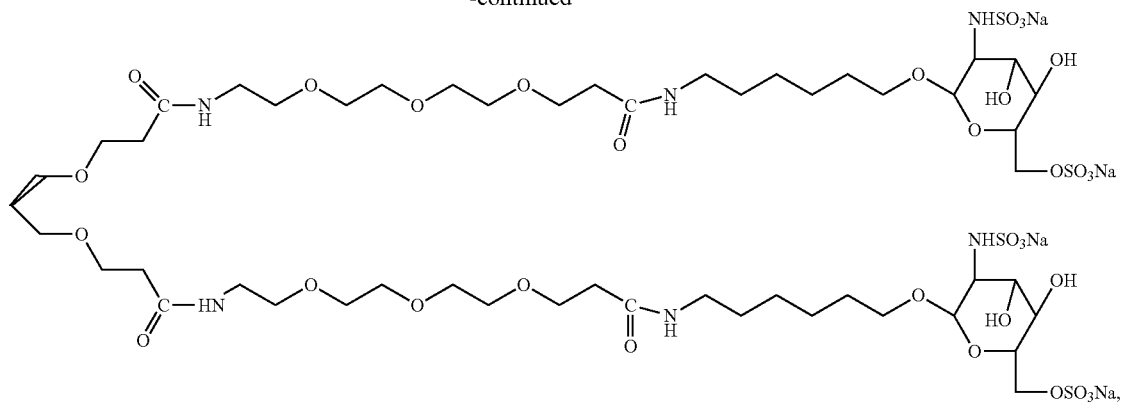
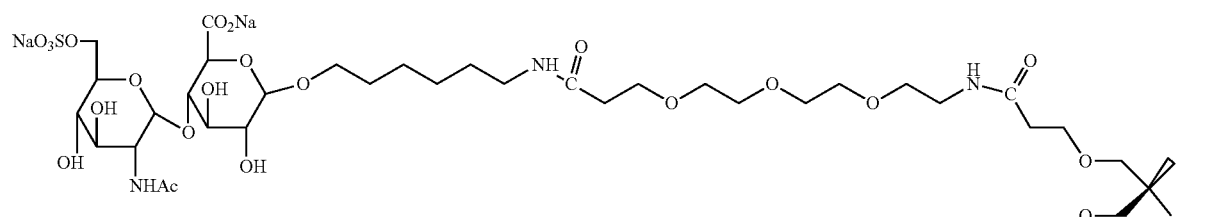
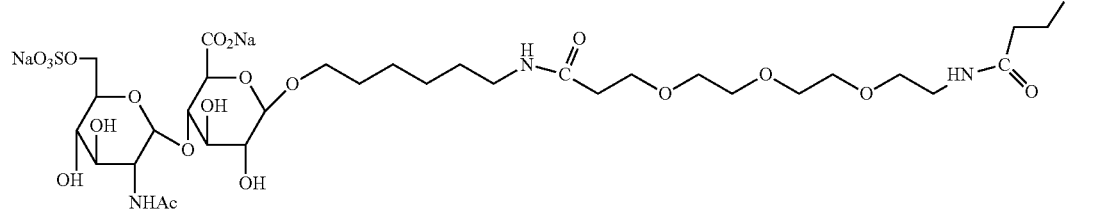
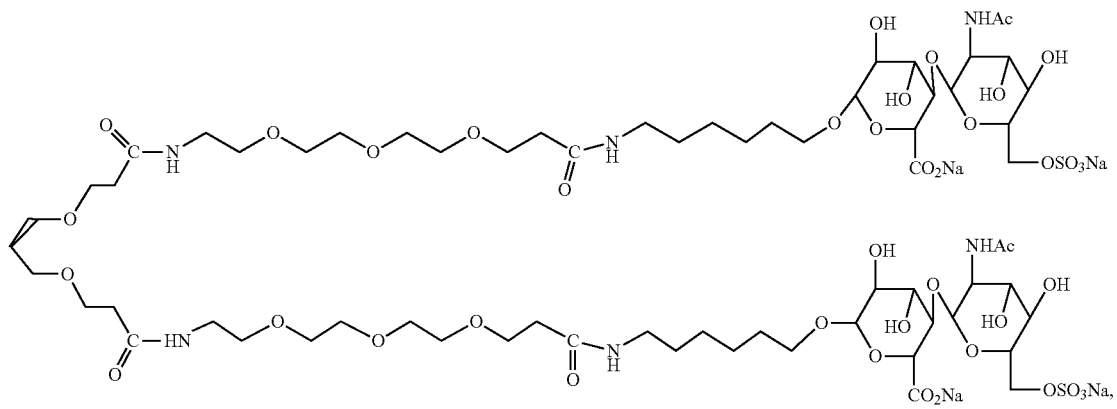
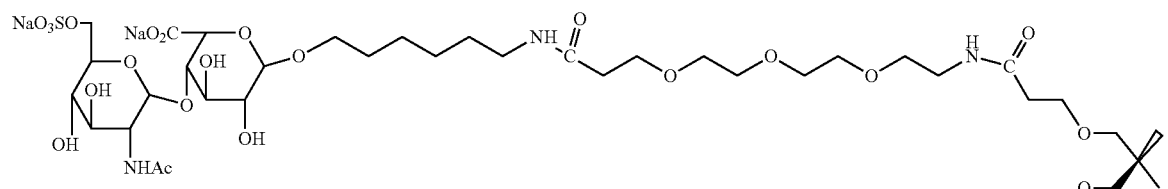
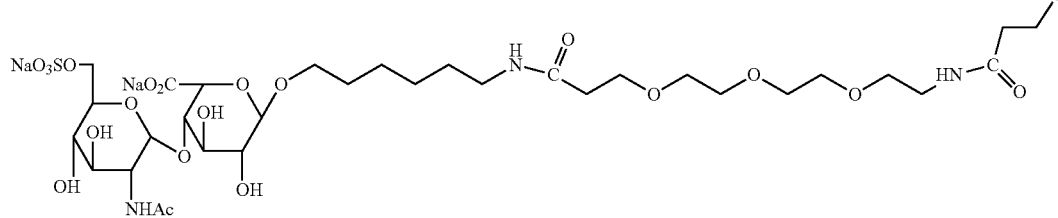

197 198
-continued
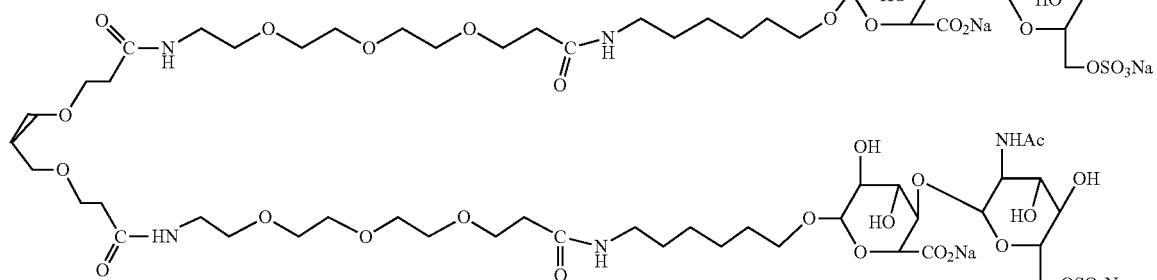
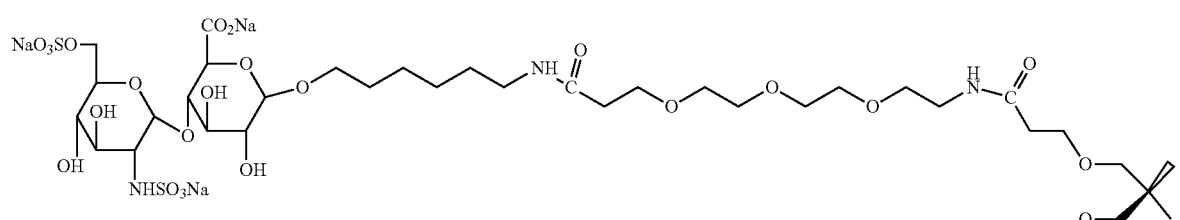
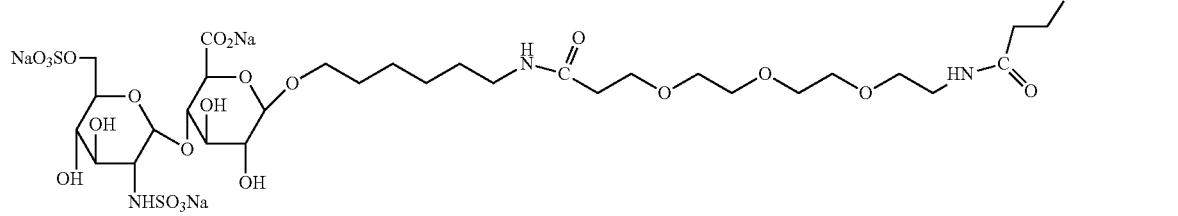
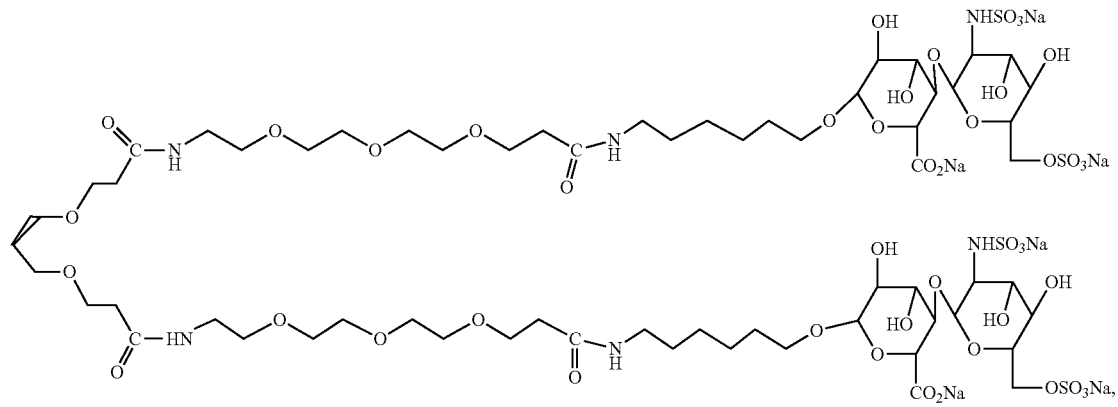
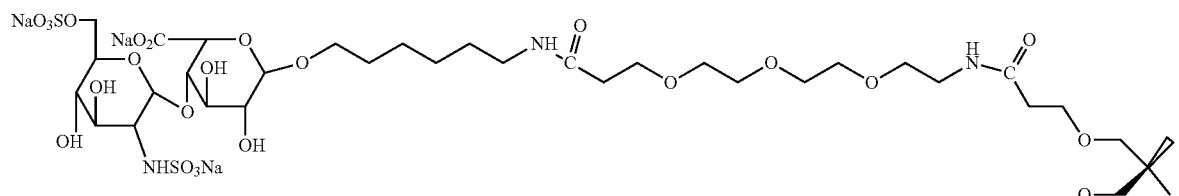
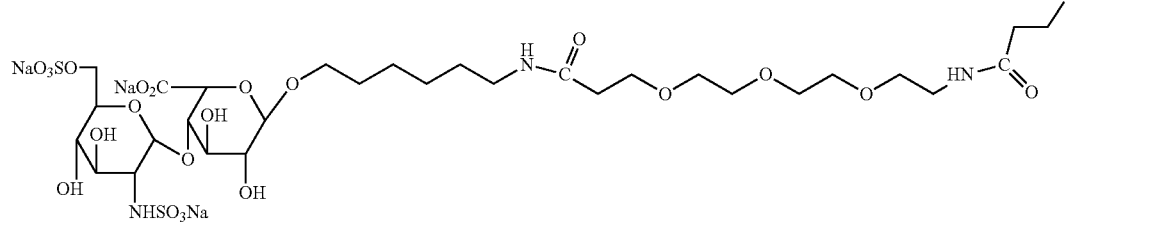

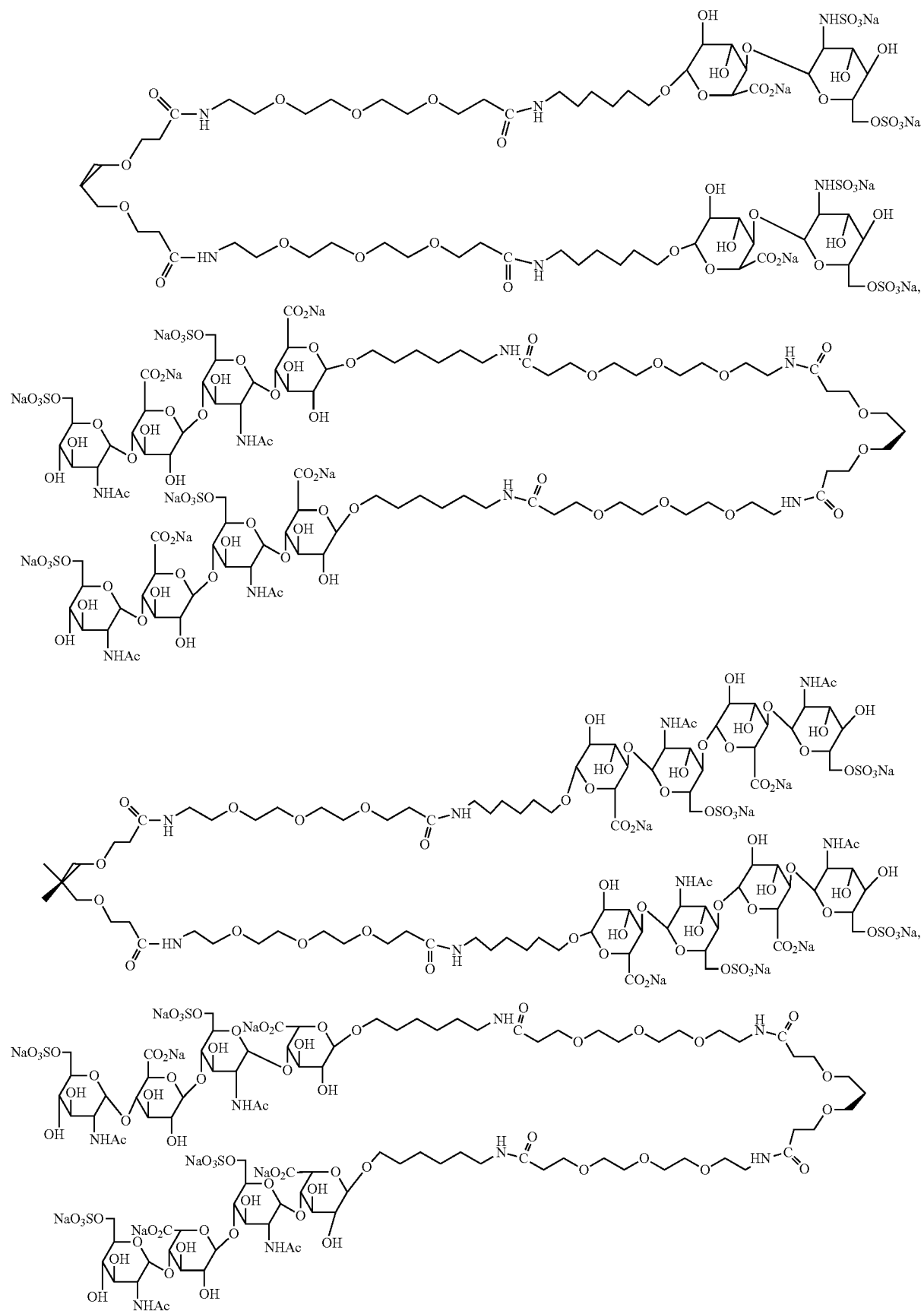

201 202
-continued
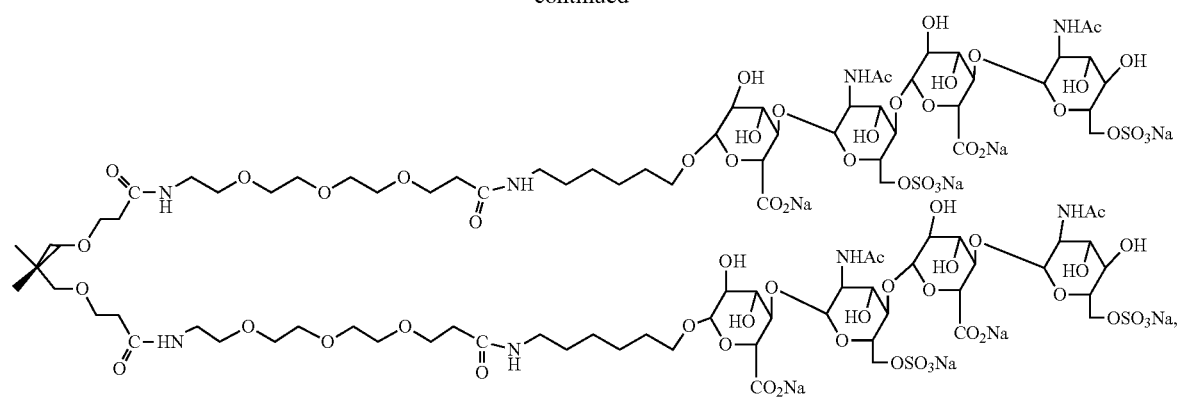
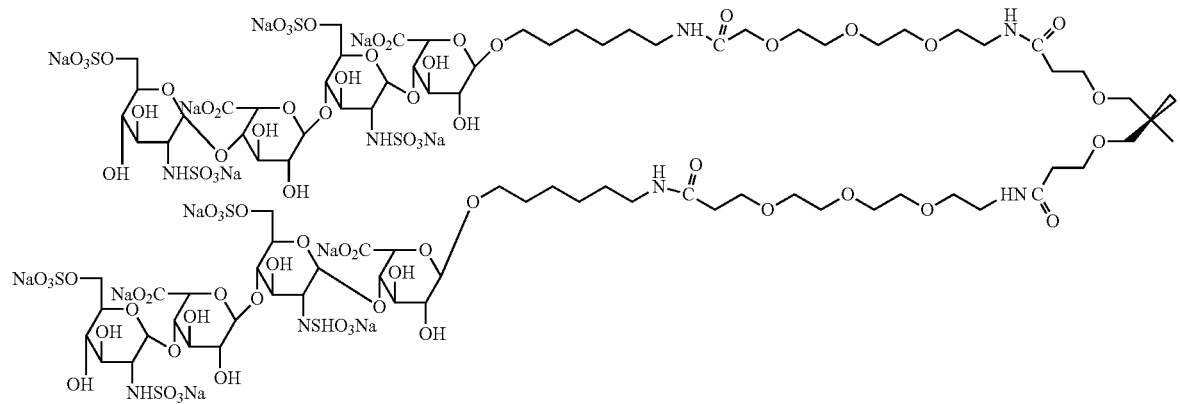
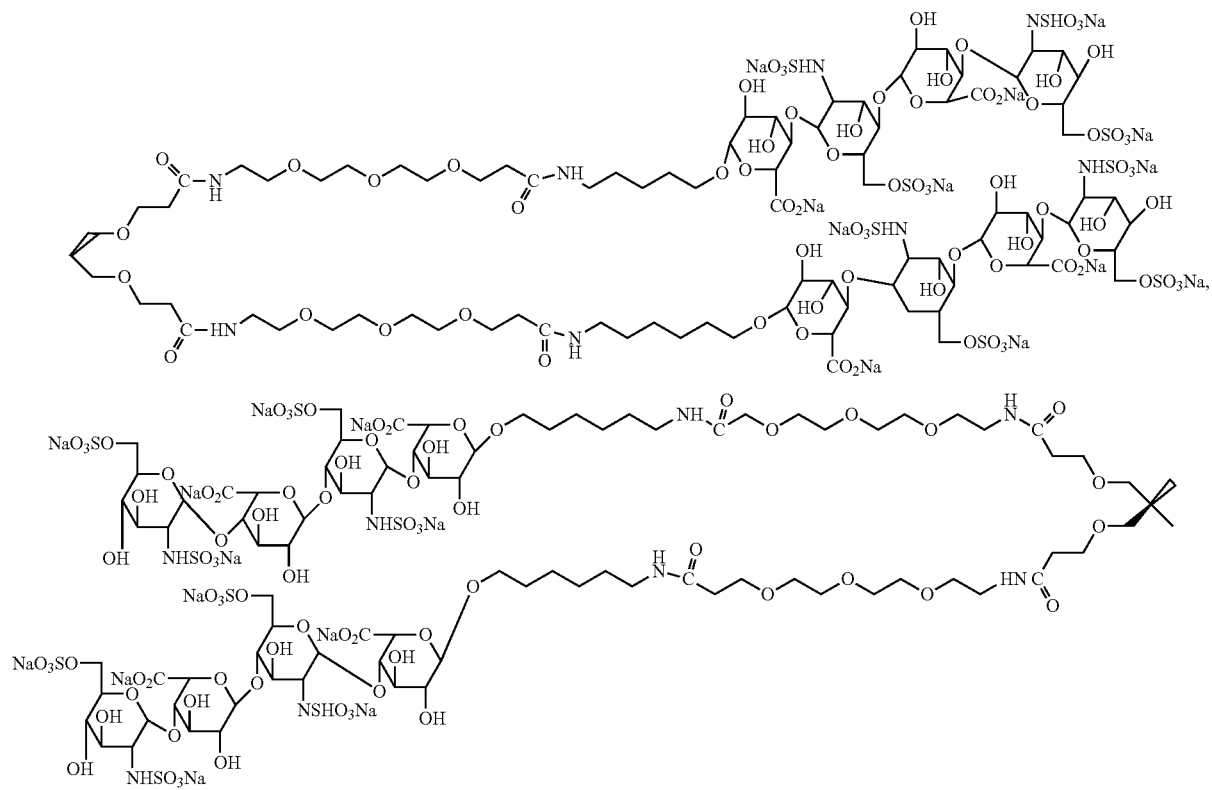

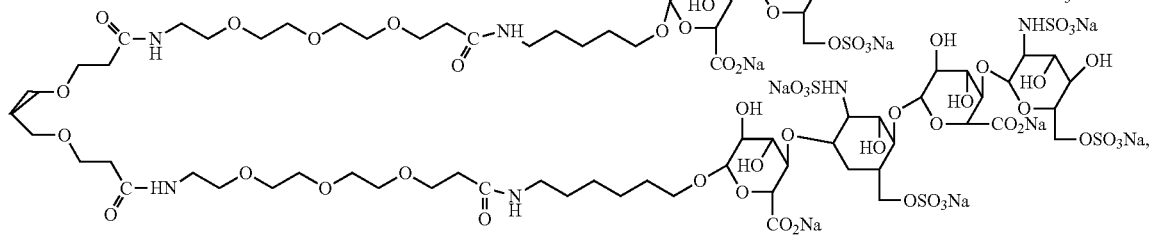
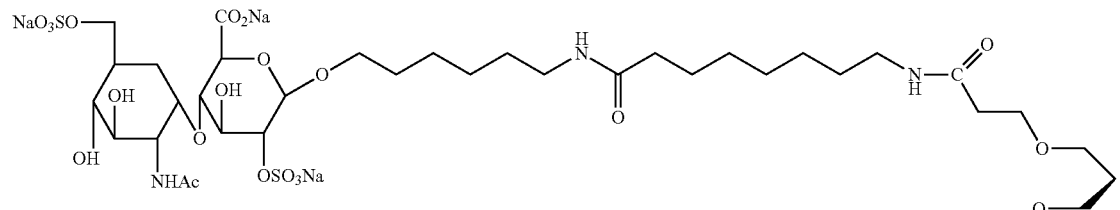
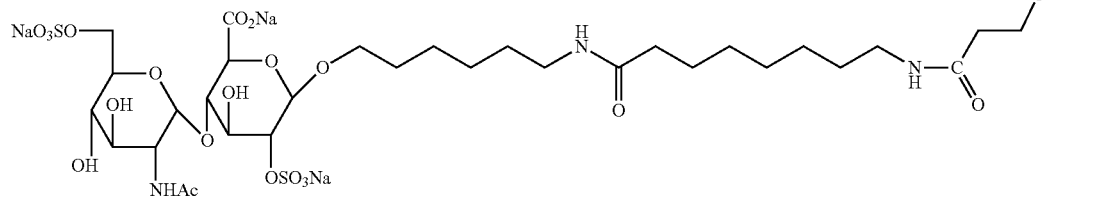
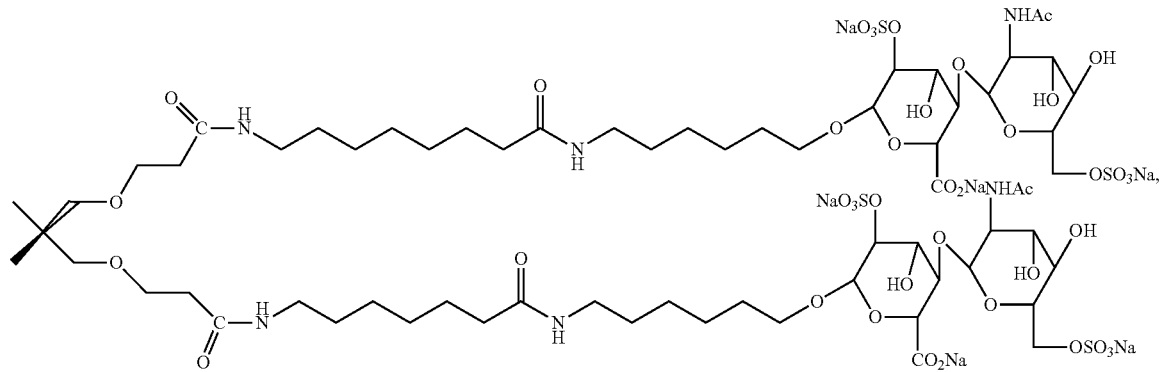
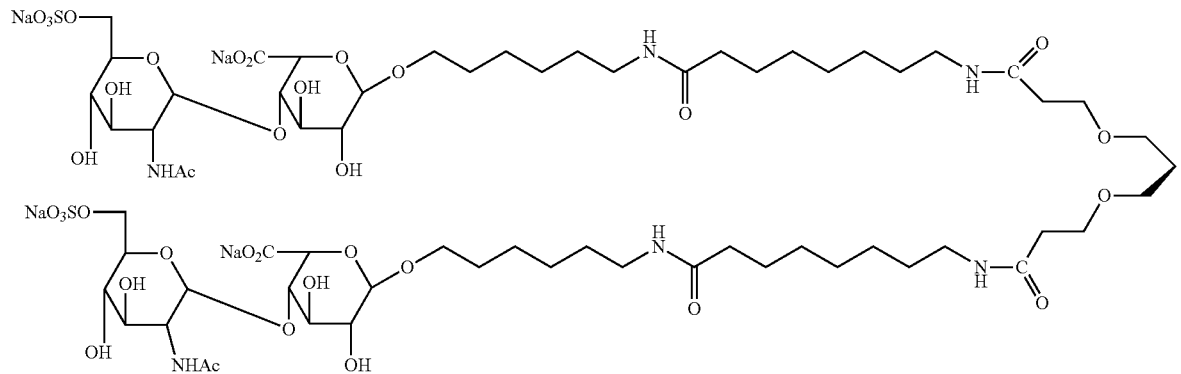

-continued
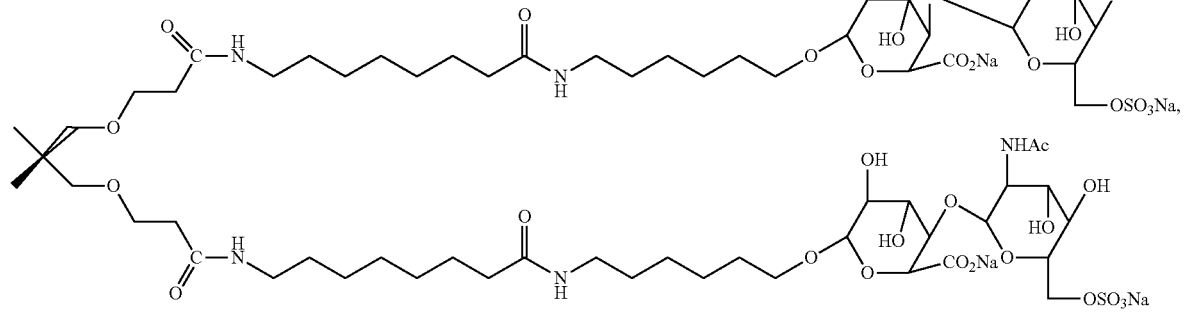
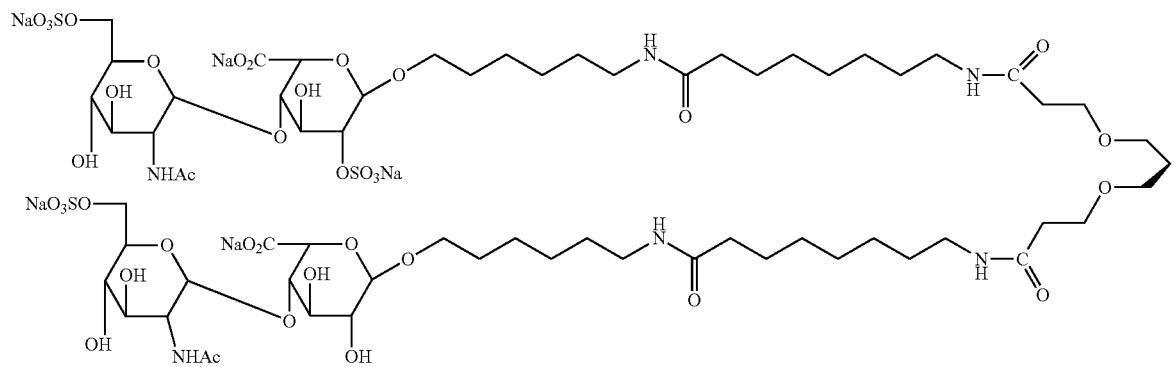
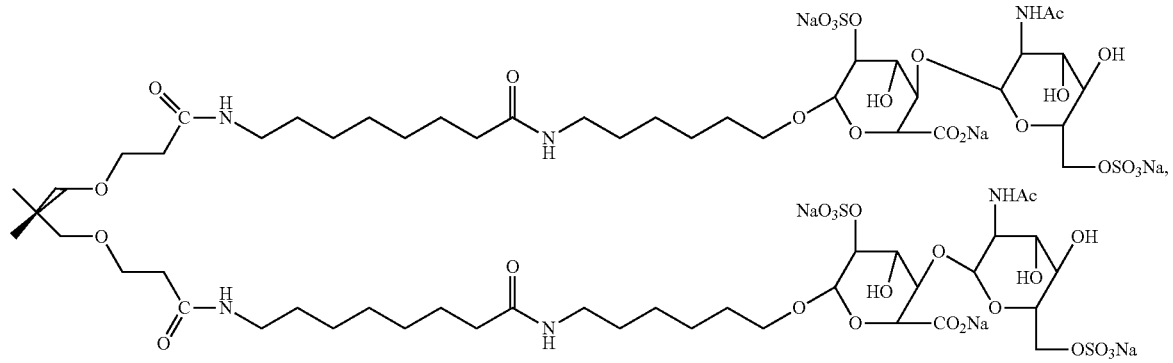
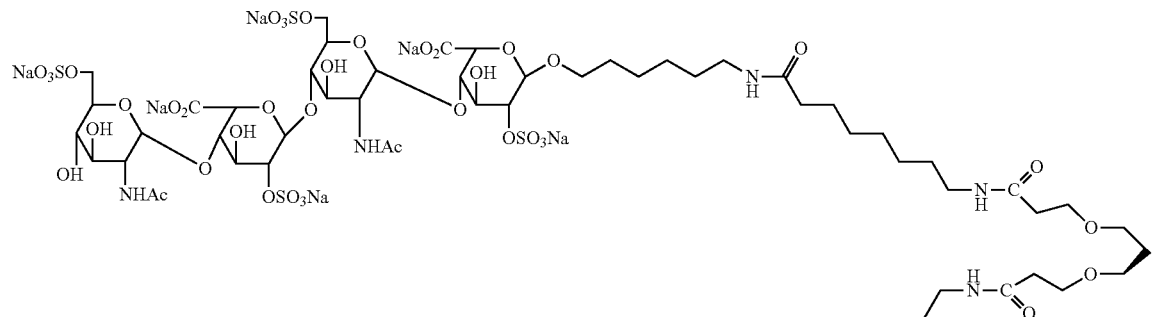
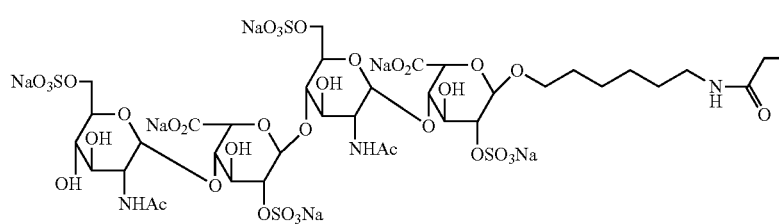

-continued
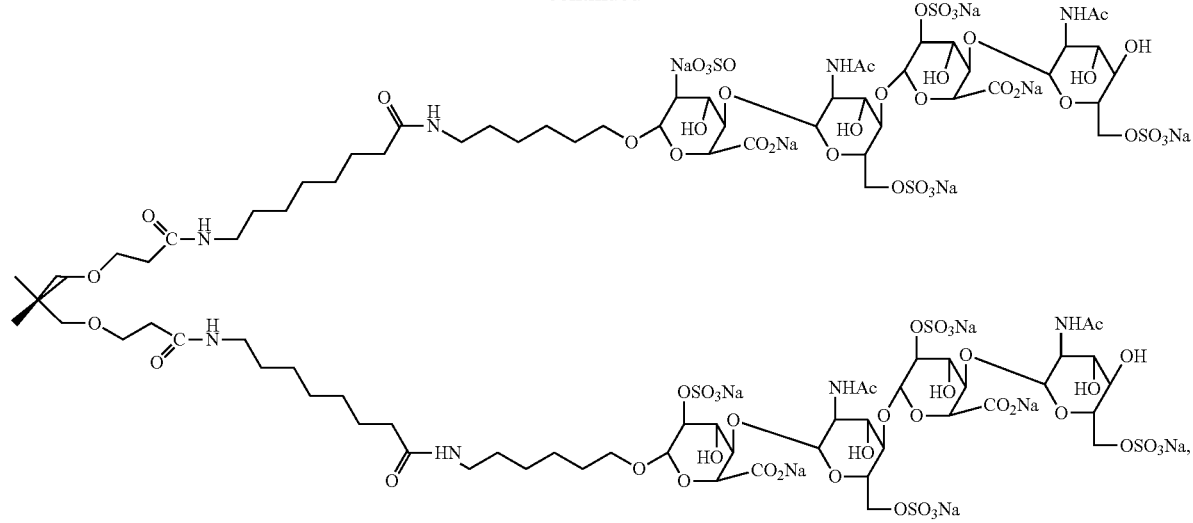
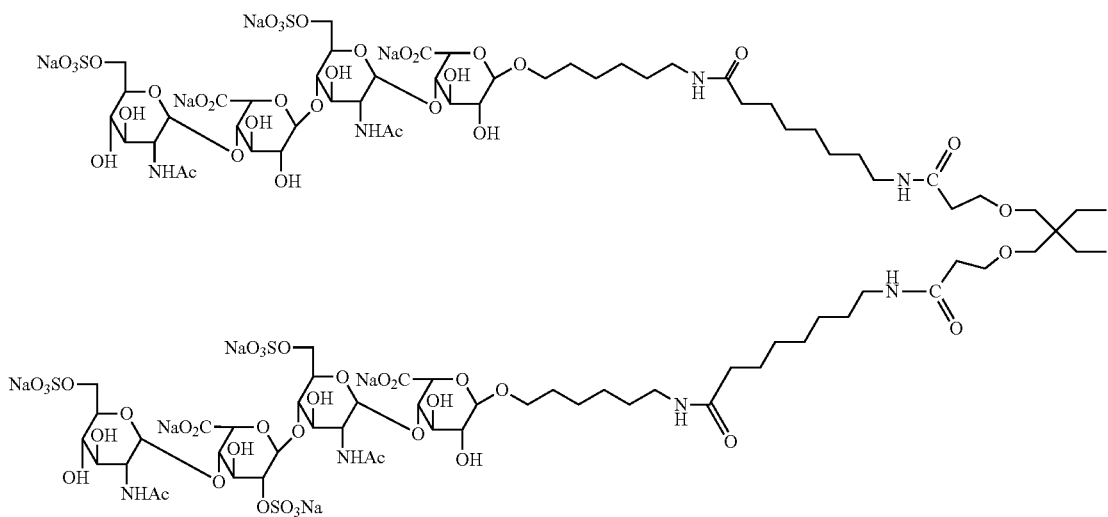
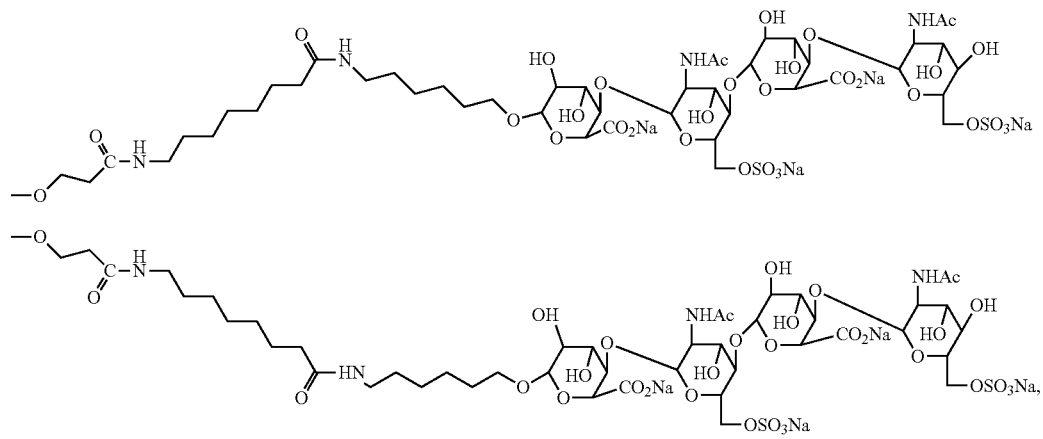

-continued
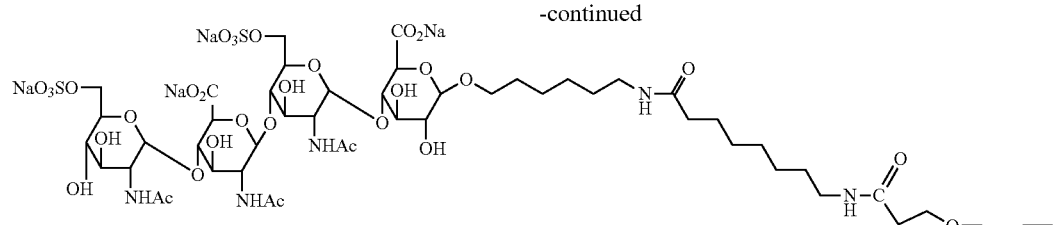
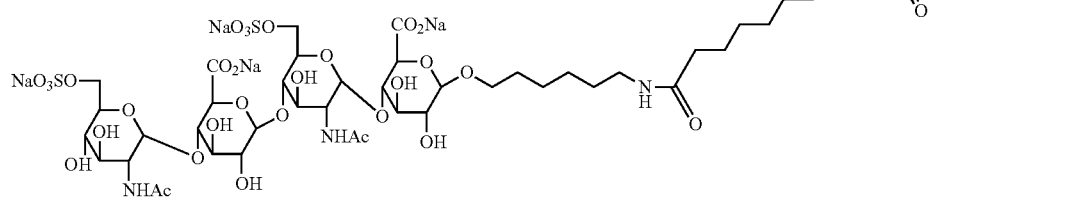
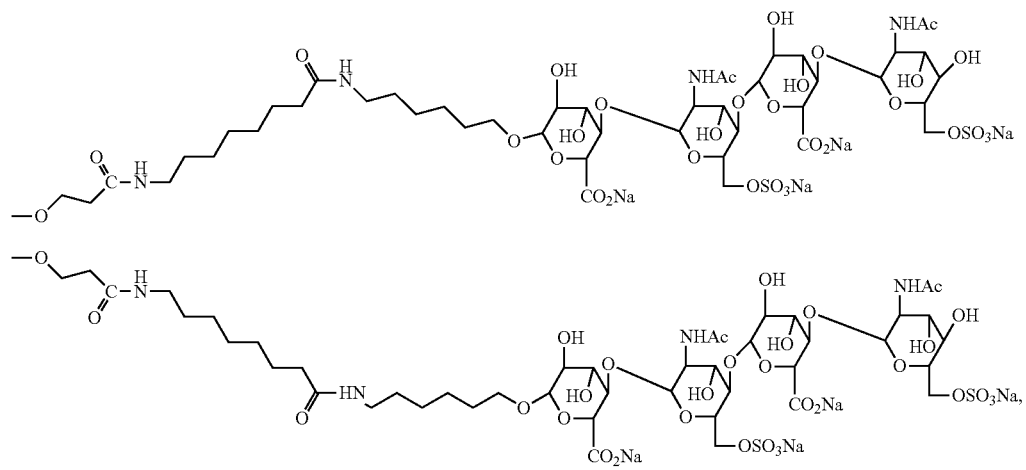
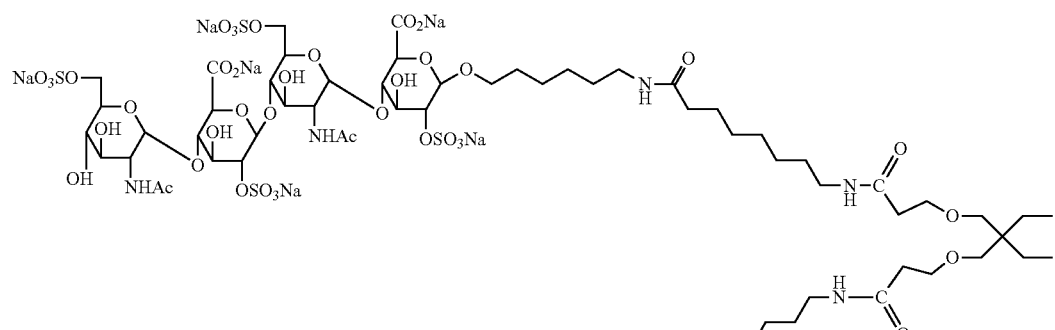
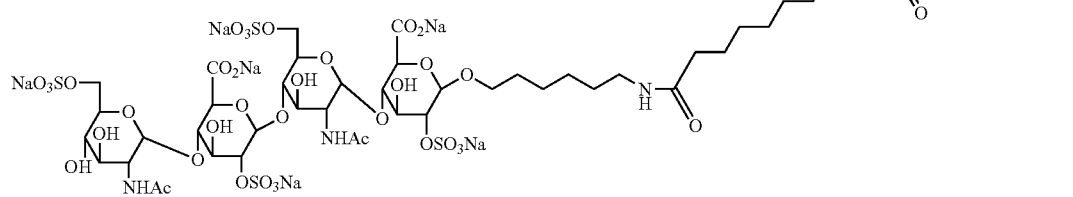

-continued
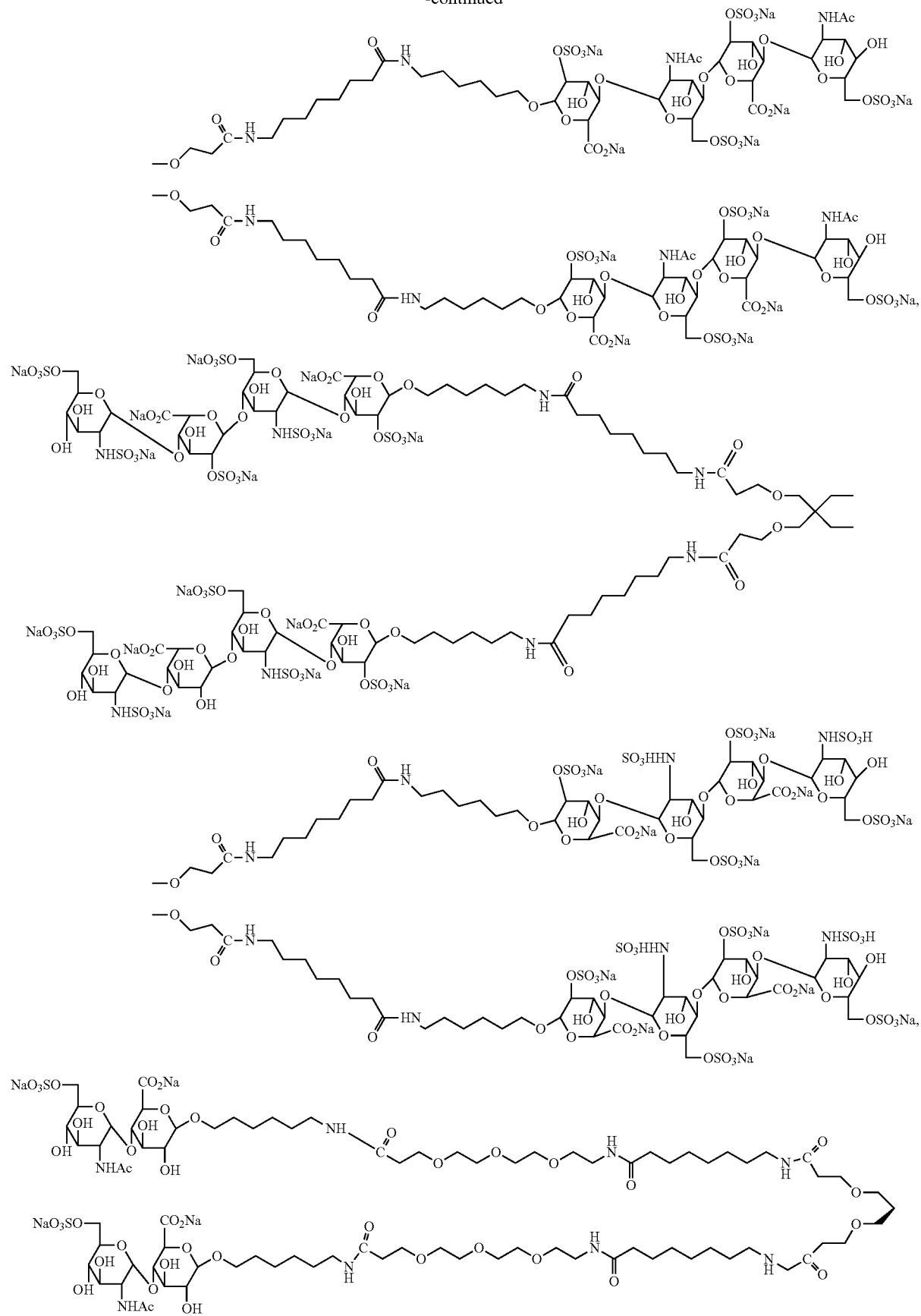

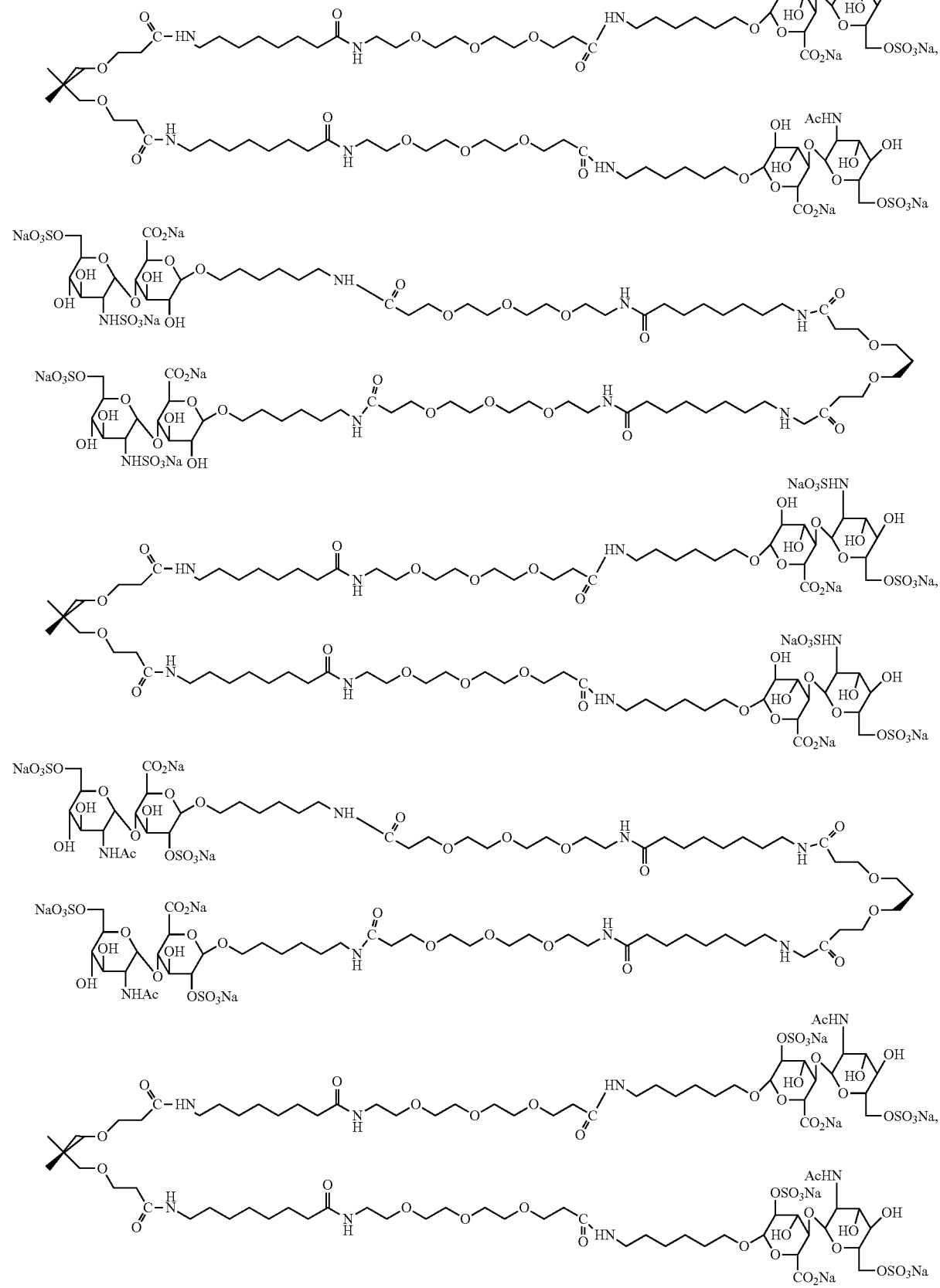

-continued
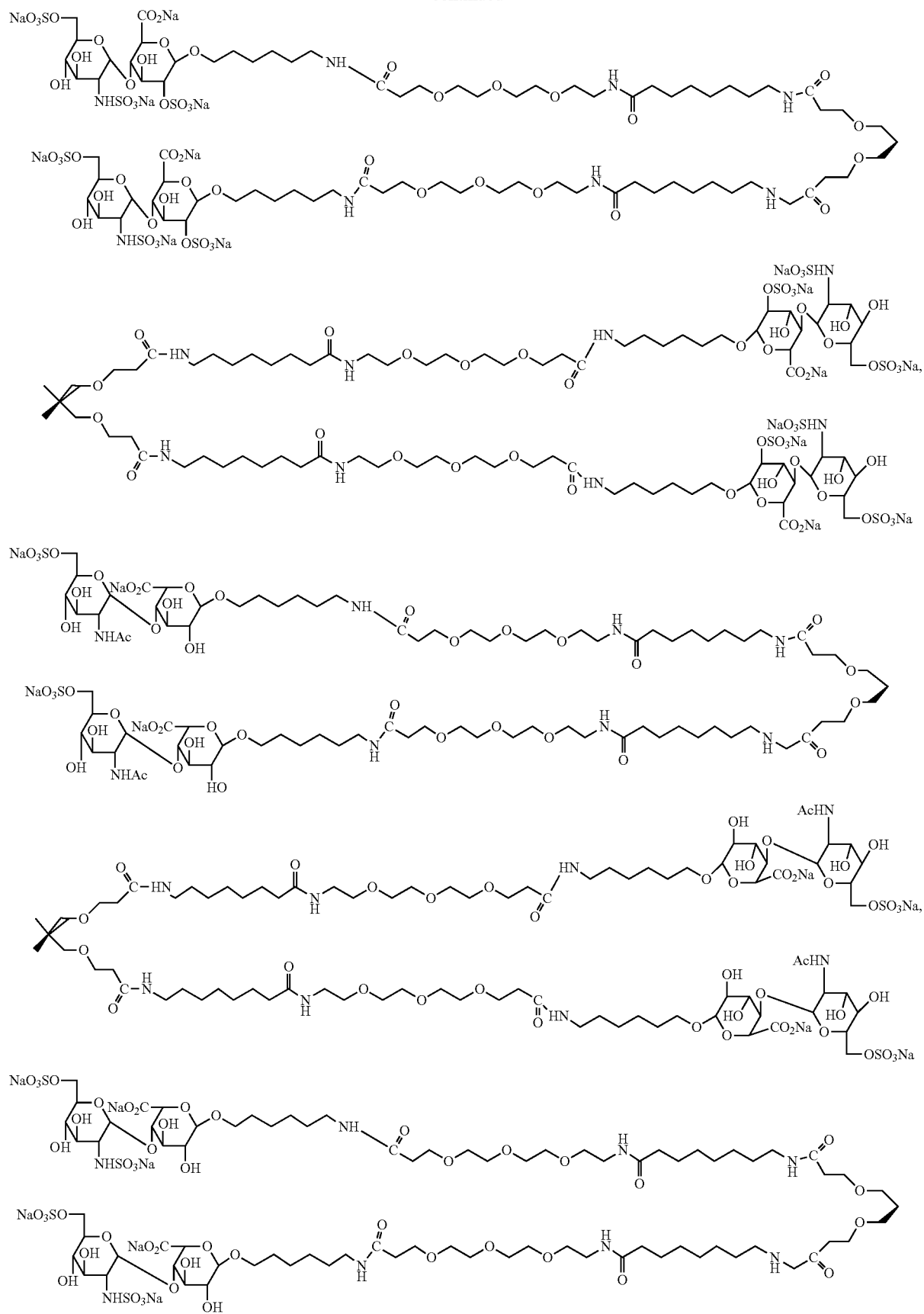

-continued
217
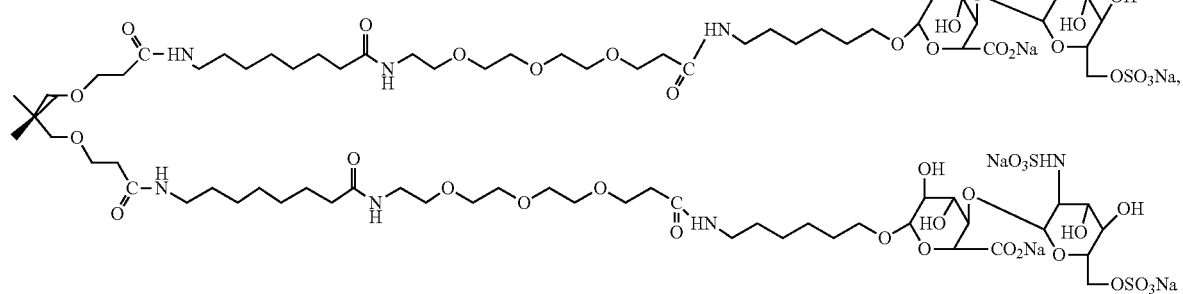
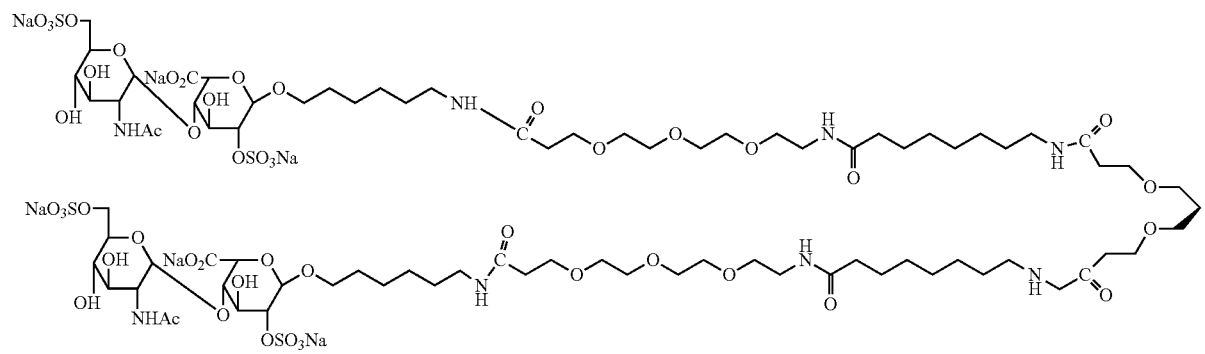
218
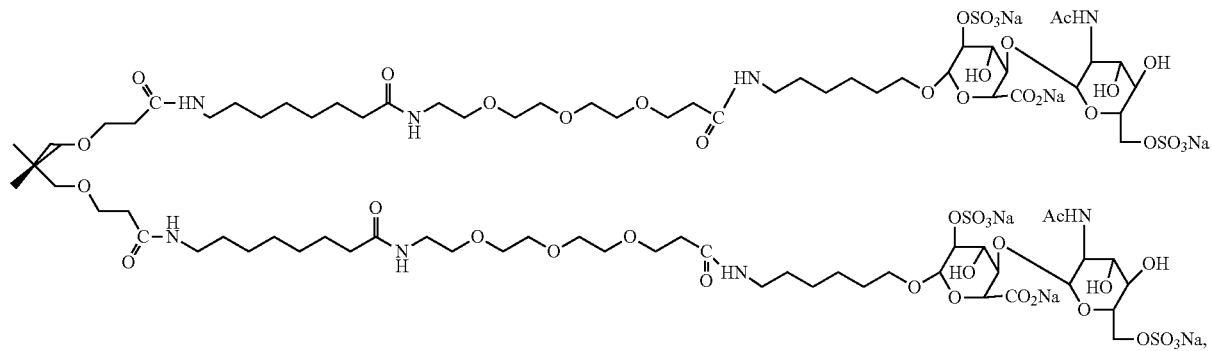
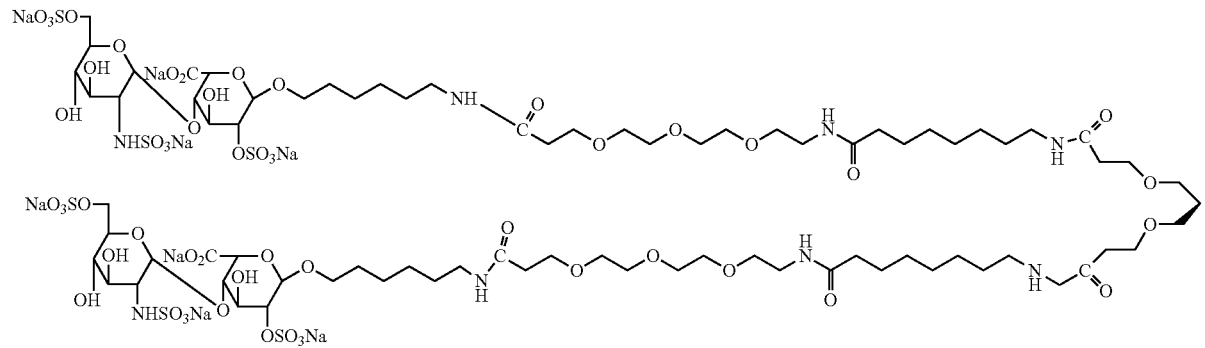

-continued
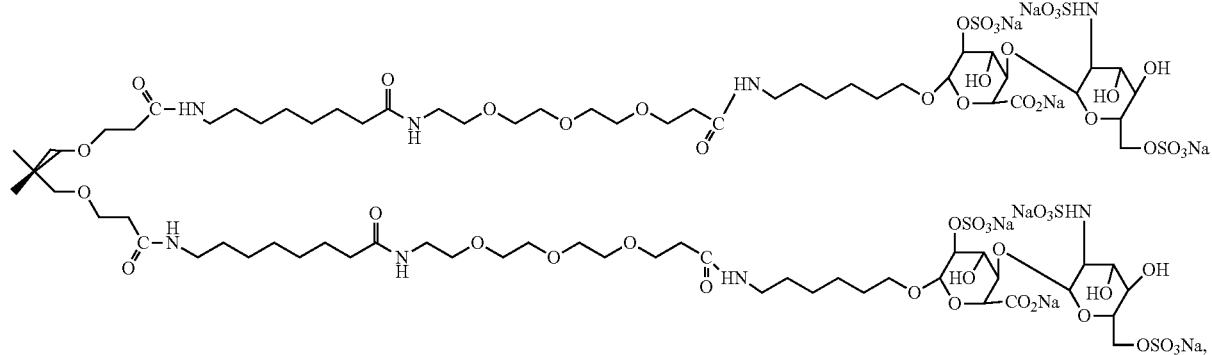
219
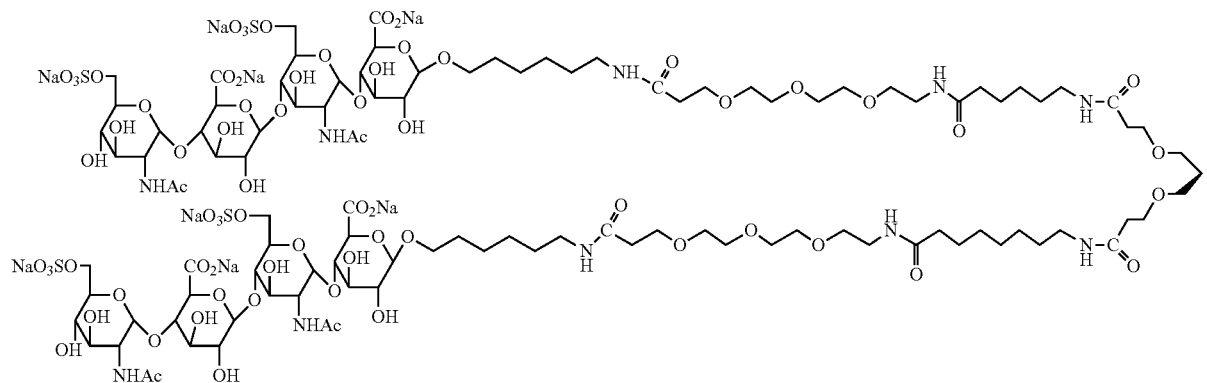
220
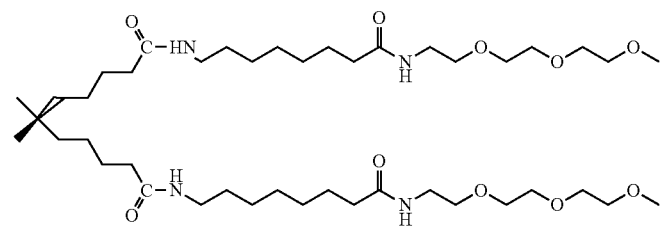
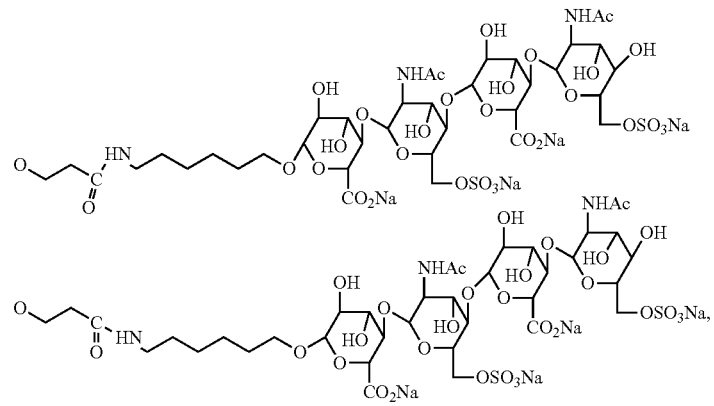

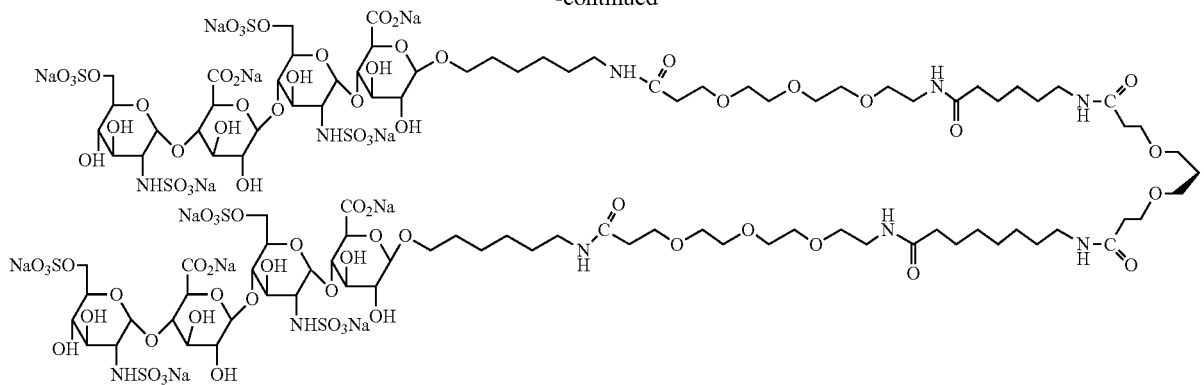
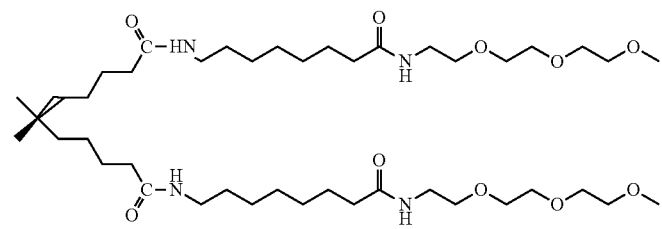
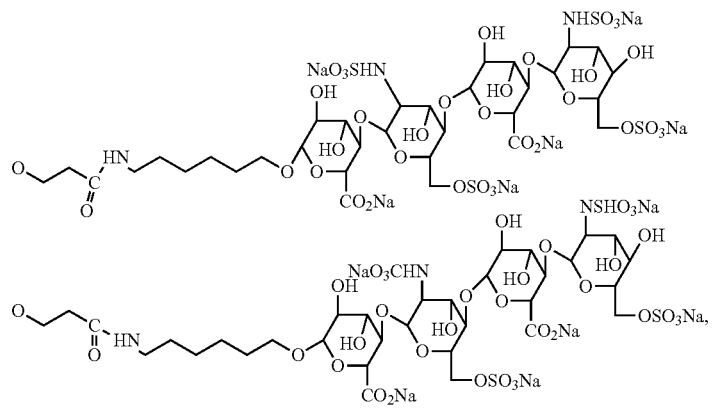
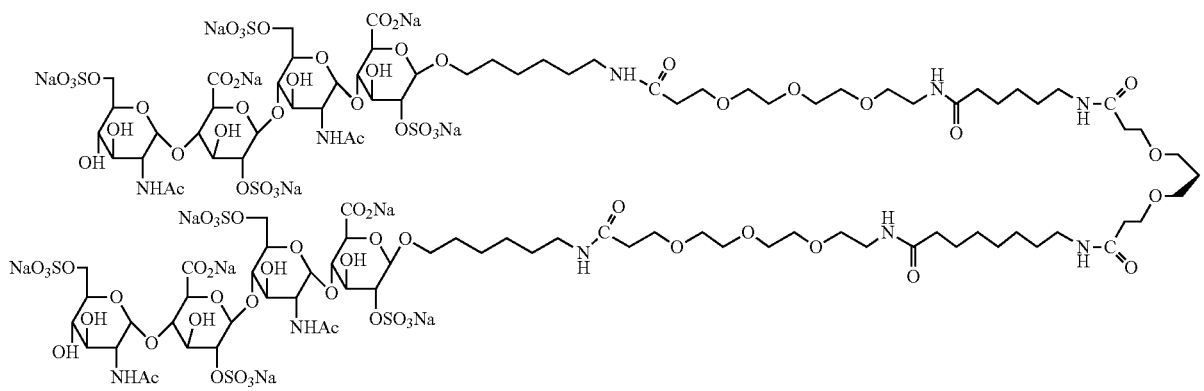
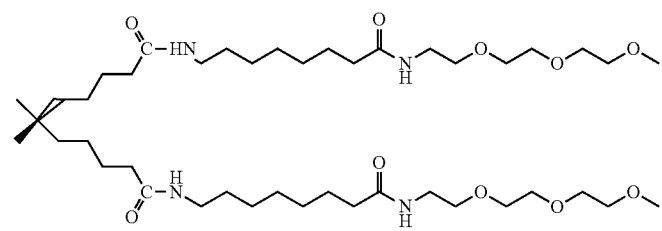

-continued
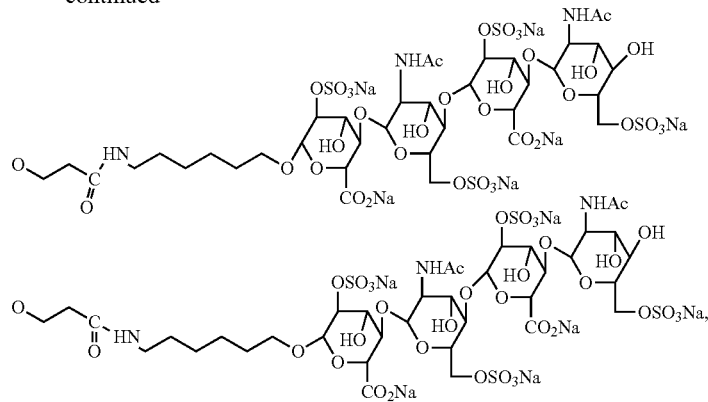
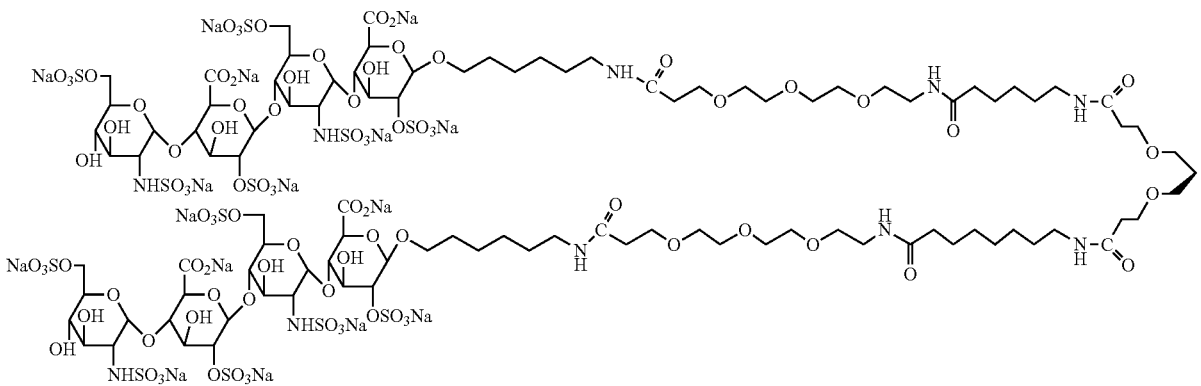
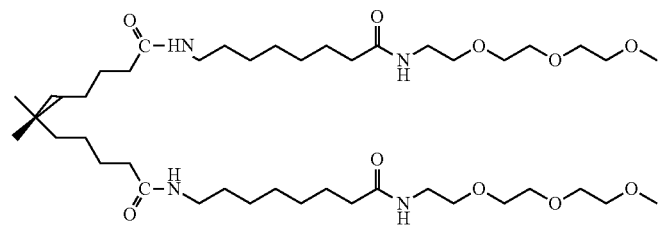
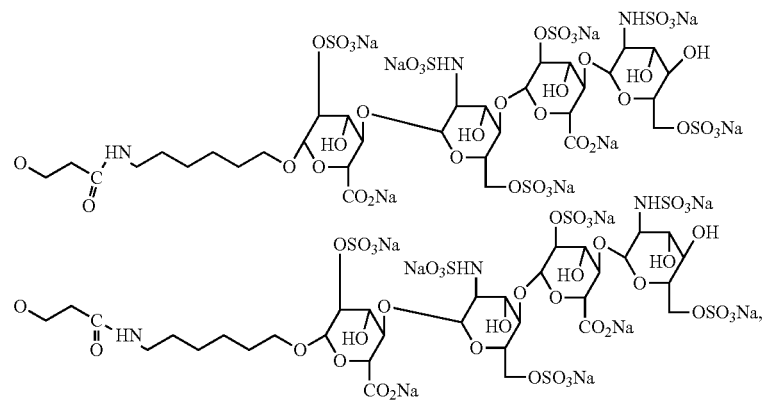

-continued
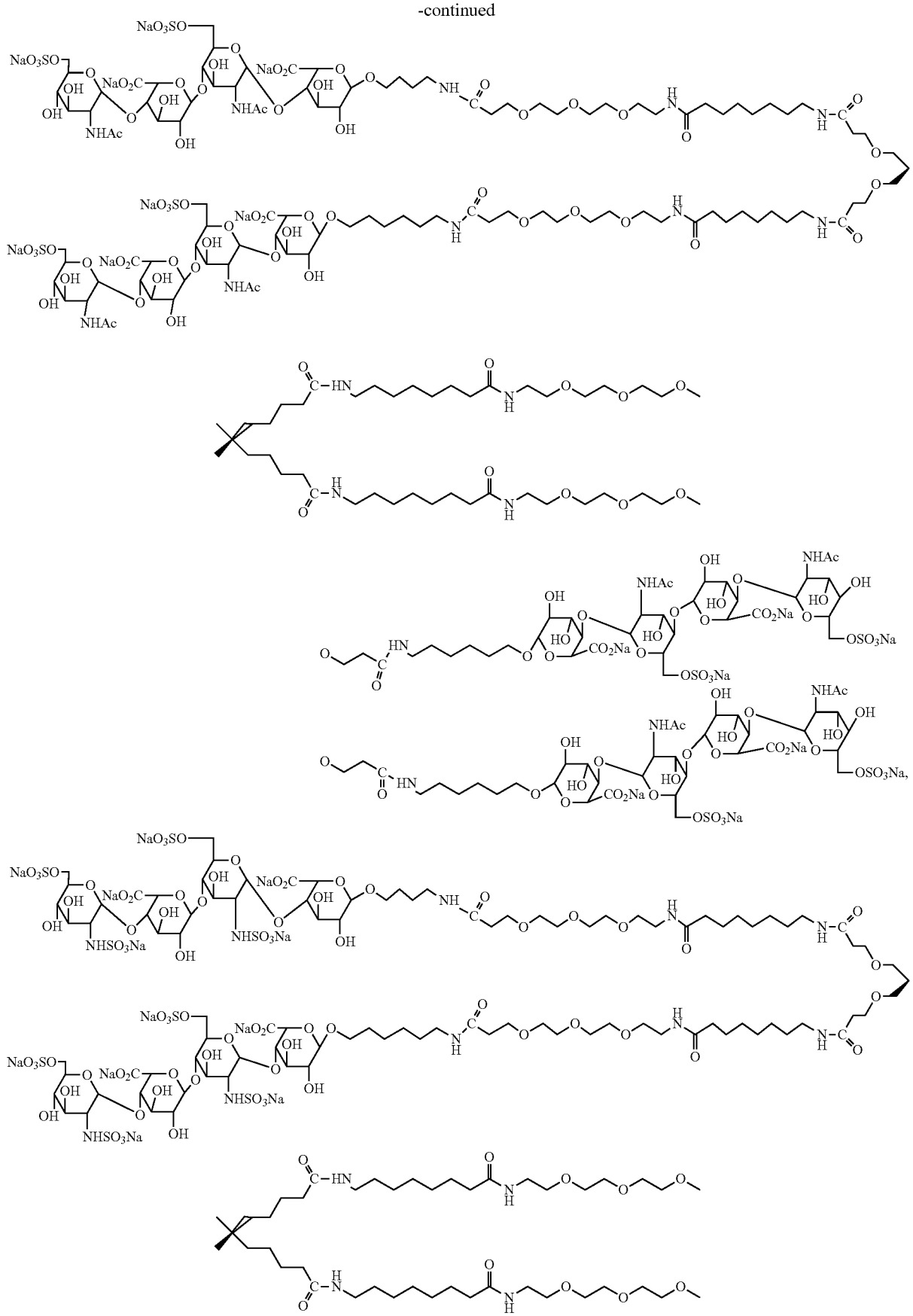

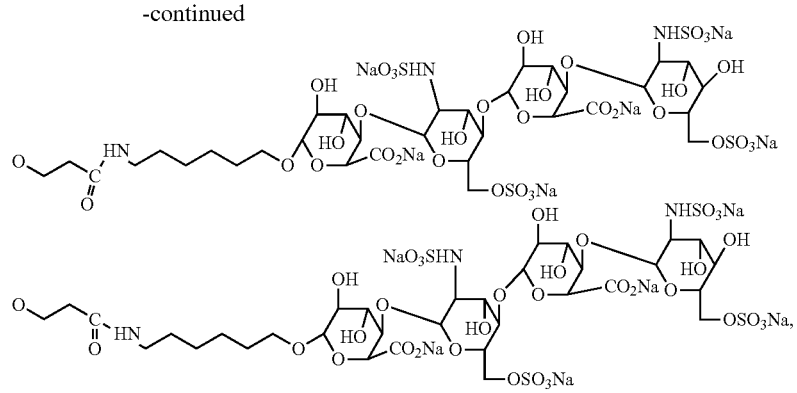
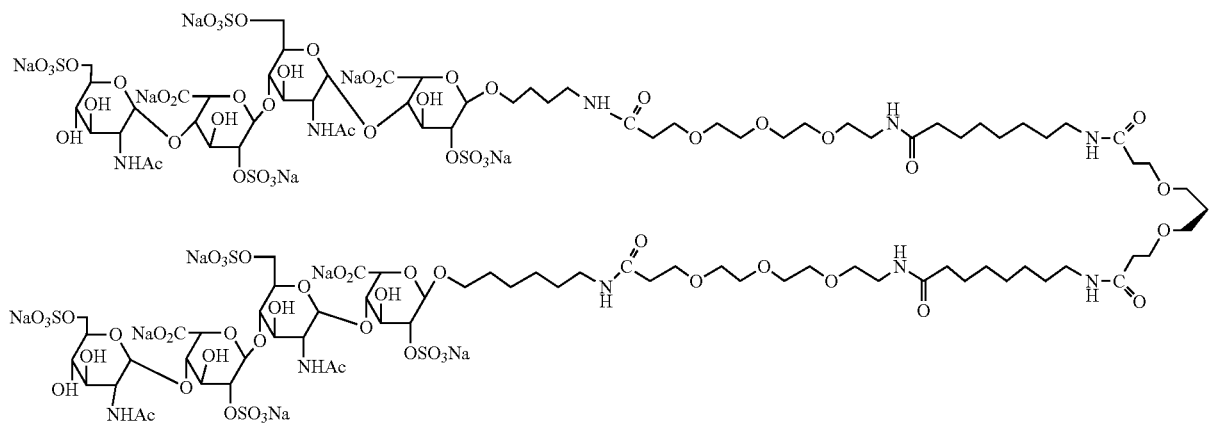
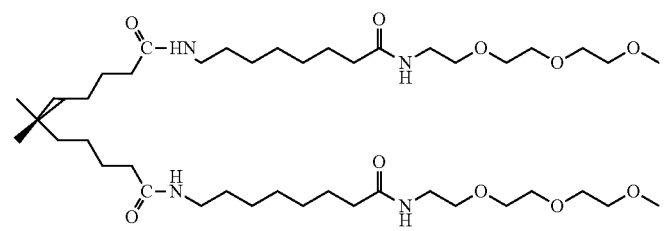
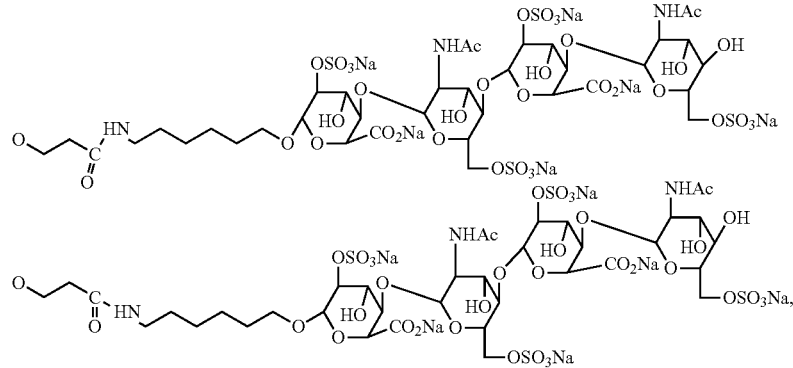

-continued
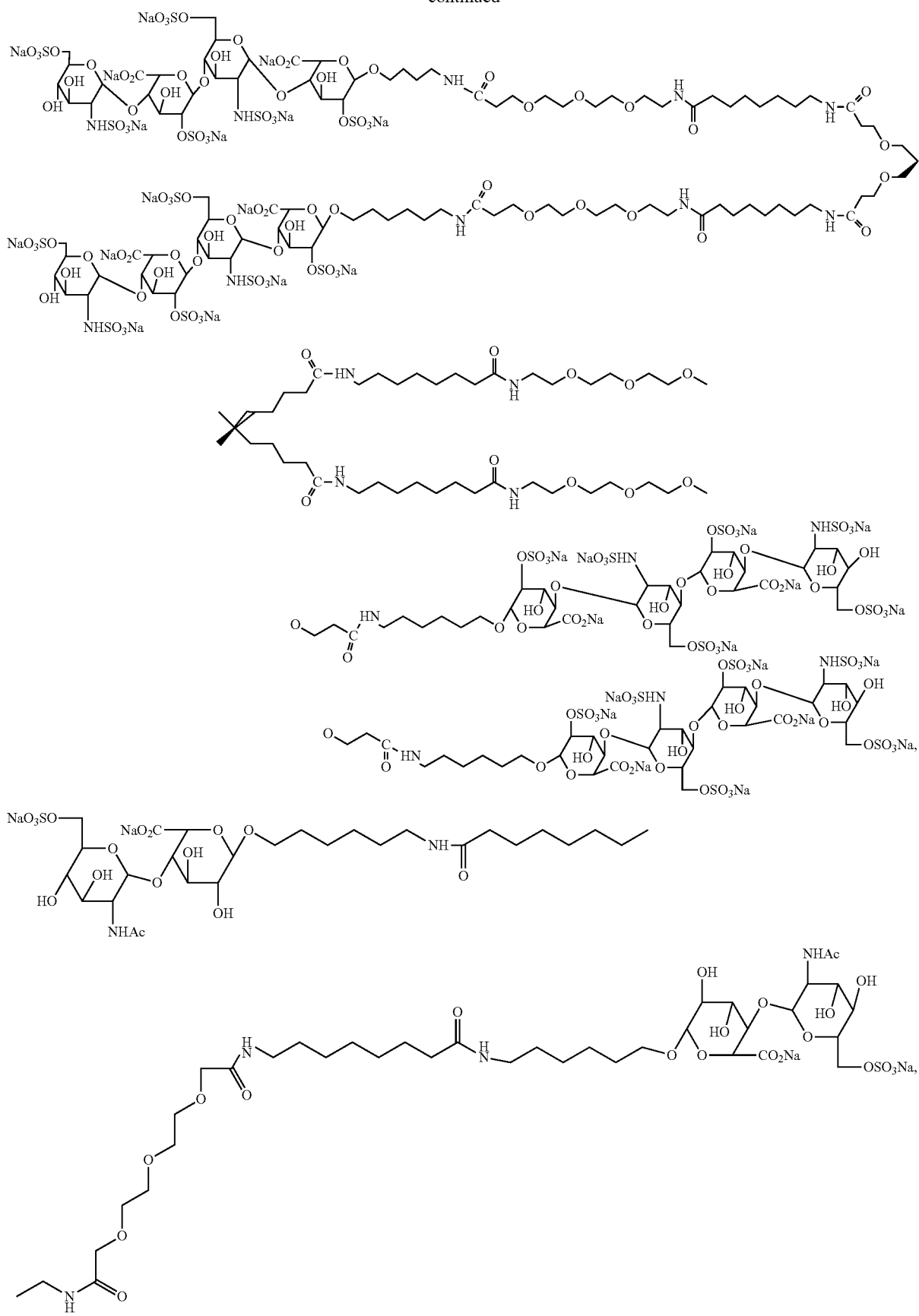

-continued
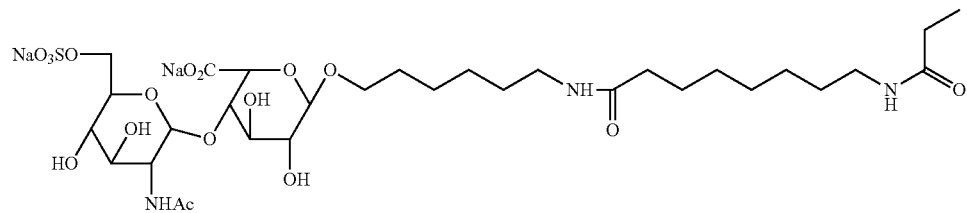
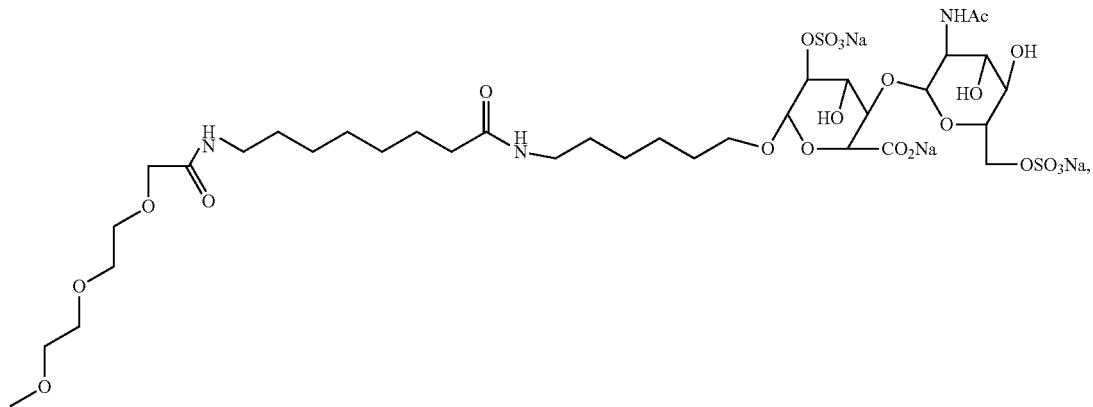
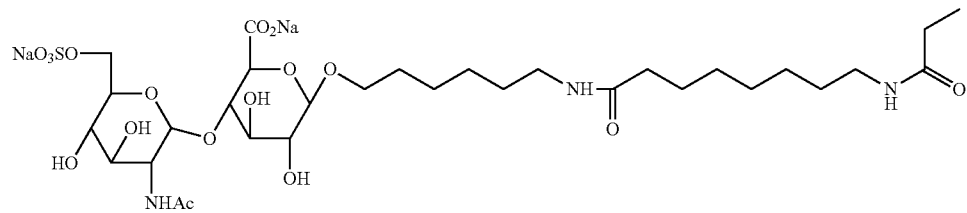
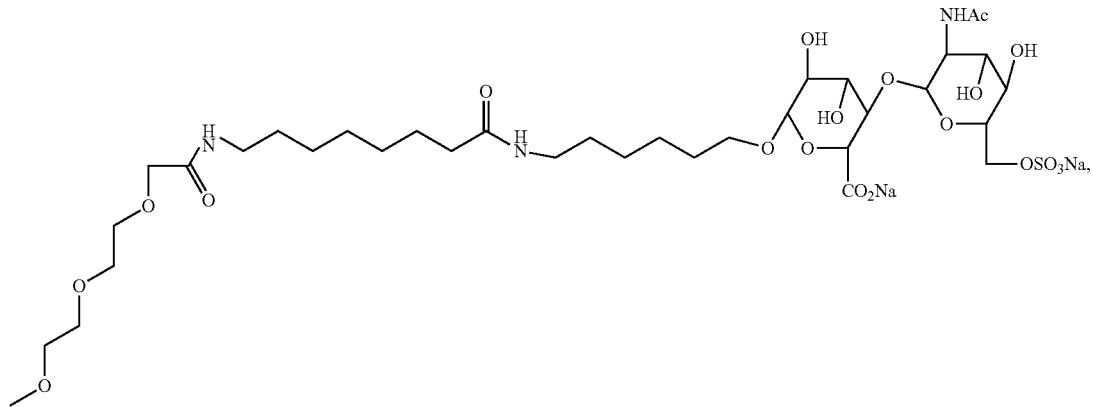
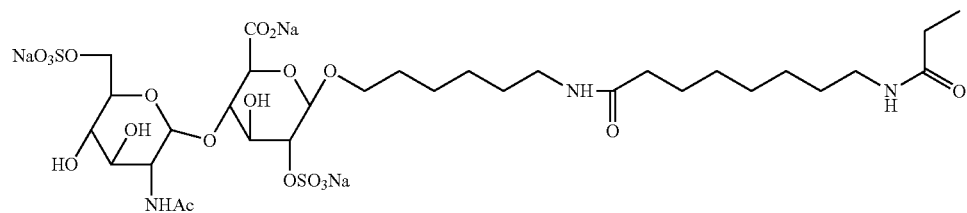

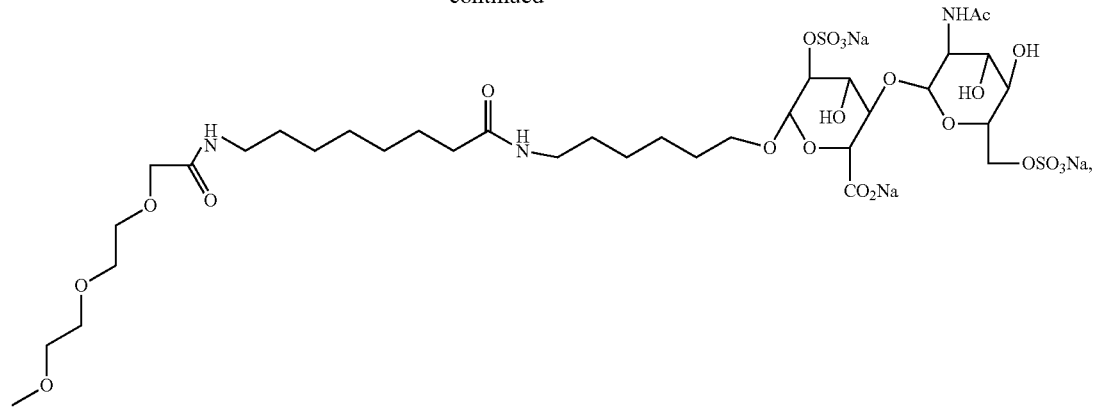
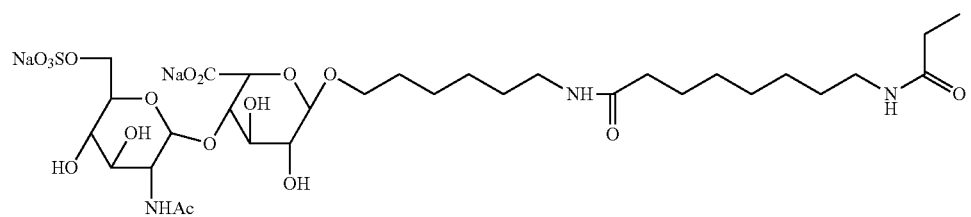
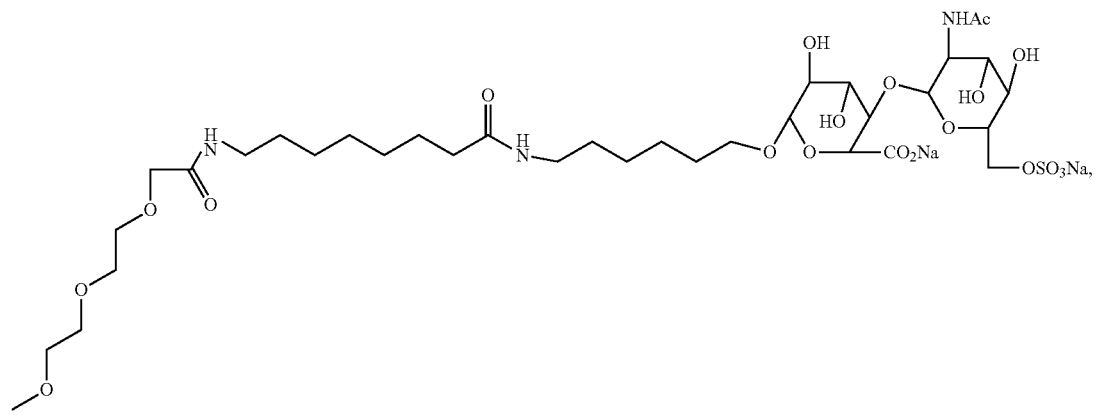
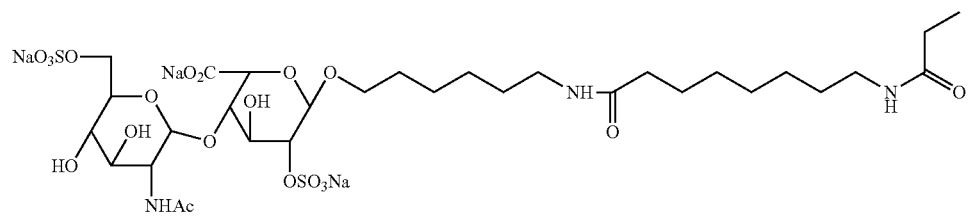
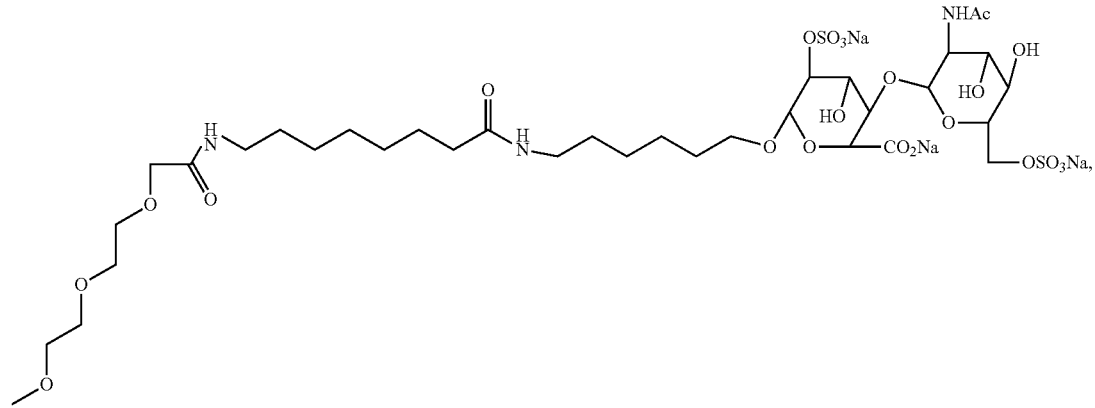

235 236
-continued
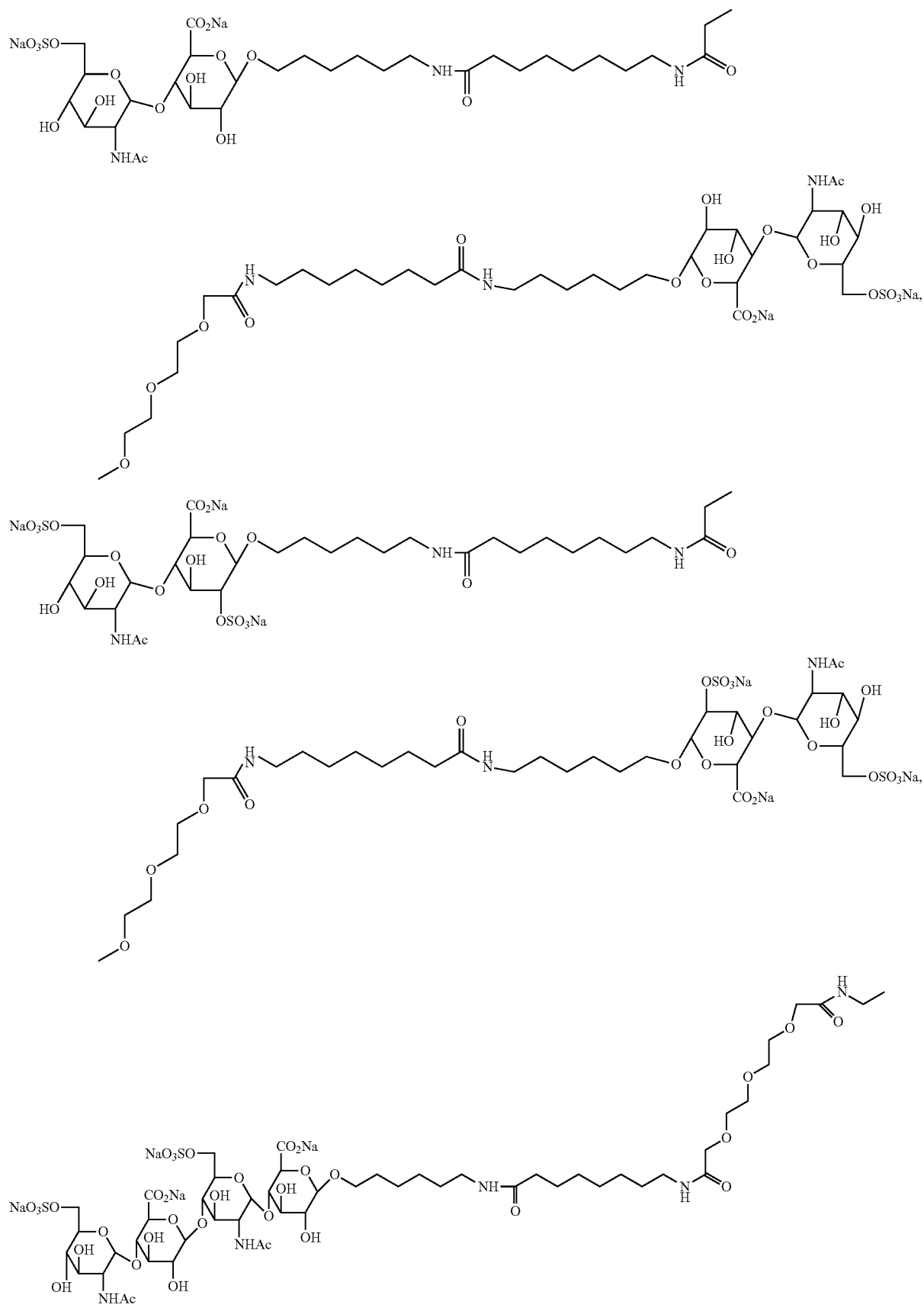

-continued
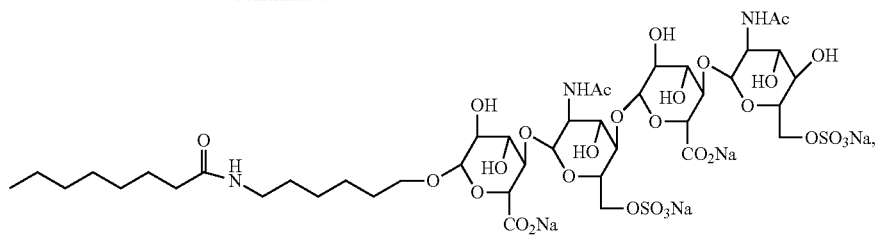
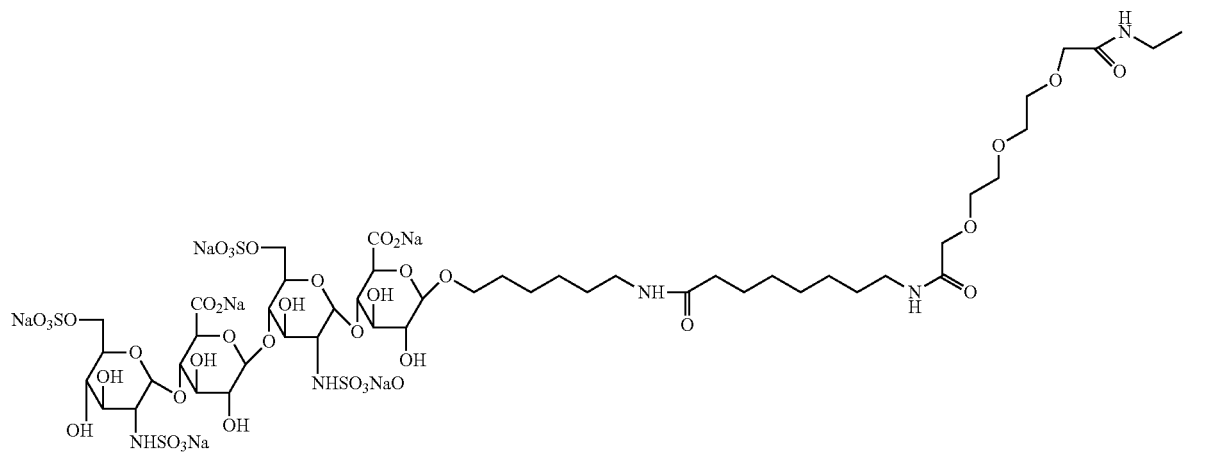
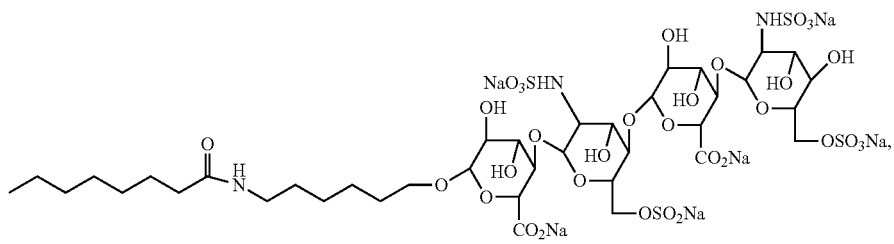
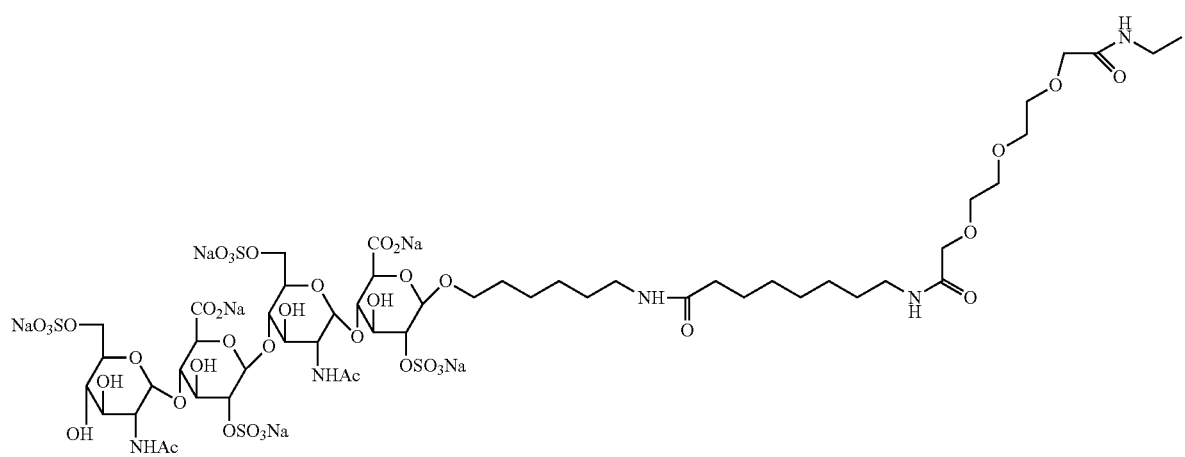
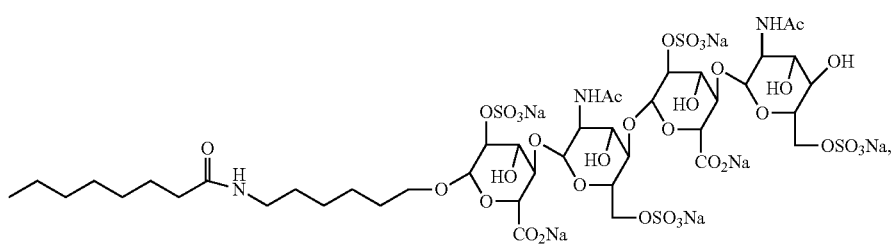

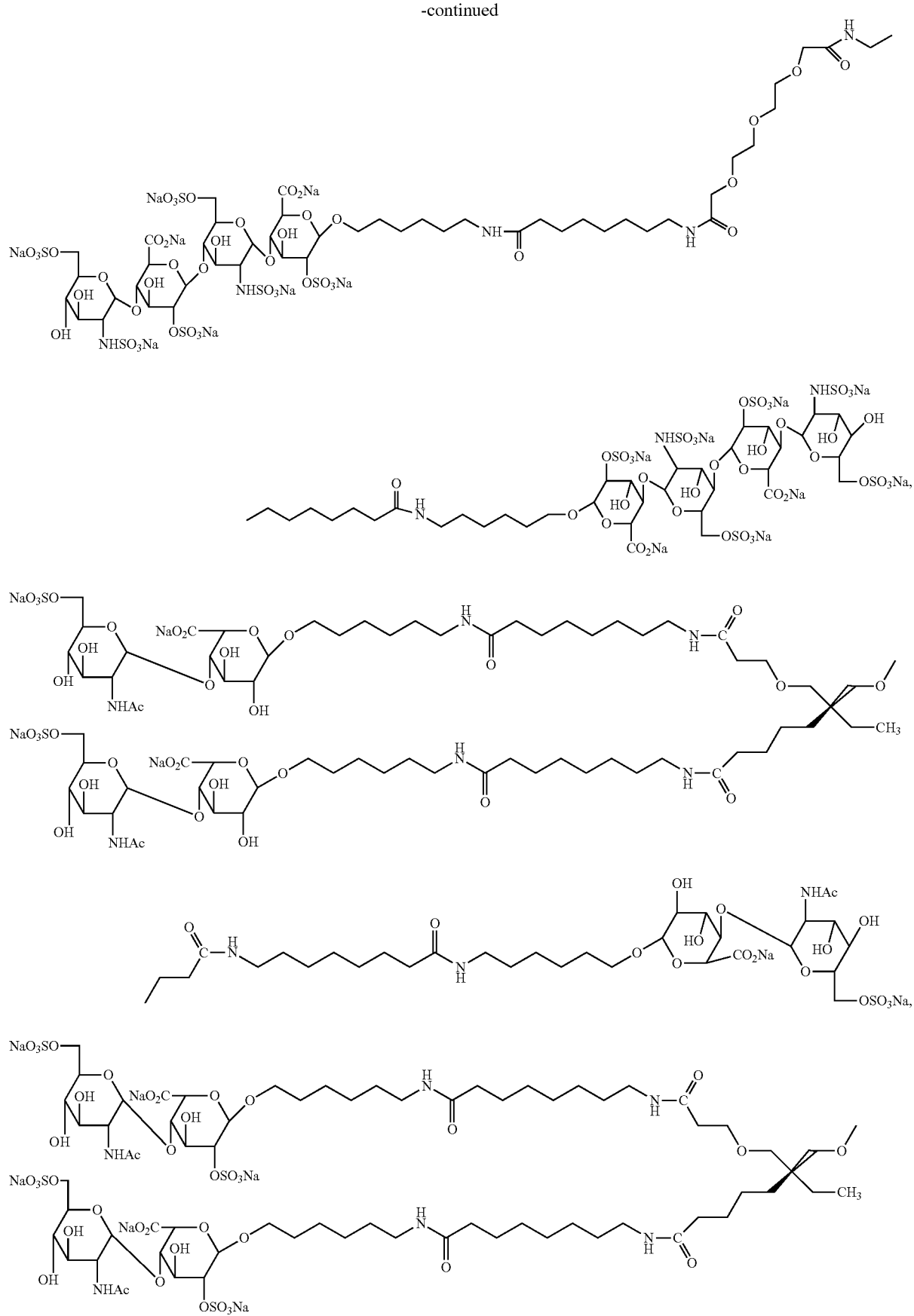

-continued
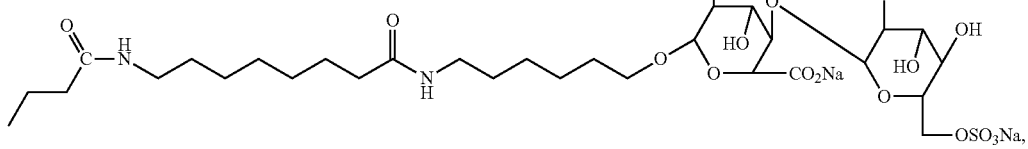
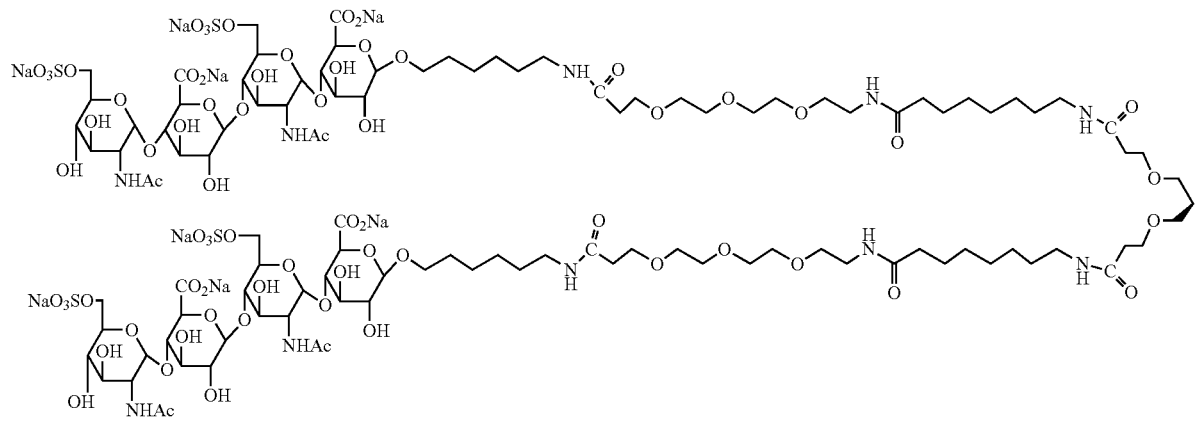
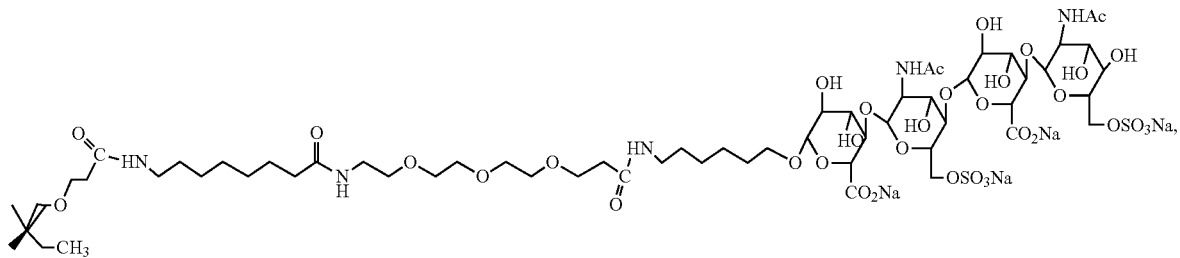
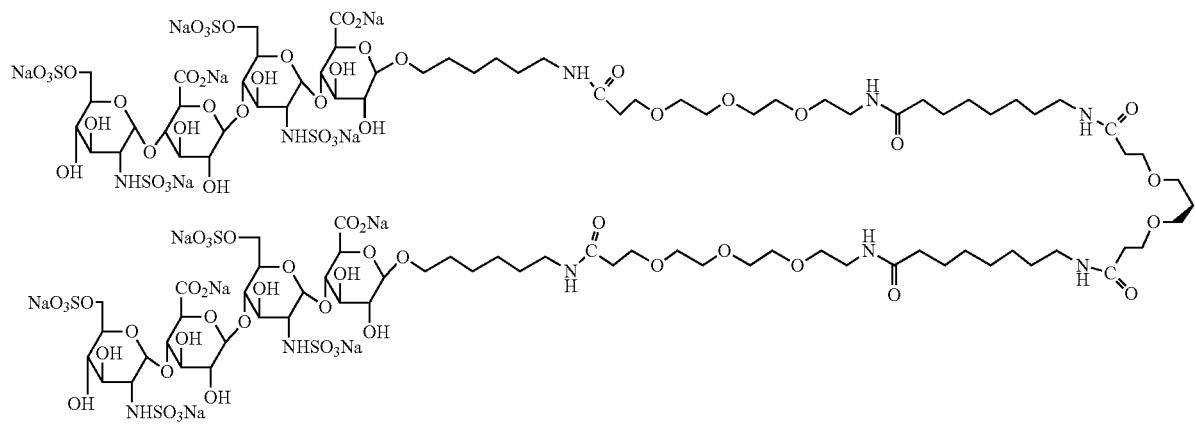
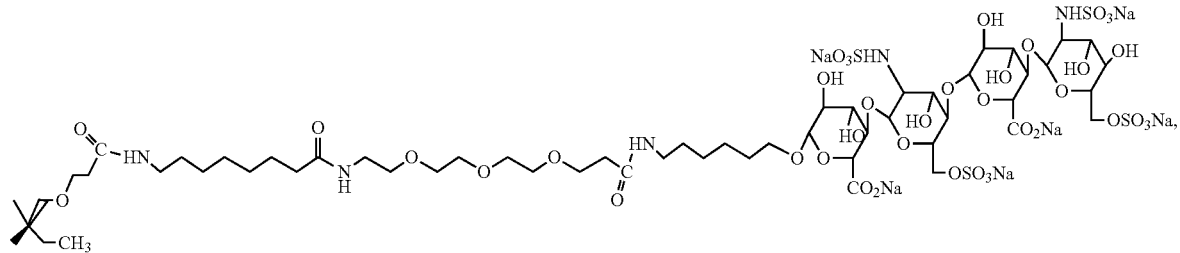

243  244
-continued
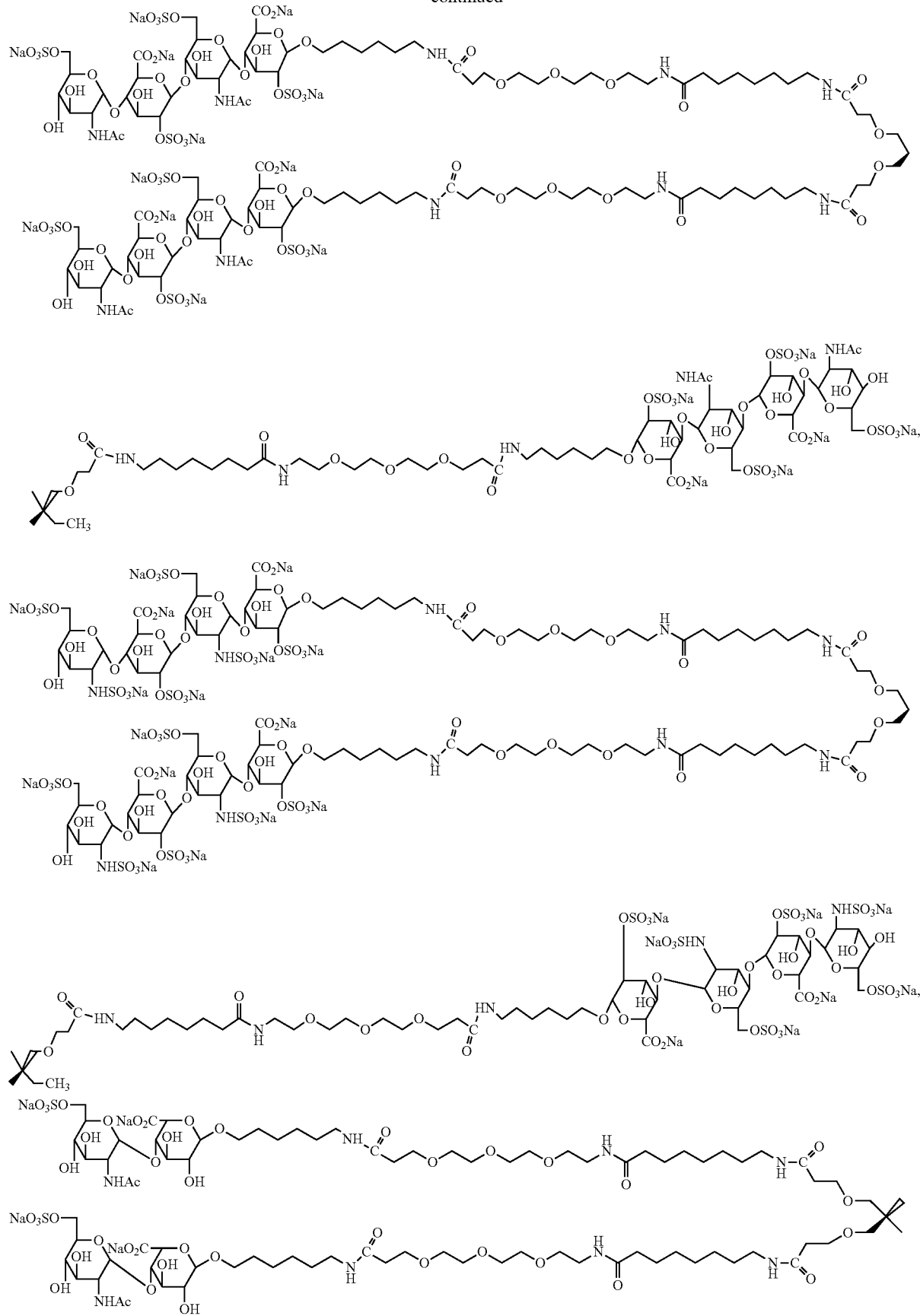

-continued
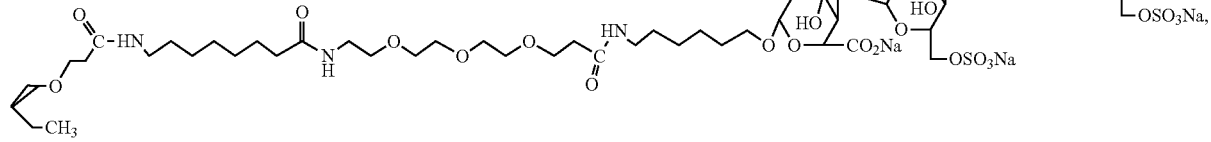
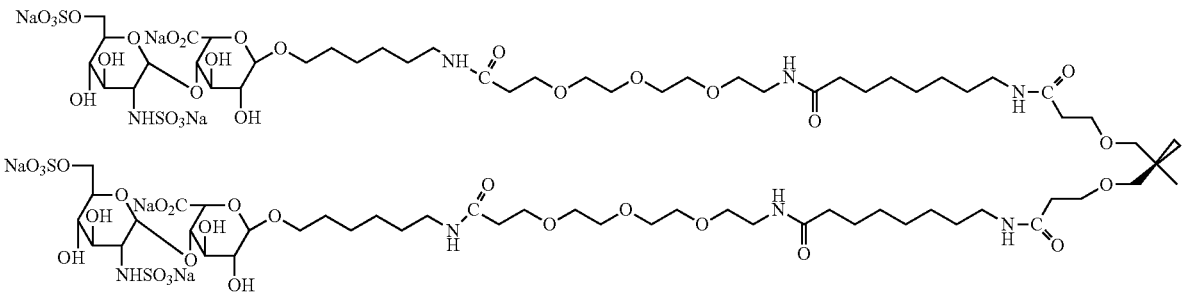
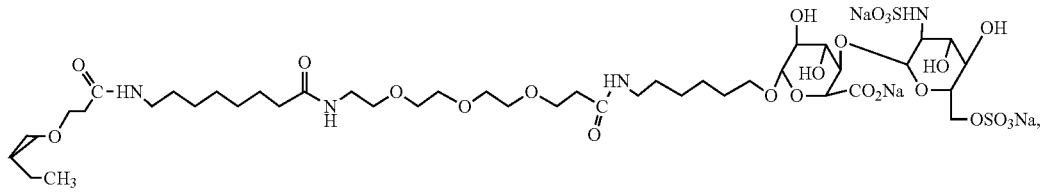
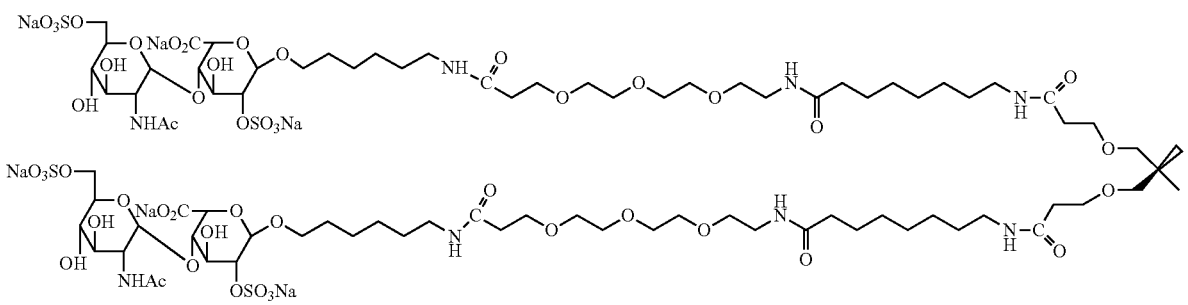
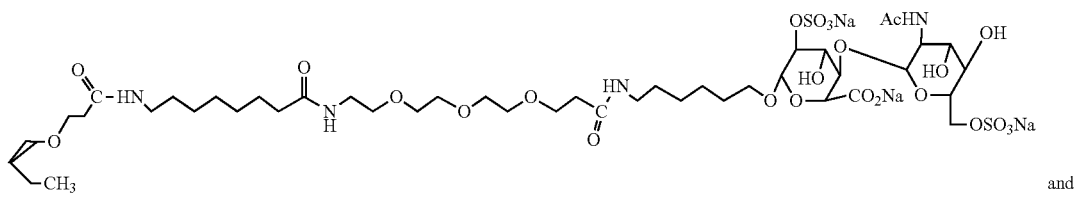
and
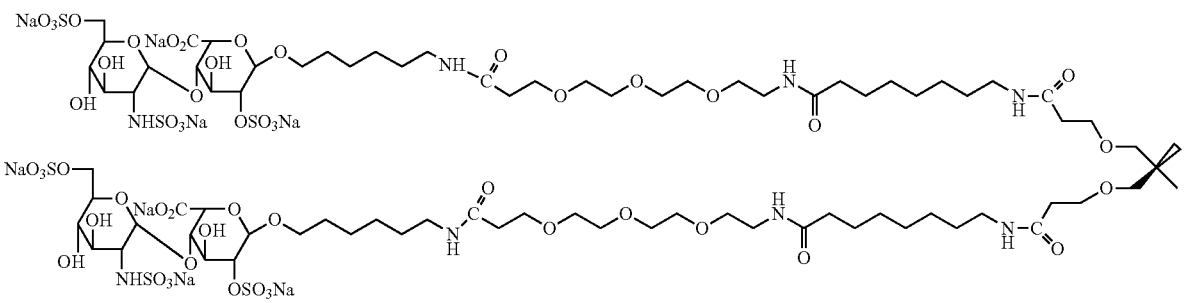

-continued

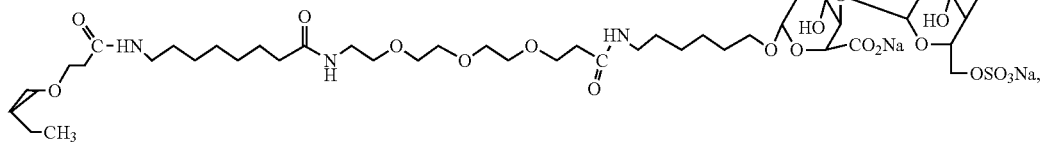

or a pharmaceutically acceptable salt thereof.

18. A pharmaceutical composition comprising a pharmaceutically effective amount of a compound of claim 1 and optionally a pharmaceutically acceptable carrier, diluent or excipient.

19. A method of treating a disease or disorder in which it is desirable to inhibit BACE-1, the method comprising administering a pharmaceutically effective amount of a compound of claim 1 to a patient requiring treatment, wherein the disease or disorder is senile dementia, pre-senile dementia, multi-infarct dementia or Alzheimer's disease.

* * * * *